US012788966B2

(12) United States Patent
Daniels

(10) Patent No.: US 12,788,966 B2
(45) Date of Patent: Nov. 10, 2026

(54) METHODS FOR MANUFACTURING WEARABLE ELECTRONICS AND SKIN CONTACT ELECTRODES

(71) Applicant: John Daniels, Madison, CT (US)

(72) Inventor: John Daniels, Madison, CT (US)

( * ) Notice: Subject to any disclaimer, the term of this patent is extended or adjusted under 35 U.S.C. 154(b) by 619 days.

(21) Appl. No.: 17/546,266

(22) Filed: Dec. 9, 2021

(65) Prior Publication Data

US 2022/0288382 A1 Sep. 15, 2022

Related U.S. Application Data

(63) Continuation of application No. 16/464,171, filed as application No. PCT/US2017/062429 on Nov. 17, 2017, now Pat. No. 11,229,787.

(60) Provisional application No. 62/549,668, filed on Aug. 24, 2017, provisional application No. 62/537,658, filed on Jul. 27, 2017, provisional application No. 62/530,888, filed on Jul. 11, 2017, provisional application No. 62/462,091, filed on Feb. 22, 2017, provisional application No. 62/445,517, filed on Jan. 12, 2017, provisional application No. 62/426,453, filed on Nov. 25, 2016.

(51) Int. Cl.

| | |
|---|---|
| ***A61N 1/04*** | (2006.01) |
| ***A61N 1/02*** | (2006.01) |
| ***A61N 1/36*** | (2006.01) |
| ***H01B 13/00*** | (2006.01) |

(52) U.S. Cl.

CPC ........... *A61N 1/0452* (2013.01); *A61N 1/025* (2013.01); *A61N 1/0484* (2013.01); *A61N 1/36031* (2017.08); *H01B 13/00* (2013.01)

(58) Field of Classification Search

CPC .. A61N 1/0452; A61N 1/36032; A61N 1/025; A61N 1/0484; H01B 13/00

See application file for complete search history.

(56) References Cited

U.S. PATENT DOCUMENTS 5,656,081 A * 8/1997 Isen ......................... B41N 1/16 118/212
7,981,508 B1 * 7/2011 Sharma .................. H05K 3/182 428/209
(Continued)

FOREIGN PATENT DOCUMENTS

CN 104768455 A * 7/2015 ............. G06F 1/163
WO WO-2004005413 A1 * 1/2004 ............. H01B 13/00
(Continued)

OTHER PUBLICATIONS

Translation of CN-104768455-A (Year: 2015).*

*Primary Examiner* — Jeffrey T Carley
(74) *Attorney, Agent, or Firm* — John J. Daniels

(57) ABSTRACT

A method of making an electrode for a wearable electronic includes providing an adhesive print media layer. A surface treatment is performed to a top surface of the print media layer. An elastic conductive ink is deposited onto the print media layer. The elastic conductive ink comprises a conductive particulate disposed in a binder. A diffusion bond is formed between the top surface of the print media layer and the elastic conductive ink. The diffusion bond forming is facilitated by the surface treatment and even after the diffusion bond is formed, the top surface of the diffusion bonded electrode remains conductive.

9 Claims, 79 Drawing Sheets

(56) References Cited

U.S. PATENT DOCUMENTS 7,989,725 B2 * 8/2011 Boddie ................ H03K 17/962 200/600
8,008,606 B2 * 8/2011 Kaiserman ............. H05B 3/342 219/548
10,064,270 B2 * 8/2018 Jur ......................... H10N 10/10
10,116,000 B1 * 10/2018 Federici ................ H01M 4/139
2004/0124957 A1 * 7/2004 Eliacin ................ B81C 1/00333 333/262
2005/0211998 A1 * 9/2005 Daniels ............. H01L 27/14625 257/89
2005/0212007 A1 * 9/2005 Daniels ..................... F21K 9/00 257/688
2005/0241949 A1 * 11/2005 Crouse ................... H05K 3/182 205/167
2008/0084449 A1 * 4/2008 Cai ........................ H05K 3/125 347/20
2008/0191174 A1 * 8/2008 Ehrensvard .............. H01R 4/04 252/500
2009/0246896 A1 * 10/2009 Kreger ................. H10K 71/611 257/E51.026
2010/0009094 A1 * 1/2010 Lochtman .............. H05K 3/185 427/554
2010/0231672 A1 * 9/2010 Joyce ................... H05K 3/1283 347/102
2011/0306921 A1 * 12/2011 Hawley .............. A61N 1/36014 604/20
2014/0318699 A1 * 10/2014 Longinotti-Buitoni ...................... H05K 1/095 156/247
2015/0125596 A1 * 5/2015 Ramakrishnan ...... C23C 18/206 427/125
2015/0250420 A1 * 9/2015 Longinotti-Buitoni ...................... A61B 5/1135 600/534
2016/0326388 A1 * 11/2016 Petcavich ............ C09D 11/101
2018/0099520 A1 * 4/2018 Hildreth ..................... B41J 2/17

FOREIGN PATENT DOCUMENTS

WO WO-2012015263 A2 * 2/2012 ............. C23C 18/02
WO WO-2018098046 A2 * 5/2018 ............... A61N 1/02

* cited by examiner

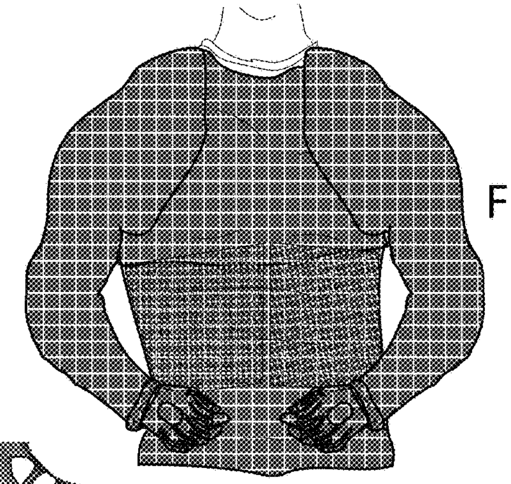
Figure 3(a)
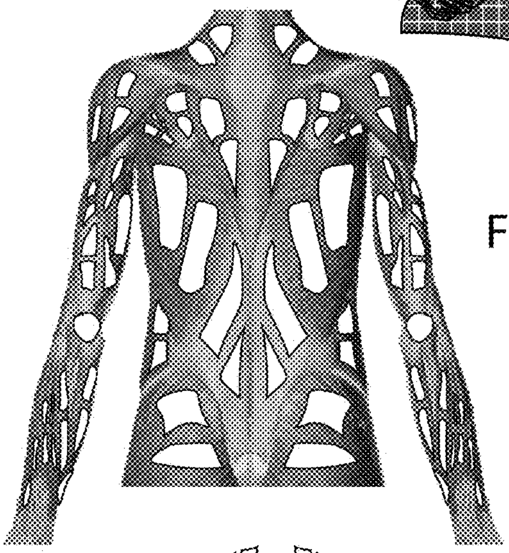
Figure 3(b)
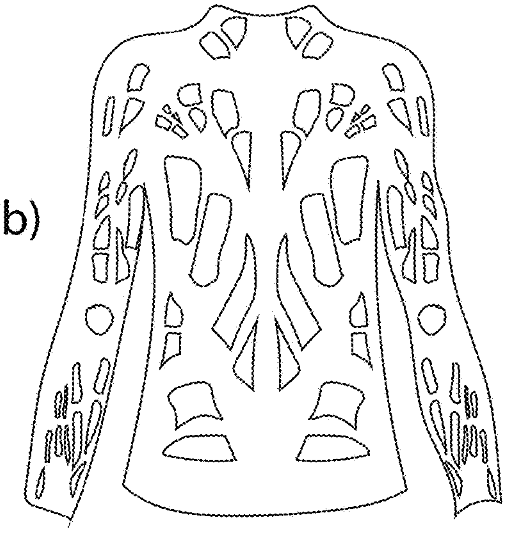
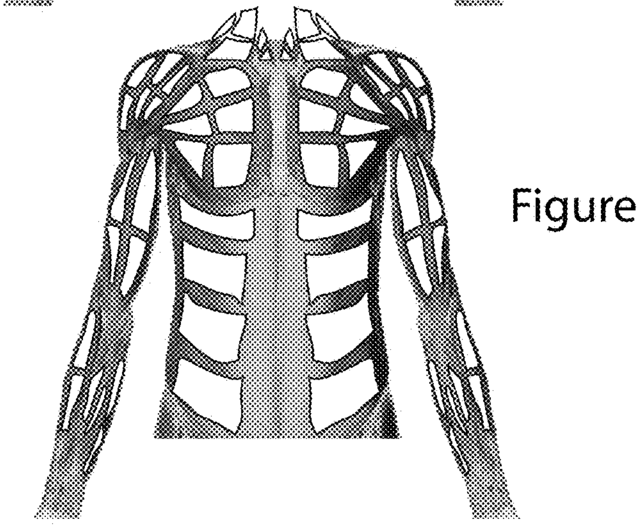
Figure 3(c)
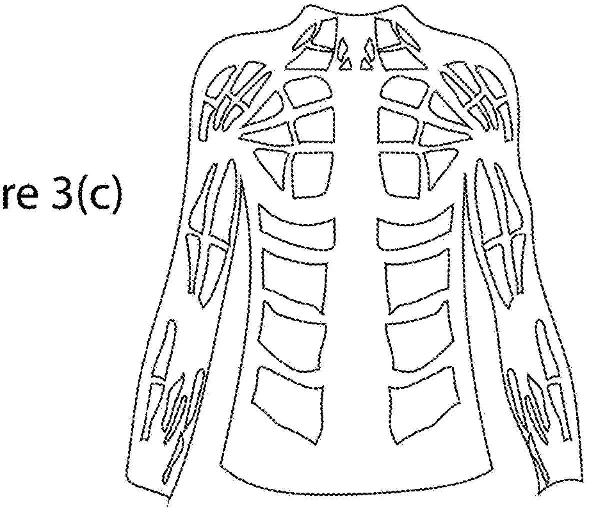

Figure 6(a)
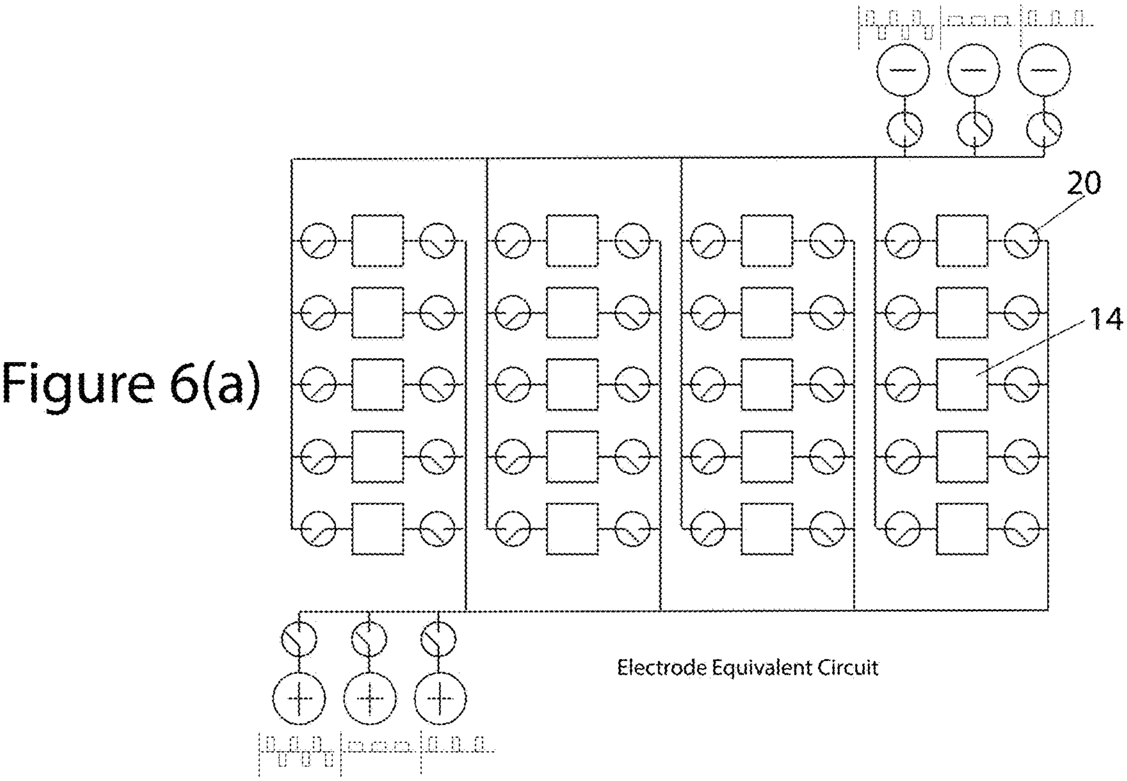
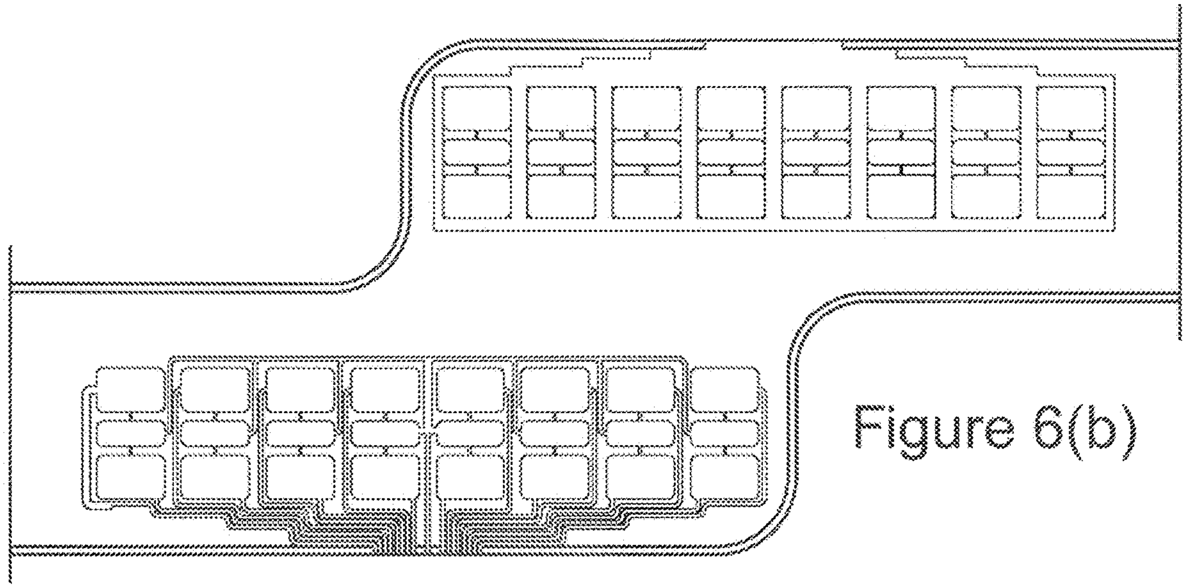
Figure 6(b)

Figure 12(a)
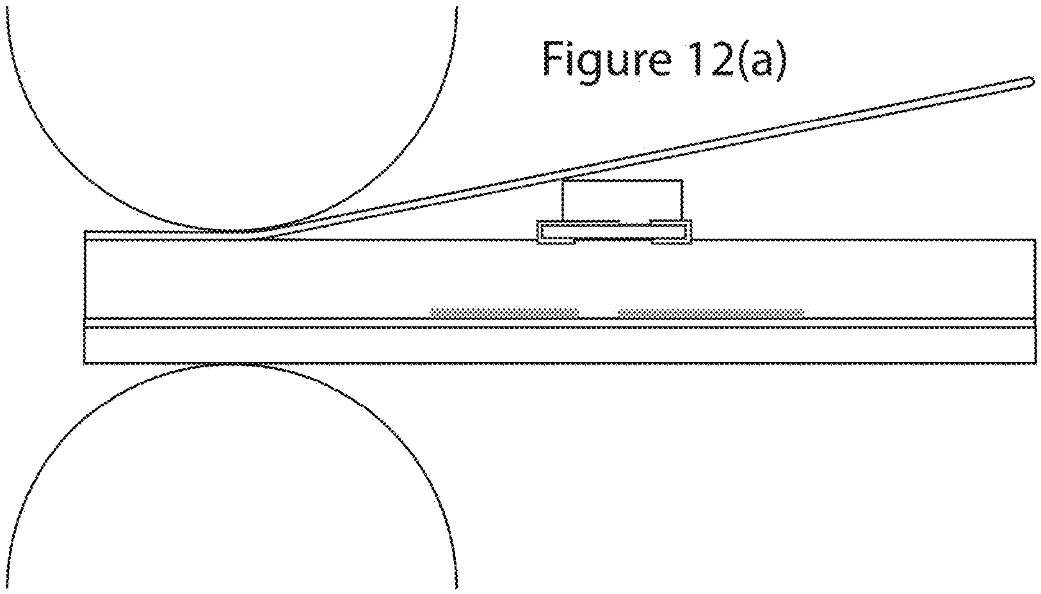
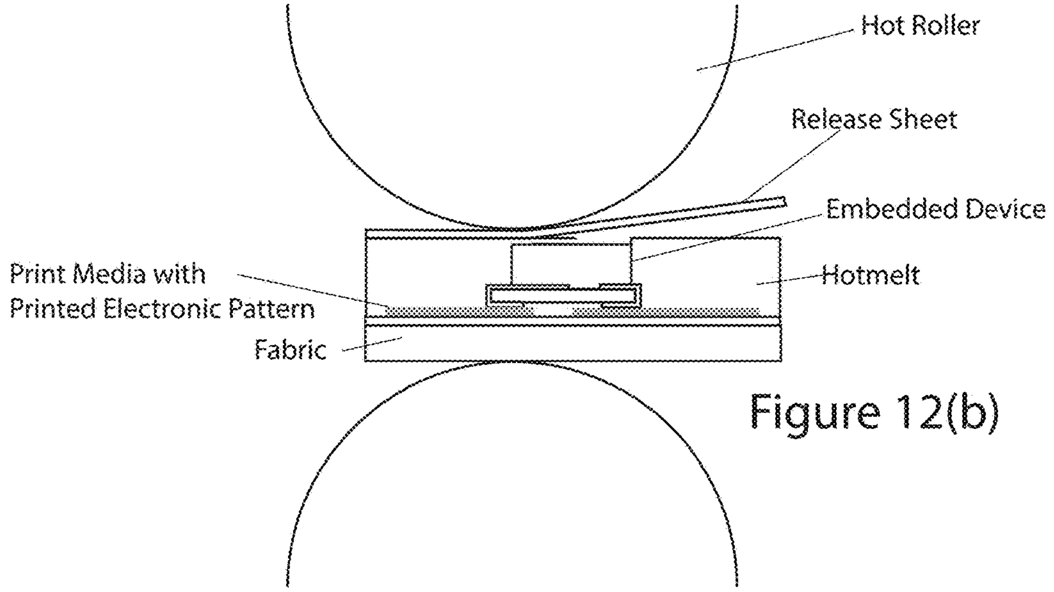
Figure 12(b)
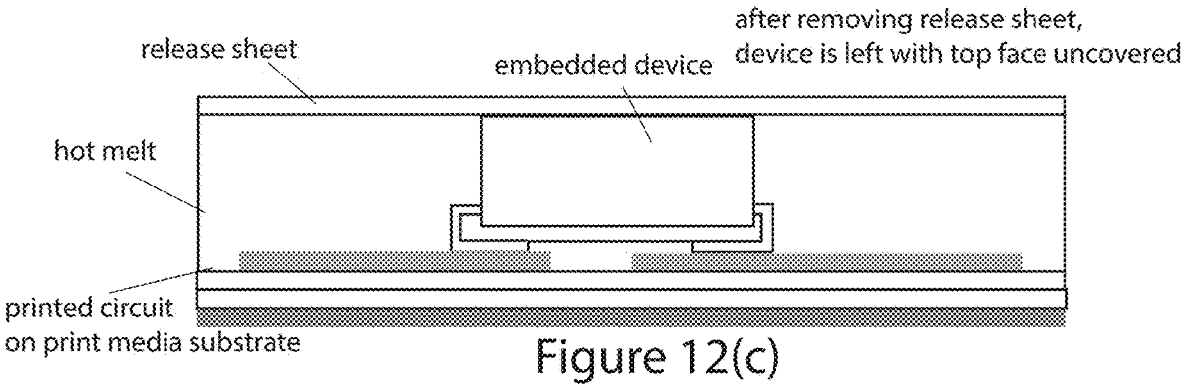
Figure 12(c)

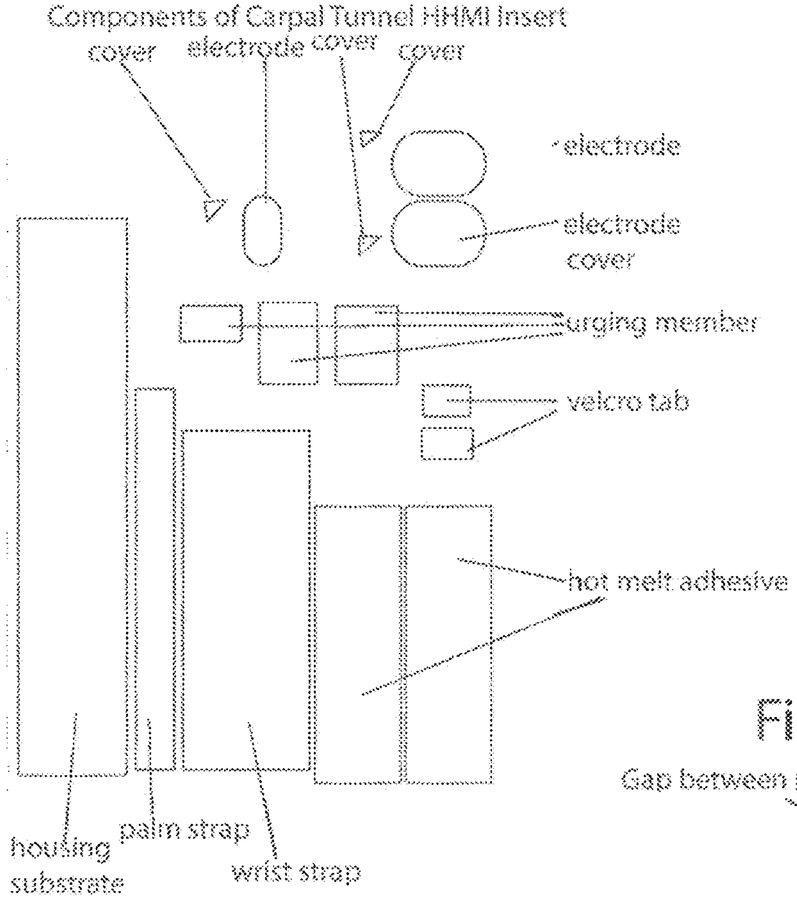
Components of Carpal Tunnel HHMI Insert
Figure 26(a)
Figure 26(b)
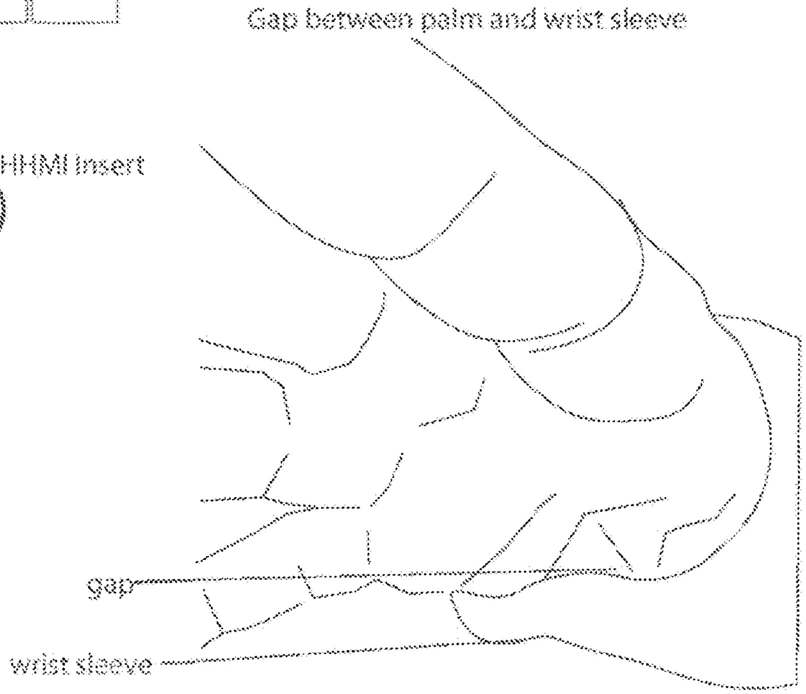

Figure 27(a)
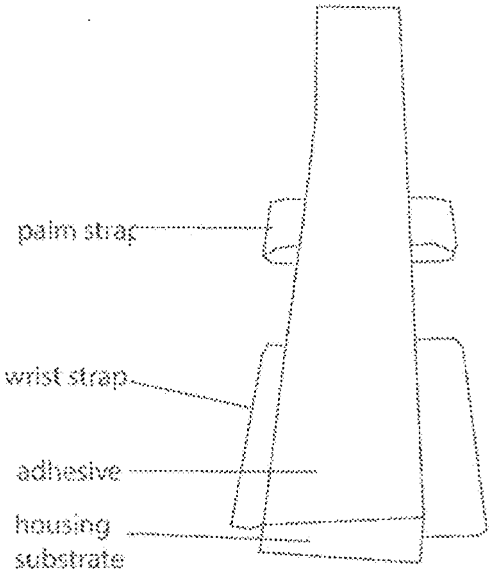
Figure 27(b)
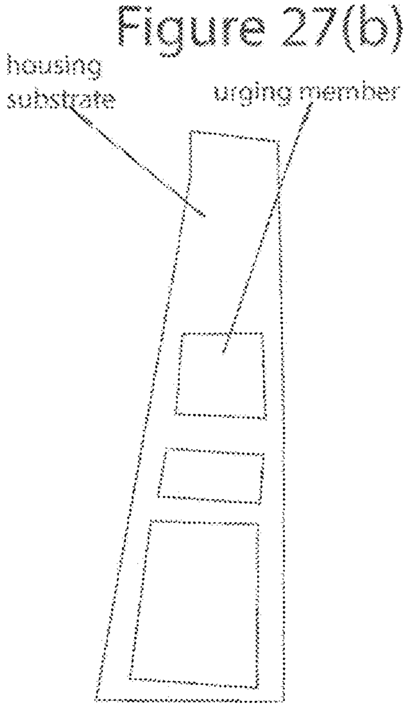
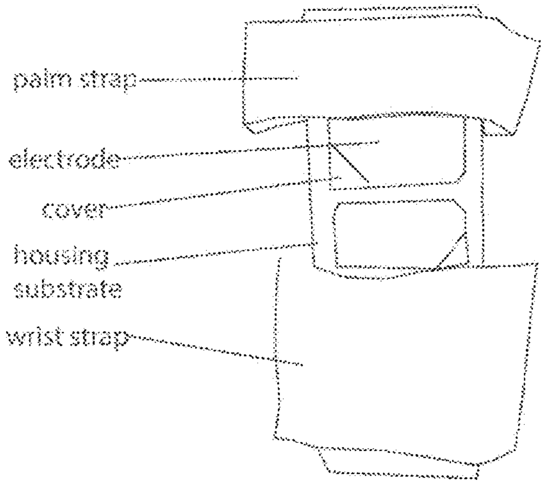
Figure 27(c)
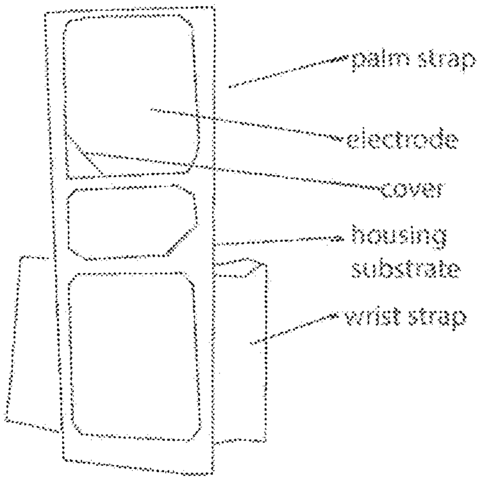
Figure 27(d)

Figure 28(a)
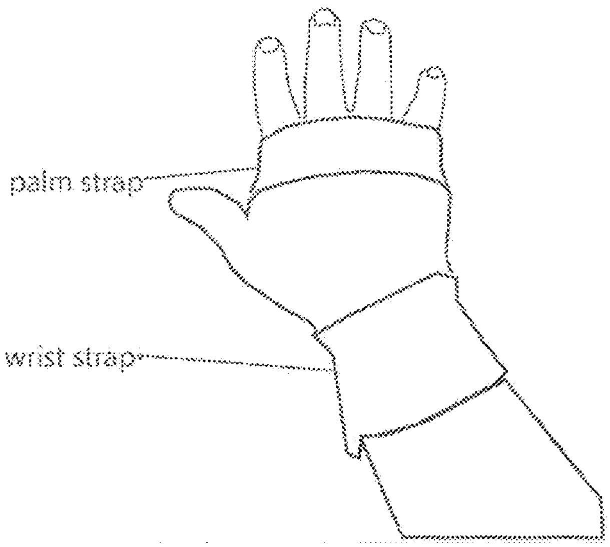
Figure 28(b)
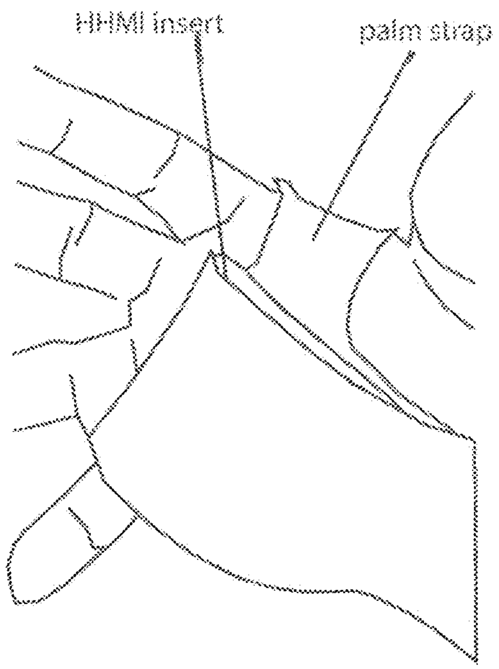
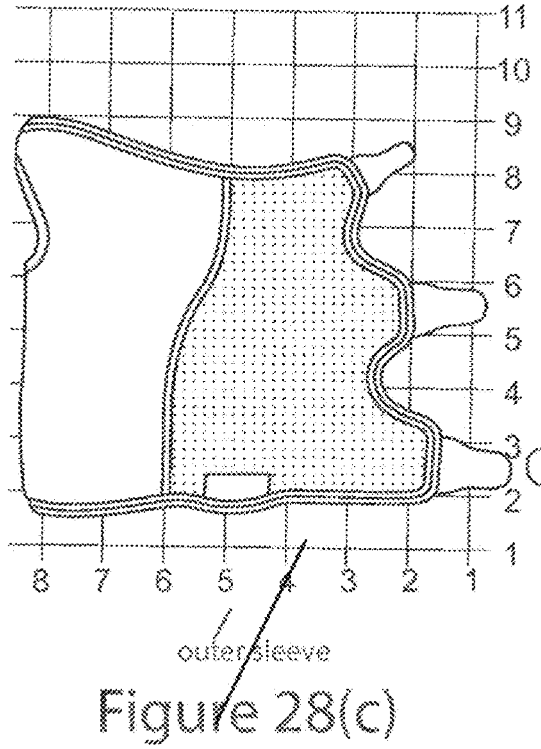
Figure 28(c)
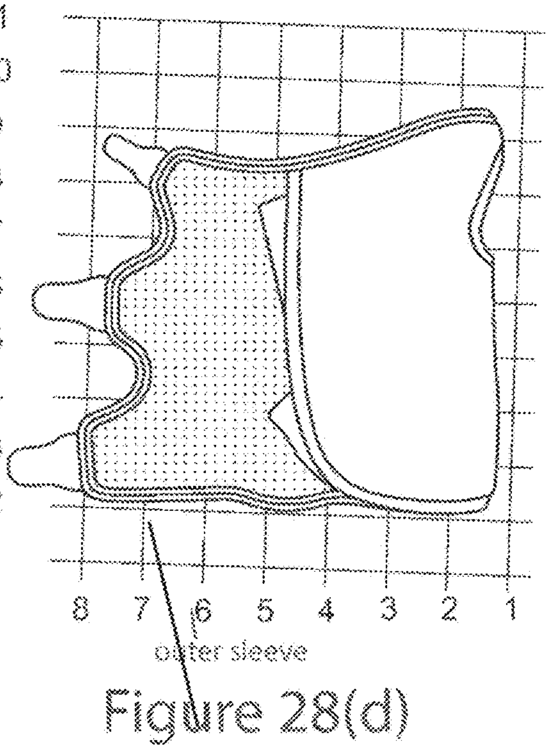
Figure 28(d)

Figure 29(a)
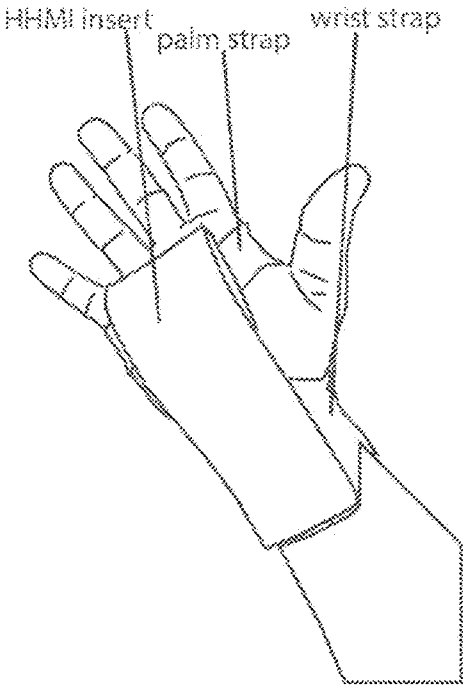
Figure 29(b)
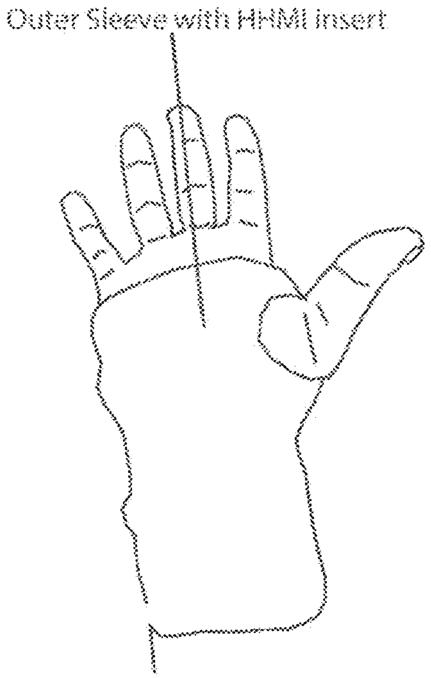
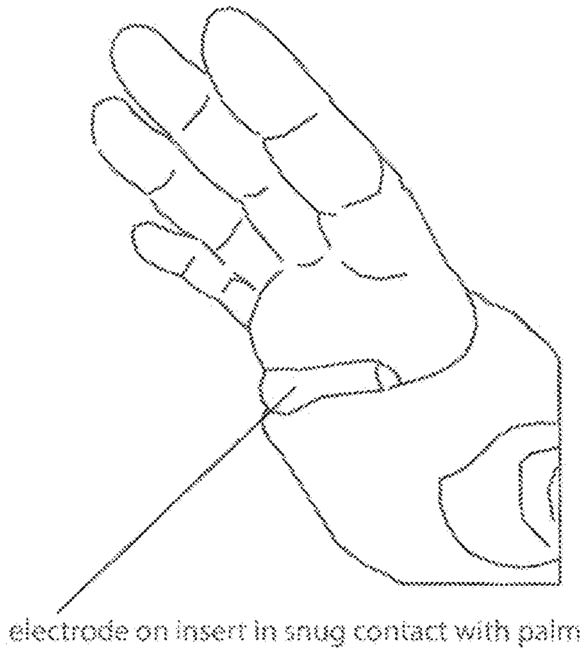
Figure 29(c)
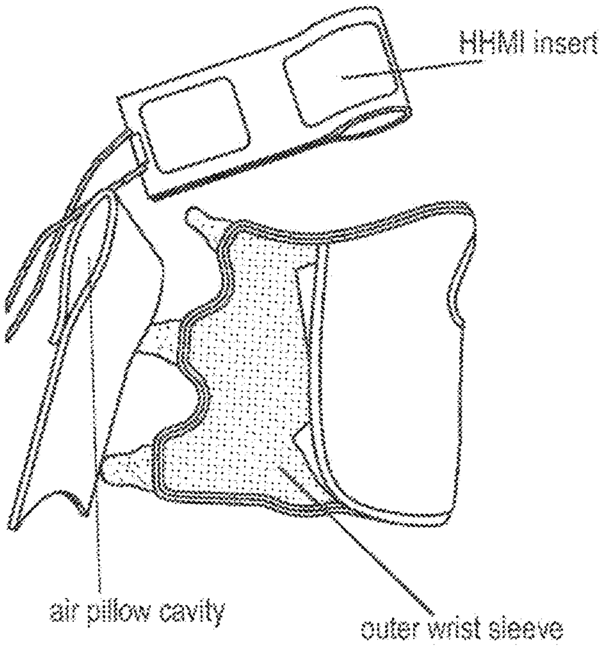
Figure 29(d)

WRAPPING THE SLEEVE

Hold Electrode Insert in hand
with one electrode against palm
and one electrode against wrist Grasp sleeve with small
velcro strap retained by
thumb Wrap sleeve around back
of hand and then wrist

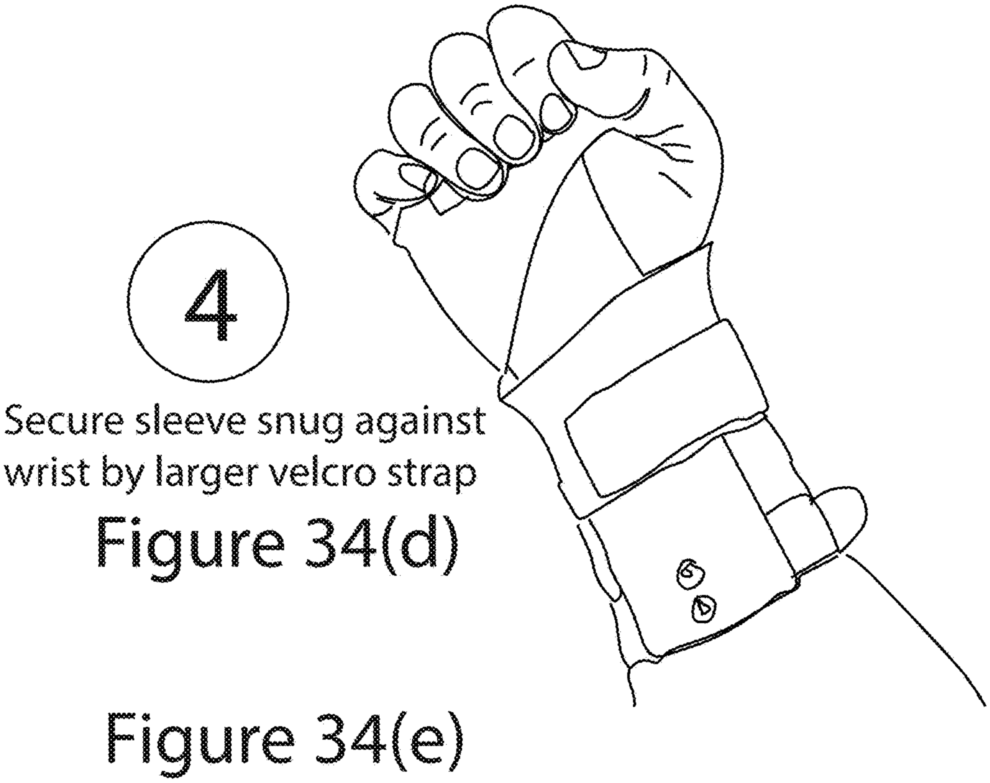
4
Secure sleeve snug against
wrist by larger velcro strap
Figure 34(d)
Figure 34(e)
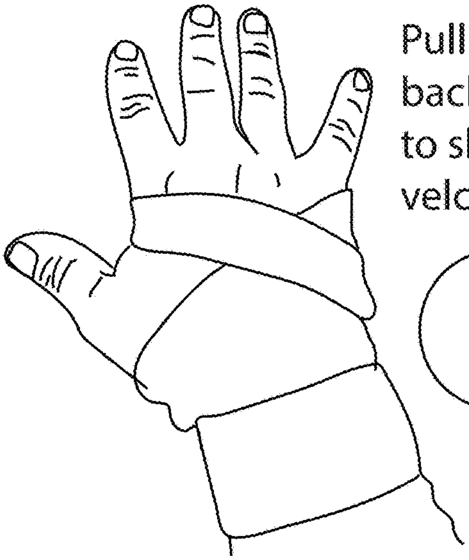
Pull small velcro strap over
back of hand and sercure
to sleeve and/or larger
velcro strap
5
6
Electrode Insert and Sleeve
correctly fit to hand
Figure 34(f)

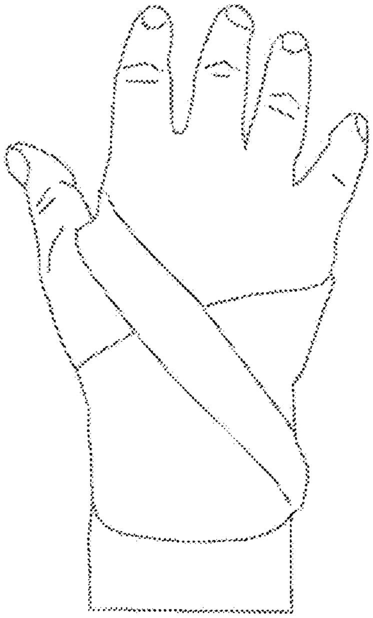
Figure 37(a)
Figure 37(b)
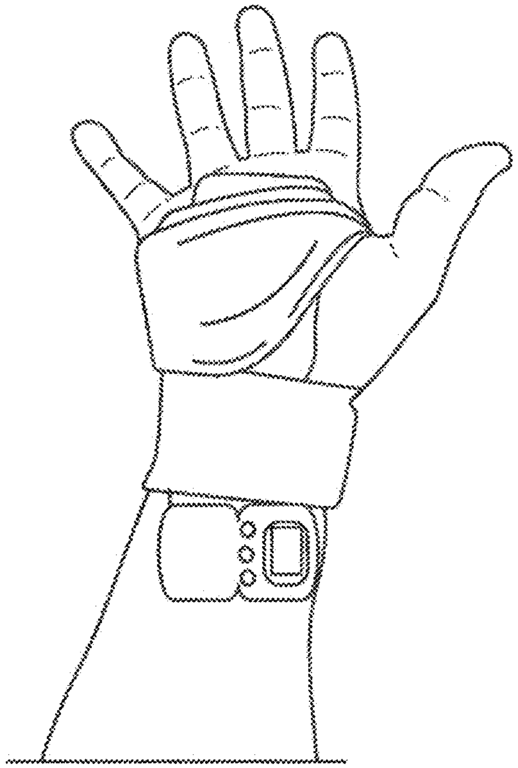

Figure 40(a)
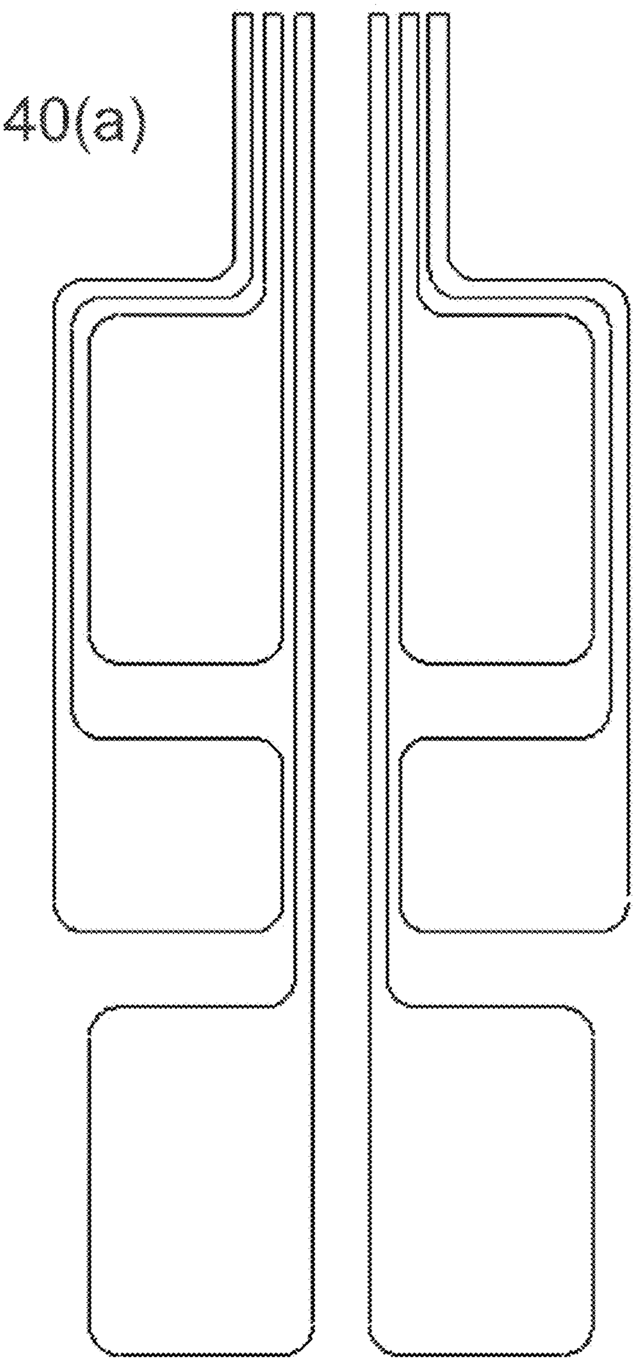
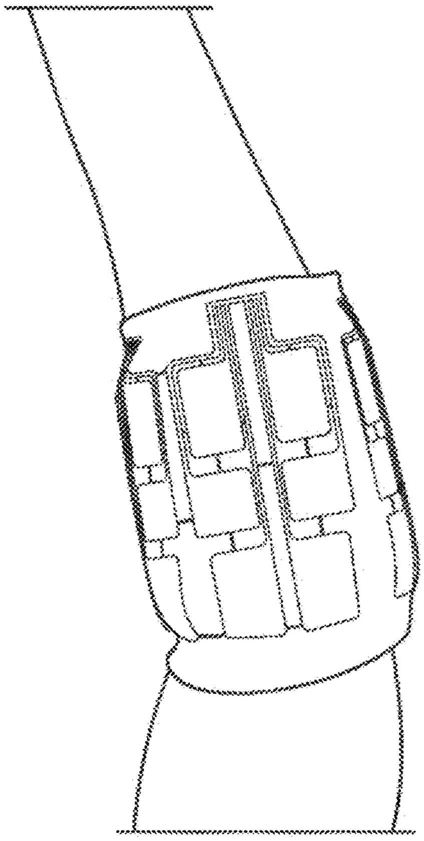
Figure 40(b)

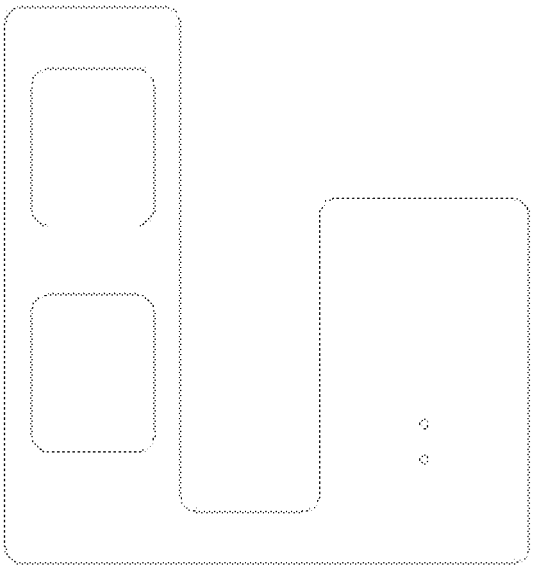
Figure 41(a)
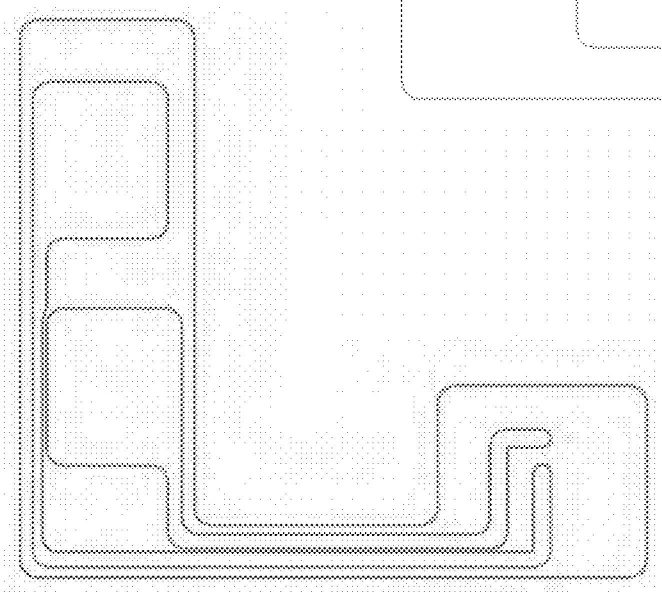
Figure 41(b)
Figure 41(c)
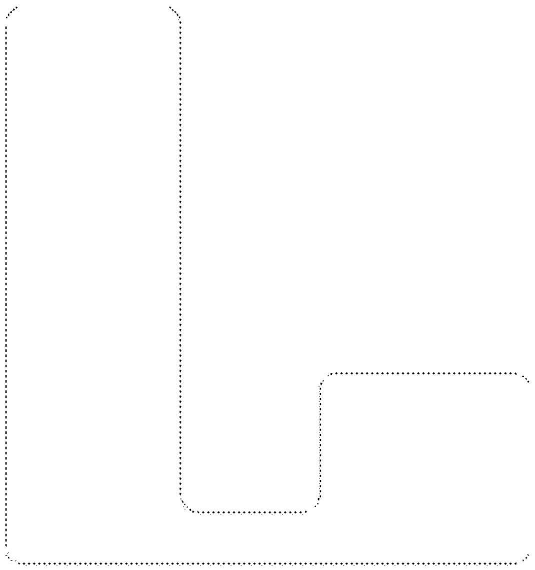

| | |
|---|---|
| outer barrier | e.g., fabric |
| circuit layer | e.g., printed ink on fabric |
| electrode layer | e.g., printed ink on fabric |
| conduction enhancement layer | e.g., gel/conductive particulate/solution |
| epidermis | e.g., user skin/tongue |

Move Forward

Come Here

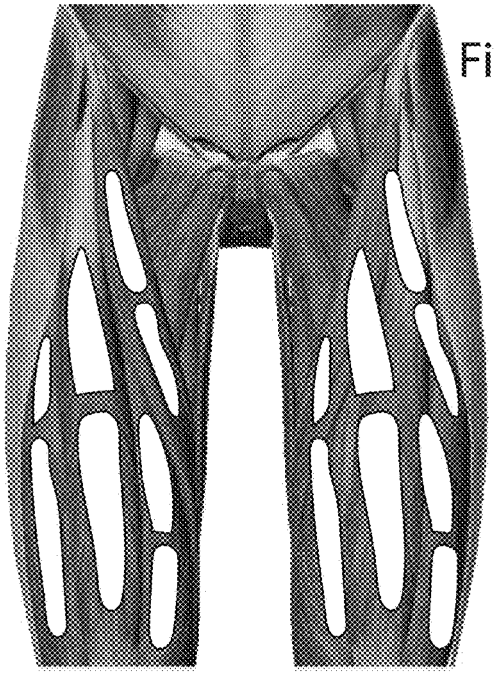
Figure 62
Figure 63
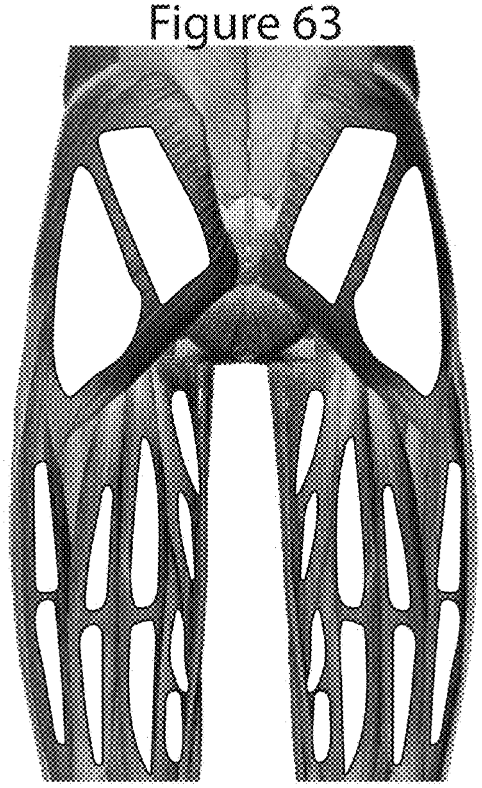
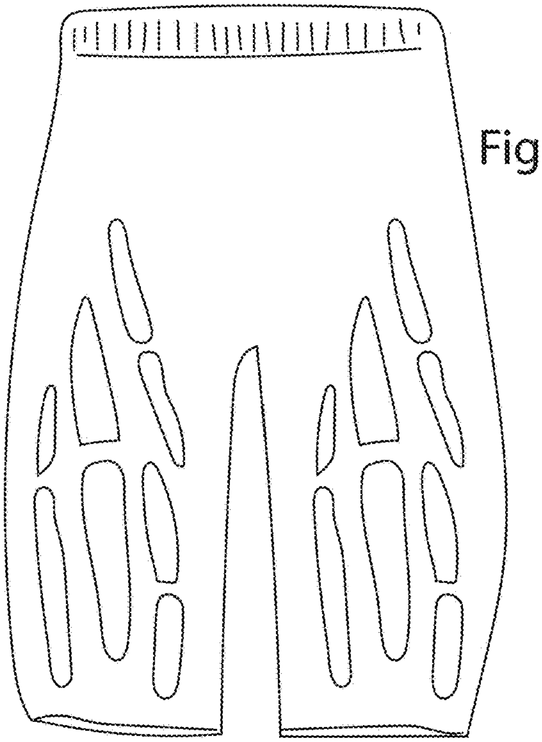
Figure 64
Figure 65
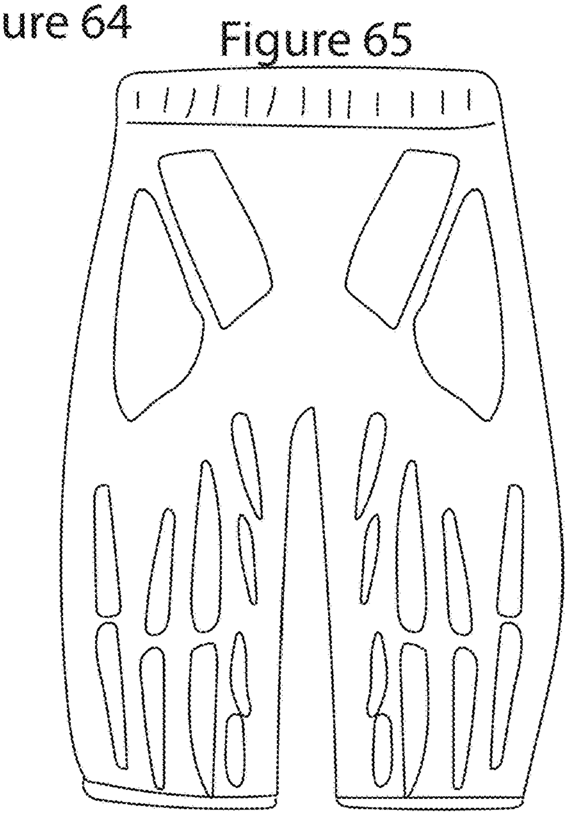

Figure 70
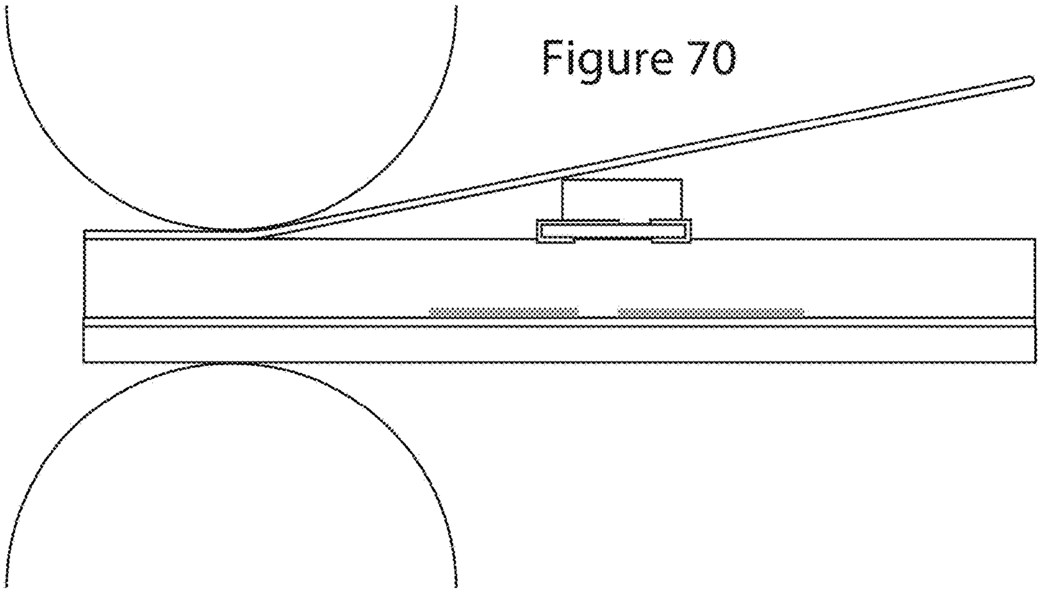
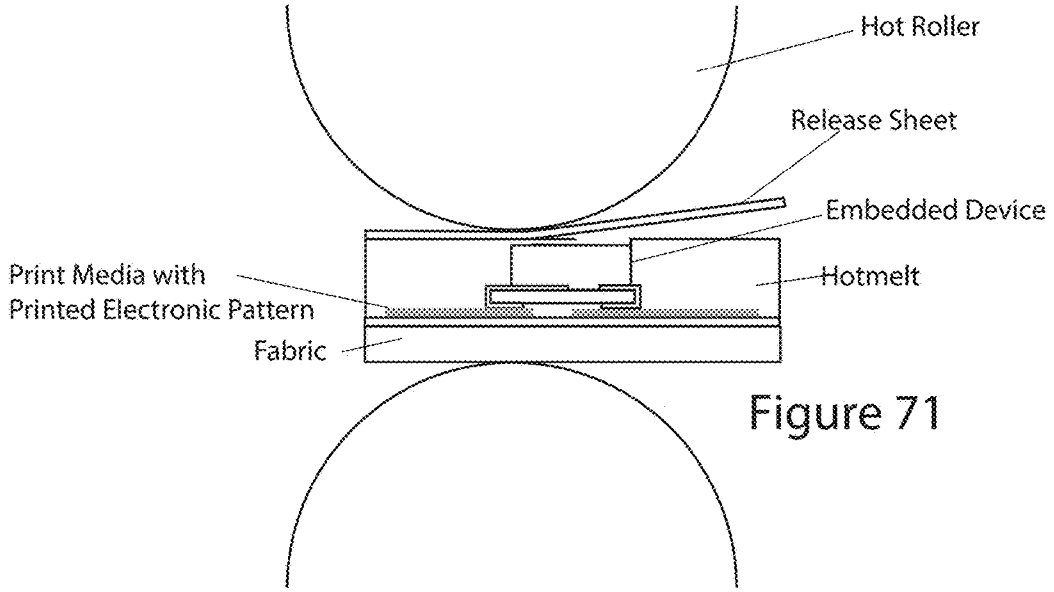
Figure 71
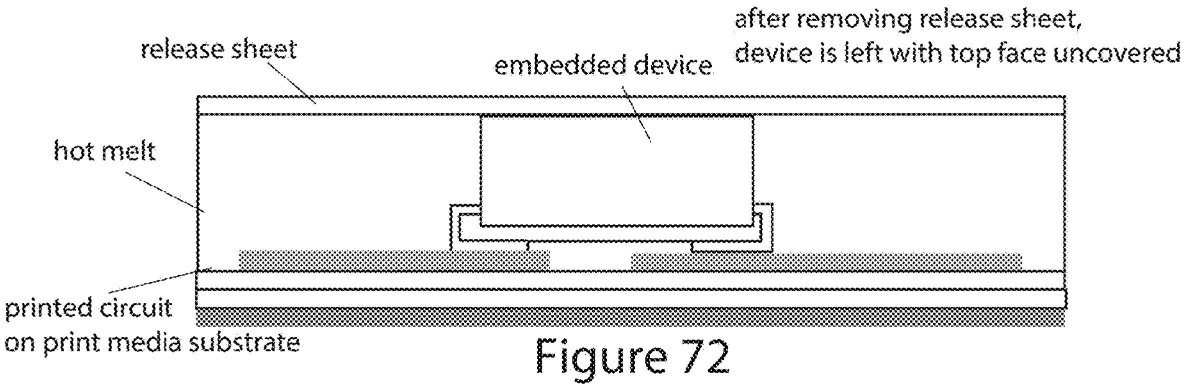
Figure 72

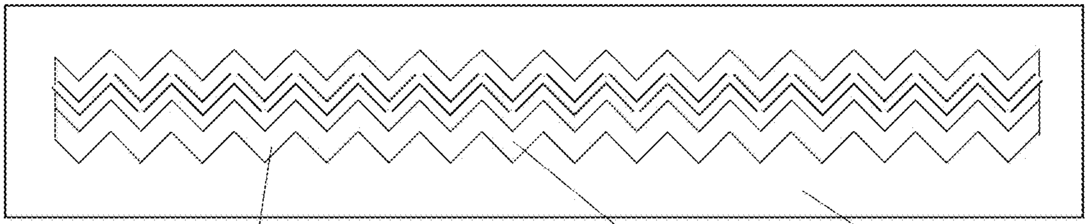
Figure 95
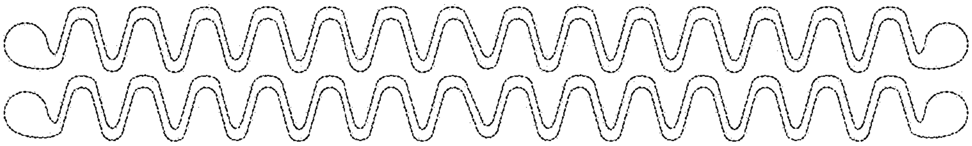
Figure 96
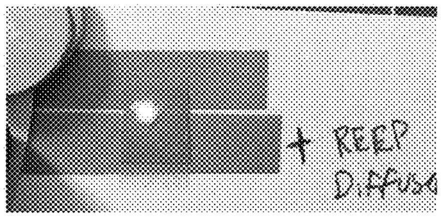
Low Temperature PCB using REEP™ material
Figure 97
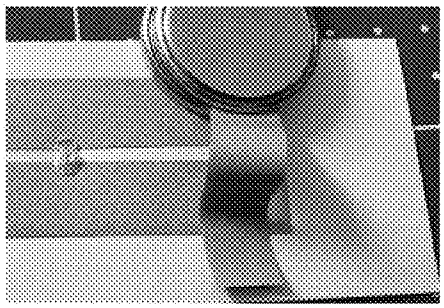
Figure 98 Low Temperature PCB using DuPont cured material
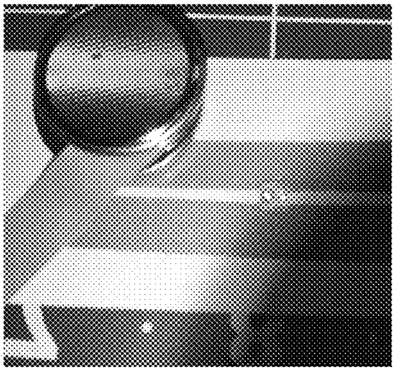
REEP™ Low Temp PCB without Light Diffuser patch
Figure 99
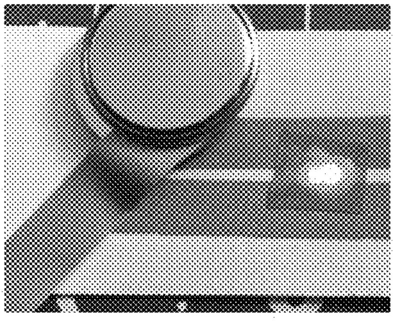
REEP™ Low Temp PCB with Light Diffuser patch
Figure 100
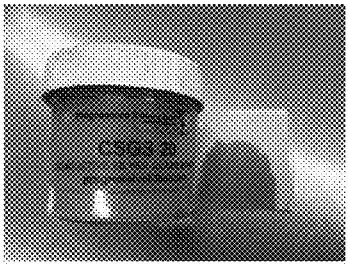
Silver Glass Spheres used to make Light Diffuser patch
Figure 101

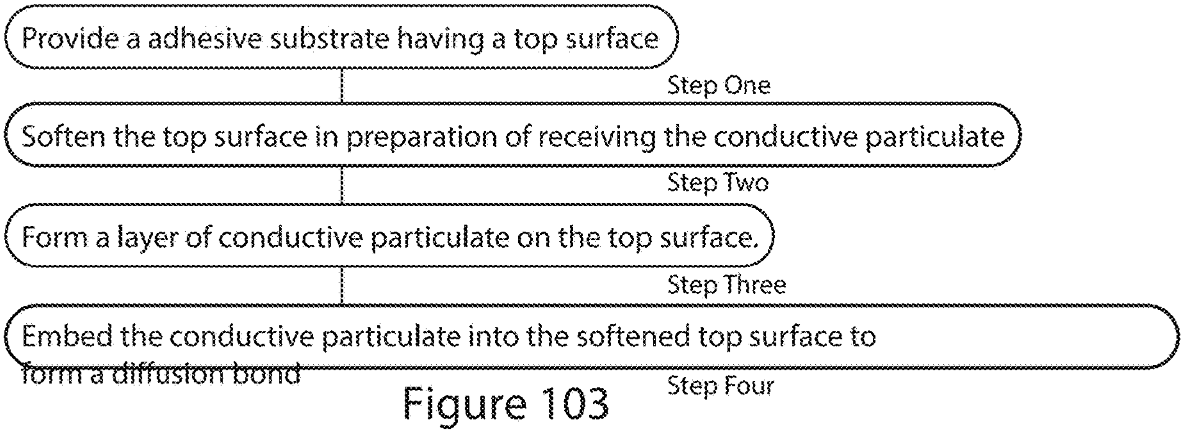
Figure 103
Figure 104
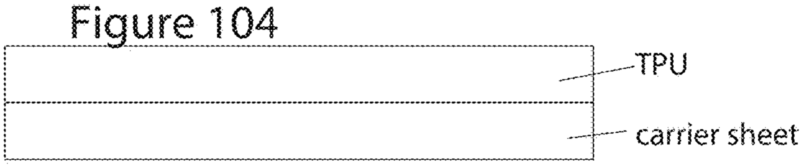
Figure 105
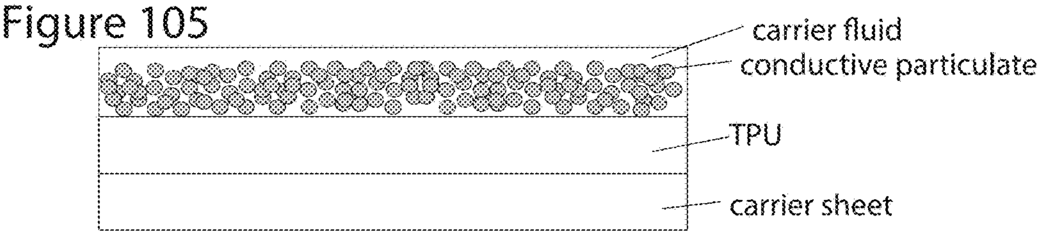
Figure 106
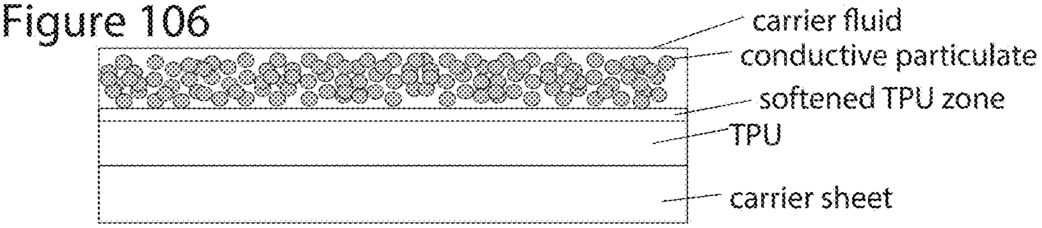
Figure 107
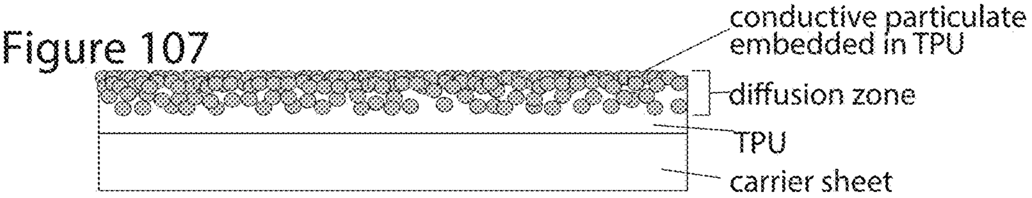

Figure 135

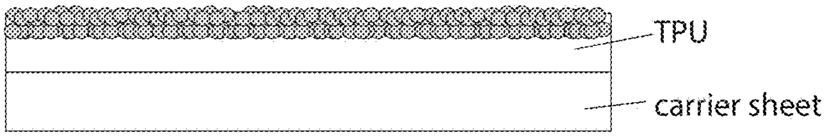

Figure 136

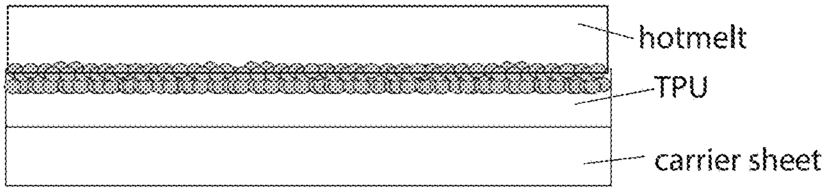

Figure 137

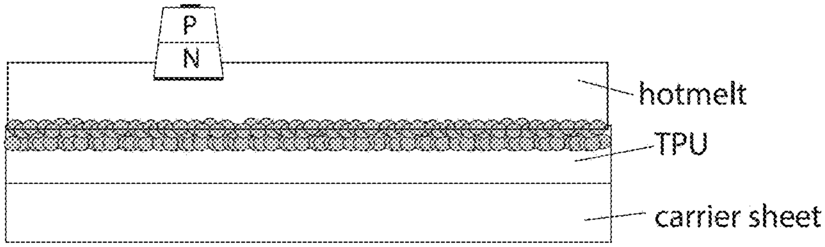

Figure 138

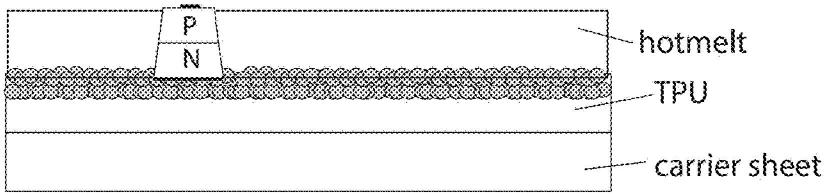

Figure 139

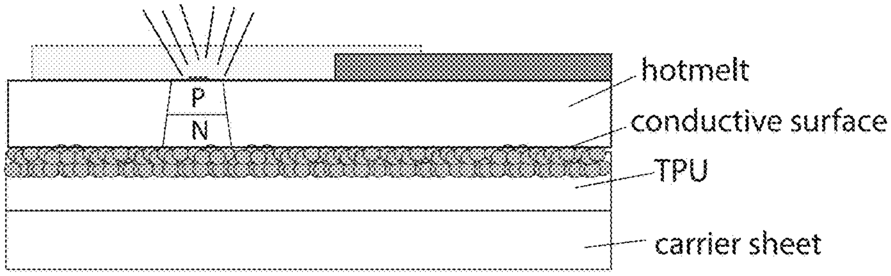

Provide a TPU substrate on carrier sheet with conductive surface — Step One

Step Two — Adhere hotmelt to embed the top conductive surface into the bottom surface of the hotmelt Place bare die LED onto softened hotmelt — Step Three Use heat and pressure to embedded bare die LED into hotmelt and connect bottom conductor with conductive suface — Step Four Print higher current capacity conductive ink line onto hotmelt sheet — Step Five Step Six — Print lower current capacity translucent conductive ink patch on hotmelt sheet and conductive ink line to electrically connect top electrode of the bare die LED to the conductive ink line

Figure 140

METHODS FOR MANUFACTURING WEARABLE ELECTRONICS AND SKIN CONTACT ELECTRODES

CROSS REFERENCE TO RELATED APPLICATIONS AND PATENTS

This is a continuation of U.S. patent application Ser. No. 16/464,171, filed May 24, 2019. This application relates to U.S. patent application Ser. No. 14/269,133, filed Jun. 6, 2016, entitled Accelerated Learning, Entertainment and Cognitive Therapy Using Augmented Reality Comprising Haptic, Auditory, and Visual Stimulation which is a continuing application of U.S. Utility patent application Ser. No. 14/269,133, filed on May 3, 2014, entitled Accelerated Learning, Entertainment and Cognitive Therapy Using Augmented Reality Comprising Haptic, Auditory, and Visual Stimulation, which claims the priority of U.S. Provisional Application No. 61/818,971, filed on May 3, 2013, entitled Accelerated Learning, Entertainment and Cognitive Therapy Using Augmented Reality Comprising Haptic, Auditory, and Visual Stimulation; and PCT Application PCT/US2016/026930, filed on Apr. 11, 2016, entitled Wearable Electronic Multi-Sensory, Human/Machine, Human/Human Interfaces which claims priority of U.S. Provisional Patent Application No. 62/147,016, filed Apr. 14, 2015, entitled Multi-Sensory Human/Machine, Human/Human Interfaces, and U.S. Provisional Patent Application No. 62/253,767, filed Nov. 11, 2015, entitled Wearable Electronic Human/Machine Interface for Mitigating Tremor, Accelerated Learning, Cognitive Therapy, Remote Control, and Virtual and Augmented Reality; and U.S. Provisional Patent Application Ser. No. 62/418,405, entitled Haptic Human Machine Interface and Applications for the Same, U.S. Provisional Patent Application Ser. No. 62/426,453 entitled Haptic Human Machine Interface and Applications for the Same, U.S. Provisional Patent Application Ser. No. 62/445,517 entitled Haptic Human Machine Interface and Applications for the Same, U.S. Provisional Patent Application Ser. No. 62/462,091 entitled Haptic Human Machine Interface and Applications for the Same, and U.S. Provisional Patent Application Ser. No. 62/530,888 entitled Roll to Roll Manufacturing for a Haptic Human Machine Interface, U.S. Provisional Patent Application Ser. No. 62/537,658 entitled Materials and Methods for Wearable and Printed Electronics. All publications, including but not limited to patents and patent applications, cited in this specification are herein incorporated by reference as if each individual publication were specifically and individually indicated to be incorporated by reference herein as though fully set forth.

TECHNICAL FIELD

The present invention relates to manufacturing methods for forming constituent parts of devices, and a method, apparatus and computer program code for providing, accelerated learning, entertainment and/or cognitive or physical therapy using augmented and/or virtual reality, comprising combined sensory cues, including, but not limited to, haptic, auditory and visual stimulation.

The present invention pertains to a device architecture, specific-use applications, and a high yield manufacturing process for wearable electronics in the form of clothing and other wearable garments with the capability to “detect, analyze and apply” the naturally occurring electrical signals of the human body. More particularly, the present invention pertains to wearable electronics for, among other things, educational, entertainment, gaming, remote unmanned vehicle control, medical and military uses. The present invention also relates to a method, apparatus and computer program code for providing accelerated learning, entertainment and/or cognitive or physical therapy using augmented and/or virtual reality, comprising combined sensory cues, including, but not limited to, haptic, auditory and visual stimulation.

The present invention also relates to a remote reality (“remotality”) interface between humans and machines, and between humans and humans. More particularly, the present invention pertains to a wearable Haptic Human/Machine Interface (HHMI) for uses including, but not limited to, mitigating tremor, accelerated learning, cognitive therapy, remote robotic, drone and probe control and sensing, virtual and augmented reality, stroke, brain and spinal cord rehabilitation, gaming, education, pain relief, entertainment, remote surgery, remote participation in and/or observation of an event such as a sporting event, and biofeedback.

BACKGROUND

This section is intended to provide a background or context to the inventions disclosed below. The description herein may include concepts that could be pursued, but are not necessarily ones that have been previously conceived, implemented or described. Therefore, unless otherwise explicitly indicated herein, what is described in this section is not prior art to the description in this application and is not admitted to be prior art by inclusion in this section.

The desire for wearable computing, where a computer/human interface is always ready for use because it is worn like clothing, has been around for decades. Now, due in large part to Moore’s Law and the continuous miniaturization of electronics, and other technologies, such as small, lightweight, ultrahigh-resolution displays, the decades-long vision for Humanistic Intelligence and wearable computing will soon be as common place as the ubiquitous cellphone.

Virtual Reality may be defined as a computer-generated simulation of a three-dimensional image or environment that can be interacted with in a seemingly real or physical way by a user using special electronic equipment, such as goggles, headphones and gloves fitted with sensory cue transducers. Augmented reality is a live, direct or indirect, view of a physical, real-world environment whose elements are augmented by computer-generated sensory input such as sound, video, graphics or GPS data. It is related to a more general concept called mediated reality, in which a view of reality is modified (possibly even diminished rather than augmented) by a computer. As a result, the technology functions by enhancing one’s current perception of reality. By contrast, virtual reality replaces the real world with a simulated one. Electroencephalography (EEG) is the recording of electrical activity along the scalp. EEG measures voltage fluctuations resulting from ionic current flows within the neurons of the brain. Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are timelocked to more complex processing of stimuli; this technique is used in cognitive science, cognitive psychology, and psychophysiological research.

An evoked potential or evoked response is an electrical potential recorded from the nervous system following presentation of a stimulus, as distinct from spontaneous potentials as detected by electroencephalography (EEG), electromyography (EMG), or other electrophysiological recording method. Signals can be recorded from cerebral cortex, brain stem, spinal cord and peripheral nerves. Sensory evoked potentials (SEP) are recorded from the central nervous system following stimulation of sense organs (for example, visual evoked potentials elicited by a flashing light or changing pattern on a monitor; auditory evoked potentials by a click or tone stimulus presented through earphones) or by haptic or somatosensory evoked potential (SSEP) elicited by haptic or electrical stimulation of a sensory or mixed nerve in the periphery. There are three kinds of evoked potentials in widespread clinical use: auditory evoked potentials, usually recorded from the scalp but originating at brainstem level; visual evoked potentials, and somatosensory evoked potentials, which are elicited by electrical stimulation of peripheral nerve. An event-related potential (ERP) is the measured brain response that is the direct result of a specific sensory, cognitive, or motor event. More formally, it is any stereotyped electrophysiological response to a stimulus. The study of the brain in this way provides a noninvasive means of evaluating brain functioning in patients with cognitive diseases.

BRIEF SUMMARY

This section is intended to include examples and is not intended to be limiting.

In accordance with an aspect of the invention, a method of making an electrode for a wearable electronic includes providing an adhesive print media layer. A surface treatment is performed to a top surface of the print media layer. An elastic conductive ink is deposited onto the print media layer. The elastic conductive ink comprises a conductive particulate disposed in a binder. A diffusion bond is formed between the top surface of the print media layer and the elastic conductive ink. The diffusion bond forming is facilitated by the surface treatment and even after the diffusion bond is formed, the top surface of the diffusion bonded electrode remains conductive.

In accordance with an aspect of the invention, a method of making a wearable electronic, a bottom substrate comprising a flexible, elastic material is provided. An adhesive print media layer is provided having a preprinted conductive pattern. The adhesive print media layer is disposed on top of the bottom substrate. The adhesive print media layer is activated to bind the preprinted conductive pattern to the flexible, elastic material. The flexible, elastic material may comprise a stretch fabric. The preprinted conductive pattern comprises electrodes may be configured for making face to face contact with the skin of user for at least one of detecting electrical signals from the skin of the user and applying electrical signals to the skin of the user.

An electronic device may be embedded in an encapsulating adhesive layer and in electrical communication with the preprinted conductive pattern. The electronic device may be embedded in the encapsulating adhesive layer and brought into electrical communication with the preprinted conductive pattern when the encapsulating adhesive layer is thermally activated.

A predetermined pattern of semiconductor devices may be fixed to the encapsulating adhesive layer. The semiconductor devices can be, for example, discrete and/or integrated circuit elements, RF, optical, sensors, transducers, and other bare die and packaged semiconductor devices. As an example, the semiconductor devices may each have a top device conductor and a bottom device conductor. A top substrate may be provided having a conductive pattern disposed thereon to form a lamination package comprising the bottom substrate, the preprinted conductive pattern on the adhesive print media layer, the encapsulating adhesive layer and the top substrate. The top substrate may be provided as a complete matching sheet or roll that matches the adhesive and preprinted adhesive print media. Alternatively, the top substrate can be a conductive patch, such as a piece of ITO coated plastic sheet, where the ITO acts as a transparent conductor. The lamination package is laminated so that the encapsulating adhesive layer insulates and binds the top substrate to the bottom substrate so that one of said top device conductor and bottom device conductor of the semiconductor devices is in electrical communication with the conductive pattern of the top substrate and so that the other of said top device conductor and bottom device conductor of each said semiconductor element is in electrical communication with the electrically conductive layer of the preprinted conductive pattern.

In accordance with another aspect of the invention, a plurality of haptic sensory cues is generated capable of being perceived by a user. The haptic sensory cues are received by the user as computer controlled serially generated electrical signals through a wearable electronic garment. The wearable electronic garment comprises a multilayered structure with the electrodes in contact with the skin of the user, insulation and wiring layers, and the sleeve covering. The layers, such as the outer covering may be, for example, a thin, multi-axial stretchable fabric. The fabric can be electrically insulating, and contain conductive threads, patches, coatings or inks to conduct the detected and applied electrical signals. The electrical signals invoke at least one of an involuntary body part movement and a perception by the user. The involuntary body part movement causing at least an urging towards at least one of a predetermined motion and a predetermined position of the body part dependent on the computer controlled serially generated electrical signals.

The perception by the user may have a predetermined somatosensory sensation dependent on the computer controlled serially generated electrical signals. The haptic sensory cues may invoke the perception by stimulating a somatosensory system of a user comprising at least one receptor including thermoreceptors, photoreceptors, mechanoreceptors and chemoreceptors to cause the user to perceive an experience of at least one of proprioception (e.g., body part position and strength of movement), mechanoreception (e.g., touch), thermoception (e.g., temperature), and nociception (e.g., pain)

In accordance with another aspect of the inventive HHMI, a method is provided for using a human/machine interface. As an example, the method may includes detecting the onset of an involuntary movement, such as a tremor of a user using a human/machine interface. The human/machine interface may be comprised of a sleeve made from a stretch material, such as Lycra, with screen, inkjet, or otherwise printed flexible conductive electrodes disposed on the interior of the sleeve and in direct face-to-face electrical contact with the skin on the arm of the user. The fabric of the outer cover or other layer may provide sufficient compression to urge the electrodes into face-to-face electrical contact with the skin of the arm. In addition, or alternatively, straps, bands, bladders, Velcro or other such mechanisms can be used for urging the electrodes into face to-face electrical communication with the user's skin. Alternatively, or in addition, foil or conductive fabrics, such as copper/polyester woven fabric, can be used to make electrode patches that are highly conductive, thin and flexible. Signal cross talk, interference from or to the electronics of the HHMI may be mitigated with shielding layers separating, as necessary, the conductive pathways and electrically active components. In this tremor mitigation example, once the electrical signals received from the human body are detected, they are analyzed and counterelectrical signals are determined having electrical characteristics effective to mitigate the involuntary tremor. The electrical signals are applied to the user using the human/machine interface.

In accordance with another aspect of the invention, electrical activity is received from at least one of muscles and nerves of a user. An electrical signal is determined having characteristics based on the received electrical activity. The electrical signal is generated and applied to an object to cause an action dependent on the received electrical activity. The object can be a biological component of the user, another user, or a remotely located machine.

In accordance with another aspect of the invention a wearable electronic includes a housing comprising a flexible, elastic material. An adhesive print media layer is provided having a preprinted conductive pattern forming a plurality of individually addressable electrodes are supported by the housing. The individually addressable electrodes are for at least one of applying stimulation electrical signals to skin of a user and detecting biometric electrical signals from the skin of the user. At least one of a signal detector for detecting the biometric electrical signals and a signal generator are provided for generating the stimulation electrical signals. An electrode multiplex circuit addresses the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls least one of the signal detector, the signal generator, the electrode multiplex circuit.

In accordance with another aspect of the invention, a method, comprises controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals.

In accordance with another aspect of the invention, an apparatus comprises: at least one processor; and at least one non-transitory memory including computer program code, the at least one memory and the computer program code configured to, with the at least one processor, cause the apparatus at least to perform: controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals. In accordance with another aspect of the invention, a computer program product comprises a non-transitory computer readable storage medium having computer-readable code embodied thereon, the computer-readable code executable by an apparatus and causing the apparatus, in response to execution of the computer-readable code, causing the apparatus to perform at least the following: controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals.

In accordance with an aspect of the invention, a method of making a wearable electronic, a bottom substrate comprising a flexible, elastic material is provided. An adhesive print media layer is provided having a preprinted conductive pattern. The adhesive print media layer is disposed on top of the bottom substrate. The adhesive print media layer is activated to bind the preprinted conductive pattern to the flexible, elastic material. The flexible, elastic material may comprise a stretch fabric. The preprinted conductive pattern comprises electrodes may be configured for making face to face contact with the skin of user for at least one of detecting electrical signals from the skin of the user and applying electrical signals to the skin of the user.

An electronic device may be embedded in an encapsulating adhesive layer and in electrical communication with the preprinted conductive pattern. The electronic device may be embedded in the encapsulating adhesive layer and brought into electrical communication with the preprinted conductive pattern when the encapsulating adhesive layer is thermally activated.

A predetermined pattern of semiconductor devices may be fixed to the encapsulating adhesive layer. The semiconductor devices can be, for example, discrete and/or integrated circuit elements, RF, optical, sensors, transducers, and other bare die and packaged semiconductor devices. As an example, the semiconductor devices may each have a top device conductor and a bottom device conductor. A top substrate may be provided having a conductive pattern disposed thereon to form a lamination package comprising the bottom substrate, the preprinted conductive pattern on the adhesive print media layer, the encapsulating adhesive layer and the top substrate. The top substrate may be provided as a complete matching sheet or roll that matches the adhesive and preprinted adhesive print media. Alternatively, the top substrate can be a conductive patch, such as a piece of ITO coated plastic sheet, where the ITO acts as a transparent conductor. The lamination package is laminated so that the encapsulating adhesive layer insulates and binds the top substrate to the bottom substrate so that one of said top device conductor and bottom device conductor of the semiconductor devices is in electrical communication with the conductive pattern of the top substrate and so that the other of said top device conductor and bottom device conductor of each said semiconductor element is in electrical communication with the electrically conductive layer of the preprinted conductive pattern.

In accordance with another aspect of the invention, a plurality of haptic sensory cues is generated capable of being perceived by a user. The haptic sensory cues are received by the user as computer controlled serially generated electrical signals through a wearable electronic garment. The wearable electronic garment comprises a multilayered structure with the electrodes in contact with the skin of the user, insulation and wiring layers, and the sleeve covering. The layers, such as the outer covering may be, for example, a thin, multi-axial stretchable fabric. The fabric can be electrically insulating, and contain conductive threads, patches, coatings or inks to conduct the detected and applied electrical signals. The electrical signals invoke at least one of an involuntary body part movement and a perception by the user. The involuntary body part movement causing at least an urging towards at least one of a predetermined motion and a predetermined position of the body part dependent on the computer controlled serially generated electrical signals.

The perception by the user may have a predetermined somatosensory sensation dependent on the computer controlled serially generated electrical signals. The haptic sensory cues may invoke the perception by stimulating a somatosensory system of a user comprising at least one receptor including thermoreceptors, photoreceptors, mechanoreceptors and chemoreceptors to cause the user to perceive an experience of at least one of proprioception (e.g., body part position and strength of movement), mechanoreception (e.g., touch), thermoception (e.g., temperature), and nociception (e.g., pain)

In accordance with another aspect of the inventive HHMI, a method is provided for using a human/machine interface. As an example, the method may includes detecting the onset of an involuntary movement, such as a tremor of a user using a human/machine interface. The human/machine interface may be comprised of a sleeve made from a stretch material, such as Lycra, with screen, inkjet, or otherwise printed flexible conductive electrodes disposed on the interior of the sleeve and in direct face-to-face electrical contact with the skin on the arm of the user. The fabric of the outer cover or other layer may provide sufficient compression to urge the electrodes into face-to-face electrical contact with the skin of the arm. In addition, or alternatively, straps, bands, bladders, Velcro or other such mechanisms can be used for urging the electrodes into face-to-face electrical communication with the user's skin. Alternatively, or in addition, foil or conductive fabrics, such as copper/polyester woven fabric, can be used to make electrode patches that are highly conductive, thin and flexible. Signal cross talk, interference from or to the electronics of the HHMI may be mitigated with shielding layers separating, as necessary, the conductive pathways and electrically active components. In this tremor mitigation example, once the electrical signals received from the human body are detected, they are analyzed and counter-electrical signals are determined having electrical characteristics effective to mitigate the involuntary tremor. The electrical signals are applied to the user using the human/machine interface.

In accordance with another aspect of the invention, electrical activity is received from at least one of muscles and nerves of a user. An electrical signal is determined having characteristics based on the received electrical activity. The electrical signal is generated and applied to an object to cause an action dependent on the received electrical activity. The object can be a biological component of the user, another user, or a remotely located machine.

In accordance with another aspect of the invention a wearable electronic includes a housing comprising a flexible, elastic material. An adhesive print media layer is provided having a preprinted conductive pattern forming a plurality of individually addressable electrodes are supported by the housing. The individually addressable electrodes are for at least one of applying stimulation electrical signals to skin of a user and detecting biometric electrical signals from the skin of the user. At least one of a signal detector for detecting the biometric electrical signals and a signal generator are provided for generating the stimulation electrical signals. An electrode multiplex circuit addresses the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls least one of the signal detector, the signal generator, the electrode multiplex circuit.

In accordance with another aspect of the invention, a method, comprises controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals.

In accordance with another aspect of the invention, an apparatus comprises: at least one processor; and at least one non-transitory memory including computer program code, the at least one memory and the computer program code configured to, with the at least one processor, cause the apparatus at least to perform: controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals. In accordance with another aspect of the invention, a computer program product comprises a non-transitory computer readable storage medium having computer-readable code embodied thereon, the computer-readable code executable by an apparatus and causing the apparatus, in response to execution of the computer-readable code, causing the apparatus to perform at least the following: controlling an electrode multiplex circuit to address a plurality of individually addressable electrodes by at least one of routing biometric electrical signals from skin of a user through more than one of the plurality of individually addressable electrodes to a signal detector and routing stimulation electrical signals from a signal generator through more than one of the plurality of individually addressable electrode to the skin of the user; and at least one of: controlling a signal generator for generating the stimulation electrical signals; and controlling a signal detector for detecting the biometric electrical signals.

In accordance with an aspect of the invention, an apparatus comprises a housing with at least one electrode supportable by the housing. The at least one electrode for applying stimulation electrical signals to skin of a user. At least one urging member is supportable by the housing adjacent to the at least one electrode for urging the at least one electrode towards the skin of the user.

In accordance with another aspect of the invention, an apparatus for detecting and or applying electrical signals to the skin of a user is fabricated by providing a housing substrate. At least one electrode is fixed to the housing substrate, the at least one electrode for applying stimulation electrical signals to skin of a user. At least one urging member is fixed to the housing substrate. The at least one urging member is disposed adjacent to the at least one electrode for urging the at least one electrode towards the skin of the user. For example, a combination of urging members and electrodes can be formed and or fixed to the house substrate along with other electrodes and or urging members formed or fixed to the electrode insert. In accordance with another aspect of the invention, an apparatus is provided for applying an electrical stimulation to skin of a user for mitigating pain. The apparatus comprises a housing with at least one electrode supportable by the housing for applying stimulation electrical signals to skin of a user. At least one urging member is supportable by the housing adjacent to the at least one electrode for urging the at least one electrode towards the skin of the user. The at least one electrode may comprise a plurality of individually addressable electrodes supported by the housing. The individually addressable electrodes are for at least one of applying stimulation electrical signals to skin of a user and detecting biometric electrical signals from the skin of the user. At least one of a signal detector for detecting the biometric electrical signals and a signal generator for generating the stimulation electrical signals. An electrode multiplex circuit for addressing the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls at least one of the signal detector, the signal generator, the electrode multiplex circuit.

In accordance with an aspect of the invention, methods of making an electrode for a wearable electronic are provided. An adhesive print media layer is provided. A surface treatment is performed to a top surface of the print media layer. An elastic conductive ink is deposited onto the print media layer. The elastic conductive ink comprises a conductive particulate disposed in a binder. A diffusion bond is formed between the top surface of the print media layer and the elastic conductive ink. The diffusion bond forming is facilitated by the surface treatment.

The adhesive print media layer can be provided as a roll of material on a carrier substrate. Performing the surface treatment to the top surface, depositing the elastic conductive ink and forming the diffusion bond may be done sequentially in a roll-to-roll process. The surface treatment may comprise at least one of heat and solvent softening of the top surface of the print media layer. The diffusion bond can be formed by at least one of a heat treatment and a pressure operation.

In accordance with another aspect of the invention, the embodiments of the inventive roll-to-roll or batch manufacturing process is used to form constituent parts of an apparatus for applying an electrical stimulation to skin of a user for mitigating pain. The apparatus comprises a housing with at least one electrode supportable by the housing for applying stimulation electrical signals to skin of a user. At least one urging member is supportable by the housing adjacent to the at least one electrode for urging the at least one electrode towards the skin of the user. The at least one electrode may comprise a plurality of individually addressable electrodes supported by the housing. The individually addressable electrodes are for at least one of applying stimulation electrical signals to skin of a user and detecting biometric electrical signals from the skin of the user. At least one of a signal detector for detecting the biometric electrical signals and a signal generator for generating the stimulation electrical signals. An electrode multiplex circuit for addressing the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls at least one of the signal detector, the signal generator, the electrode multiplex circuit.

BRIEF DESCRIPTION OF THE DRAWINGS

In the Attached Drawing Figures:

FIG. 1(*b*) illustrates the arm without skin showing a location of electrode relative to the muscle groups of the arm;

FIG. 1(*c*) illustrates the arm with a sleeve of an inventive haptic interface;

FIG. 1(*d*) illustrates the arm with gel electrodes targeting individual muscles or muscle groups;

FIG. 1(*e*) illustrates the arm with the sleeve of the inventive haptic interface including an x-y grid of relatively smaller signal receiving transducers and relatively larger signal applying electrodes targeting individual muscles or muscle groups;

FIG. 2(*b*) shows the arm of the user wearing the inventive haptic interface with the targeted muscle groups involuntarily contracted;

FIG. 3(*a*) shows the inventive HHMI configured as an undergarment and having clusters of more densely packed electrodes and clusters of less densely packed electrodes;

FIG. 3(*b*) shows an image of the back of a human torso showing the muscles underlying the skin and locations on an HHMI garment with electrode locations that match the muscles;

FIG. 3(*c*) shows an image of the front of a human torso showing the muscles underlying the skin and locations on an HHMI garment with electrode locations that match the muscles;

FIG. 4(*b*) illustrates the fishnet elastic fabric material having a printed elastic ink electrode and trace line formed on the fishnet elastic fabric material;

FIG. 4(*c*) illustrates a printed elastic ink insulator formed over the trace line;

FIG. 5(*b*) shows the artwork for an example inkjet-printed three electrode pattern for detecting and applying electrical signals, with a central electrode for acting as a reference electrode relative to two outer detecting electrodes;

FIG. 6(*a*) schematically illustrates an electrode equivalent electronic circuit for applying and detecting electrical signals;

FIG. 6(*b*) is a photograph of a prototype showing individually addressable electrodes, each electrode having a trace terminating at a connection header laminated onto an elastic fabric adjustable sleeve;

FIG. 7(*b*) is a schematic showing a repeatable circuit section for individually addressing a respective electrode and a corresponding electrode of a plurality of electrodes to at least one of selectively apply, detect or switch on/off signals to the addressable electrodes;

FIG. 7(*c*) is a schematic showing another repeatable circuit section for individually addressing a respective electrode and a corresponding electrode of a plurality of electrodes to at least one of selectively apply, detect or switch on/off signals to the addressable electrodes;

FIG. 8(*b*) illustrates a use of the HHMI in a virtual reality game where the impact of a virtual lance during gameplay triggers an involuntary movement and haptic sensation;

FIG. 8(*c*) illustrates a use of the HHMI in a virtual reality game where the action of a virtual bow and arrow during gameplay is used as a trigger for generating involuntary movement and haptic sensations replicating the action and sensations from a real-world bow and arrow;

FIG. 11(*b*) shows a roll of HHMI preform formed in the roll-to-roll manufacturing process laser trimmed and sewn into an HHMI sleeve;

FIG. 12(*a*) illustrates an inventive manufacturing process where a packaged SMT semiconductor device is connected to a pre-printed electronic circuit trace formed on an adhesive print media layer prior to being embedded in an encapsulating adhesive layer during a lamination process for driving the SMT LED through the hot melt encapsulating adhesive;

FIG. 12(*b*) illustrates an inventive manufacturing process where a packaged SMT semiconductor device is connected to a pre-printed electronic circuit trace formed on an adhesive print media layer being embedded in an encapsulating adhesive layer during a lamination process for driving the SMT LED through the hot melt adhesive;

FIG. 12(*c*) illustrates a packaged SMT LED embedded in a thermally active encapsulating adhesive layer and in direct face-to-face electrical contact with the pre-printed electronic circuit trace;

FIG. 14(*b*) is an isolated cross-sectional view showing an HHMI configuration formed on a stretch fabric substrate with an adhesive print media layer having a printed conductive trace pattern for forming an electronic circuit with a CPU packaged semiconductor electronic device embedded in an encapsulating adhesive layer;

FIG. 24(*b*) illustrate a die, laser or knife cut electrode patch having individually addressable electrodes and non-electrode conductive traces, with grouping portions for retaining the grouping of the electrodes and traces to enable transfer and lamination.

FIG. 25(*b*) is a front view of the dry electrode insert;

FIG. 26(*a*) illustrates the material components of an embodiment of an inventive electrical signal detector and/or applier system;

FIG. 26(*b*) illustrates a gap between the housing sleeve and palm of the user;

FIG. 27(*a*) illustrates a material stack of components of the inventive electrical signal detector and/or applier system showing the adhesive and bottom housing substrate;

FIG. 27(*b*) illustrates a material stack of components of the inventive electrical signal detector and/or applier system showing foam urging members and top housing substrate;

FIG. 27(*c*) illustrates the laminated material stack of components showing the printed electrodes fixed to the housing substrate; showing palm and wrist straps FIG. 27(*d*) illustrates the laminated material stack of components showing the printed electrodes fixed to the housing substrate;

FIG. 28(*a*) shows the back of the user's hand wearing an embodiment of the electrode insert; insert;

FIG. 28(*b*) shows the palm of the user's hand wearing an embodiment of the electrode;

FIG. 28(*c*) shows a front side of an outer housing sleeve;

FIG. 28(*d*) shows a back side of an outer housing sleeve;

FIG. 29(*a*) shows the electrode insert worn on the hand of the user;

FIG. 29(*b*) shows the outer housing sleeve and electrode insert worn on the hand of the user;

FIG. 29(*c*) shows the electrode insert filling the gap between the housing sleeve and the palm of the user;

FIG. 29(*d*) shows components of an embodiment of the electrical signal detector and/or applier system;

FIG. 30(*b*) shows the back of another embodiment of the inventive electrical signal detector and/or applier system;

FIG. 31(*b*) shows the upper substrate fabric shell of an electrode insert; FIG. 31(*c*) show foam urging members;

FIG. 31(*d*) shows the lower substrate fabric sheet of the electrode insert;

FIG. 32(*b*) is a perspective view of the assembled electrode insert having laminated electrodes;

FIG. 34(*b*) shows a second step for applying the embodiment of the inventive electrical signal detector and/or applier system;

FIG. 34(*c*) shows a third step for applying the embodiment of the inventive electrical signal detector and/or applier system;

FIG. 34(*d*) shows a fourth step for applying the embodiment of the inventive electrical signal detector and/or applier system;

FIG. 34(*e*) shows a fifth step for applying the embodiment of the inventive electrical signal detector and/or applier system;

FIG. 34(*f*) shows a sixth step for applying the embodiment of the inventive electrical signal detector and/or applier system;

FIG. 36(*b*) illustrates a back view of the electrode insert; FIG. 36(*c*) illustrates a side view of the electrode insert;

FIG. 37(*a*) shows the back of the hand of user wearing an embodiment of the inventive electrical signal detector and/or applier system;

FIG. 37(*b*) shows the palm and wrist of the user wearing an embodiment of the inventive electrical signal detector and/or applier system;

FIG. 39(*b*) shows the front and back of dry electrode units;

FIG. 40(*a*) illustrates an electrode pattern for the electrical signal detector and/or applier system;

FIG. 40(*b*) shows a gesture control cuff turned inside out to show the electrodes of the electrical signal detector and/or applier system;

FIG. 41(*a*) shows a back substrate of an embodiment of the electrical signal detector and/or applier system;

FIG. 41(*b*) shows an electrical substrate of an embodiment of the electrical signal detector and/or applier system;

FIG. 41(*c*) shows a front substrate of an embodiment of the electrical signal detector and/or applier system;

FIG. 42(*b*) shows a section of a sleeve illustrating a large number array of individually addressable electrodes;

FIG. 44(*c*) illustrates a roll-to-roll direct-to-fabric printing for forming a patterned elastic conductive ink print over a patterned elastic thread filler ink formed directly on fabric;

FIG. 62 shows the location of TENS or NMES signal applying electrodes on the large muscles of the lower body of a diabetic user;

FIG. 63 shows the location of TENS or NMES signal applying electrodes on the large muscles of the lower body of a diabetic user;

FIG. 64 shows an HHMI configuration as diabetes shorts with electrodes located for applying TENS or NMES signals to the large muscles of the lower body of a diabetic user;

FIG. 65 shows the location of TENS or NMES signal applying electrodes on the large muscles of the lower body of a diabetic user;

FIG. 70 illustrates an inventive manufacturing process where a packaged SMT semiconductor device is connected to a pre-printed electronic circuit trace formed on an adhesive print media layer prior to being embedded in an encapsulating adhesive layer during a lamination process for driving the SMT LED through the hot melt encapsulating adhesive;

FIG. 71 illustrates an inventive manufacturing process where a packaged SMT semiconductor device is connected to a pre-printed electronic circuit trace formed on an adhesive print media layer being embedded in an encapsulating adhesive layer during a lamination process for driving the SMT LED through the hot melt adhesive;

FIG. 72 illustrates a packaged SMT LED embedded in a thermally active encapsulating adhesive layer and in direct face-to-face electrical contact with the pre-printed electronic circuit trace;

FIG. 75 is an isolated cross-sectional view showing an HHMI configuration formed on a stretch fabric substrate with an adhesive print media layer having a printed conductive trace pattern for forming an electronic circuit with a CPU packaged semiconductor electronic device embedded in an encapsulating adhesive layer;

FIG. 76 illustrates a roll-to-roll manufacturing process for manufacturing a robust exposed electrode material using a print media surface pre-treatment, an elastic ink printing, and a heat and pressure post-treatment;

FIG. 77 illustrates a roll-to-roll manufacturing process for making a robust exposed electrode formed as a patterned elastic conductive ink on TPU adhered to fabric;

FIG. 78 illustrates a roll-to-roll direct-to-fabric printing for forming a patterned elastic conductive ink print over a patterned elastic thread filler ink formed directly on fabric;

FIG. 79 shows a step in the process of forming a robust exposed electrode showing the step of providing a TPU print media on a carrier sheet;

FIG. 80 shows a step of pre-treating the top surface of the TPU print media using a solvent mist;

FIG. 81 shows a step of the pre-treatment creating a softened top surface of the TPU print media;

FIG. 82 shows a step of applying an elastic conductive ink coating on the softened top surface of the TPU print media;

FIG. 83 shows a step of providing a release sheet on top of the uncured elastic ink coating on the softened top surface of the TPU print media;

FIG. 84 shows a step forming a diffusion bond between the elastic ink and the TPU print media by applying heat and pressure to cure the elastic conductive ink coating, drive off at least a portion of any remaining solvents from the top surface pre-treatment and from within the coating of elastic conductive ink;

FIG. 85 illustrates the roll-to-roll process of forming a diffusion bond by applying heat and pressure to cure the elastic conductive ink coating using heated rollers;

FIG. 86 shows the diffusion bond formed by applying heat and pressure to uncured elastic conductive ink coated on the softened top surface of a pre-treated TPU print media;

Figure 32A:
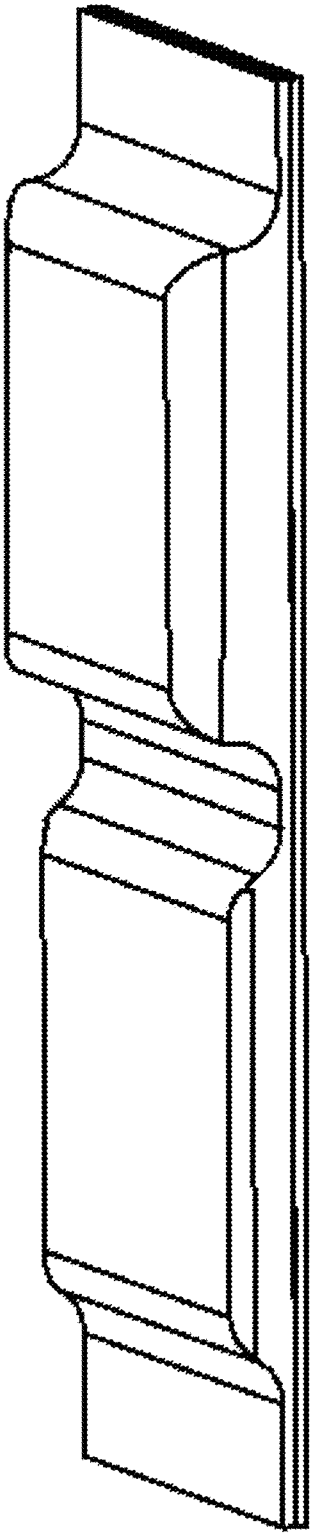
FIG. 32(*a*) shows a perspective view of the assembled shell, foam urging members and bottom substrate of the electrode insert.
Figure 32B:
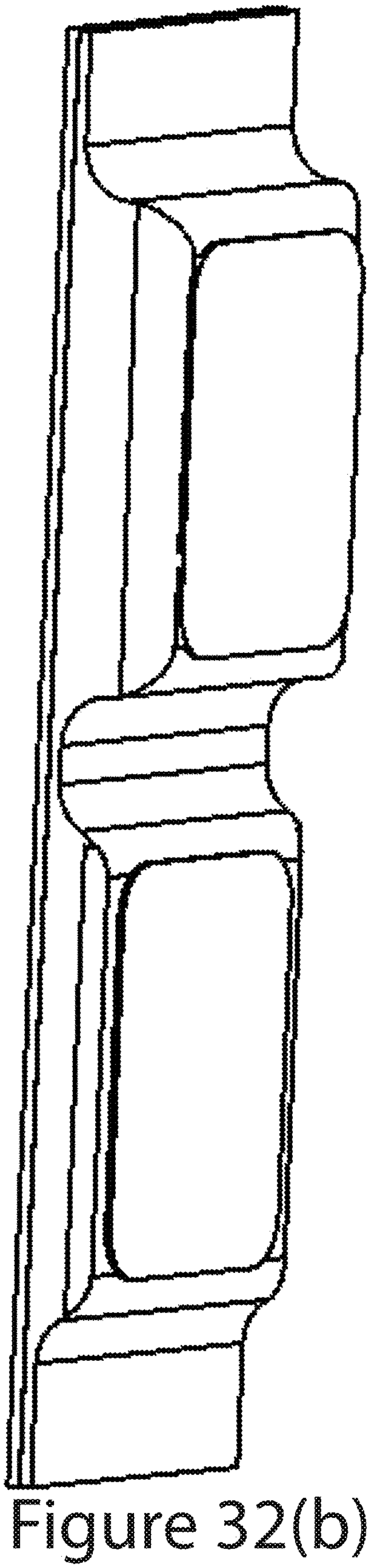
Figure 33:
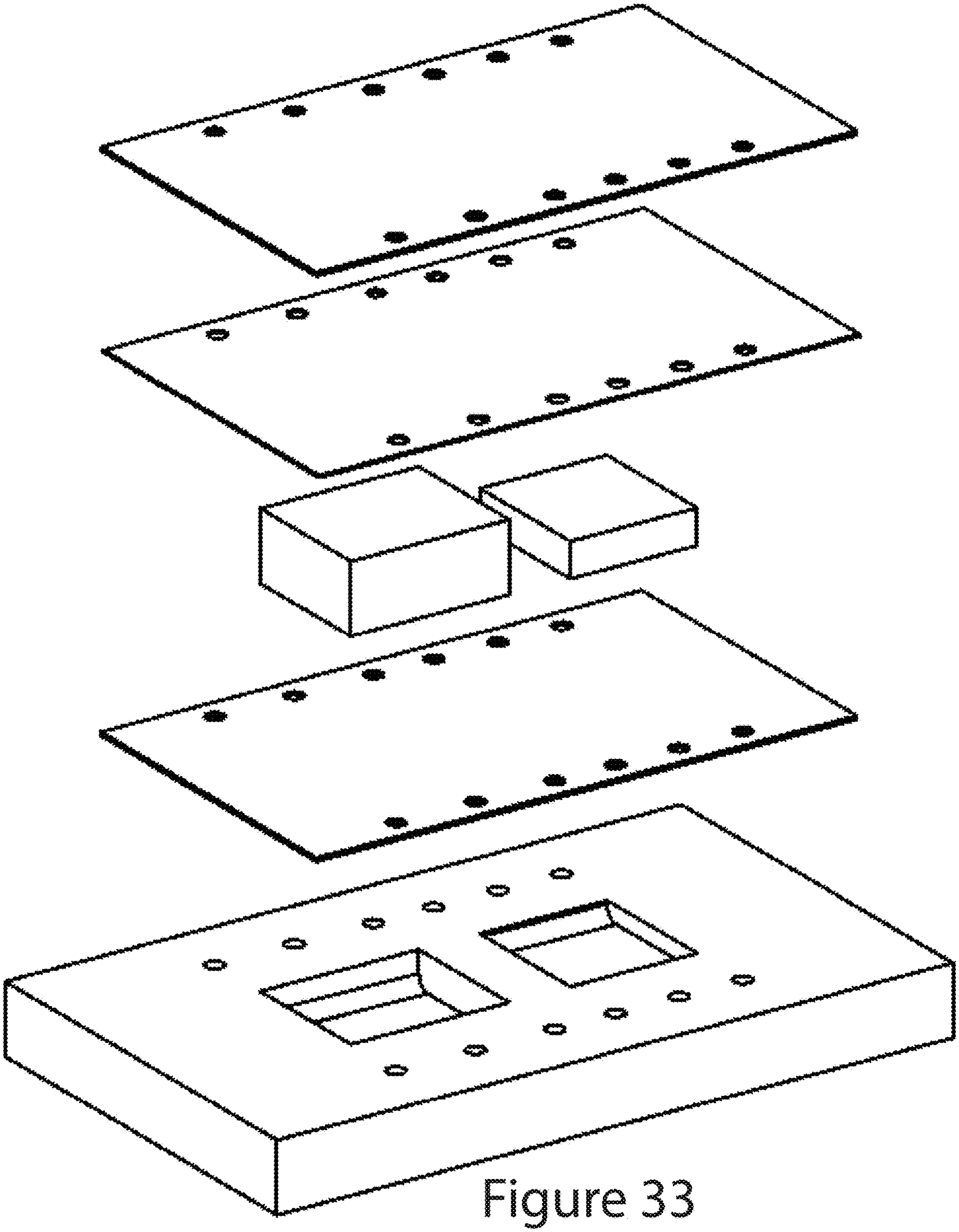
FIG. 33 shows a material stack and lamination press form mold.
Figure 34A:
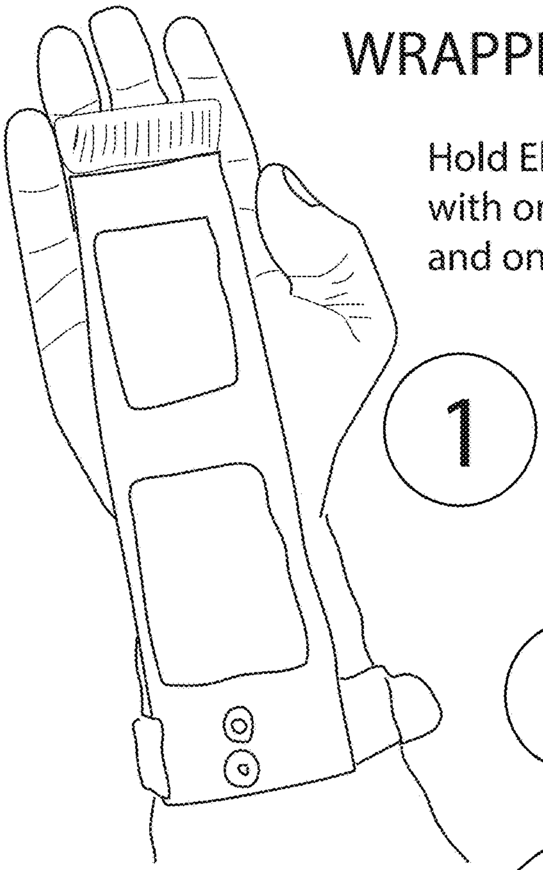
FIG. 34(*a*) shows a first step for applying an embodiment of the inventive electrical signal detector and/or applier system.
Figure 34B:
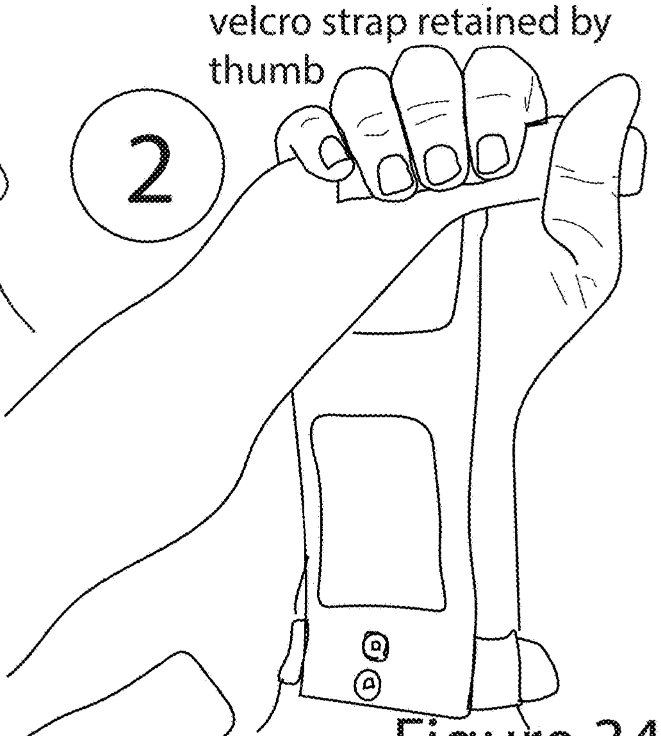
Figure 34C:
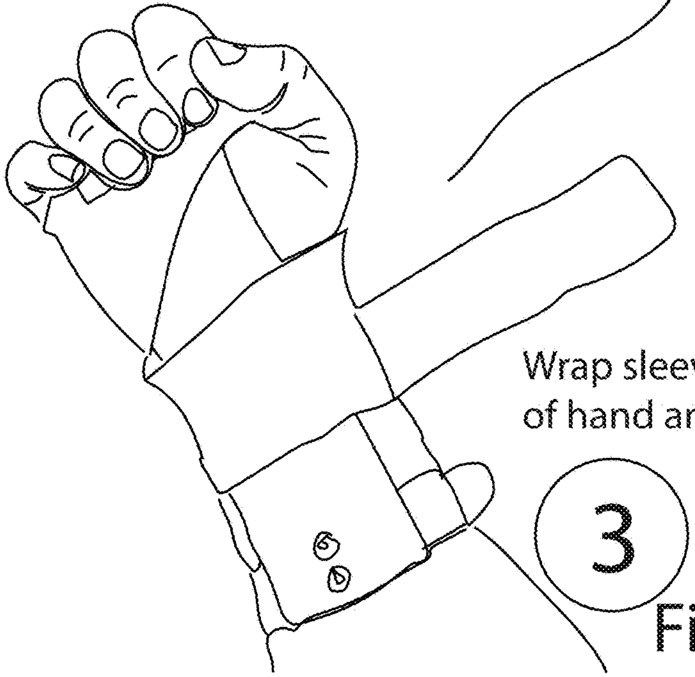
Figure 35:
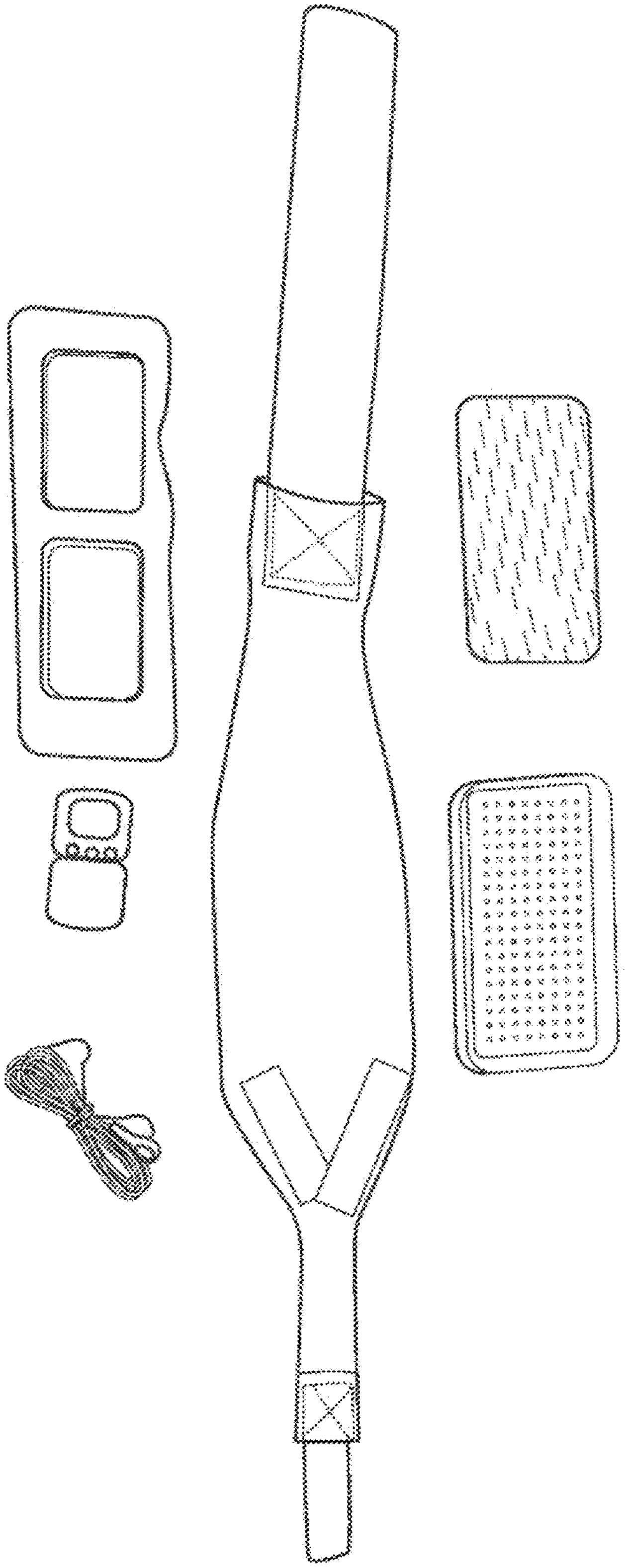
FIG. 35 illustrates the components of an embodiment of the inventive electrical signal detector and/or applier system.
Figure 36A:
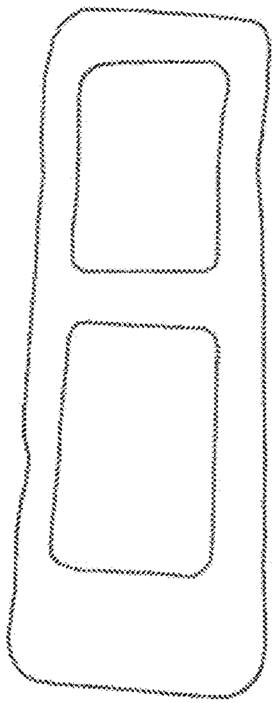
FIG. 36(*a*) illustrates a front view of the electrode insert.
Figure 36B:
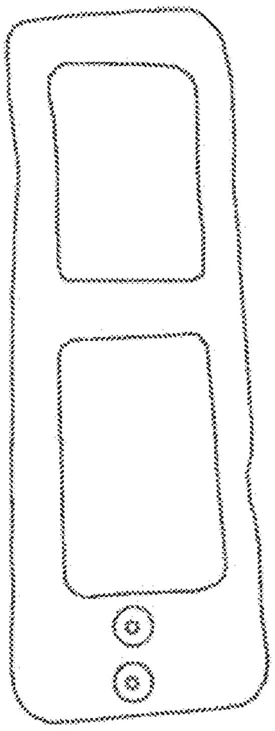
Figure 36C:
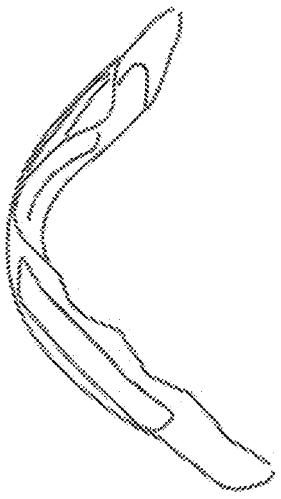
Figure 87:
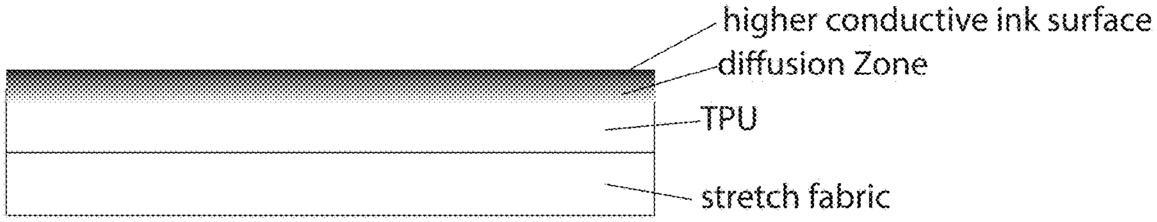
Figure 88:
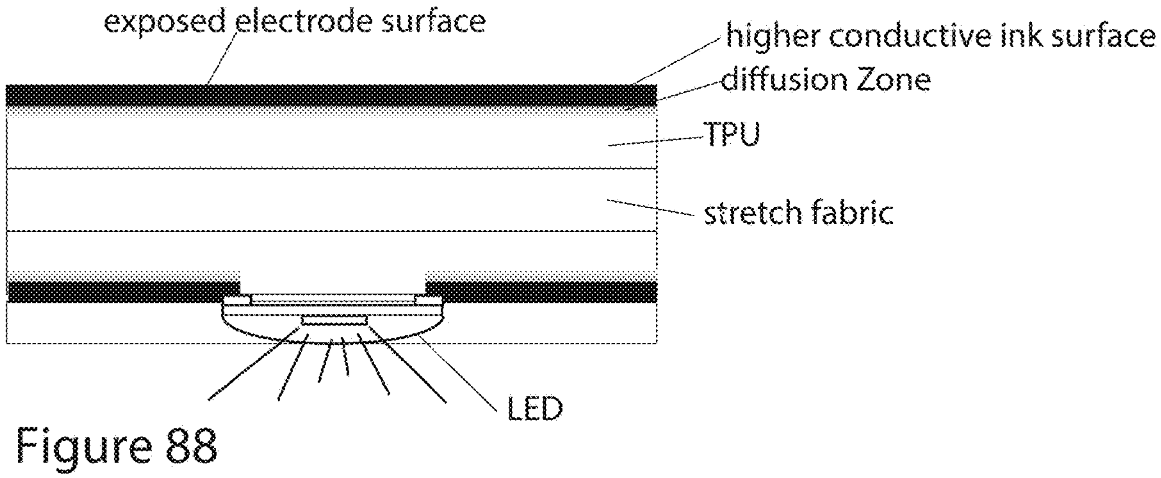
Figure 89:
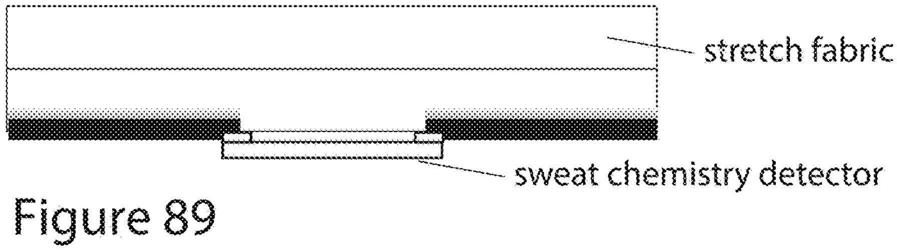
Figure 90:
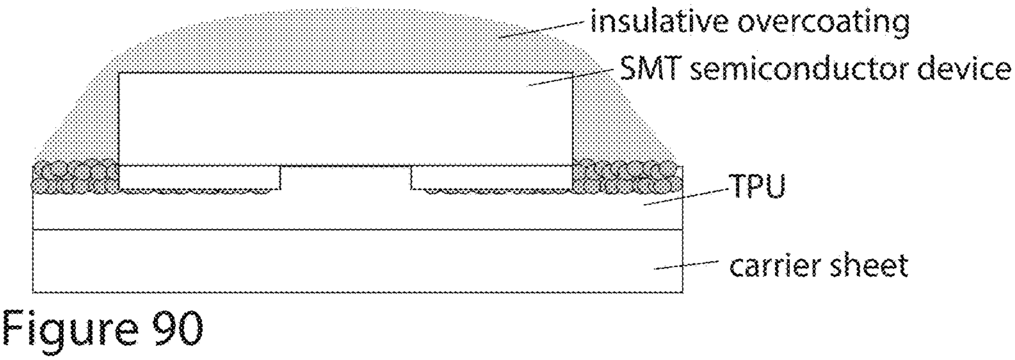
Figure 91:
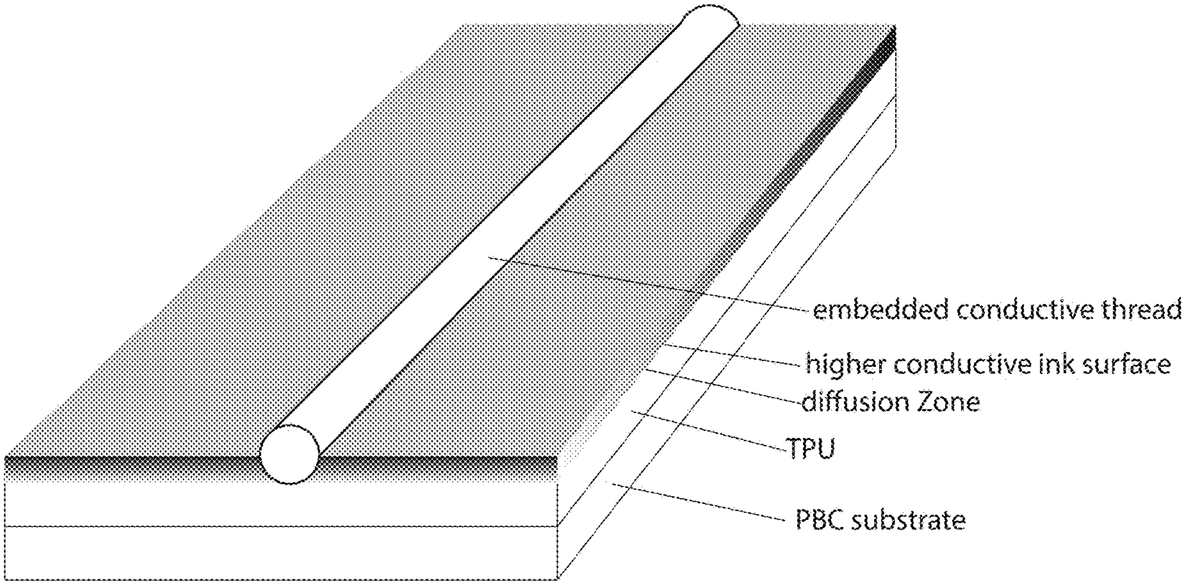
Figure 92:
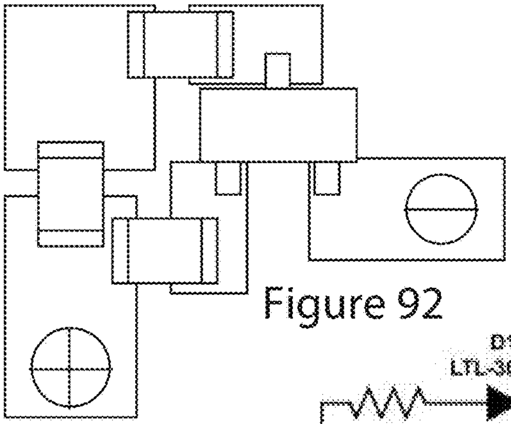
Figure 94:
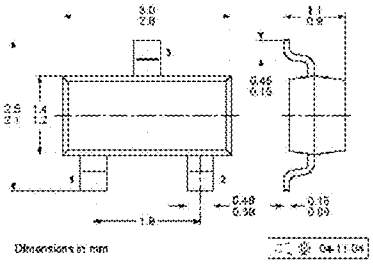
Figure 93:
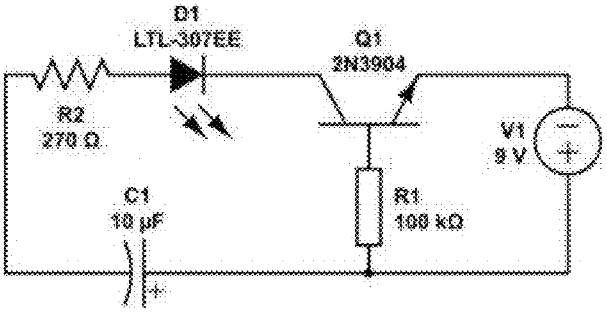
Figure 102:
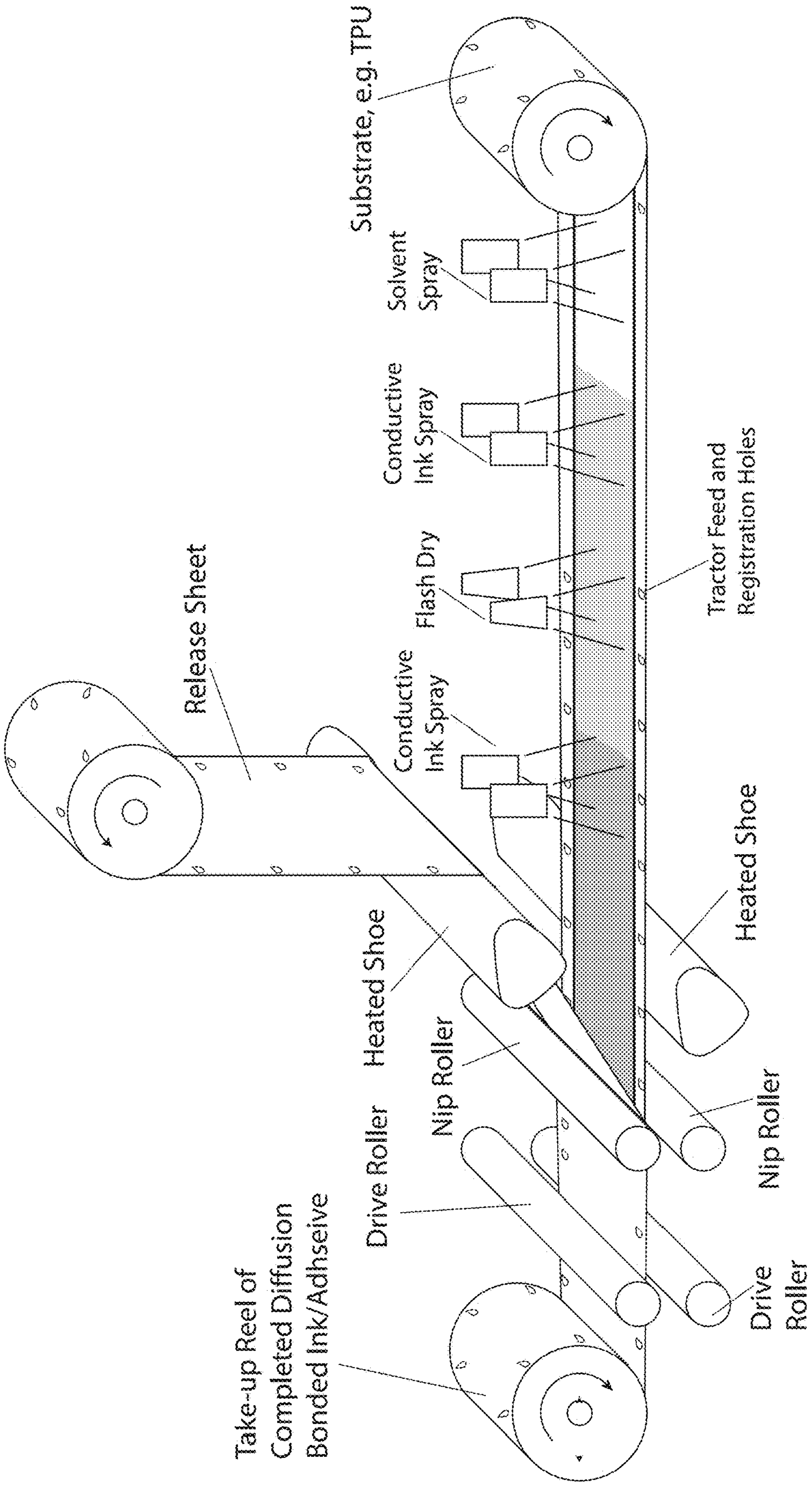
Figure 108:
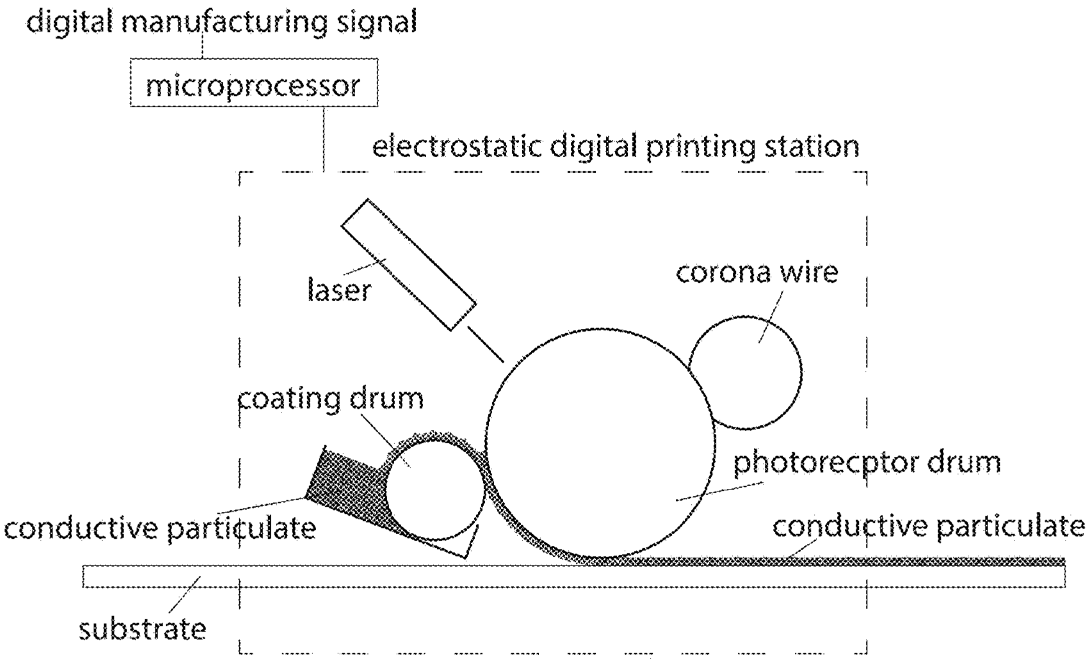
Figure 109:
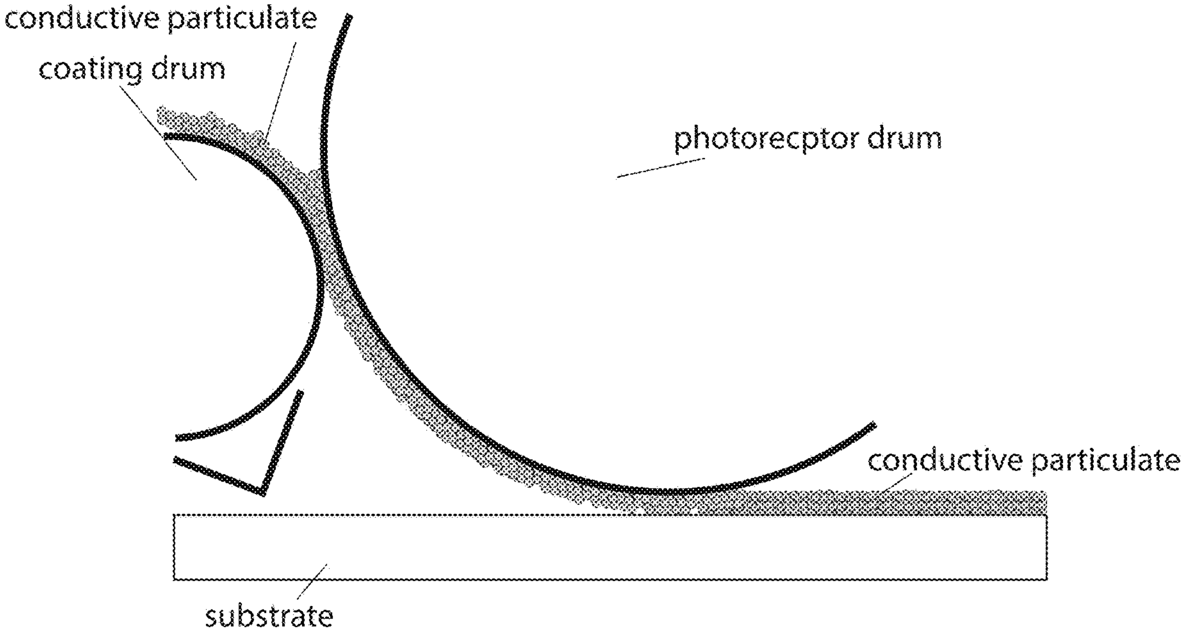
Figure 110:
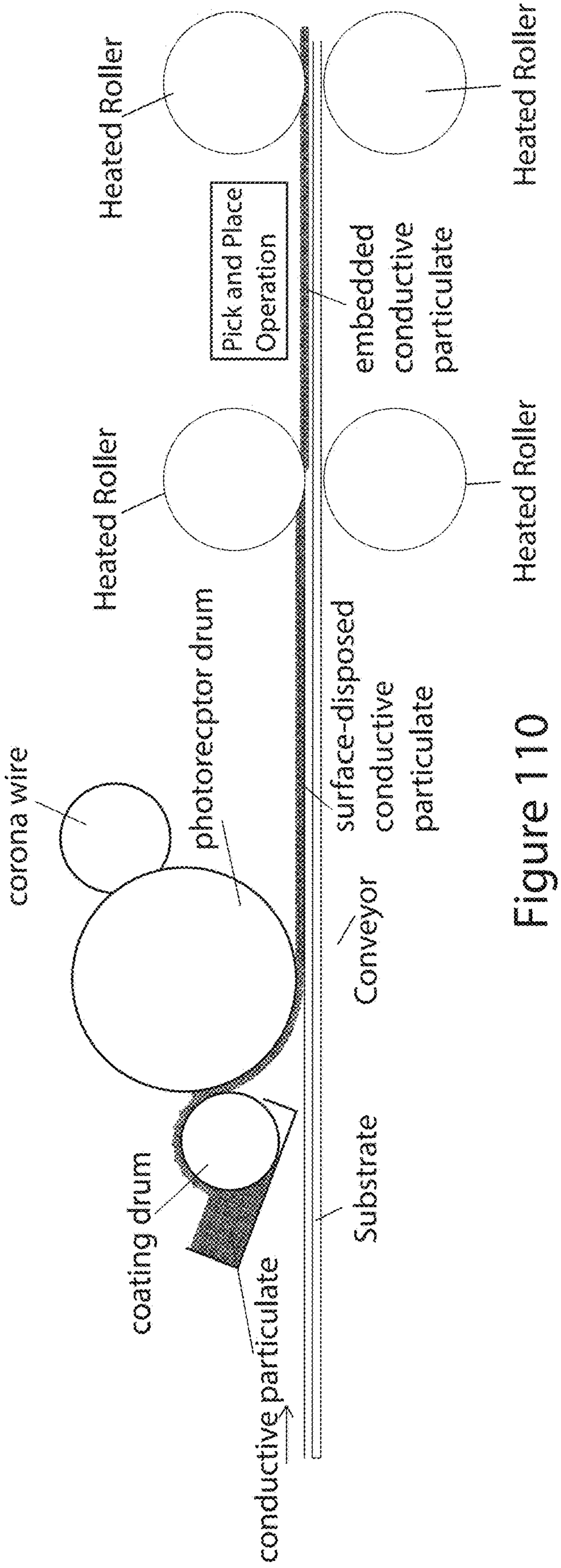
Figure 111:
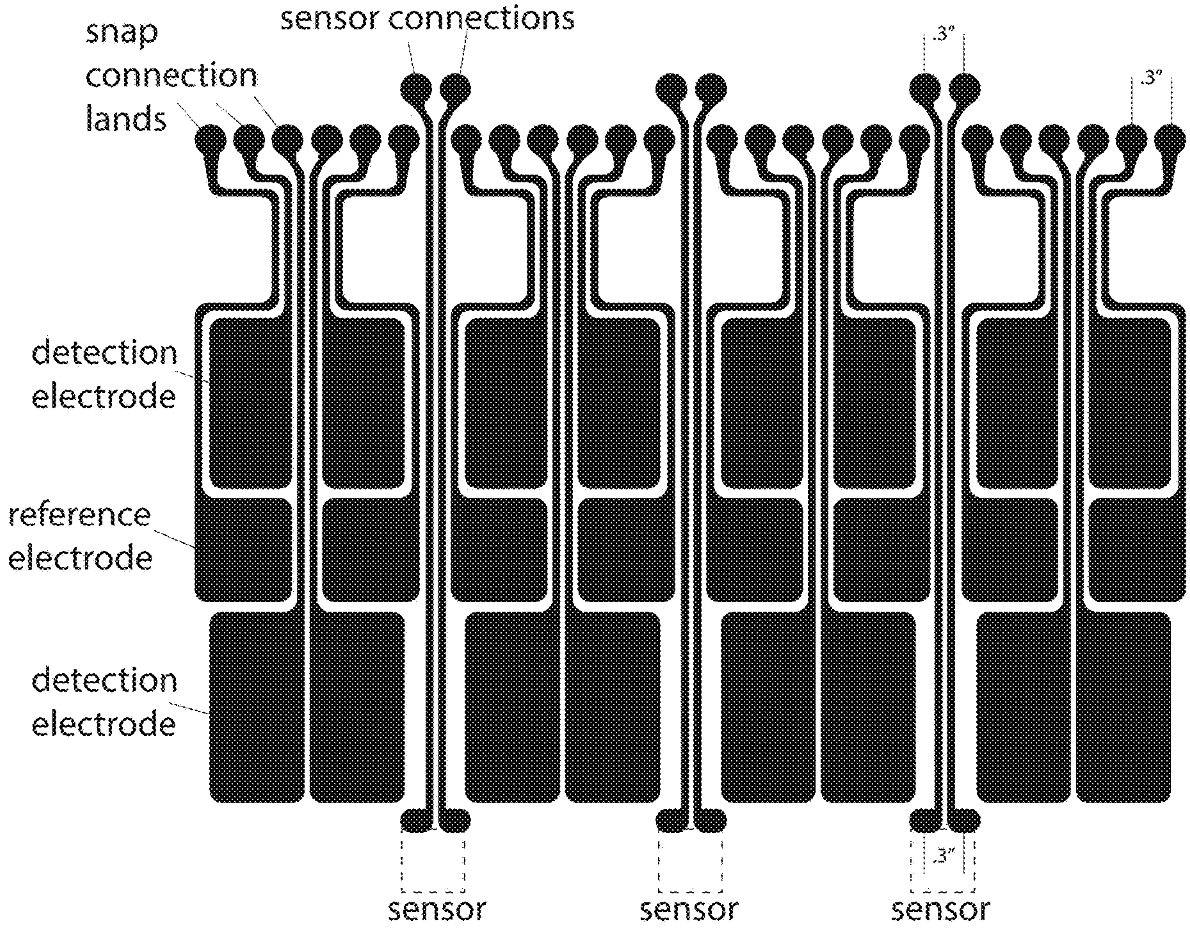
Figure 112:
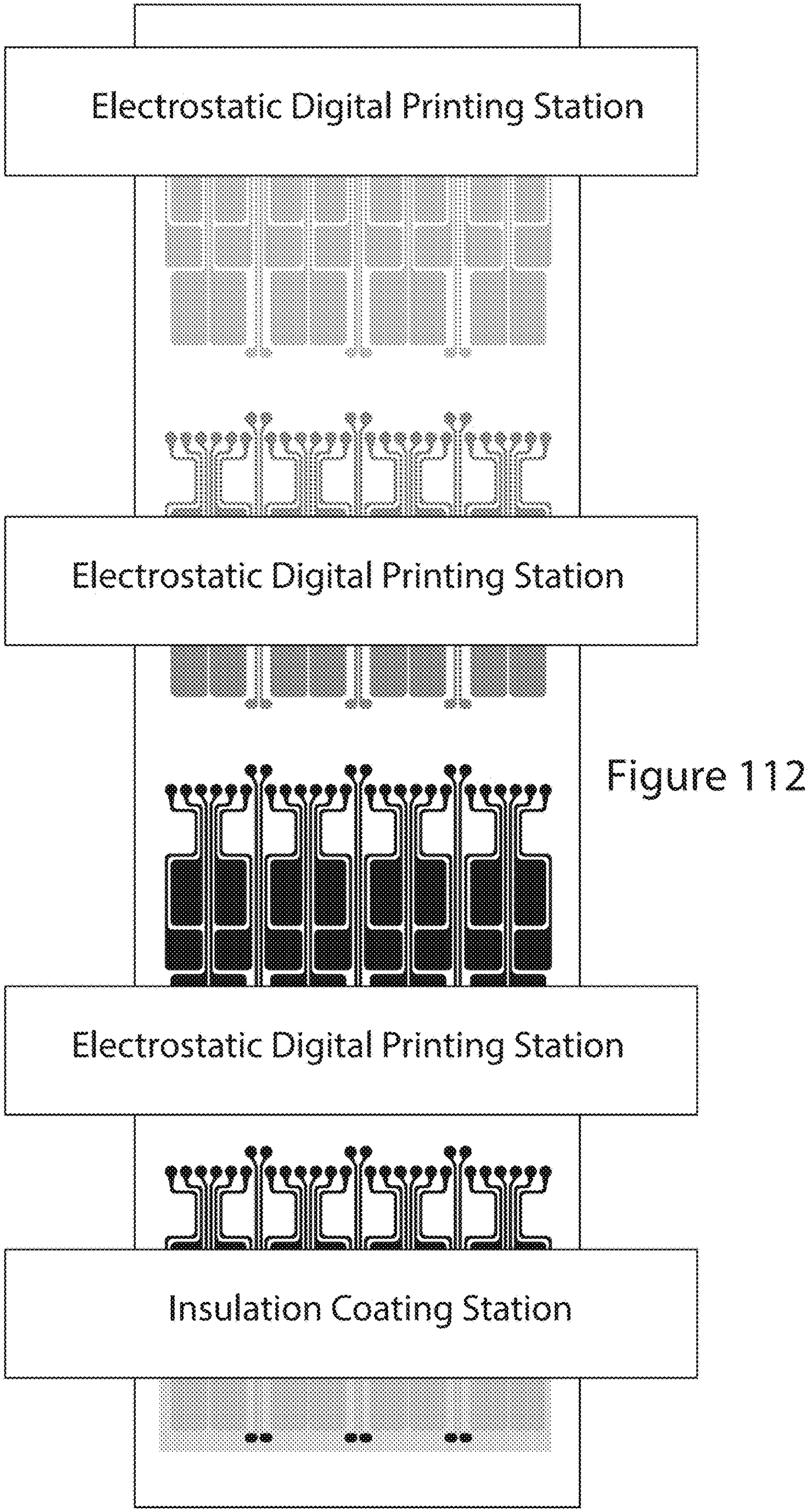
Figure 113:
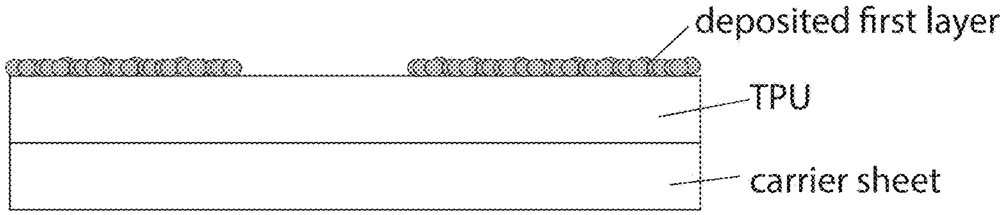
Figure 114:
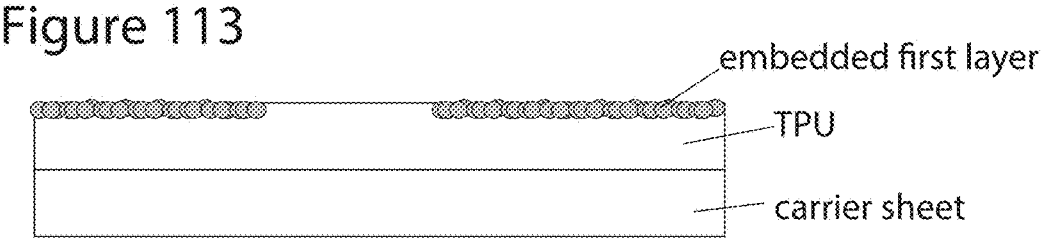
Figure 115:
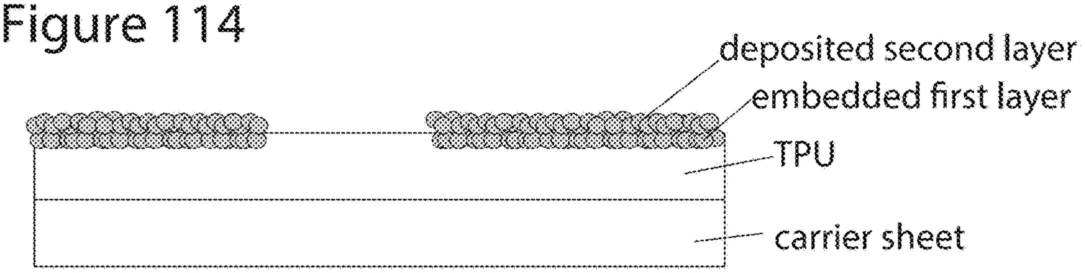
Figure 116:
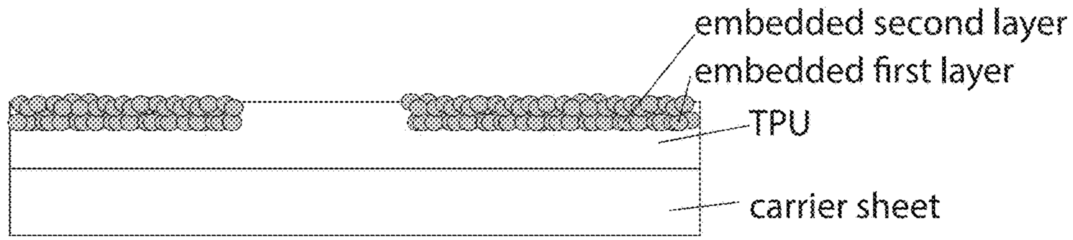
Figure 117:
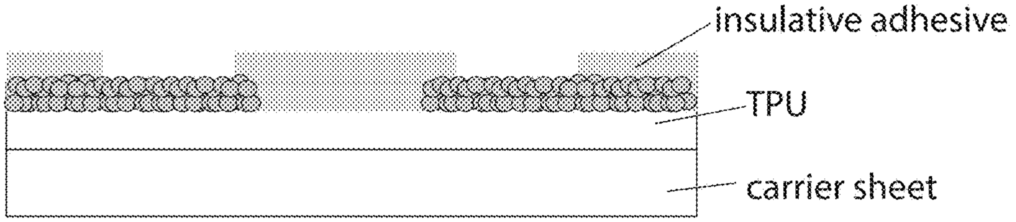
Figure 118:
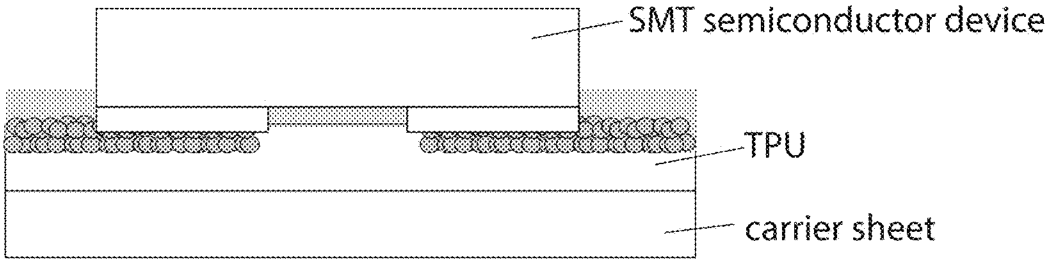
Figure 119:
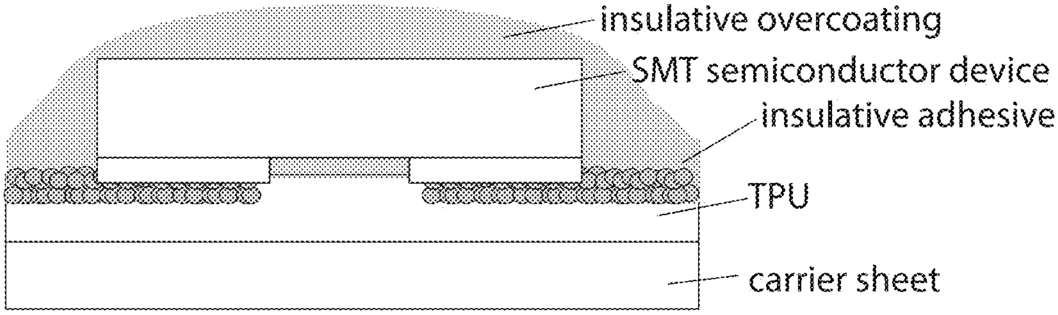
Figure 120:
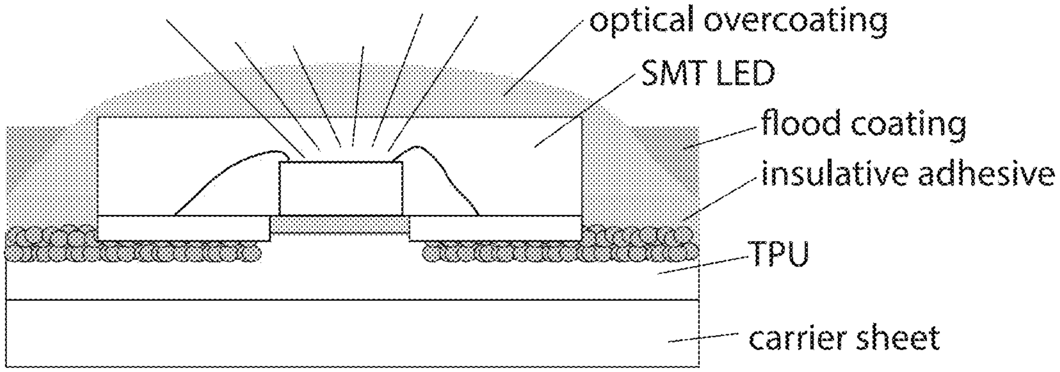
Figure 121:
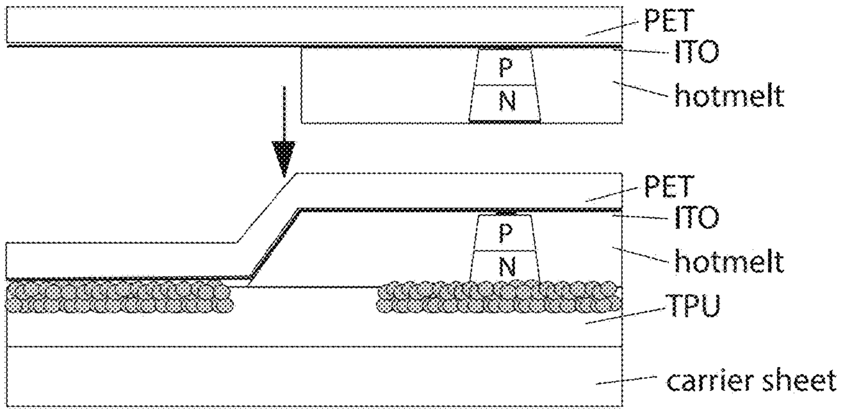
Figure 122:
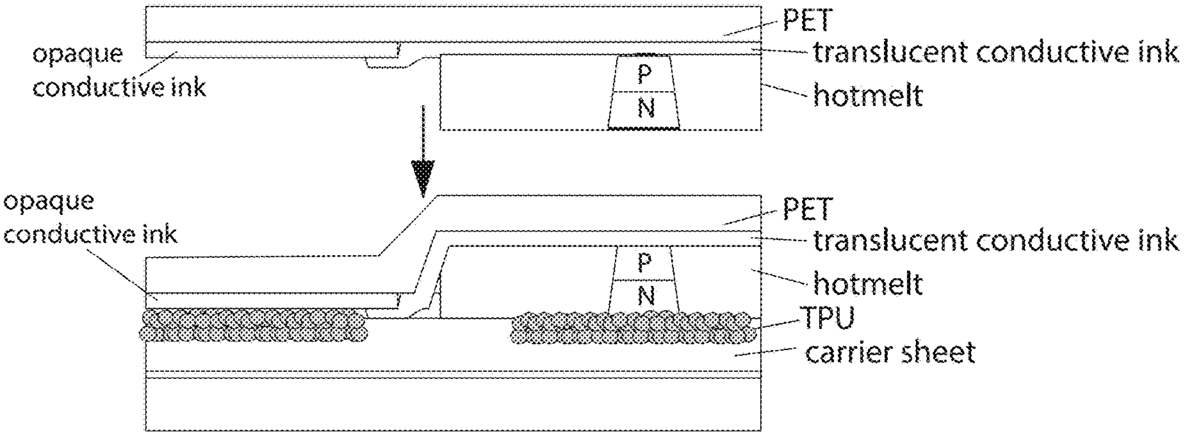
Figure 123:
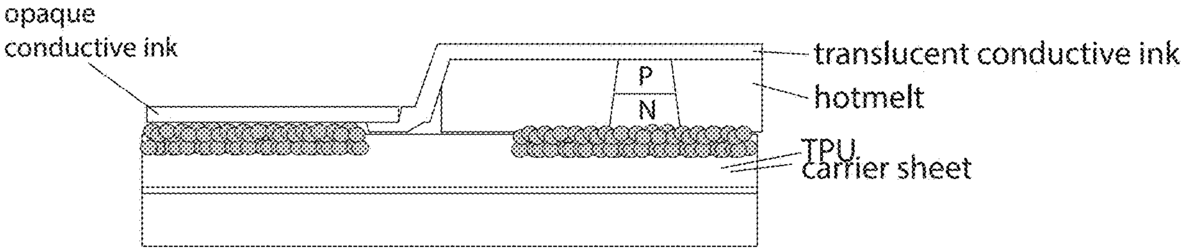
Figure 124:
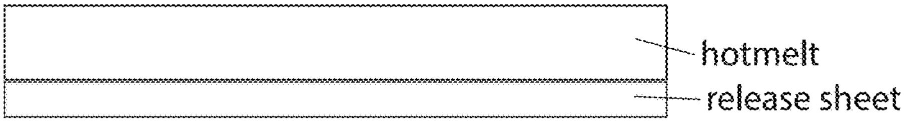
Figure 125:
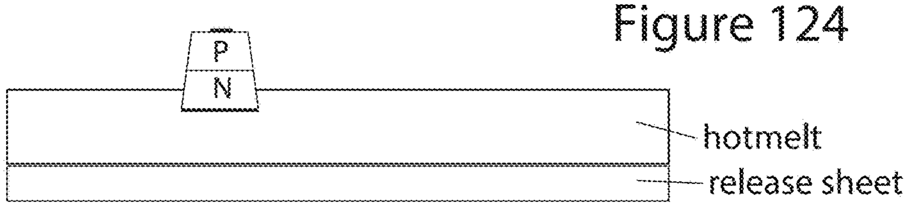
Figure 126:
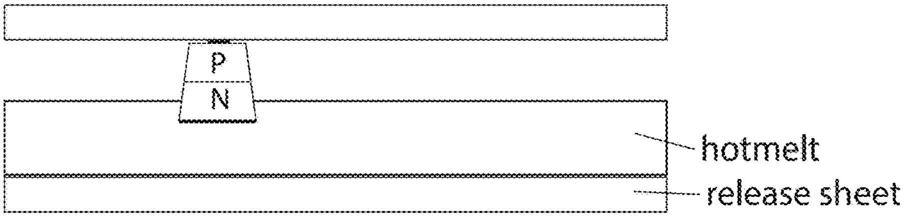
Figure 127:
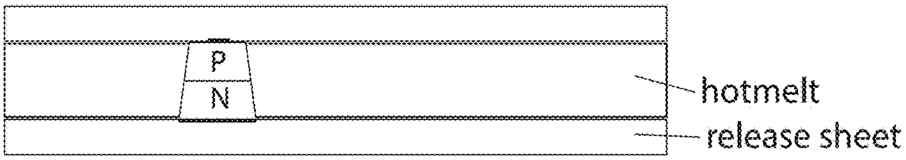
Figure 128:
Figure 129:
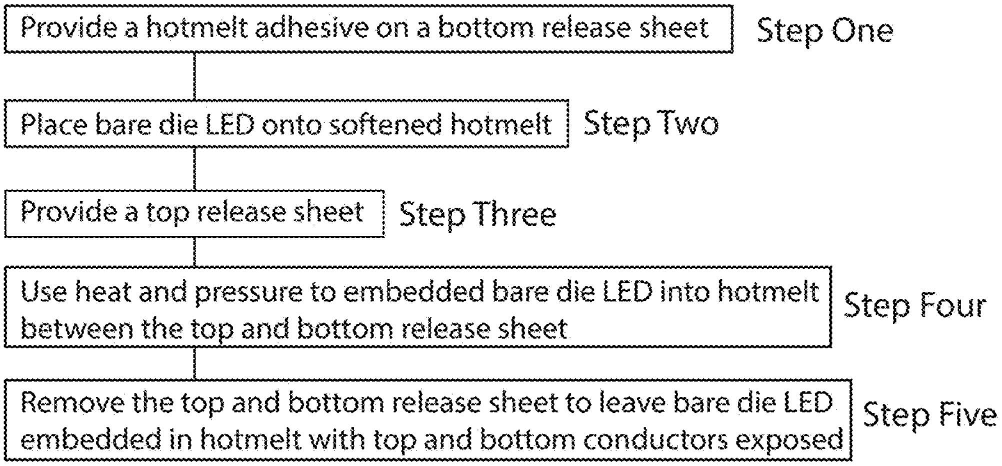
Figure 130:
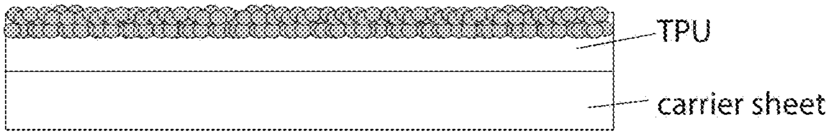
Figure 131:
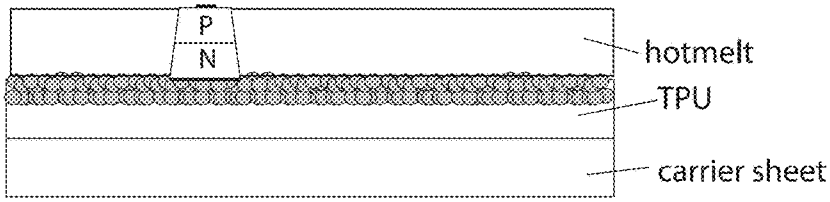
Figure 132:
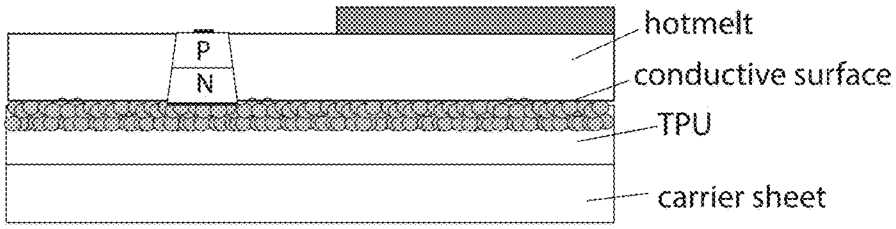
Figure 133:
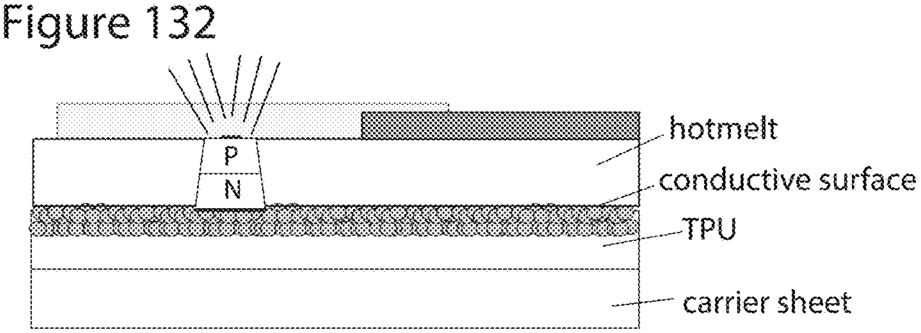
Figure 134:
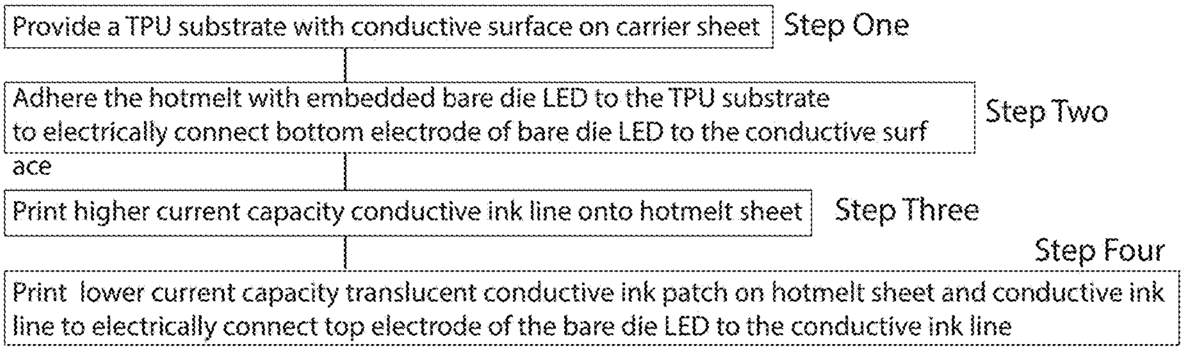

FIG. 87 shows a robust exposed electrode having a higher conductive ink surface bonded through a diffusion bond to the TPU print media adhered to a stretch fabric;

FIG. 88 shows a configuration of a robust exposed electrode facing inwards towards the skin of a user and adhered to a stretch fabric with an embedded LED adhered to the stretch fabric and facing outward from the skin of the user;

FIG. 89 shows a configuration of a robust sweat chemistry detector fixed to printed electric leads formed from an elastic conductive ink diffusion bonded to a TPU print media and adhered to a stretch fabric;

FIG. 90 is a cross-sectional view showing a surface mount electronic device electrically and mechanically connected without conductive glues or solder to REEP™ processed conductive leads disposed on a thermoplastic insulative adhesive and/or disposed on a PCB substrate;

FIG. 91 illustrates REEP™ processed conductive lead having an embedded conductive thread for providing a lower resistance electric pathway;

FIG. 92 illustrates a low temperature printed circuit made from an all-additive process;

FIG. 93 is a schematic of an electronic circuit that includes a resistor/capacitor timing circuit for controlling a transistor to cause an LED to blink;

FIG. 94 illustrates an example of a surface mount transistor;

FIG. 95 shows an example of a sine wave shape printed conductive circuit line made using the REEP™ process and laminated to a fabric PCB substrate suitable for making a wearable electronic device;

FIG. 96 shows a sine way printed circuit line formed using the REEP™ processed material;

FIG. 97 shows a low temperature printed circuit board built on a paper substrate using the REEP™ processed materials for connecting a surface mount LED, where the LED includes a connection enhancing additional TPU patch that includes a light diffusing particulate, showing that the LED has been put into electrical communication with a battery without the use of an additional conductive glue or solder;

FIG. 98 shows an experimental attempt to connect a surface mount LED to conductive lines using the same TPU and conductive ink as used in the REEP™ processed material shown in FIG. 32;

FIG. 99 shows a low temperature printed circuit board with a blue LED and a green LED electrically connected through a simple one-step heat and pressure lamination process directly onto conductive lead lines formed from REEP™ processed materials having an elastic conductive ink diffusion bonded to an adhesive print media;

FIG. 100 shows the blue and green LED shown in FIG. 99 having a patch of light diffusion material applied in a heat and pressure lamination process, which also more securely fixes the surface mount electronic devices to the REEP™ processed material;

FIG. 101 shows an experimental light diffusion patch made from silver-coated glass spheres bonded to the same TPU and similar processing steps as used in the REEP™ processed materials;

FIG. 102 illustrates a roll-to-roll process with multiple spray coating passes for creating a completed roll of diffusion bonded elastic conductive ink on adhesive;

FIG. 103 is a flow chart showing the steps for forming an adhesive with particulate in an adhesive substrate;

FIG. 104 is a cross section of a TPU substrate on carrier sheet;

FIG. 105 is a cross section showing a carrier fluid with dispersed conductive particulate disposed on the top surface of the TPU substrate;

FIG. 106 is a cross section showing a softened TPU zone formed on the top surface of the TPU substrate;

FIG. 107 is a cross section showing the conductive particulate embedded in the TPU substrate with a diffusion zone formed between a more conductive top surface and the bulk of the TPU substrate;

FIG. 108 illustrates an electrostatic digital printing station of a wearable electronic digital manufacturing process;

FIG. 109 is a close-up view showing the transfer of conductive particulate from a coating drum to a photoreceptor drum to a substrate of the electrostatic digital printing station;

FIG. 110 illustrates a roll-to-roll wearable electronic digital manufacturing process;

FIG. 111 is a digitally printable exposed electrode pattern;

FIG. 112 illustrates a multiple pass, roll-to-roll digital manufacturing line for building up high density conductive particulate into a digitally printed electronically conductive pattern;

FIG. 113 is a cross section showing an embedded first layer of conductive particulate on the TPU substrate;

FIG. 114 is a cross section showing the embedded first layer and a patterned deposited second layer of conductive particulate on the TPU substrate;

FIG. 115 is a cross section showing the embedded first layer and an embedded second layer of conductive particulate on the TPU substrate;

FIG. 116 is a cross section showing the embedded first layer and the embedded second layer of conductive particulate with a patterned insulative adhesive overcoat on the TPU substrate;

FIG. 117 is a cross section showing the embedded first layer and the embedded second layer of conductive particulate with the patterned insulative adhesive overcoat having an SMT semiconductor device adhered to the insulative adhesive and electrically connected to the embedded first and second layers of conductive particulate on the TPU substrate;

FIG. 118 is a cross section showing the SMT semiconductor device adhered to the insulative adhesive and further fixed and protected with a protective insulative overcoating;

FIG. 119 is a cross section showing the SMT semiconductor device that has been brought into face to face electrical communication with the patterned embedded conductive particulate and fixed in place on the TPU substrate through the application of heat and pressure, and further fixed and protected with a protective insulative overcoating;

FIG. 120 is a cross section showing an SMT LED adhered to the insulative adhesive, with an optical overcoating and further fixed and protected with a protective insulative flood coating;

FIG. 121 is a cross section showing a bare die electronic element, such as an LED, connected to a conductive transparent surface of a top patch or sheet of transparent substrate applied to a TPU having a conductive surface;

FIG. 122 is a cross section showing a bare die electronic element, such as an LED, connected to a printed ink conductive translucent surface of a top patch or sheet of transparent substrate applied to a TPU having a conductive surface;

FIG. 123 is a cross section showing a bare die electronic element, such as an LED, connected to a printed ink conductive translucent surface and printed ink higher conductivity lead lines printed on a TPU having a conductive surface;

FIG. 124 is a cross section showing a hotmelt adhesive on a bottom release sheet;

FIG. 125 is a cross section showing a bare die LED partially embedded in a softened top surface of the hotmelt adhesive;

FIG. 126 is a cross section showing a top release sheet forming a lamination package with the hotmelt adhesive on the bottom release sheet;

FIG. 127 is a cross section showing the bare die LED driven thorough the hotmelt adhesive;

FIG. 128 is a cross section showing the top and bottom release sheets removed from the hotmelt adhesive with the bare die LED embedded having a top and bottom electrode expose;

FIG. 129 is a flow chart of a process for forming a sheet of adhesive with embedded bare die LED, each LED having its top and bottom electrode exposed;

FIG. 130 is a cross section showing a TPU substrate with a conductive surface on a carrier sheet;

FIG. 131 is a cross section showing a hotmelt adhesive with embedded bare die LED adhered to the conductive surface;

FIG. 132 is a cross section showing a conductive lead line printed on atop surface of the hotmelt;

FIG. 133 is a cross section showing a translucent printed conductor connecting the top electrode to the conductive lead line;

FIG. 134 is a flow chart of a process for forming an electronic circuit by printing a translucent conductive ink and conductive lead lines on a sheet of hotmelt adhesive with embedded bare die LED;

FIG. 135 is a cross section showing a TPU substrate with a conductive surface on a carrier sheet;

FIG. 136 is a cross section showing an adhesive hotmelt adhered to the TPU substrate to embed the conductive surface into a bottom surface of the hotmelt adhesive;

FIG. 137 is a cross section showing a bare die LED partially embedded in a softened top surface of the hotmelt adhesive;

FIG. 138 is a cross section showing the bare die LED driven thorough the hotmelt adhesive with a bottom electrode connecting with the conductive surface;

FIG. 139 is a cross section showing a conductive lead line and a translucent printed conductor connecting the top electrode of the LED to the conductive lead line printed on a top surface of the hotmelt; and FIG. 140 is a flow chart of a process for forming an electronic circuit by printing a translucent conductive ink and conductive lead lines on a sheet of hotmelt adhesive with embedded bare die LED.

DETAILED DESCRIPTION OF THE INVENTION

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

The exemplary embodiments herein describe methods, apparatus, computer code, applications and techniques for a haptic human/machine and human/human interface.

Figures 1A, 1B, 1C, 1D, 1E:
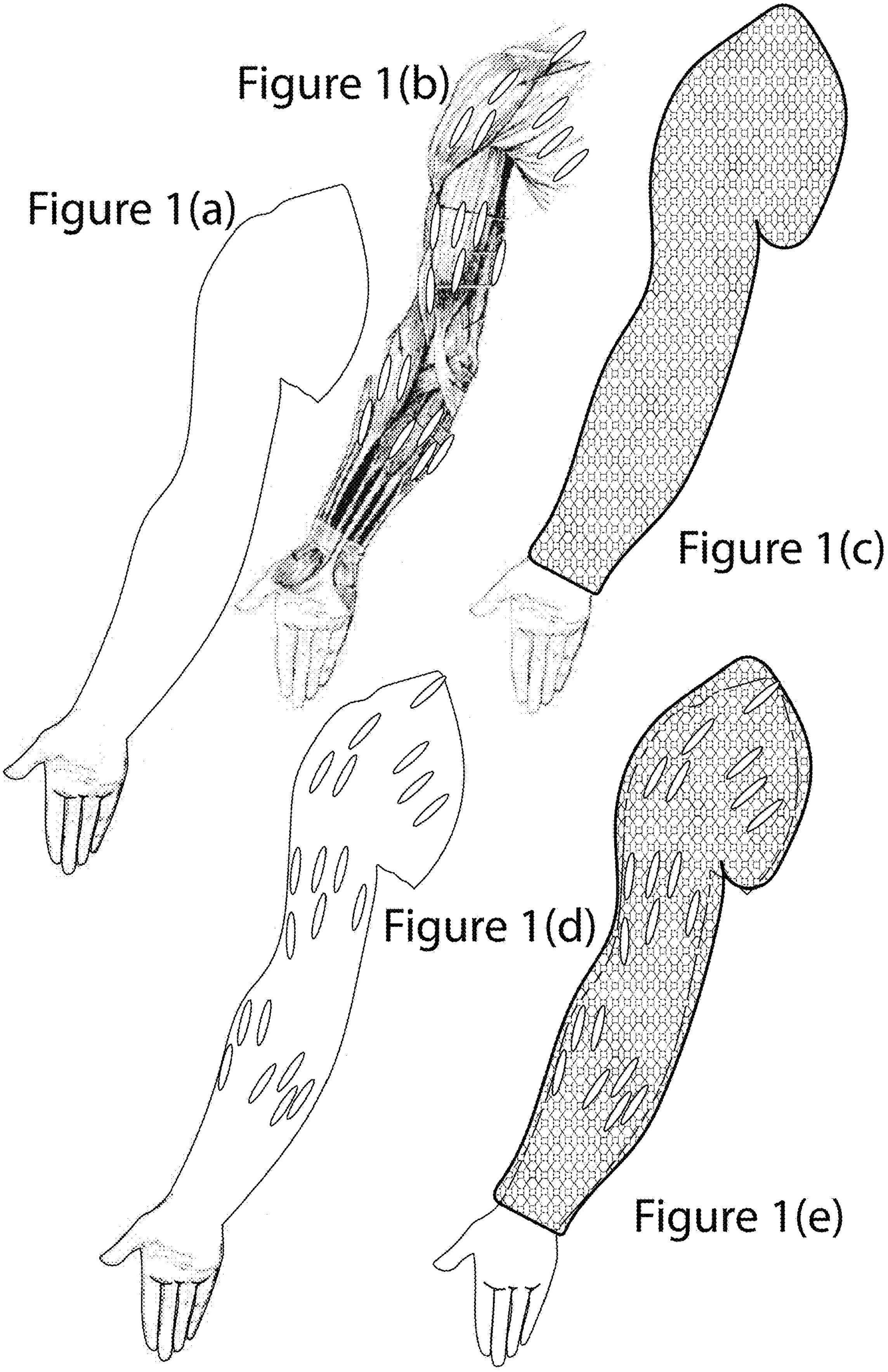
FIG. 1(*a*) illustrates a user's bare arm.

A non-limiting exemplary embodiment of an inventive haptic interface is configured as a sleeve that can be worn by a user, with the detection and application of electrical signal activity obtained through a user-calibrated grid of conductive patches or electrodes. FIG. 1(*a*) illustrates a user's bare arm. FIG. 1(*b*) illustrates the arm without skin showing a location of electrode relative to the muscle groups of the arm.

FIG. 1(*c*) illustrates the arm with a sleeve of an inventive haptic interface. FIG. 1(*c*) illustrates the arm noting locations for electrodes targeting individual muscles or muscle groups. FIG. 1(*d*) illustrates the arm with electrodes targeting individual muscles or muscle groups. FIG. 1(*e*) illustrates the arm with the sleeve of the inventive haptic interface including a grid of addressable electrodes. The electrodes may include relatively smaller signal receiving electrodes/transducers and relatively larger signal applying electrodes/transducers targeting individual muscles or muscle groups.

Figure 2A:
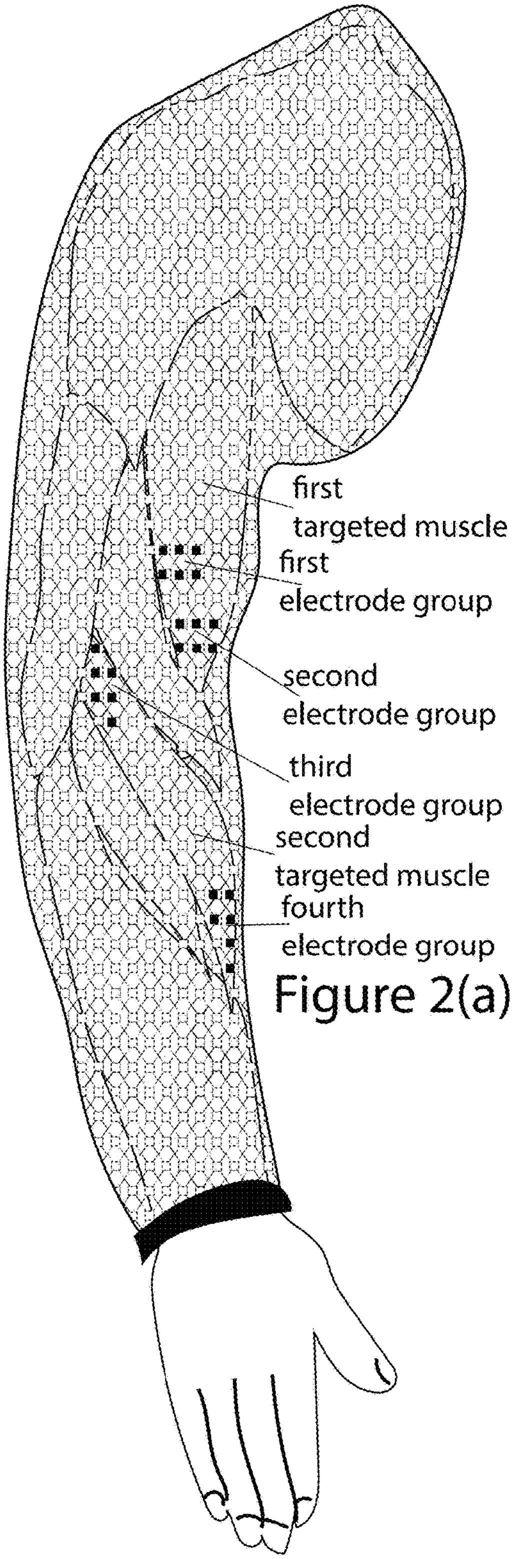
FIG. 2(*a*) shows an arm of the user wearing the inventive haptic interface targeting specific muscle groups for applied electrical stimulation.
Figure 2B:
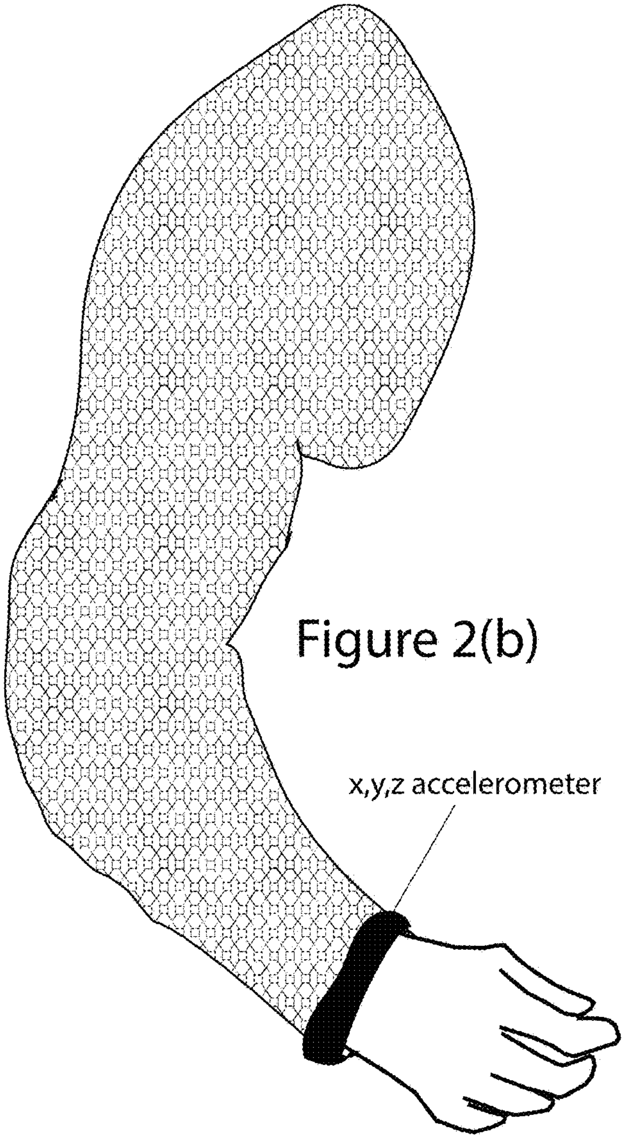

FIG. 2(*a*) shows an arm of the user wearing the inventive haptic interface targeting specific muscle groups for applied electrical stimulation. FIG. 2(*b*) shows the arm of the user wearing the inventive haptic interface with the targeted muscle groups involuntarily contracted.

The haptic interface may be in the form of a comfortable, easily worn garment that a user wears with little or no restriction of movement. Also, a full body garment may be formed having a similar construction as shown herein.

This inventive interface is applicable to a wide range of techniques and applications, including, but not limited to entertainment, sporting, military, gaming, computer control, home automation, space and deep sea probes, as well as the remote-control drone or robot operation. The inventive interface can also provide an immersive way to communicate between two people remotely located from each other, or to experience an activity being performed or observed by another, in real time and from previously detected and recorded data.

The use of the HHMI technology as the membrane between man and machine has application for swarming UAVs. For example, a number of squadrons of drones can go out on patrol of a wide area with hotspot potentials. Each squadron can be commanded by a respective remote from-the-battlefield soldier who controls a master drone with the rest of the drones in his squadron flying autonomously along side the master in formation. When a hotspot is identified, this squadron of drones is in place for other soldier-pilots to jump in and take command of an individual drone so that each drone in the squadron is immediately in place and now has the human "wetware" interfacing the remote drone for focused control and an orchestrated response to the hotspot."

In accordance with an exemplary embodiment, the HHMI is configured as a therapeutic wearable electronic device that interfaces the user with a small, mobile microprocessor, portable communication device, smart phone, tablet or the like. The HHMI includes electrodes in contact with the skin surface of the user, connected via conductive leads and individually addressable. In accordance with exemplary embodiments, the same electrodes may be used to detect and apply electrical signals from/to the muscles and nerves, and/or electrodes may be specific for the detection and application function. The application of haptic sensory cues can be selective and include a variety of stimulation in accordance with a desired interface, learning or entertainment enhancement. For example, the fingers (and/or the muscles controlling the fingers and/or the nerves communication with those muscles) can receive haptic stimulation in the form of a pressure, vibration, electrical impulse or other stimulation.

As will be logically foreseeable to one ordinarily skilled in the art from the teachings herein, an event or action can be replicated in a virtual or augmented reality, and can be many different activities and actions, including controlling at least one of a sports related object, a musical instrument, a weapon, a video gaming controller, a remotely controllable system including a space probe, a drone aircraft, an underwater probe, a robot. Also, at least one of a first and a second plurality of sensory cues can be remotely determined from measurements or sensed data corresponding to an event that is performed, the preformed event being remote in at least one of time and location relative to the user experiencing the event as part of a virtual or augmented reality. At least one of the first and the second plurality of sensory cues stimulates a brain processing center for at least one of the five senses of hearing, seeing, smelling, feeling and taste. The HHMI opens new avenues in human-automation interaction and control, including impacting the areas of accelerated learning, physical training and rehabilitation. The ability to identify muscle groups at a sufficient level of definition, and the ability to apply electrical signals at a similar level results in a system in which previously-known actions and muscle movements could be developed for improved physical training and correction of physical motion. Muscle memory and pattern recognition associated with nearly all kinds of human activities can be more quickly developed to learn, for example, a musical instrument or sport technique. For military applications, rapid muscle memory and pattern recognition build up could enhance the training of soldiers in basic and advanced weapons. Additionally, new forms of safety restraints could be provided in which the human user is prevented through the HHMI-applied electrical signals from taking an action that may result in injury or undesired action. Medical use examples include noninvasive, non-chemical means to counteract involuntary tremors caused by movement disorders, such as Parkinson's disease; stroke injury and other brain damage rehabilitation through rewiring of the damaged brain by the synchronized application of computer-controlled haptic, audio and visual cues. Also, the HHMI may be used in the treatment of autism by providing a sensation replicating light pressure thereby providing therapeutic benefits using a custom-calibrated, mobile and convenient system.

FIG. 3(*a*) shows the inventive HHMI configured as an undergarment and having clusters of smaller, more densely packed electrodes at the solar plexus and clusters of larger, less densely packed electrodes located elsewhere. FIG. 3(*b*) shows an image of the back of a human torso showing the muscles underlying the skin and locations on an HHMI garment with electrode locations that match the muscles. FIG. 3(*c*) shows an image of the front of a human torso showing the muscles underlying the skin and locations on an HHMI garment with electrode locations that match the muscles.

The solar plexus is a complex of ganglia and radiating nerves of the sympathetic nervous system at the pit of the stomach, and core functions of the body can be detected by monitoring these structures and/or the muscles in this region such as the diaphragm. The sympathetic nervous system's primary process is to stimulate the body's fight-or-flight response.

In accordance with a military use, the HHMI undergarment can be worn by a soldier for adding a new layer of perception during, for example, a combat situation. Typically, the visual and auditory senses of a soldier are saturated during the high intensity of a combat situation. The HHMI undergarment can add a new way to convey information to the soldier using tactile information that can be a supplement to the audio and visual information being received. The tactile information may be, for example, an indication of the location of a rallying point or where the soldier's comrades are located. The location of an enemy, such as by detecting a muzzle blast, can be sensed, for example, using audio sensors that are tuned to detect the muzzle blast, and the direction of the enemy can be conveyed using the HHMI undergarment, through a haptic sensation or even by causing an involuntary turning or urging of the soldier. Sensors and transmitters or other data links can be used as well to convey details about the soldier's physical condition including heart rate, blood pressure, body temperature and other vital signs and health related conditions.

The HHMI is made from a multilayered, flexible and light weight structure. The layers of the HHMI include compression layers that bias inward and can be formed in a shape that wraps around an object, such as an arm, when configured as a sleeve, or the user back, shoulders, stomach and torso when configured as a shirt. The HHMI may thus be configured as a wearable electronic with the individually addressable electrodes urged into effective face-to-face electrical contact with the skin of the user. The HHMI may be configured as a light weight, wireless, high resolution electrical signal sensing/applying wearable electronic for the detection of the user control intentions (for example, to control a robot's flight) and for the application of enhanced haptic cues (for example, to experience the robot's flight conditions). The interface is in the form of a comfortable, easily worn garment that the operator wears with limited weight and bulk, and controllable restriction of movement.

The HHMI may be constructed as a conformable, comfortable, but fairly tight fitting garment to hold the electrodes in direct face-to-face electrical contact with the skin. The HHMI is used to apply electrical stimulation through the skin to provide haptic cues.

The HHMI can be configured as a full body undergarment that can be a component of a virtual reality interface that deepens the immersion for the operator by tying in real-time head and body movements to a three dimensional, perceived visual sphere. High quality, binaural, audio provided through sound canceling headphones replicate the actual, real-time sounds that are ambient, for example, to a remote robot, a computer-generate game or learning scenario, or the experience of another human or animal.

There are applications where full body haptic stimulation combined with simultaneously applied sensory cues can be effective for learning, entertainment or rehabilitation. For example, exemplary embodiments can be used as a rehabilitation device, to induce movement in the individual fingers on a hand or invoke involuntary movement of leg muscles. The full body haptic interface can be segmented depending on the need, and the resolution of the applied electrical signals can be as refined or course as necessary. That is, for example, the muscles that control movement of each finger can be separately targeted.

The haptic, visual and audio experiences of one user may be transferred to another user. The user also wears a skullcap constructed as an EEG hairnet and along with a full body haptic suit the other user's experience is mapped through detected electrical signals received from that user's brain. In accordance with an exemplary utilization, the audio, visual and haptic data of another individual can be collected and used to replicate for the user an experience perceived by the other.

In accordance with an exemplary non-limiting embodiment of the inventive human/machine interface, the haptic sensory cues can be utilized along with the visual and/or audio sensory cues to create a new kind of entertainment, whereby, a song or visual piece, such as a painting or movie, can be utilized to create the pattern of sensory cues perceivable by the human through two or more senses, such as sight, hearing, touch, taste and smell. In accordance with other embodiments of the inventive human/machine interface, the haptic sensations can be applied to one or more parts of the body, such as the legs, thighs, arms, ribs, torso, neck, head, etc.

Figure 4A:
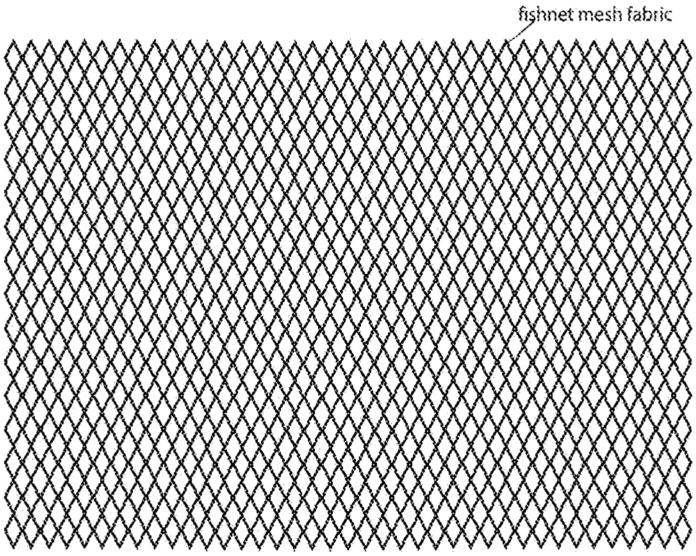
FIG. 4(*a*) illustrates a fishnet elastic fabric material.
Figure 4B:
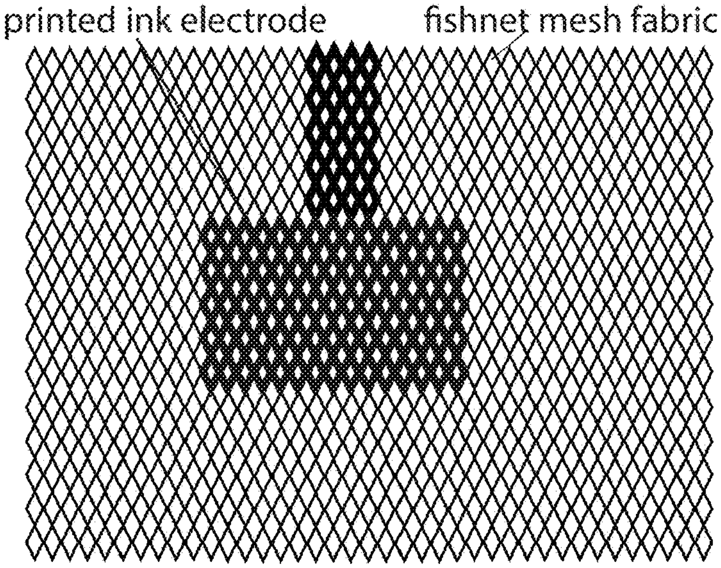
Figure 4C:
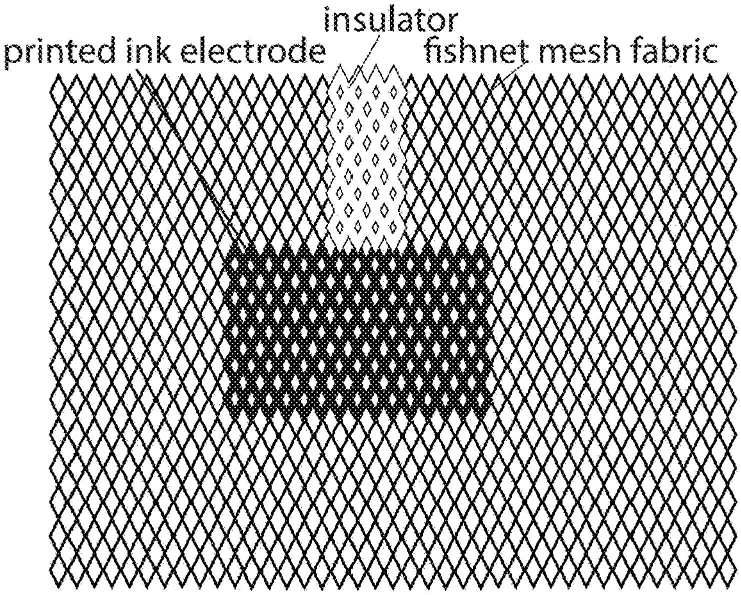

FIG. 4(*a*) illustrates a fishnet elastic fabric material. FIG. 4(*b*) illustrates the fishnet elastic fabric material having a printed elastic ink electrode and trace line formed on the fishnet elastic fabric material. FIG. 4(*c*) illustrates a printed elastic ink insulator formed over the trace line. In accordance with an embodiment of the HHMI configured to provide airflow over the skin of the user, the fishnet elastic fabric material is used as a substrate upon which elastic, conductive electrodes are formed directly through a printing operation and/or through the lamination process as described, for example, herein. The relatively larger electrode area may be formed through a single or multiple print of a conductive ink, such as the DuPont elastic, conductive ink described herein. Alternatively, the electrode area can be formed by first printing the conductive ink onto a print media, such as the Bemis material described herein, then perforated (or left unperforated) and laminated to the fishnet elastic fabric material. A conductive trace that electrically connects the electrode area with an electronic circuit (not shown) may be insulated by printing, laminating or otherwise forming an insulator onto the conductive trace (or formed on the side of the material that is not in contact with the user's skin).

Figure 5A:
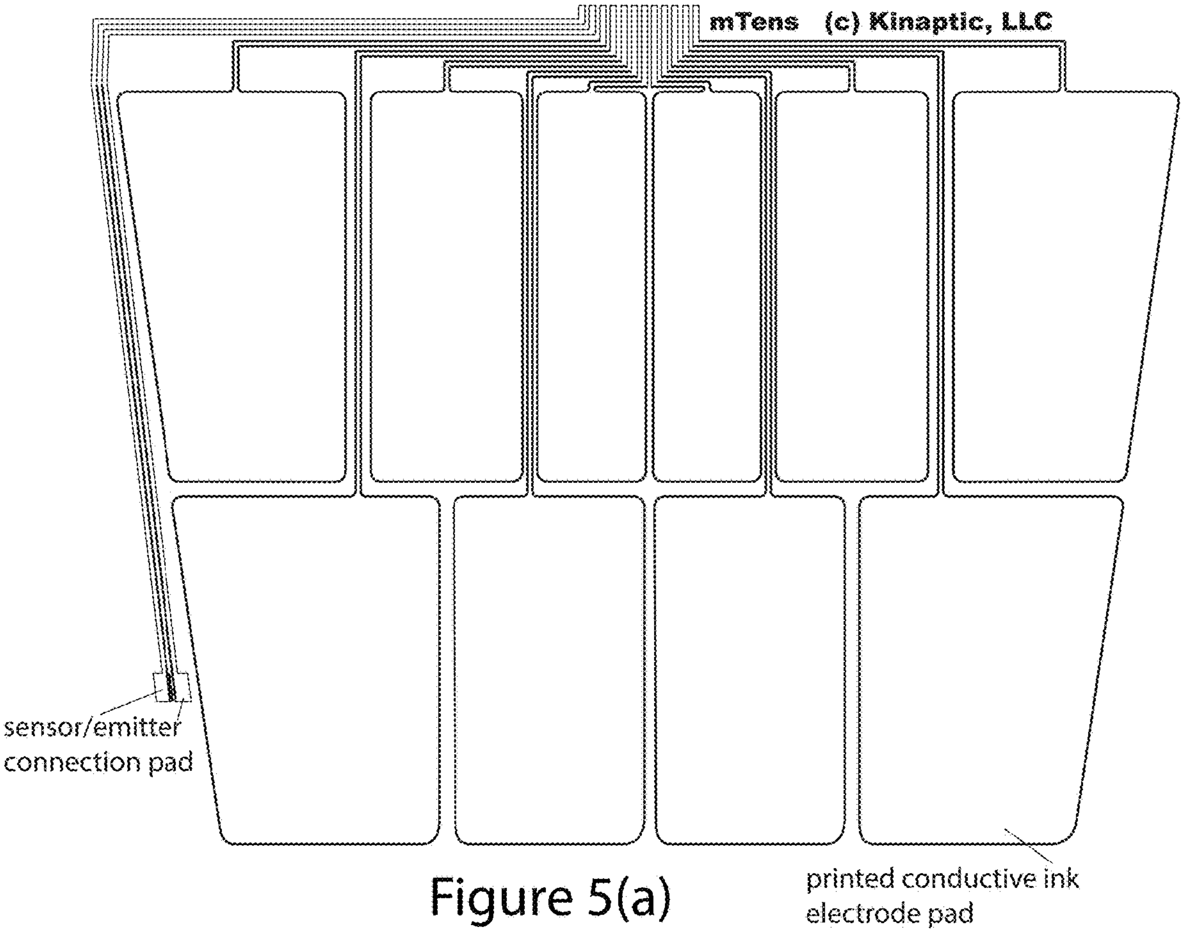
FIG. 5(*a*) shows the artwork for an example screen printed electrode pattern having conductive ink forming individually addressable electrodes, each electrode having a trace terminating at a connection header.
Figure 5B:
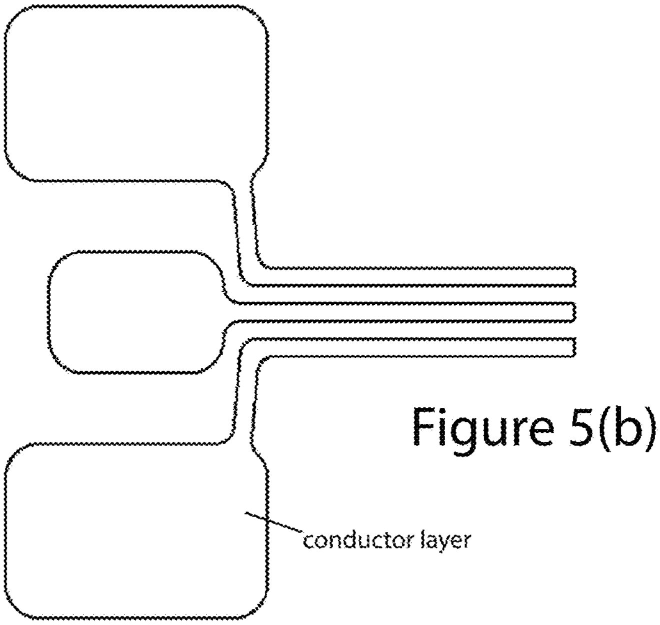

FIG. 5(*a*) shows the artwork for an example screen printed electrode pattern having conductive ink forming individually addressable electrodes, each electrode having a trace terminating at a connection header. The artwork includes connecting pads for electrically connecting to, for example, an embedded sensor, detector or transducer (such as a vibrator). FIG. 5(*b*) shows the artwork for an example inkjet-printed three electrode pattern with a central electrode for acting as a reference electrode relative to two outer detecting electrodes.

In an example use to mitigation involuntary movement, such as tremor, electrical signals are determined by a microprocessor to have electrical characteristics effective to mitigate the involuntary tremor. The electrical signals are applied to the user. The electrical signals may be applied to the user via a plurality of electrodes where each electrode is disposable, for example, using the haptic sleeve, garment or body suit shown herein. Each electrode is in electrical communication with one or more biological components of the user, such as the skin of the user and through the skin the nerves and muscles. As an alternative, or in addition to skin surface contact, one or more of the electrodes may be disposed subcutaneously, for example, to apply or detect electrical signal at muscles or nerves that are deep beneath the skin layer. These subcutaneous electrodes may be permanently or semi-permanently left in place, or they may be, for example, acupuncture-type needles that are applied and then removed when not in use. FIG. 6(*a*) schematically illustrates an electrode equivalent electronic circuit for applying and detected electrical signals. In an example use of the inventive HHMI, the exemplary embodiments include electrical circuits, such as those shown here or equivalents, that are used to detect, for example, the onset of an involuntary tremor of a user, control intentions of a remote unmanned vehicle operator, the best practice of an expert for an accelerated learning application, and other applications of the HHMI described herein as well as other applications that are or will become available from being enabled by the HHMI.

At least one electrode may be individually addressable to be selectively in an on-state or an off-state. In the electrical equivalent electronic circuit switches are symbolically shown. In an actual circuit, the on/off state can be controlled through electronic switch mechanisms that include, but are not limited to transistors, reed switches, relays, optoisolators, and the like. A combination of known electrical circuit components and microprocessor controlled devices can be used, some or all of which can be embedded within a barrier layer as described herein. In the onstate the electrical signals flow through the at least one electrode to at least one biological component of the user and in the off-state the electrical signals do not flow through the at least one electrode to the at least one biological component of the user.

FIG. 6(*b*) is a photograph of a prototype showing individually addressable electrodes, each electrode having a trace terminating at a connection header laminated onto an elastic fabric adjustable sleeve.

A flexible grid of screen printed or otherwise formed flexible conductive electrodes have the geometry and size that are optimized to enable multiplexed, high resolution signals to be detected and applied. For example, the electrical activity of the body of the user (particularly, the nerves and muscle) can be detected and used to determine the user's control intentions. These control intentions can be machine-implemented actions such as moving a cursor on a display screen, selecting a button for a hyperlink in an HTML document, controlling home automation equipment, gaming, remote control of unmanned vehicles, control of deep space and deep sea probes, etc.

Embodiments of the HHMI are configured to enable the wearable electronic circuit and electrodes to allow for high resolution of the detected and applied signal, while minimizing cost, battery consumption, bulk, weight, volume that much be made water tight, etc.

The individually addressable electrodes of the conductive ink pattern can be as small as necessary. Each electrode is connected through a conductive trace. As described herein, and as shown, nearly 100% packing density of the electrode surface area can be achieved. That is, the entire surface area of the skin under the HHMI garment may be covered by individually addressable electrodes, and the electrodes can be grouped and driven (or detected from) to create an electrode grouping that matching the underlying muscle/nerve structure. The geometry and number of electrodes may be optimized, for example, to match the underlying muscles and nerves.

Figure 7A:
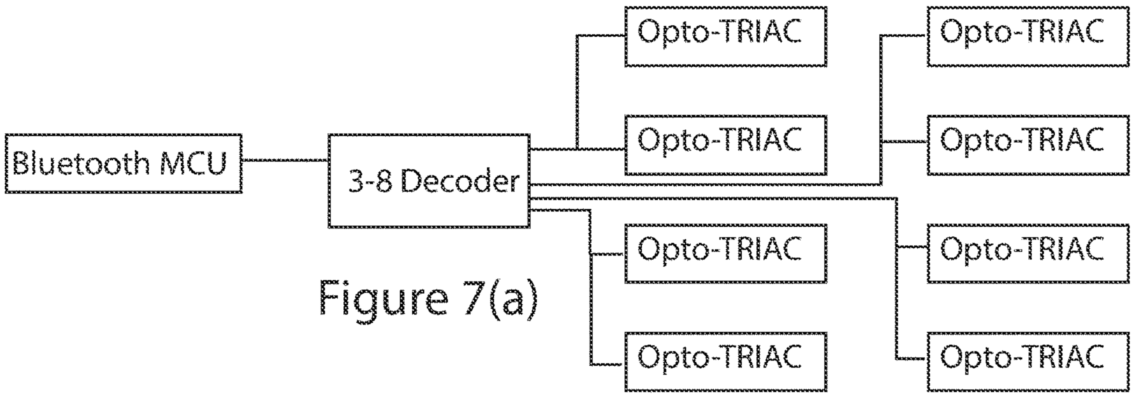
FIG. 7(*a*) is a schematic showing a circuit for selectively applying an electrical signal through electrodes disposed in face-to-face contact with the skin of a user.
Figure 7B:
Figure 7C:
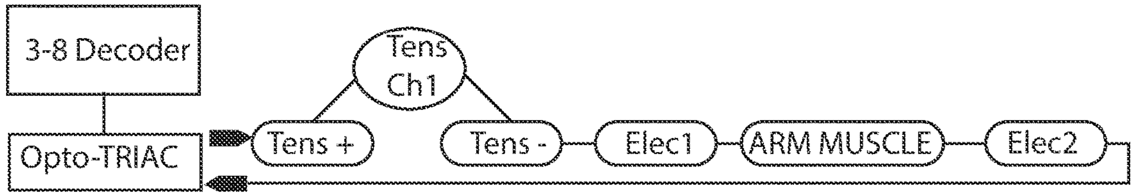

FIG. 7(*a*) is a schematic showing a prototype circuit for selectively applying an electrical signal through electrodes disposed in face-to-face contact with the skin of a user. FIG. 7(*b*) is a schematic showing a repeatable circuit section for individually addressing a respective electrode and a corresponding electrode of a plurality of electrodes to selectively apply, detect or switch off signals to the addressable electrodes. FIG. 7(*c*) is a schematic showing another repeatable circuit section for individually addressing a respective electrode and a corresponding electrode of a plurality of electrodes to selectively apply, detect or switch off signals to the addressable electrodes.

Figure 8A:
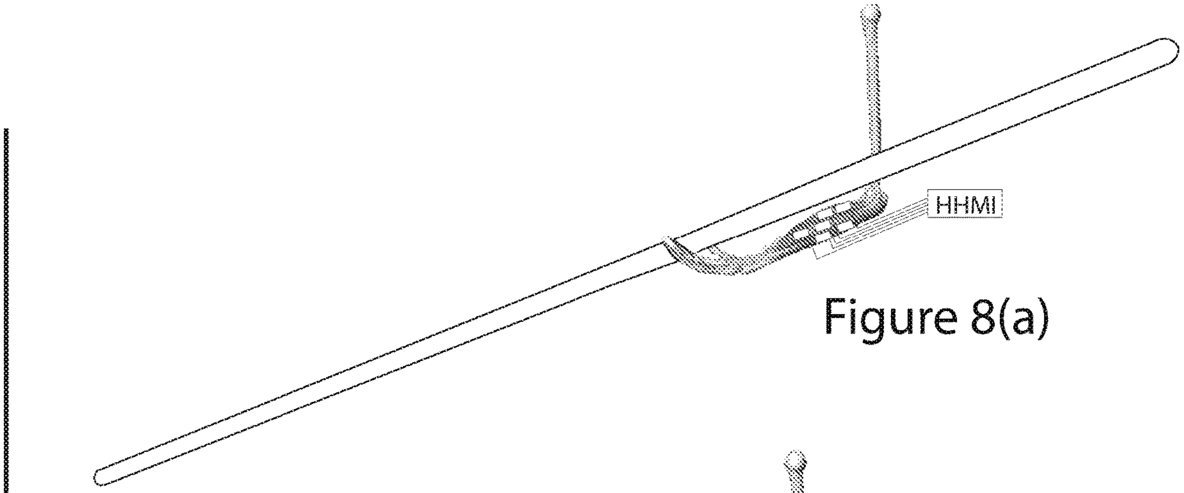
FIG. 8(*a*) illustrates a use of the HHMI in a virtual reality game where the impact of a virtual lance during gameplay is about to trigger an involuntary movement and haptic sensation.
Figure 8B:
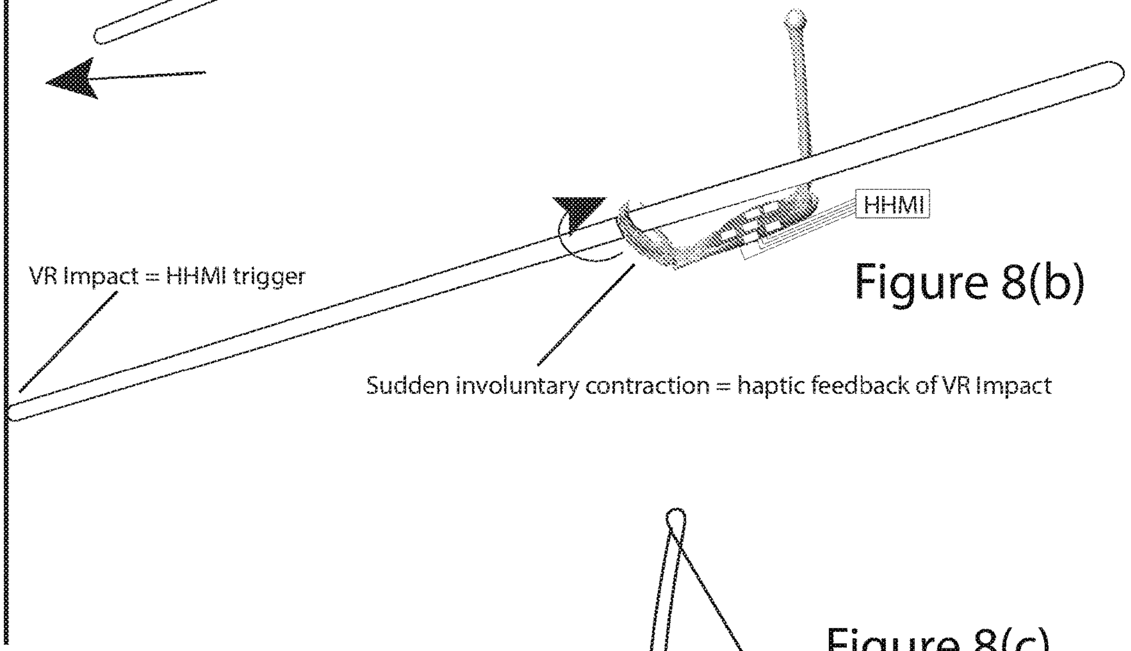
Figure 8C:
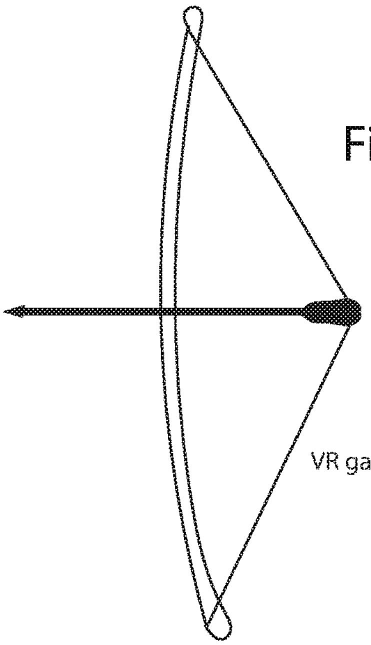

FIG. 8(*a*) illustrates a use of the HHMI in a virtual reality game where the impact of a virtual lance during gameplay is used as a trigger for generating an involuntary movement and haptic sensation. FIG. 8(*b*) illustrates a use of the HHMI in a virtual reality game where the impact of a virtual lance during gameplay is used as a trigger for generating an involuntary movement and haptic sensation. In this example VR gaming embodiment, a virtual lance is held in the user's hand as if cradled by the user's forearm. A head-on impact is a detected game event that triggers the HHMI to create a jarring movement and sensation by causing involuntary muscle contractions in the muscles of the user's forearm. FIG. 8(*c*) illustrates a use of the HHMI in a virtual reality game where the action of a virtual bow and arrow during gameplay is used as a trigger for generating involuntary movement and haptic sensations replicating the action and sensations from a real-world bow and arrow. In this example VR gaming embodiment, "real-world" bow string tension is translated to HHMI generated muscle contractions so player feels the arrow being drawn back in the draw arm, in the bow arm, the HHMI generates the sense of opposing the bow string tension. When the arrow is let loose, both arms experience the vibration and sudden release of tension caused by the loosening of the arrow.

Figure 9:
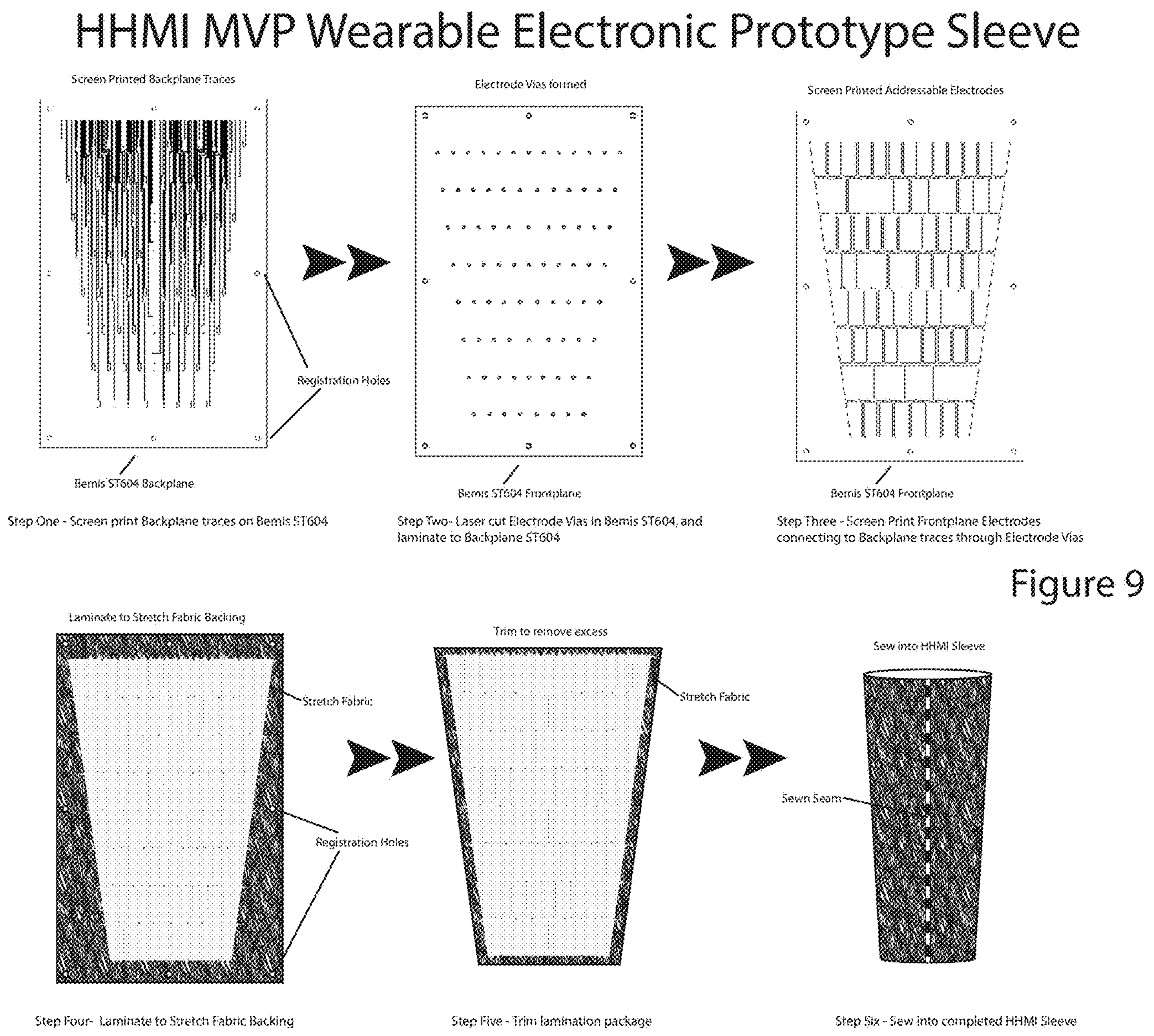
FIG. 9 shows a construction of an HHMI configuration using an adhesive layer having a preprinted electrode pattern, where the adhesive layer is laminated to a stretch fabric substrate and sewn to form an HHMI sleeve.

FIG. 9 shows a construction of an HHMI configuration using an adhesive layer having a preprinted electrode pattern, where the adhesive layer is laminated to a stretch fabric substrate and sewn to form an HHMI sleeve.

Example Configuration (Step One): A 12"×18.5" sheet of Bemis ST604 is laser cut with registration holes and placed on a screen printing jig to form the Backplane. DuPont 973 Elastic Conductive Ink is screen printed to form the Backplane Traces on the Backplane.

(Step Two): A second 12"×18.5" sheet of Bemis ST604 is laser cut with registration holes and electrode vias, then placed on the screen printing jig to form the Frontplane.

(Step Three): The Backplane and FrontPlane are assembled on lamination jig and laminated together forming a lamination package and sandwiching the Backplane Traces between layers of Bemis ST604. The lamination package is placed on the screen printing jig. DuPont 973 Elastic Conductive Ink is screen printed to form the Addressable Electrodes on the Frontplane.

(Step Four): A 12"×18.5" piece of Lycra stretch material is laser cut with registration holes. The Lycra stretch material and the lamination package are assembled on the lamination jig and laminated together to form the HHMI sleeve preform.

(Step Five): The HHMI sleeve preform is laser cut to trim excess materials.

(Step Six): The trimmed HHMI sleeve preform is sewn to form the completed HHMI sleeve.

The HHMI may be provided as a wearable housing supporting the apparatus to provide a user-wearable electronic device. The wearable housing may comprise a multilayered flexible electronic circuit including an electrode layer comprised of a plurality of electrodes having a conductive face disposed for making electrical contact with a biological system of the user and at least one additional layer including at least one of an electrical circuit layer, an electrical insulating layer, an electrical conducting layer, and a flexible covering. A rigid or semi-rigid outer housing may be provided, which may also incorporate other useful devices such as a display, TENS signal generator, RF communication transmit/receiver, battery, memory, central processing unit (CPU) and a wired or wireless computer interface. All or some of these devices can be embedded within the HHMI garment as described herein.

The HHMI is constructed of layers of thin flexible materials, such as conductive stretchable fabrics, flexible insulators, flexible circuit boards, and the like. The materials may be woven, spun, closed cell, open cell, thin film, or other suitable structure. Layers, bonded layers, and constituent elements of the HHMI may be printed using a 3D printer, or formed by a batch or roll-to roll manufacturing process including lamination, screen printing, ink jet printing, self-assembly, vapor deposited, sprayed or dip coated. The HHMI can be fabricated as a sleeve, glove, legging, shirt, full body suit, etc., and has a flexible and comfortable snug fit that urges the electrodes into face-to-face surface contact with the skin of the user. The electrode construction described herein provides thin, flexible structures designed specifically for compression face-to-face contact.

Whatever the case, the transference of the electrical signal between the electrically conductive surface of the electrode and the skin of the user is effectively accommodated.

An exemplary embodiment of the HHMI is constructed as a thin, flexible sleeve unobtrusively worn by the user, and the connection between the sleeve and microprocessor can be direct or via wireless networking, such as optical, or RF (e.g., Bluetooth, WiFi, etc.). The HHMI may be embodied in a lightweight, comfortable, haptic sleeve having electrode size and density enabling automatic calibration to the unique physiology of a user.

Figure 10:
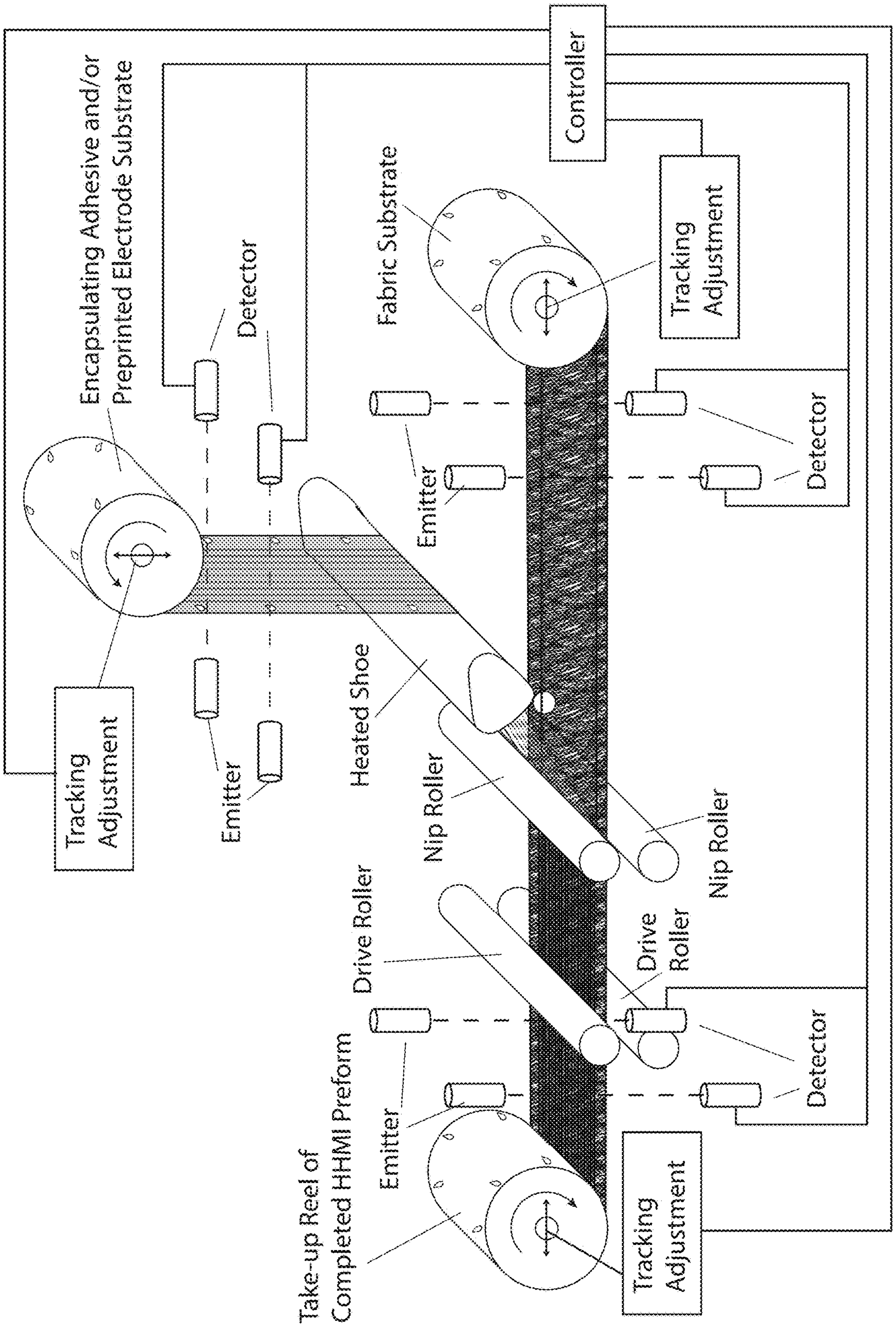
FIG. 10 schematically illustrates a roll-to-roll lamination process for mass producing an HHMI preform including an adhesive print media layer having a preprinted electrode pattern laminated to a stretch fabric substrate.

FIG. 10 schematically shows a roll-to-roll manufacturing process for manufacturing, for example, at least one of the exemplary embodiments shown herein. The HHMI can be configured as a sleeve, legging, jumpsuit, coverall, jacket, trouser, cap, glove or other wearable electronic. The HHMI may be comprised of a multilayered structure with the electrodes in contact with the skin of the user, insulation and wiring layers, and the sleeve covering. The layers, such as the outer covering may be, for example, a thin, multi-axial stretchable fabric. The fabric can be electrically insulating, and contain conductive threads, patches, coatings or inks to conduct the detected and applied electrical signals. In some of the drawings the electrodes are illustrated as being on the outside of the sleeve to show the concept of electrode size and location. In an exemplary embodiment, the sleeve is made from an opaque Lycra material with flexible conductive fabric electrodes disposed on the interior of the sleeve and in direct face-to-face electrical contact with the skin on the arm of the user. The fabric of the outer cover or other layer provides sufficient compression to urge the electrodes into face-to-face electrical contact with the skin of the arm. In addition, or alternatively, straps, bands, bladders, Velcro or other such mechanisms can be used for urging the electrodes into face-to-face electrical communication with the user's skin. Flexible and conductive fabrics and/or threads, such as mixes of one or more of copper/stainless steel/nylon/polyester fabric and/or threads can be used to make electrode patches and/or traces that are highly conductive, thin and flexible. Signal cross talk, interference from or to the electronics of the HHMI may be mitigated with shielding layers separating, as necessary, the conductive pathways and electrically active components.

An exemplary embodiment pertains to a method of making a wearable electronic. The inventive roll-to-roll fabrication process starts with a supply roll of bottom substrate material, such as an elastic fabric. A supply roll of a hotmelt adhesive sheet, which may include one or more layers of pre-printed print media and embedded electronic and mechanical devices, is brought into contact with the bottom substrate. An embedded device die (or other mechanical, RF, semiconductor or electronic circuit elements) can be pre-embedded into the hotmelt adhesive sheet off-line in a separate operation, or in-line as described elsewhere herein. A warm tacking pressure roller system can be used to soften the hotmelt adhesive and secure it to the bottom substrate. The hotmelt adhesive sheet can include a release sheet that protects the embedded semiconductor elements and keeps the adhesive from sticking to itself in the roll. A top substrate having a conductive layer can be provided, and/or additional layers of conductor, insulators, devices, etc., can be provided to create a multilayered circuit board-type of structure. The hotmelt adhesive sheet with the printed electrodes, traces and embedded device(s) is inserted between the elastic fabric and any additional top layer(s) (if any) to form a lamination package. The lamination package is run through hot fusing pressure rollers to melt the hotmelt adhesive sheet and electrically insulate and connect (as determined by the conductive print and the embedded devices) and bind the lamination package materials together. The rollers may be heated, or separate heating zones can be provided for heat activating the adhesive.

In accordance with an inventive method of making a wearable electronic, a bottom substrate comprising a flexible, elastic material is provided. An adhesive print media layer is provided having a preprinted conductive pattern. The adhesive print media layer is disposed on top of the bottom substrate. The adhesive print media layer is activated to bind the preprinted conductive pattern to the flexible, elastic material.

The flexible, elastic material may comprise a stretch fabric. The preprinted conductive pattern comprising electrodes may be configured for making face to face contact with the skin of user for at least one of detecting electrical signals from the skin of the user and applying electrical signals to the skin of the user.

An electronic device may be embedded in an encapsulating adhesive layer and in electrical communication with the preprinted conductive pattern. The electronic device may be embedded in the encapsulating adhesive layer and brought into electrical communication with the preprinted conductive pattern when the encapsulating adhesive layer is thermally activated.

A predetermined pattern of semiconductor devices may be fixed to the encapsulating adhesive layer. As an example, the semiconductor devices may each have a top device conductor and a bottom conductor. A top substrate may be provided having a conductive pattern disposed thereon to form a lamination package comprising the bottom substrate, the preprinted conductive pattern on the adhesive print media layer, the encapsulating adhesive layer and the top substrate. The top substrate may be provided as a complete matching sheet or roll that matches the adhesive and preprinted adhesive print media. Alternatively, the top substrate can be a conductive patch, such as a piece of ITO coated plastic sheet, where the ITO acts as a transparent conductor. The lamination package is laminated so that the encapsulating adhesive layer insulates and binds the top substrate to the bottom substrate so that one of the top device conductor and bottom device conductor of the semiconductor devices is in electrical communication with the conductive pattern of the top substrate and so that the other of said top device conductor and bottom device conductor of each said semiconductor element is in electrical communication with the electrically conductive layer of the preprinted conductive pattern.

At least one of the bottom substrate, the adhesive print media layer, the encapsulating adhesive layer are provided as respective rolls of material. The step of disposing may comprise fusing at least two of the bottom substrate the adhesive print media layer, the encapsulating adhesive layer are provided as respective rolls of material together in a continuous roll lamination process.

The semiconductor device may be at least one of electrostatically and magnetically attracted onto the adhesive layer. The semiconductor device may be placed onto the adhesive layer using a pick and place machine. The semiconductor device may be placed onto the adhesive layer by transferring said semiconductor device from a relatively lower tack adhesive to a relatively higher tack adhesive.

Figure 11A:
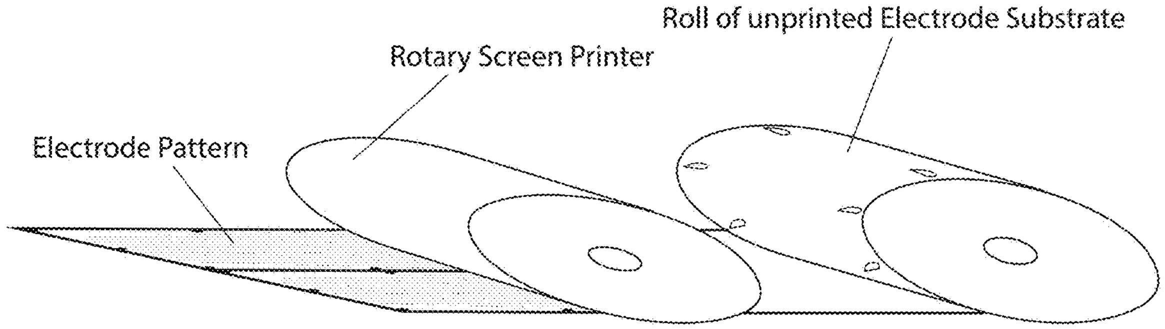
FIG. 11(*a*) shows a roll of an adhesive print media layer having an elastic conductive ink electrode pattern printed thereon through a rotary screen printing process.
Figure 11B:
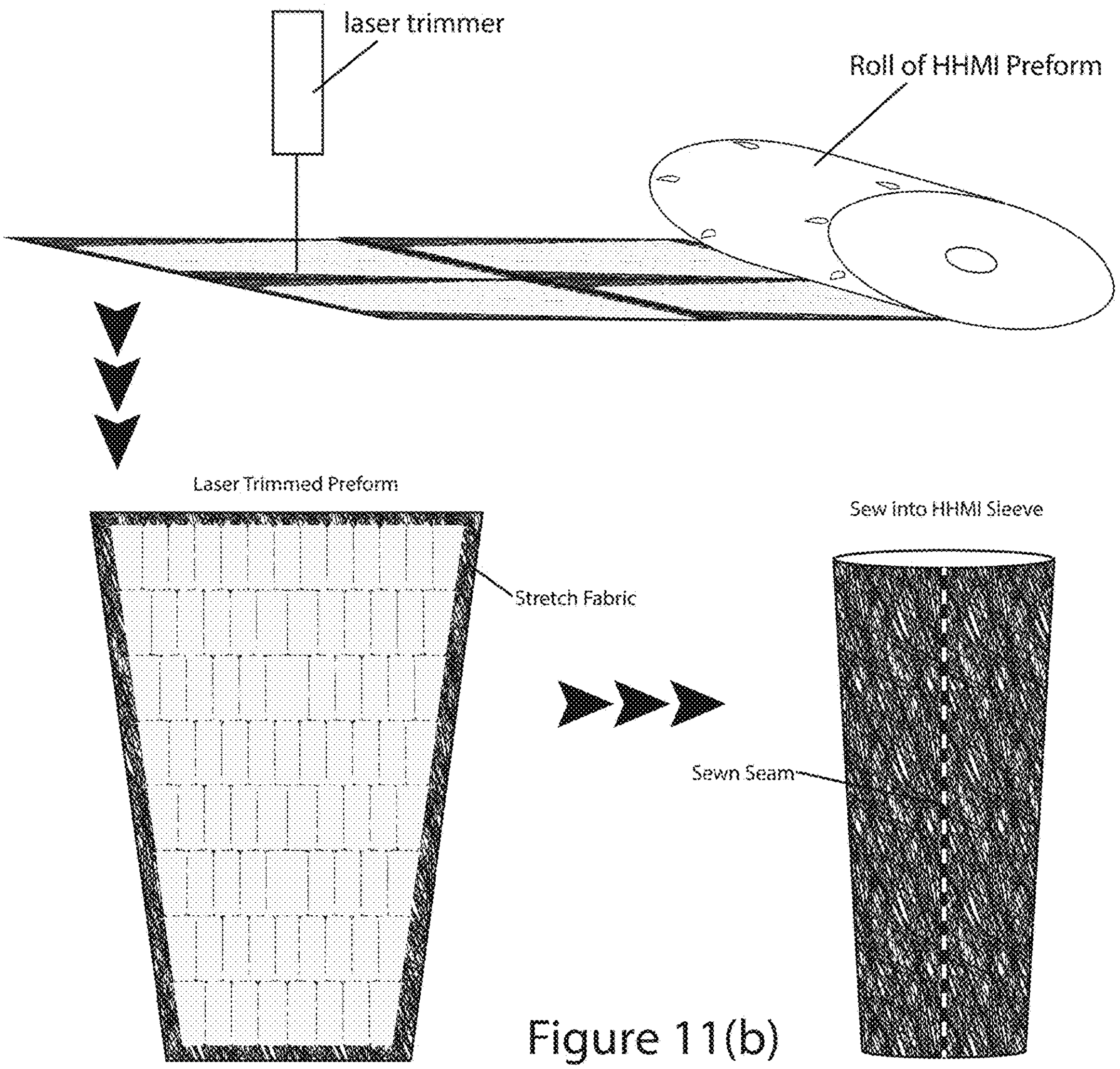

FIG. 11(*a*) shows a roll of adhesive layer having an elastic conductive ink electrode pattern printed thereon through a rotary screen printing process. FIG. 11(*b*) shows a roll of HHMI preform formed in the roll-to-roll manufacturing process laser trimmed and sewn into an HHMI sleeve.

In an optional manufacturing technique, bare die and packaged semiconductor devices can be connected during the lamination process. Applicant has discovered that as the hotmelt sheet is softened, for example, during a roll lamination process, the embedded device die breakthrough the adhesive so that an electrode of the device comes into electrical contact with the conductive layers in the lamination package (for example, the conductive pattern printed on the print media, or other layer in another lamination material that is oriented and positioned to make contact with the conductor when the device breaks through the hot melt adhesive layer that it is embedded within). Thus, for example, in the case of a simple semiconductor device, a pn junction diode, the p and n sides of each embedded diode device die are automatically connected to a top conductive layer and a bottom conductive surface that is strategically disposed in the lamination package for making such contact. Each embedded device can be completely encapsulated within the hotmelt adhesive and the substrates for a waterproof and robust construction. In addition, the embedded device die is each permanently secured between the substrates fully encased within the flexible, hotmelt adhesive sheet layer and substrates.

The protective barrier of the adhesive provides a water proof, dust proof thermally advantageous protection of, for example, a package SMT device and also secures the electrical connection of the two bottom conductors (or multiple conductors). However, for example, in the case of an LED or optical sensor, the optical properties of the protective barrier are not likely to be a better light transmission match than the lens material or optical stack that makes up the packaged lamp from the emissive LED surface to the top of the lens open to the outside. Accordingly, FIG. 12(*a*) shows a release sheet that is removed exposing a light emitting lens or a detecting top face while leaving the rest of a packaged SMT LED embedded in a thermally active adhesive and in face-to-face electrical contact with a conductor(s) of one or more of the materials in the lamination package. FIG. 12(*b*) illustrates the embedding the packaged SMT LED in a thermally active adhesive and forcing it under the pressure of the lamination rollers into direct faceto-face electrical contact with a printed electronic pattern. In accordance with this aspect of the invention, the emitting face of packaged lamps or the detecting face of, for example, an optical detector, is left exposed while leaving the vulnerable SMT LED (or bare die) nearly fully embedded in a barrier and/or thermally advantageous binding film (the adhesive, adhesive/phase change material layers, adhesive with phase change domains, adhesive with phase change wells, etc., as shown and described herein and also as might otherwise logically be used to achieve the intended purpose of tending to maximize light output, lower cost, ease manufacturing, reduce manufacturing capital equipment, reduce failure modes and provide device protection)

FIG. 12(*c*) shows an embedded packaged semiconductor device having the top face (which can be an emitter or detector, transducer, or other active portion) exposed once the release sheet is removed, with the rest of the device embedded in a thermally active adhesive and in direct face-to-face electrical contact with the printed flex circuit conductors. When the release sheet is peeled away, for example, in the case of an LED, the light emitting lens is exposed while leaving the rest of a packaged SMT LED embedded in a barrier layer of thermally active adhesive.

As shown and described herein, sensor, emitter, bare die and packaged semiconductor electronics can be embedded within the construction of the HHMI garment. The hot-melt materials provide barrier, shock absorbing and retention properties making the emitted device protected and robust. The embedded device can act as a sensor, indicator, emitter, detector, for uses including, but not limited to pulse, oxygen, moisture, blood chemistry (including glucose, salt, alcohol, pathogen, toxic actors, and other health conditions obtainable from the body).

Figure 13:
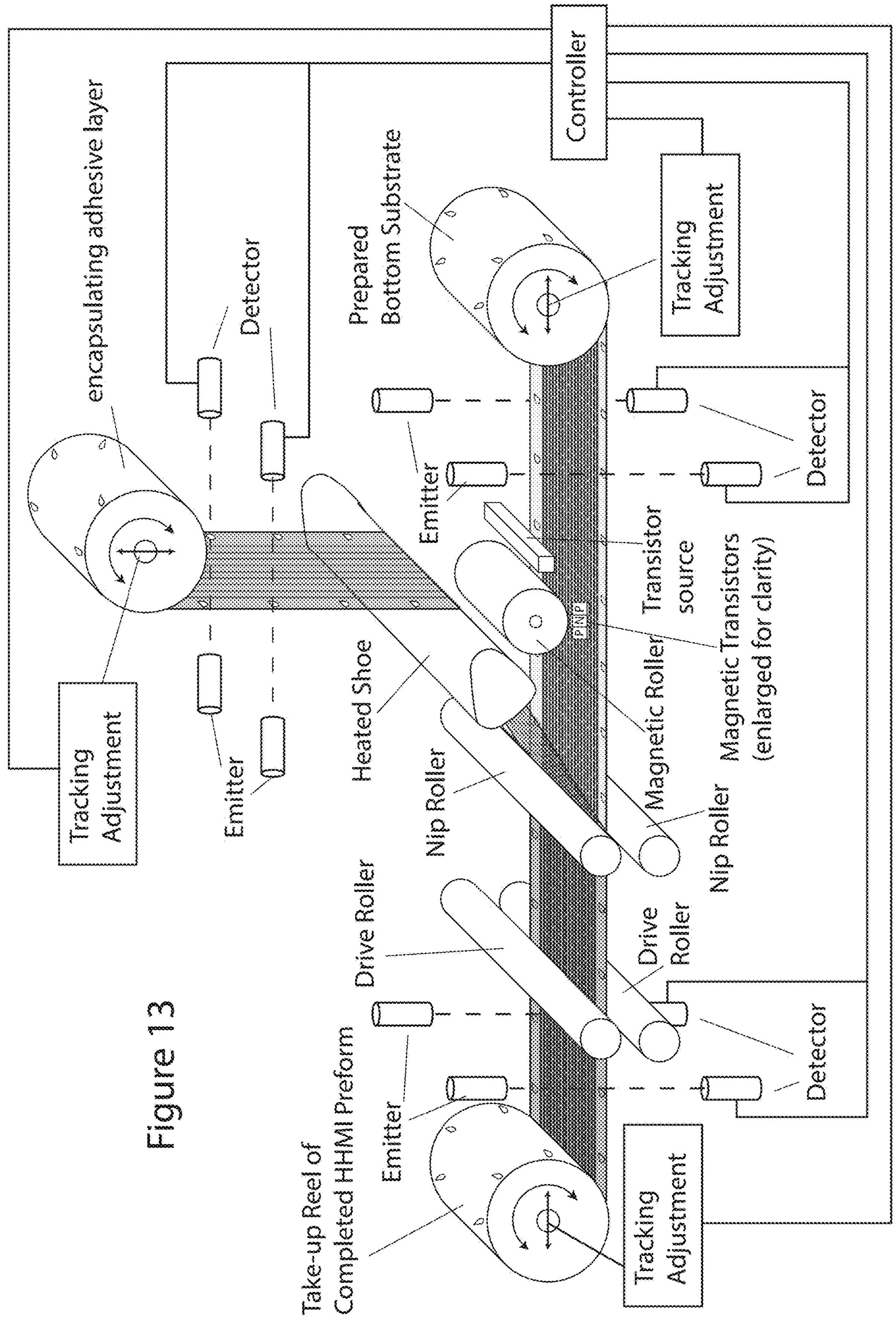
FIG. 13 schematically shows a roll-to-roll manufacturing process for manufacturing, for example, at least one of the exemplary embodiments shown herein, where a magnetically attractive semiconductor device is magnetically attracted and placed onto the encapsulating adhesive layer or the adhesive print media during the roll-to-roll manufacturing process.

FIG. 13 schematically shows a roll-to-roll manufacturing process for manufacturing, for example, at least one of the exemplary embodiments shown herein. In accordance with the exemplary roll-to-roll manufacturing process, an electronic device, such as a bare die or packaged semiconductor detector, emitter, sensor, electronic circuit element, or other small device (collectively, "embedded device") that can be beneficially embedded in the HHMI wearable electronic construction is made available. For example, the embedded device may be attracted to a magnetic (or electrostatic) rotating drum and transferred to an adhesive or transfer sheet. An embedded device source provides a hopper located adjacent to a rotating drum, similar to a toner cartridge of a conventional laser printer or copier and the many different conventional mechanisms for selectively directing toner onto a flexible substrate (e.g., paper sheet), can be utilized in accordance with the exemplary roll-to-roll manufacturing process to create a rapid, low cost, wearable electronic assembly process without the need to individually pick and place, for example, a bare die or packaged semiconductor, or many other fabrication steps that would be typically associated with creating a printed circuit embedded within a wearable electronic.

The inventive wearable electronic can have a very simple device architecture including a bottom substrate (typically, a stretch fabric such as Lycra or Spandex), a hotmelt adhesive (which may include an embedded device) can include a conductive electrode and circuit pattern screen printed ink, such as DuPont PE971, pre-printed onto a roll of print media such as BemisST604. The Bemis ST604 includes a hotmelt adhesive layer which can be provide as, or in addition to, the hotmelt encapsulating adhesive and vice versa. A top substrate may also be provided that can include, for example, insulated and non-insulated sections that allow for the direct face-to-face electrical communication between the skin of a wearer of the wearable electronic and an element of the wearable electronic such as the individually addressable electrodes, sensor and the like. The pre-printed print media and the hotmelt adhesive can be prepared ahead of time as a completed roll of materials that includes conductive electrodes, circuit patterns, and packaged and/or bare die electronics fixed to the circuit patterns. The bottom substrate, the hotmelt adhesive (with the embedded device) and the top substrate can thus be provided as rolls of material. The rolls are brought together in a continuous roll fabrication process, resulting in the high-speed production of a wearable electronic device. The inventive roll-to-roll fabrication process enables a high yield, lower cost manufacturing of a wearable electronic garment that can optionally include embedded semiconductor electronic circuits. Also, the exemplary embodiment results in devices with a unique, very thin form factor that is extremely flexible, waterproof and highly robust.

Figure 14A:
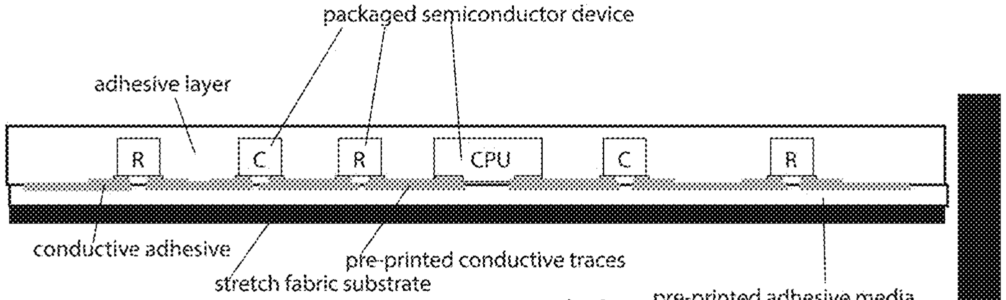
FIG. 14(*a*) is a cross sectional view showing an HHMI configuration formed on a stretch fabric substrate with an adhesive print media having a printed conductive trace pattern for forming an electronic circuit with packaged semiconductor electronic devices embedded in an encapsulating adhesive layer.
Figure 14B:
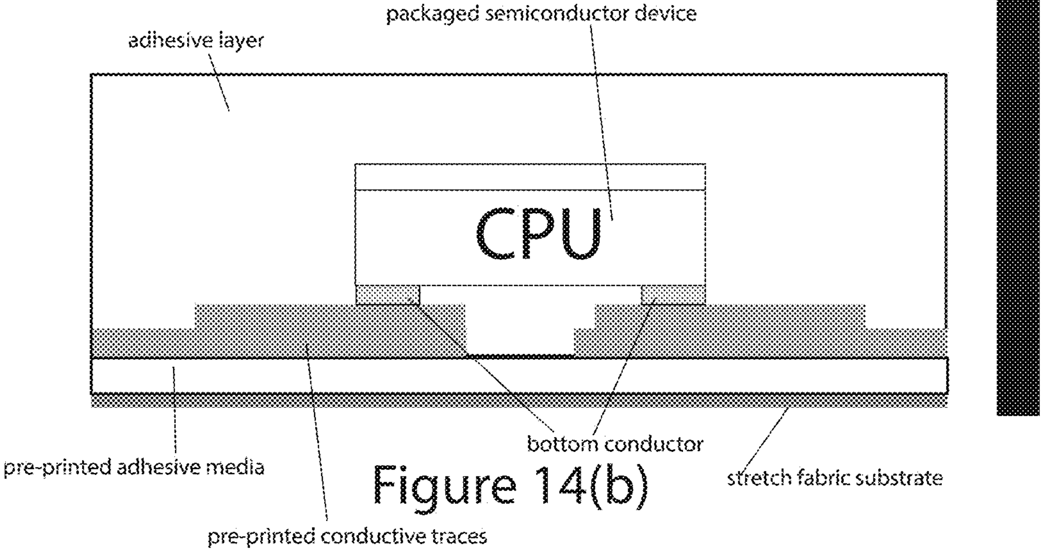

FIG. 14(*a*) is a cross sectional view showing an HHMI configuration formed on a stretch fabric substrate with an adhesive media having a printed conductive trace pattern for forming an electronic circuit with packaged semiconductor electronic devices embedded in an encapsulating adhesive layer. FIG. 14(*b*) is an isolated cross-sectional view showing an HHMI configuration formed on a stretch fabric substrate with an adhesive media having a printed conductive trace pattern for forming an electronic circuit with a CPU packaged semiconductor electronic device embedded in an encapsulating adhesive layer. Another exemplary utilization of the HHMI is rehabilitation of a stroke victim or other brain injury or deficiency victim enabling more rapid rerouting or rewiring of the various communication signals between areas of the brain. For example, if the portions of the brain related to auditory processing are damaged or otherwise defective, the visual and sensory cues, along with the audio cues, generated to stimulate the various processing centers of the brain of the stroke victim will help to reinforce newly learned auditory responses as the brain rewires those specific portions related to auditory processing. Another exemplary utilization can be to enhance the rehabilitation of spinal cord and/or nerve damage patients. In this case, the haptic stimulation in conjunction with the auditory and visual stimulation or sensory cues will enable a nerve and or spinal cord damaged patient to begin the association of the sense of touch with the audible and visual sensory cues, thereby strengthening the neural pathways that create either new muscle memory or help repair damaged pathways and memory associations.

Various portions of the brain related to the processing of sound, touch and vision can be controllably and simultaneously stimulated so that a weakened brain sensory, motor or cognitive processing center can be strengthen or rewired through the support of stronger brain sensory stimulation processing centers. For example, a stroke victim with damage to right side of the brain may have a loss of function in the motor control of the fingers of the left hand. In this case, the haptic sensory cues applied to the fingers of the left hand provide touch sensory stimulation to the dam-aged portions of the brain, while the corresponding visual and audio cues reinforce the re-learning or rewiring of the damaged portions of the brain through the touch sensory stimulation.

The plasticity of the human brain is only now being realized. This therapeutic use of the HHMI may strengthen the neurological pathways in addition to re-enforcing the patient's ability to combat resting tremor. This rewiring of the patient's brain may be effective in further combating cognitive problems including dementia and thinking difficulties; and emotional changes, such as depression, fear, anxiety and loss of motivation. In accordance with this aspect of the invention, the sensory cues can be utilized to provide rehabilitation to a victim of a brain injury or other brain damage or learning dysfunction. The HHMI can be configured to mitigate the physical and emotional difficulties of a patient suffering from a movement disorder, exemplified by, but not limited to, Parkinsonian tremor. Parkinsonian tremor is typically asymmetric, occurs at rest, and becomes less prominent with voluntary movement. The inventive HHMI offers a mechanism to conveniently apply a feedback-regulated, computer controlled, electrical signal only when needed to automatically counter the changing characteristics of a Parkinsonian tremor. As a non-limiting example, the received electrical activity may be the result of an involuntary tremor of a user having Parkinson's disease. The characteristics of the control signal are determined based on the involuntary tremor to cause involuntary muscle movement that counteracts the involuntary tremor. The control signal is generated as an electrical signal having the characteristic to cause the involuntary muscle movement that counteracts and the control signal is applied to the user to cause the muscle movements that counteract the involuntary tremor.

An embodiment of the HHMI can be configured so that EMG and limb movements are used as biomarkers for early diagnosis of PD and other movement disorders or health aspects that are discernible from information obtained from detection and analysis of EMG and limb movements.

Nearly 200 years after Parkinson's disease was first described doctors are still subjectively measuring Parkinson's disease largely the same way as Dr. James Parkinson did in 1817. This embodiment of the HHMI enables data science and wearable computing to capture and objectively measure patients' actual experience of disease and to enable much earlier detection of the onset of movement disorder diseases.

For example, the HHMI uses the naturally occurring electrical signals emitted by the human body as biomarkers indicative of PD. In this use example, the HHMI is configured as a wearable electronic diagnostic tool for directly and objectively measuring muscle contractions and mechanical limb movement. Analysis of the resultant data is used as very early indicators of possible PD or other movement disorders, as well as for disease monitoring and treatment efficacy testing. Data logging, cloud storage, and analysis enables anonymous, wide spread collection from PD patients and the population at large.

Using available EMG research-grade equipment, researchers have had very good success at measuring PD tremor directly from the skin surface. Physiological tremor is measured in healthy individuals as a low amplitude postural tremor with a modal frequency of 8-12 Hz. This healthy tremoring is very slight, and can be measured in a healthy individual at rest as a normally occurring, low amplitude oscillation determined by mechanical limb properties. The degree of regularity, measured by approximate entropy, in the limb acceleration signal (measured movement data) and the coherence between limb acceleration and muscle output (measured EMG data) has also been shown to be useful in characterizing both physiological and pathological tremors.

In accordance with an exemplary embodiment, the HHMI is configured with precision EMG, lost cost, highly sensitive acceleration and inertia sensors, low energy wireless data transmission, low cost, powerful, microprocessors, high speed electronics, and cloud computing for data logging and analysis. These components and features are, are integrated into a wearable electronic used as, for example, a diagnostic tool for very early indication of otherwise unnoticed motor unit firings that are characteristic with PD.

In this exemplary embodiment, the HHMI is configured as a wearable electronic having a grid of small, individually addressable electrodes, with a high-speed electronic multiplex circuit that is computer controlled to enable on-the-fly selection of the electrode pattern that best fits the detection of electrical signals from selectable muscles, nerves and motor units. By obtaining and analyzing data on the electrical signals that create involuntary tremor oscillations, objective individual-specific and population-based determinations are made of genetic and/or environmental factors associated with dopaminergic neuronal loss. This same data enables new metrics for evaluating therapeutic agents related to proteins like alpha-synuclein, and parkin, and enzymes like glucocerebrosidase and LRRK2.

In this diagnostic HHMI modality, the analysis of data collected from the HHMI can be used for early diagnosis of impending movement disorders. As a convenient wearable electronic, the HHMI can be part of routine wellness physical examinations, providing advanced knowledge for individual treatment options and a population-based source for Cloud-based, Big Data analysis.

In an "accelerated learning mode", the sensory stimulation is applied as haptic (touch), visual and audio cues applied to the senses of a student, where the sensory cues correspond to a performance being learned (e.g., piloting a drone). The sensory cues replicate and/or augment the tactile, visual and audio sensations experienced during the control of an actual drone flight. An enhanced flight simulator is obtained where the student pilot experiences the visual and audio information associated with the control of the drone, with the addition of haptic sensations that create the muscle-memory necessary for a learned action to quickly become an instinctive response. In the case of a "performance mode", such as an actual remote drone flight, the sensory cues provide real-time feedback of the ambient environment and stresses on the aircraft. The inventive human/human interface can be used for accelerated learning, entertainment and other human sensory and cognitive interactions. For example, in the case of a haptic information transducer, a vibration buzzer (such as a piezo or motor driven mechanical vibrator) and/or electrical signals can be applied to the individual fingers and arm muscles and nerves of the user, for example, a student during a lesson learning session. In the case of the display, it may be, for example, specially constructed eyeglasses that display visual information that has been collected or artificially created corresponding to the learned event or entertainment session. Specially constructed VR goggles or eyeglasses may display visual information as an overlay, picture in a picture, or other simultaneously displayed video information while the user also sees the real-world imagery. For example, when learning to play the piano, the student may be sitting at the piano and able to see a sheet of music and also see the piano keys with his hand and finger positions in real time, while also seeing visual sensory cues that is being generated and supplied to the specially constructed eyeglasses. Also, the inventive human/human interface can be used for accelerated learning that takes place remote in time and/or location from the instrument or teacher, so that the student feels, hears and sees sensory cues corresponding to the learning of the event at any time and place remote from the instrument. This accelerated learning system is designed to create associative memory in the user corresponding to muscle memory (haptic information), auditory memory (auditory information), and visual memory (visually display information).

The HHMI can be used to indirectly or directly transfer the nuances of a performer's musical skills and passion to students, and to multitudes of people, young and old, throughout the world and down through the generations. The HHMI may be used as a component in an Accelerated Learning System (ALS) that uses computer-controlled sensory stimulation that is synchronized and received by multiple senses of the student to more quickly build the muscle memory and pattern recognition necessary to learn an instrument. For example, audio cues (a piano melody) are combined with visual cues (image of a performer's fingers and hands correctly playing the piano melody) and haptic cues (vibration and/or electro-stimulation of the muscles/nerves of the student's fingers corresponding to the relevant muscles/nerves of the performer). This ALS stimulates the separate sensory processing centers of the brain to re-enforce and hardwire the brain/nerves/muscles needed to learn and master the instrument, and the learning session can be done at any time, at the instrument or away, even while en-gaged in another activity.

The inventive HHMI configured as a sleeve and applied as a retrofit modification or OEM device in signal communication with a gaming controller. The HHMI may communicate over a wireless or wired connection with a console or hand controller, such as an X-box, Playstation, Wii, Nintendo, or other gaming platform. The typical gaming controller includes a vibrating element (sometimes called a "rumble pack"). Much of the gaming software makes use of the rumble pack to provide haptic feedback, for example, to provide a somatic vibrating sensation when a grenade explodes, or a rocket ship takes off, or a car engine revs. In accordance with this aspect of the invention, the HHMI can make use of the control of the rumble pack during game play of an existing game or using code written specifically for the HHMI so that a haptic cue is applied to the user. A microprocessor may be used to generate a specific haptic cue corresponding to the software code making up the game.

The exemplary embodiments show an inventive Haptic Human/Machine Interface (HHMI). The HHMI is a wearable electronic garment having a grid of individually addressable dry electrodes that detects muscle and nerve activity, analyzes the detected signal, and generates a corresponding activation signal that is applied via the same electrode grid to create movement and touch sensations.

In accordance with an exemplary embodiment, a wearable electronics device architecture and fabrication method are provided for generating an HHMI wearable electronic that includes a high speed multiplexing electronic circuit connecting a large array of many individually addressable electrodes to small number of detection and application electronic units. The architecture of the HHMI is adapted to mass production as a roll-to-roll manufactured printed electronic garment with embedded sensors and transducers.

An exemplary embodiment of the HHMI utilize existing stretch fabrics (such as Lycra and Spandex), printing techniques (including screen printing, stamping and inject printing), and mature roll-to-roll lamination processing technology that has previously been used, for example, in the sign making industry. In accordance with an exemplary manufacturing process, these previously known manufacturing techniques are modified to create a new high yield batch and roll-to-roll manufacturing process for fabricating wearable electronics products.

The exemplary embodiments of the HHMI can be used for example, for accelerated learning, imparting muscle memory and pattern recognition through the simultaneous stimulation of the auditory, vision and haptic (touch and motion) processing centers of the brain. The exemplary embodiments of the HHMI can be configured as wearable electronic products that use screen printed elastic, conductive electrodes and a high speed, multiplexing circuit that significantly reduces costs, failure modes, bulk, battery consumption and weight of the wearable electronic.

An exemplary embodiment of a roll-to-roll manufacturing process is disclosed for mass producing wearable electronics with embedded sensors and transducers at high throughput and yield and at significantly lower costs as compared to other manufacturing techniques conventionally used to make wearable electronic devices.

The exemplary embodiments of the HHMI empower wearable electronics with the capability to detect, analyze and apply the electrical signals of the human body. Unlike any other wearable architecture, the large array of small addressable electrodes create easy user-customization, calibration and change in the use of the garment. Location and placement of the garment on the body does not have to be precise, can shift around, and automatically accommodates for different sizes and user physiologies.

Uses of the HHMI wearable electronics include the secure aggregation of biometric data, nonopioid pain relief, accelerated learning, sports augmentation and training, and military applications such as remote unmanned vehicle sensing and control.

Figure 15:
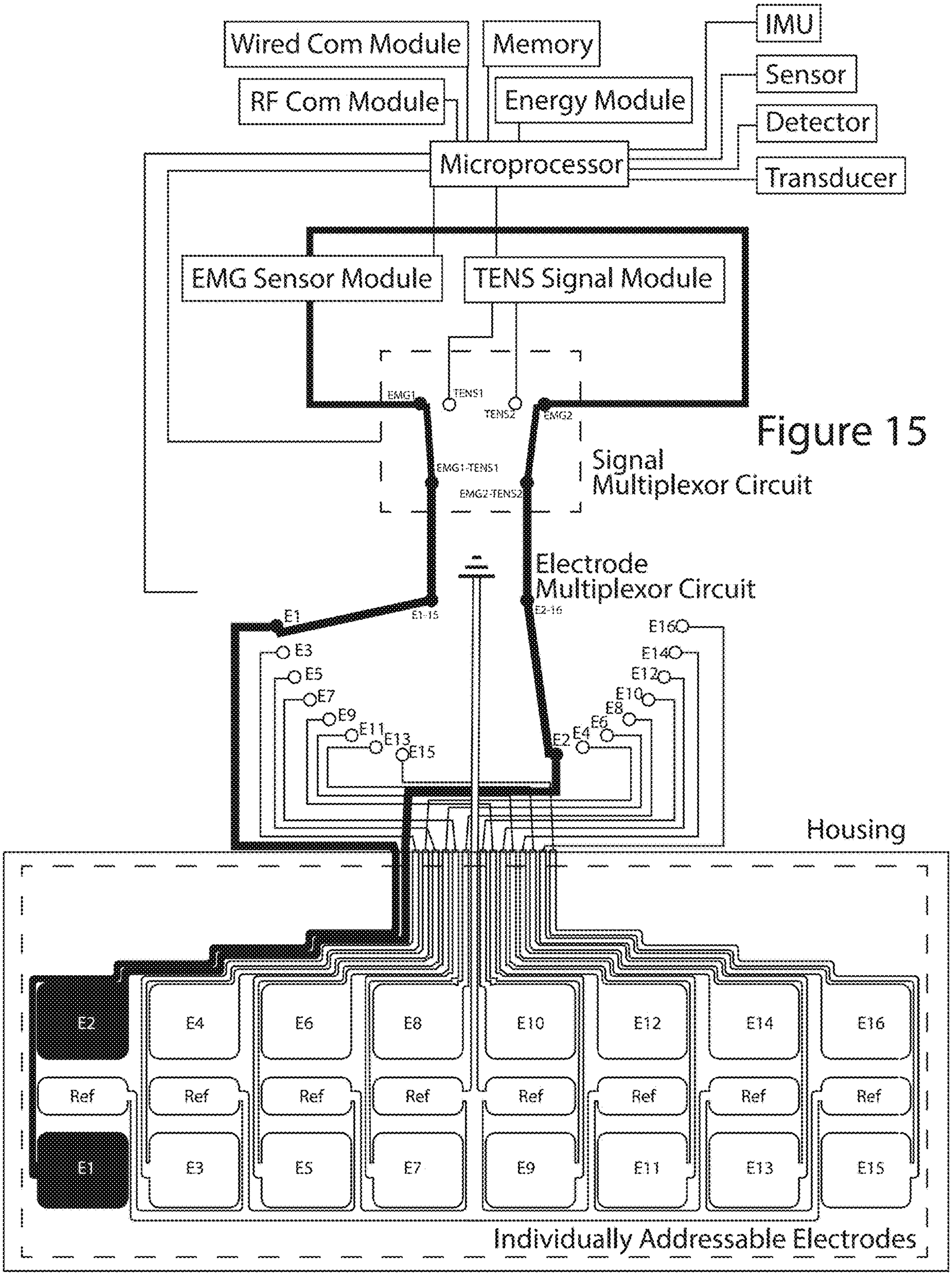
FIG. 15 illustrates an exemplary embodiment showing electrical signals to a plurality of individually addressable electrodes routed through an electrode multiplex circuit and a signal multiplex circuit.

As shown in FIG. 15, in accordance with an aspect of the invention a housing is provided. A plurality of individually addressable electrodes are supported by the housing. The individually addressable electrodes are for at least one of applying stimulation electrical signals to skin of a user and detecting biometric electrical signals from the skin of the user. At least one of a signal detector for detecting the biometric electrical signals and a signal generator are provided for generating the stimulation electrical signals. An electrode multiplex circuit addresses the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls least one of the signal detector, the signal generator, the electrode multiplex circuit.

Figure 16:
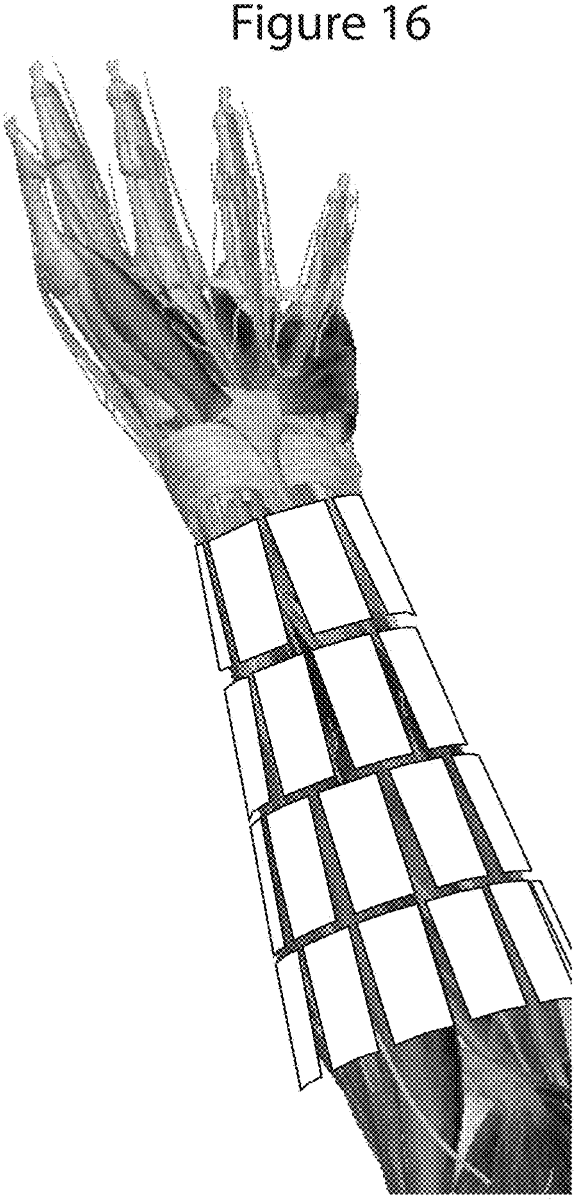
FIG. 16 illustrates a plurality of individually addressable electrodes disposed for receiving biometric electrical signals from motor units underlying the skin of a user.
Figure 17:
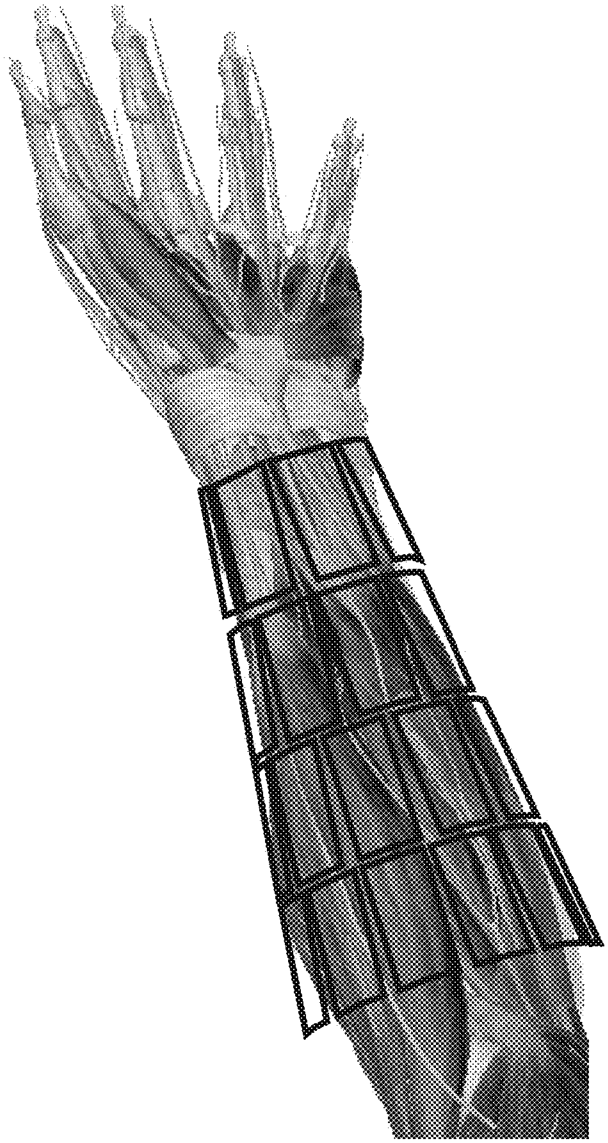
FIG. 17 illustrates the plurality of individually addressable electrodes showing the muscles and nerves underlying the skin of the user.
Figure 18:
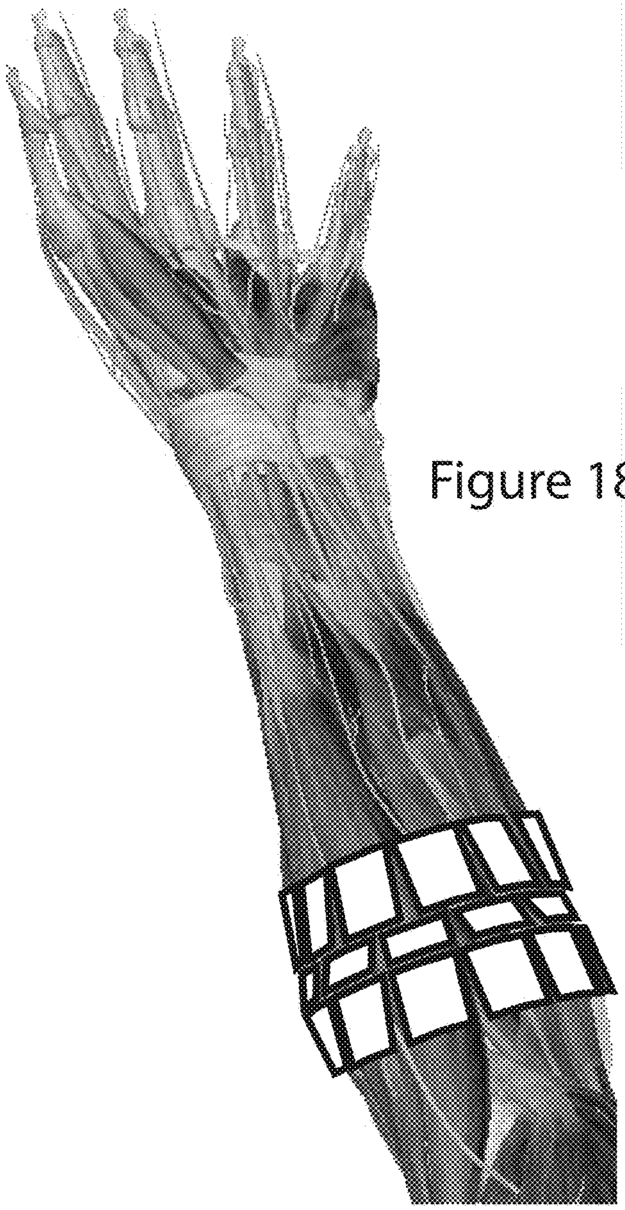
FIG. 18 shows a configuration of a plurality of individually addressable electrodes having biometric signal detection electrodes disposed in pairs that approximately line up with the long axis of muscles in the forearm of a user, along with reference electrodes disposed between the electrode pairs.
Figure 19:
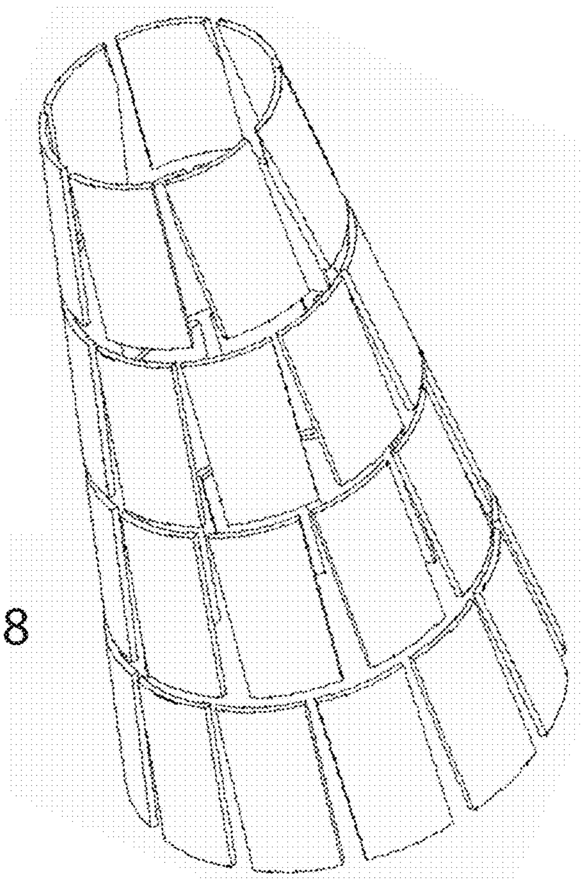
FIG. 19 shows a three-dimensional representation of a pattern of individually addressable electrodes for an HHMI forearm sleeve.

FIG. 16 illustrates a plurality of individually addressable electrodes disposed for receiving biometric electrical signals from motor units underlying the skin of a user. FIG. 17 illustrates the plurality of individually addressable electrodes showing the muscles and nerves underlying the skin of the user. FIG. 18 shows a configuration of a plurality of individually addressable electrodes having a biometric signal detection electrodes disposed in pairs that approximately line up with the long axis of muscles in the forearm of a user, along with reference electrodes disposed between the electrode pairs. FIG. 19 shows a three-dimensional representation of a pattern of individually addressable electrodes for an HHMI forearm sleeve.

The microprocessor can control the electrode multiplex circuit to route the biometric electrical signals from the skin of the user sequentially through more than one of the plurality of individually addressable electrodes to the signal detector. The microprocessor can control the electrode multiplex circuit to route the biometric electrical signals from the skin of the user simultaneously through more than one of the plurality of individually addressable electrodes to the signal detector. The microprocessor can control the electrode multiplex circuit to route the stimulation electrical signals from the signal generator simultaneously through more than one of the plurality of individually addressable electrodes to the skin of the user. The microprocessor can control the electrode multiplex circuit to route the stimulation electrical signals from the signal generator sequentially through more than one of the plurality of individually addressable electrodes to the skin of the user. The microprocessor can control the electrode multiplex circuit to route the stimulation electrical signals from the signal generator simultaneously through more than one of the plurality of individually addressable electrodes to the skin of the user.

Figure 20:
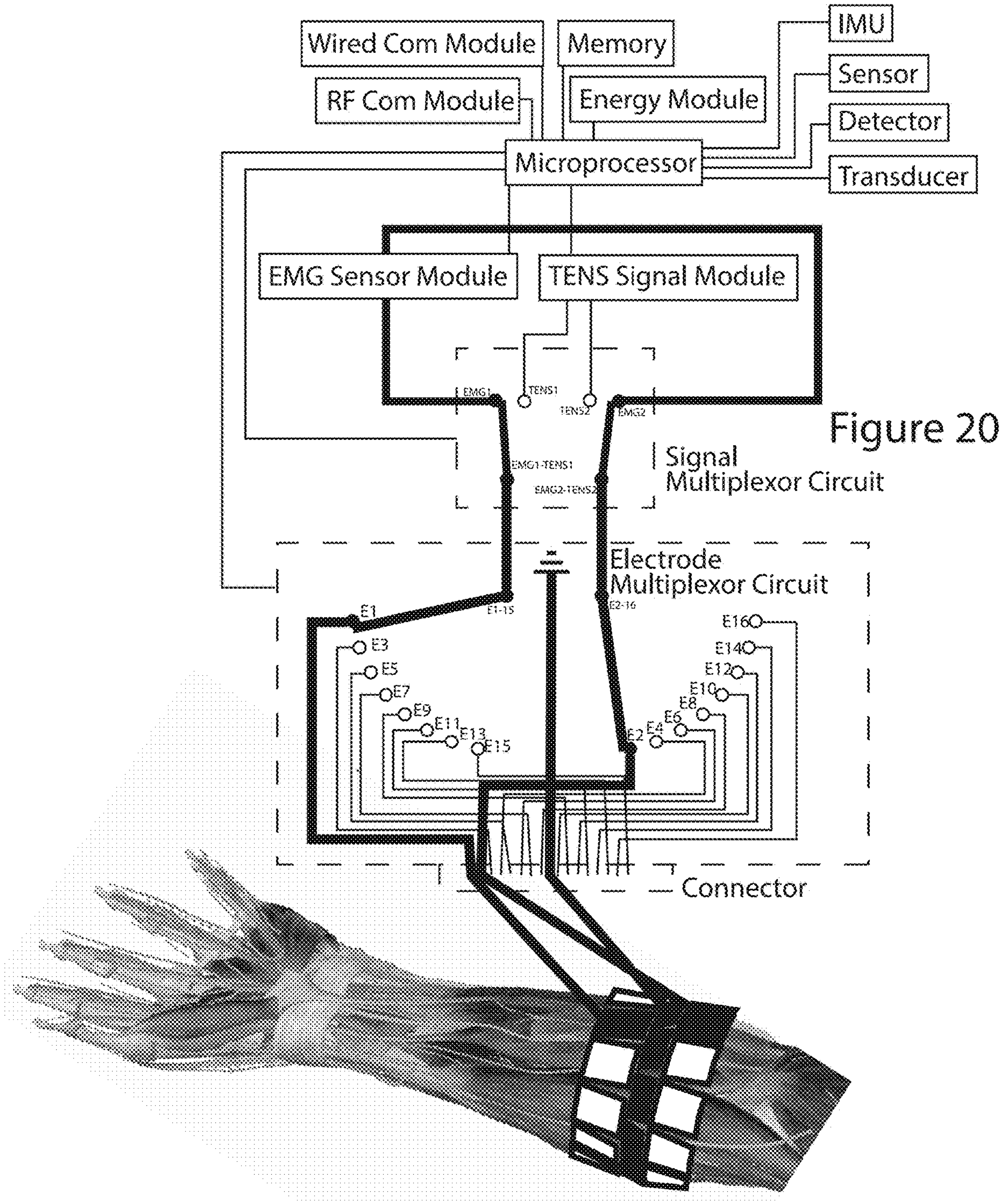
FIG. 20 illustrates an electrode pattern for an HHMI forearm sleeve for detecting and applying electrical singles using a single signal detector and a single signal generator, with a multiplexor circuit system for routing the electrical signals.
Figure 21:
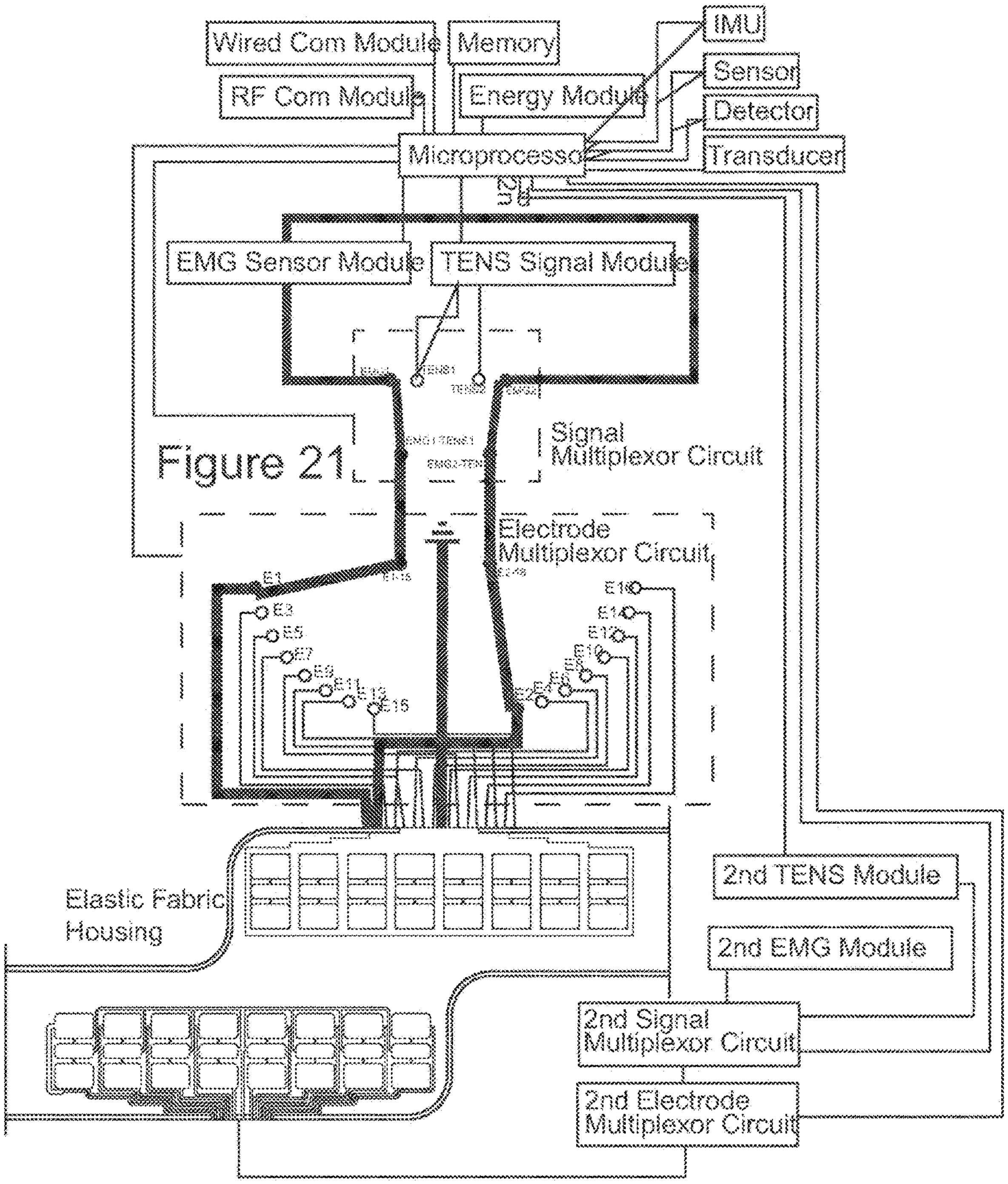
FIG. 21 shows a prototype HHMI sleeve having two sets of individually addressable electrodes, with each set having a multiplexor circuit system for routing electrical signals so that a small number of costly signal detection and signal generation electronics are usable with a large number of screen printed and laminated low cost individually addressable electrodes.

FIG. 20 illustrates an electrode pattern for an HHMI forearm sleeve for detecting and applying electrical singles using a single signal detector and a single signal generator, with a multiplexor circuit system for routing the electrical signals. FIG. 21 shows a prototype HHMI sleeve having two sets of individually addressable electrodes, with each set having a multiplexor circuit system for routing electrical signals so that a small number of costly signal detection and signal generation electronics are usable with a large number of screen printed and laminated low cost individually addressable electrodes.

A signal multiplex circuit may be provided controlled by the microprocessor for routing the electrical signals from the signal generator to skin of the user through the electrode multiplex circuit and to the signal detector from the skin of the user through the electrode multiplex circuit.

A memory may be provided controlled by the microprocessor for storing data dependent on the biometric electrical signals; and a communication module for transmitting the stored data for analysis by a remote network device.

The housing may be comprised of an elastic fabric material, and the individually addressable electrodes are dry electrodes may be formed by printing elastic conductive ink. A same individually addressable electrode of the plurality of individually addressable electrodes can both detects the biometric electrical signals from the skin and applies the stimulation electrical signals to the skin. The microprocessor can control the electrode multiplex circuit to address the plurality of electrodes for sampling the biometric electrical signals at a sampling rate effective for the detection by the signal detector of the biometric signals as electromyographic signals originating from subcutaneous motor units indicative of muscle contractions from two or more muscles of the user.

The microprocessor can control the electrode multiplex circuit to address the plurality of electrode for applying the stimulation electrical signals as application pulses at a pulse rate effective to cause involuntary contractions of the muscles of the user. The microprocessor can control the electrode multiplex circuit to address the plurality of individually addressable electrodes by at least one of sequentially and simultaneously routing both the biometric electrical signals from the skin of the user through more than one of the plurality of individually addressable electrodes to the signal detector and routing the stimulation electrical signals from the signal generator through more than one of the plurality of individually addressable electrode to the skin of the user. At least one of a inertial measurement unit, a sensor, a detector and a transducer may also be provided supported by the housing.

Figure 23:
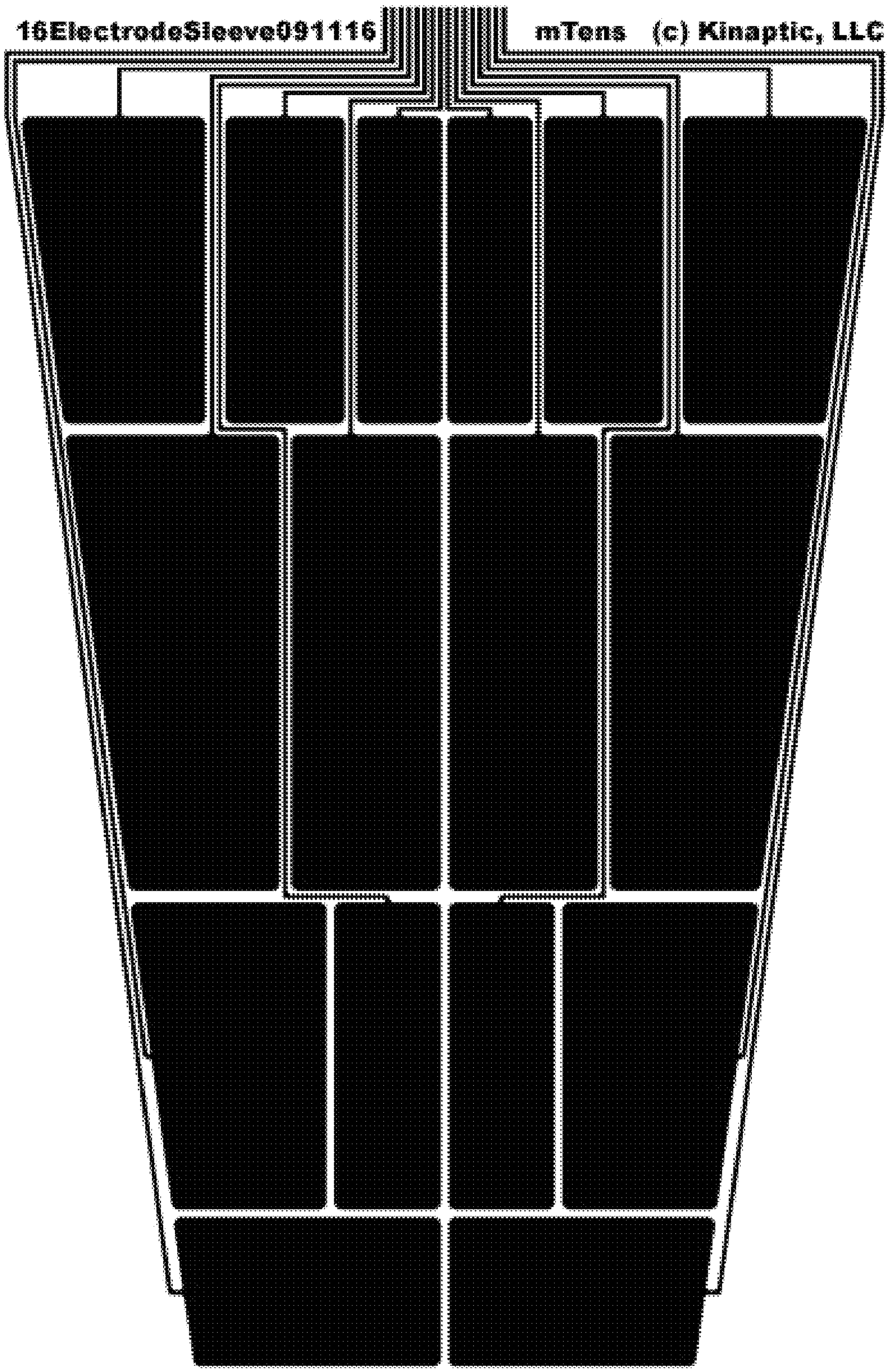
FIG. 23 illustrates a screen print artwork for printing an elastic conductive ink onto a print media for transfer and lamination onto a housing comprised of an elastic fabric material.
Figure 24A:
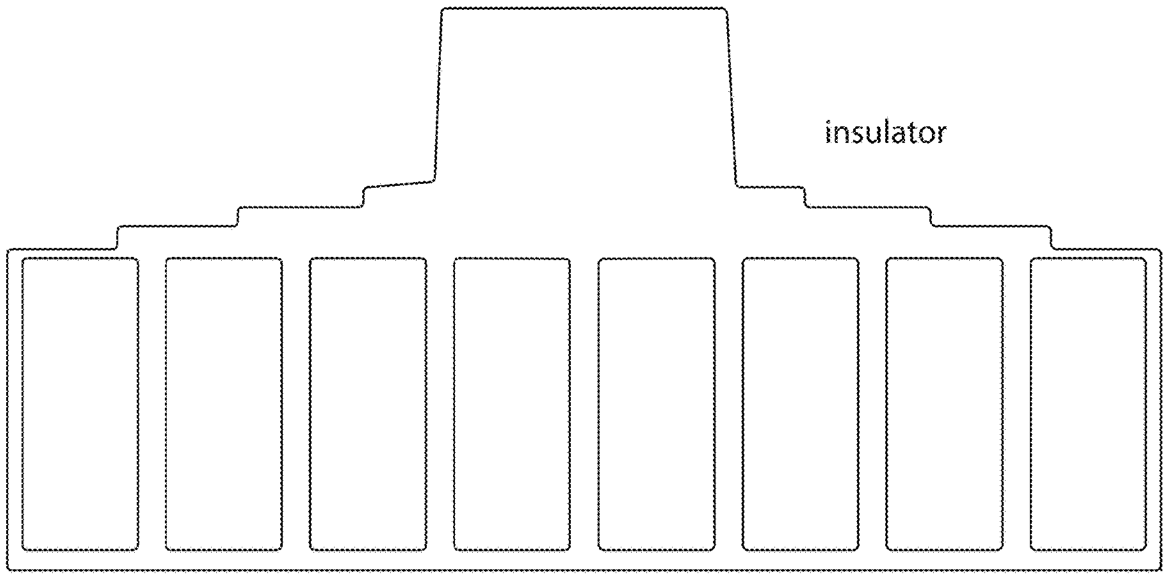
FIG. 24(*a*) illustrates a die, laser or knife cut insulator patch for allowing individually addressable electrodes to contact the skin of a user while insulating from electrical communication with the skin non-electrode conductive traces.
Figure 24B:
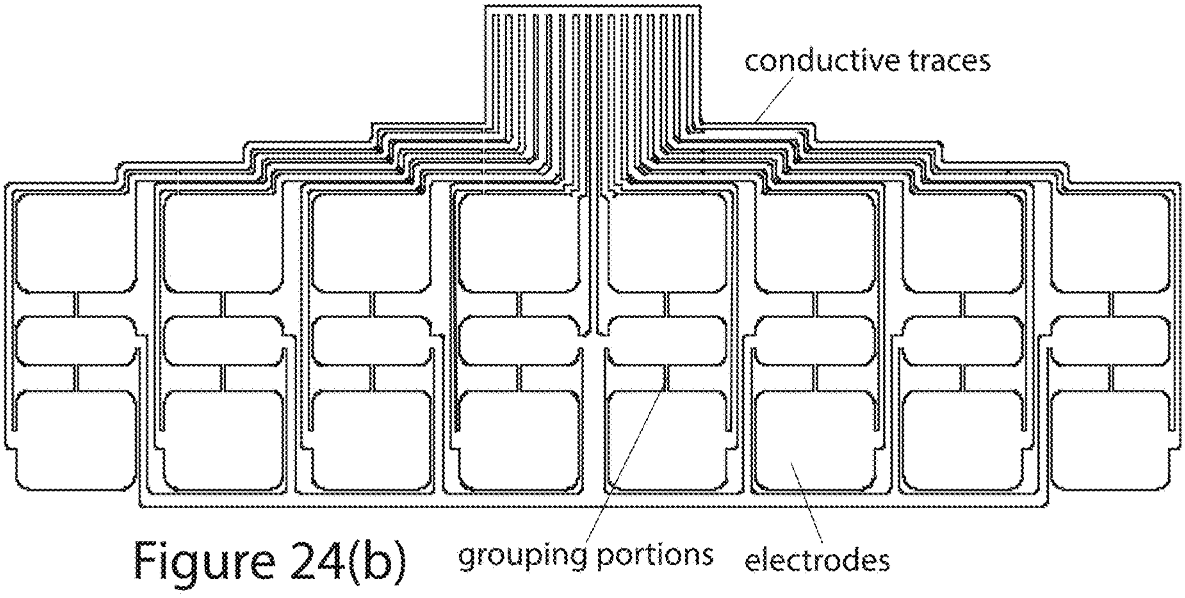

FIG. 23 illustrates a screen print artwork for printing an elastic conductive ink onto a print media for transfer and lamination onto a housing comprised of an elastic fabric material. FIG. 24(*a*) illustrates a die, laser or knife cut insulator patch for allowing individually addressable electrodes to contact the skin of a user while insulating from electrical communication with the skin non-electrode conductive traces. FIG. 24(*b*) illustrate a die, laser or knife cut electrode patch having individually addressable electrodes and non-electrode conductive traces, with grouping portions for retaining the grouping of the electrodes and traces to enable transfer and lamination.

Figure 22:
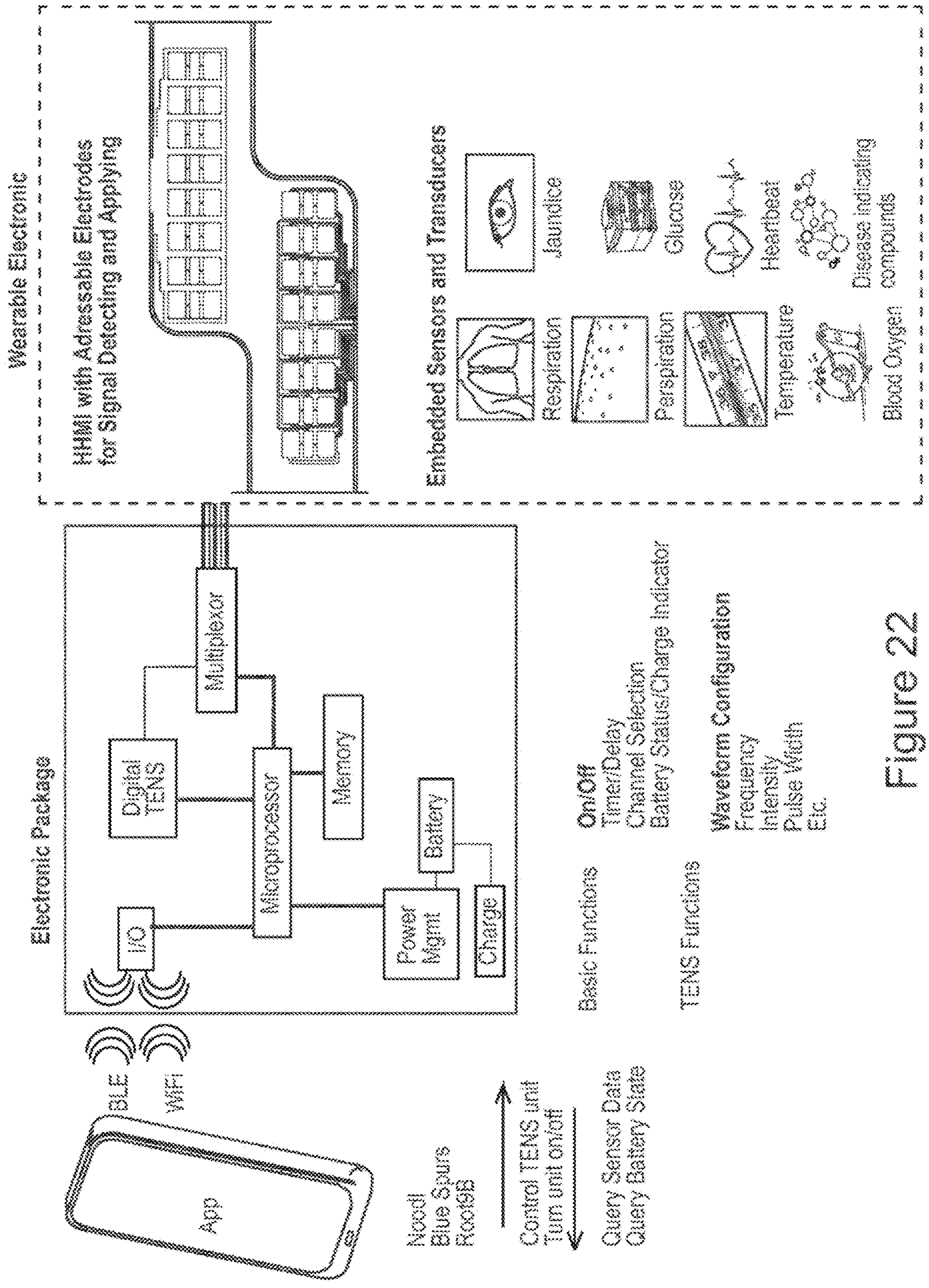
FIG. 22 illustrates an HHMI system including a smartphone app, an electronics package removably connected with an HHMI elastic fabric sleeve having individually addressable electrodes and embedded sensors, detectors and transducers.

FIG. 22 illustrates an HHMI system including a smartphone app, an electronics package removably connected with an HHMI elastic fabric sleeve having individually addressable electrodes and embedded sensors, detectors and transducers.

As shown in FIG. 22, an exemplary embodiment includes an Electronic Package with a powerful but low cost Arduino-based Microprocessor. The Microprocessor controls the operations of the electronic components and device functions. A Digital TENs device allows for the generation of instantaneously varied electrical signals, under the control of the Microprocessor. The TENS signal waveform can be varied in frequency, intensity, pulse width and other signal characteristics depending on the application and circumstances. The HHMI Wearable Electronic includes a grid of individually addressable electrodes that are configured and dimensioned for both signal application and detection.

Under microprocessor control a Multiplexor routes the detected and/or applied to the electrodes enabling only a single TENs source and a single EMG Detector to be selected for applying and sampling signals from any of the multitude of electrodes. When this multiplexed individually addressable electrode system is scaled up to a very large array of dozens or hundreds or even thousands of electrodes, the advantage of the HHMI patent-pending multiplexor becomes significant, resulting in a beneficial cycle of lower component count, failure modes, bulk, weight, power consumption and cost. This system also allows the HHMI Wearable Electronic to be custom configurable through a calibration routine to any user's specific physiology, and is very orientation and position tolerant.

The HHMI can be used for IoT, and a host of other applications, and can utilize Blue Tooth Low Energy (BLE) and WiFi signal input and output to provide a convenient user interface as well as opening the technology for future uses such as Cloud-based data logging and Big Data analysis. The HHMI wearable electronic may include embedded small semiconductor-based sensors, detectors and transducers within a durable barrier thermal plastic, that also acts to bind and connect the embedded devices to the printed electronic circuit.

Specific HHMI Applications: Listed below are specific applications for exemplary embodiments of the HHMI. This is in now way to be construed as an exhaustive list. Additional hardware in the form of embedded detectors, sensors, and transducers may be necessary to obtain one or more of the features listed in the specific use applications. Some of the hardware is described herein, while other components and their use will be readily understood by one skilled in the art.

Medical Applications The drugs most used to treat Parkinson's disease, such as Levodopa, have terrible long term side effects including a condition called dyskinesia where the patient has uncontrolled highly exaggerated movements. The HHMI configured for tremor mitigation detects the electrical activity of tremor contractions, analyzes the detected signal, and applies a counteracting electrical signal to steady the tremor. Our next-generation diagnostic tool measures heartbeat, blood-flow, muscle tone and strength, along with disease characteristics like oscillatory muscle contractions. The HHMI also enables a new form of non-invasive imaging, myographic imaging, where the motor units (muscle/nerve cells combination) that cause muscle contractions are depicted as 3D moving images.

Drones and Robots The unmanned vehicle industry has been using a "good enough" approach to the feedback and control of remote devices, often still relying on basic joystick and computer monitors. The advent of virtual and augmented reality is poised to change the conventional joystick and computer monitor interface. The addition of haptic feedback and control completes the VR immersion, with the ultimate potential that the operator will feel as if he or she has become the remotely controlled vehicle. Cognitive Therapy Applications The concept is to apply a haptic sensory cue using a comfortable wearable electronic while simultaneously applying audio and visual cues that are all synchronized to a learned task. Muscle memory and new neural pathways are created by simultaneous stimulation of the brain's processing centers, for example, to "rewire" a damaged brain using a pleasant and goal oriented effort, such as learning to play the piano.

Virtual and Augmented Reality As an essential part of a deep immersion VR/AR system, the HHMI brings the third sensory mode, by adding the sense of touch along with motion to significantly enhance the VR experience. This HHMI product concept is on the evolutionary progressions of radio-to-television-to-Internet and telegraph-to-telephone-to-smartphone. Those are all big and lasting markets. VR/AR is at the intersection of those progressions and the HHMI technology is poised to be a significant game changer. Not far behind VR/AR gaming, the "next big thing" may be telepresence across time and space, with the HHMI providing the third constituent of the ultra-deep immersion triad of auditory, visual and haptic senses. Music Instruction The HHMI is combined with a 3D VR headset and creates involuntary muscle movements (e.g., urging the fingers into a particular musical chord pattern) along with haptic sensation (e.g., indicating which fingers are to be used to play the chord pattern). The HHMI combines the simultaneous stimulation of three of the brain processing centers by applying synchronized sensory cues. The sensory cues stimulate the audio, visual and motor processing centers and quickly build the muscle and motor pattern necessary for learning an instrument.

Sports Training The HHMI technology can be used for any muscle memory and pattern recognition teaching or training, such as perfecting a golf swing or as a flight trainer. The idea is to record the body position "best practices" of an expert, determine a sensory cue (such as haptic stimulation), and apply the sensory during a learning session to quickly build up pattern recognition and/or muscle memory so the best practice is learned by the student.

Virtual Reality Controller In accordance with an exemplary embodiment, an HHMI configuration includes at least one of embedded sensors, detectors, emitters and transducers to enable a wearable electronic that can be tracked for game play and other virtual reality uses. As an exemplary configuration, a number of Light to Digital Sensors (for example, a photodiode plus aTS3633 integrated circuit from Triad Semiconductor). In this exemplary HHMI configuration, a wearable electronics sleeve can be formed having between 20 to 30 or more Light to Digital sensors. An IMU can be included with the HHMI configuration where the location information from the IMU gets included with light-to-digital angle information. A microprocessor forms the data into transmittable information sent to a Host Processor over a wired (e.g. USB) and/or wireless (e.g., BlueTooth or 2.4 GHz WiFi) communications link. Software, such as SteamVR software enables a "position engine" to computes the position and the orientation of tracked HHMI sleeve as the user's forearm moves through three-dimensional space.

Pulse-Oximeter Among the uses of an exemplary embodiment of the HHMI wearable electronic include, blood oxygen measurement and monitoring using pulse oximetry built into the HHMI. Pulse oximetry is a noninvasive method for monitoring a person's oxygen saturation (SO2). Its reading of SpO2 (peripheral oxygen saturation) is not always identical to the reading of SaO2 (arterial oxygen saturation) from arterial blood gas analysis, but the two are correlated enough within an acceptable deviation such that the safe, convenient, noninvasive, inexpensive pulse oximetry method is valuable for measuring oxygen saturation in clinical use. For example, a sensor device embedded within the HHMI construction is located so that is will come into contact or become adjacent to a part of the wearer's body. The embedded device passes two wavelengths of light through the body part, such as the skin of the forearm, to a photodetector that is located in the HHMI construction so that there is adequate transmission of the emitted wavelengths. The embedded transmitter/sensor pair is then used to measure the changing absorbance at each of the wavelengths, allowing the determination of the absorbances due to the pulsing arterial blood alone, excluding venous blood, skin, bone, muscle, fat, etc.

Glucose Monitoring Glucose monitoring can be achieved similar to a currently available product such as Dexcom (e.g., Dexcom G5 Mobile Continuous Glucose Monitoring System), which gives real-time glucose levels. Such a system may not be conveniently secured in place on the body and/or requires the use of inconvenient tapes and adhesives. In accordance with the construction and wearing of the HHMI devices, glucose monitoring embedded devices are disposed in secure, snug, face-to-face contact with the skin minimizing the likelihood of the device being knocked loose during user activity. As with other embedded sensing devices described herein and others that are not necessarily described explicitly but can be incorporated within the HHMI construction, the live monitoring of biometric readings from the wearer can be logged and made available, for example, on a smart phone app, computer, or become part of a cloud-based data collection and analysis system. Other envisioned embedded sensor uses can include body temperature measurement, allergy/histamine, urine abnormality, and shock, for example, where an abnormally low blood pressure may be detected along with a faster than normal heart beat.

Hypoglycemia Monitoring hypoglycemia during night hours or anytime can be achieved, for example, by monitoring body temperature and sweat. During episodes of potentially dangerous low blood glucose patients will experience hyperhidrosis (excessive sweating) without elevated body temperature. The embedded devices within the HHMI construction can include moisture absorbing pods/sensors that detect an increase in sweating while embedded temperature sensors can detect that no corresponding elevation of body temperature occurs. An alarm can be provide, contained within the HHMI or sent from the HHMI as a wireless signal to an alerting device such as a smart phone, to alert the wearer and set of events (deliver noxious stimulus to try and wake the user, sound an alarm, contact another persons cell phone, etc.) This use of the HHMI can be a life saving as when glucose levels dip to 40 and below the patient can become non-responsive. A measurement of sweat compared to outdoor temperature and in conjunction with other factors such as skin temperature, blood pressure can be used to help track hydration and other biometric conditions. Body Mass Index Body fat ratio may be obtained using an embedded sensor that detects electrical impedance. A current that is sent in on one side of the body (hand, forearm, feet) and the amount of time it take to be detected on the contralateral limb, along with metrics such as height, weight, age, gender can be used for a body mass index calculation. Weight can be measured by pressure upon a surface, the ground, in a full HHMI suit or stocking configuration. In this exemplary embodiment, the HHMI can be outfitted with a digital scale as a type of electronic weighing machine, which is used to measure many readings including body fat, BMI, lean mass, muscle mass, water ratio along with body weight. Further, sensors can be embedded to identity the HHMI owner so that encrypted data of that particular owner that contains sensitive HIIPA controlled info is sent, for example, through a secure network connection. Heart Rate Variability As an example of an embedded sensor for heart rate variability, a sensor similar to a product called the Polar H7 chest strap can be used to monitor and measure, for example, the time between r waves of the heart beat and detect an increase in sympathetic and parasympathetic activity. There may be incorporated a second level of branching logic in detecting disease, stress, low blood sugar in the case of increase sympathetic activity with hyperhidrosis and normal body temperature. HRV can be used to detect when your body is able to handle more stress or needs recovery. As an example, in sport training, embedded sensors included some or all listed herein can be used to detect overtraining and to optimize a training regimen.

Drug Delivery As another example, the embedded device may be used for drug delivery, in the form of iontophoresis that uses as an example, a polarized electrical current to push same charged medications into the blood stream through the skin. Liquid medications are either positive or negatively charged, then providing the medication with the same polarity current forces medication into the body. The medication can be forced subcutaneously according to a timer, or in response to a sensed condition, such as blood sugar level or heart beat, or in response to a user activation.

Other embedded devices may include, for example, a GPS unit. In a medical use example, an Alzheimer's patient can be tracked using GPS, alerting authorities and family when the patient wanders. The embedded GPS can connect WiFi or cellular hotspots, satellite or other wireless communication system, marking the location of the user. In this example use, when the GPS information that marks the individual as outside a set of preselected coordinates, an alarm triggers to emergency personnel, who at the time of the alert also receive wirelessly the coordinates of the sufferer from the HHMI.

Other embedded devices may be used for hazards warning (including but not relegated to traffic, danger, obstruction, hazmat, radiation, toxins). Disabled (deaf, blind or wheelchair bound) individuals all share the ability to feel a haptic stimulus. Intersection walk signaling systems, can be equipped to send wireless data as well as visual and/or audible information. In this example, use, the embedded device or the user's smartphone or other wireless devices, receives the data and communicates to the wearer as a haptic stimulus using the mechanisms described herein, vibrations, etc. For example, the wireless information from a hazard may convey specific information, such as an intersection stop/go indicator. An onboard microprocessor can be provided to determine what haptic stimulus characteristic (pulse, intensity, location) to apply to provide the wearer with the specific information to stimulate in a known way that conveys the information.

Other embedded devices may include, for example, devices intended to protect (insect killer, attack response such as mace, motion detection, and deliver electric shock as to an attacking dog). Power generated by the HHMI user and saved in suit can be elected by wearer to deliver mild electric shock to a attacking dog, or can be delivered from battery pack. Mace can be stored in receptacle in sleeve and motion of users hand causes mechanism to release mist or targeted spray. Again hand commands can be translated by microprocessor to HHMI and HHMI receives command to release mace, electric shock, raid. Off the shelf Motion detection could be installed in HHMI, possible uses could be for hunting, safari, walking through dark areas.

Other Uses:

Threats to individual and communication to police (choking, falling) A sensor indicates the individual is in a prone position for a certain amount of time. Breathing and or blood pressure becoming suddenly rapid indicates trauma, such as choking.

Circulation and compression stockings tens muscle activation is used in a wave pulse from distal to proximal to help circulation of the legs during long drive, flights or during the day for people with circulator diseases. Prevention of DVTs.

Athletic Performance Potentiation Muscle priming to increase motor unit recruitment and excitability of tissue prior to competition. Henneman's size principle: at the lowest levels of activation, only the smallest motor units are recruited and minimal power is generated. As this level of activation increases, the recruitment thresholds of larger motor units are surpassed, resulting in a greater number of motor units recruited and successively greater force and power production. Rate coding or the frequency of signaling from the central nervous system to the motor unit is also an essential element of power production. Increasing signal frequency can result in greater power production because of an increase in the firing rate of motor units and a continual increase in a stepwise fashion of force.

Functional Movement Screening An HHMI suit or garment can evaluate EMG during a series of pre tested movements. The suit can map and access the symmetry of muscle activation throughout the movement screen. This will serve as a baseline for an athlete or individual and over the course of a season they can re test to rule out compensatory patterns taking place that may lead to injury due to muscle imbalance. Tool for Injury risk management and over training monitoring. Very practical for return to play post injury. This may be utilized with head injury screening.

Neuroprosthetic Sleeve Using the bidirectional nature the "sleeve" can detect nerve impulses from a proximal muscle to control a distal prosthetic. An example would be a HHMI shoulder girdle for a below the elbow amputee. The activation of the upper trapezius during a shrug of the shoulder could give a signal to flex the prosthetic wrist. Using force sensors in the fingers of a robotic hand prosthetic will deliver a tactile feedback back to the shoulder girdle. This will allow a cutaneous feedback to the user from the prosthetic hand. This ability to sense pressure from the robotic prosthetic will improve the ability to gain dexterity and fine motor control.

Atrial Fibrillation Detecting Kinaptic Shirt The shirt will be lined with conductive ink sensors located under the left pectoral muscle. The sensors will detect the electrical impulses that trigger your heartbeats. Body temperature sensor will also be embedded in the arm pits of the shirt. A phone app or watch like device will analyze the data collected and alert the wearer of any abnormal heart rhythms such as but not limited to atrial fibrillation. The app will alert the user or surrounding persons of the medical emergency. The app will have the ability to contact 911 and give the location of the event, shirt wearers' identification and vitals such as body temp and heart rate.

Posture Correction Shirt Upper cross syndrome is a common condition that leads to discomfort of the shoulders, neck and back. Forward head positions with kyphosis of the thoracic spine are two of the common physical postural traits. In this position the posterior neck musculature is in a short stiff position and the upper traps tend to live in a state of splinting and spamming (increased tone). This causes the forward head position. The anterior chest muscles are also in a tighten short position leading to a look of forward shoulders. To counter this position strengthening of the scapular depressors and retractors are required and stretching of the chest muscles and upper traps. The shirt will have conductive ink electrodes that will create a neuromuscular stimulus to activate the correct muscles to maintain proper posture position. The shirt will be controlled wirelessly by a Bluetooth device that the user adjust intensity, treatment time and location of activation.

Exercise Suit with Virtual Trainer App The low profile spandex-type material of embodiments of the HHMI includes conductive ink EMG sensors and TENS signal applying electrodes, along with embedded sensors, detectors and transducers which may include one or more accelerometers located on strategically mapped anatomical landmarks. An exercise user can be guided through a series of exercises shown on a smart phone app. The exercise user mimics the virtual trainers movements at the same time as watching them being performed. The HHMI garment can monitor the muscle firing and joint position of the exerciser to ensure correct form. The suit can detect if the virtual trainer movements and the exercisers' are similar. If incorrect movement the virtual trainer can give corrective cues, and/or through the application an appropriate TENS signals urge the exercise towards the correct movement.

Vicarious Entertainment A scheduled event on social media, such as the following of a celebrity, who is wearing a HHMI, may be purchased. The celebrity for instance wears an HHMI and is outfitted with a 360 degree high definition camera, such as the Nikon KeyMission360. The celebrity, or other person or object to be tracked and followed, wears this equipment to, for instance, a party after the Oscars. Haptic, auditor and visual data is captured by a microprocessor, memory, etc., and transmitted wirelessly to social media platform via a network connection, such as the internet. The social medial platform may have some of the attributes, for example, of Twitter, Snapchat, Facebook, and the like, but with a more robust application and interface built to stream copious amount of data. Additionally, or alternatively, compression techniques may be used to facilitate the transmission of the haptic, auditory and visual data needed. The system architecture captures the data at an event (for example, the sights and sounds, plus haptic cues such as handshakes, picking up items, putting down items, walking, hugging, etc., and wirelessly transmit this data to SAN or local storage attached to a virtual machine cluster. To control usage, purchasers or other users of the vicarious entertainment experience may be streamed information based on their unique haptic identity, such as a fingerprint, or a device serial number. The information flows out as data as a service, or similar to how tweets flow out from an individual followed to those following. The users wear an HHMI garment with augmented or virtual reality systems for vision and auditory cues. The event begins, and ends, unlike the following of a twitter account, a scheduled following event has a start time and date, and a end time and date, after which the data aforementioned flowing to those following the celebrity at the event ceases. In another example of Vicarious Entertainment, a performer (for example, an entertainer) wears a HHMI and a high definition camera, and during the performance the visual, auditory and haptic cues of the performer's experience are wirelessly transmitted. A virtual concert attendee likewise wears an HHMI garment and AR/VR system for the remotality experience. The haptic cues of the entertainer's use of props or instruments is processed and uploaded to SAN or local storage to, for example, a Cloud clusters of virtual machines passing the data on to a data as a service provider such as Factual. When the performer plays their instrument the HHMI garment fitted on the performer sends haptic data via the aforementioned method to the virtual concert attendee and the positioning and use of the performers detected body movements while playing an instrument is felt by the virtual attendee. If that attendee is seated at a drum kit, or holding a guitar, it is likely that some much lower proficiency of the instrumental performance is duplicated by the virtual attendees HHMI.

As an example, a user can attend an event that a friend is going to and is not going to, in this case, the friend wearing the HHMI attends the event. The user follows the friend as per the examples related to social media. The HHMI garment helps translate a deep immersion in the virtual experience. The event can be pre-stored information, or information received concurrently with the actual timing of the event. For example, networked virtual machines may be assigned to and wait for the event start, and handle the processing of the data and manage the transmission in conjunction with a data as a service or streamed data engine to the virtual attendee.

This is of course not limited to events, wishing to follow another and experience what they are feeling would be desirable under many conditions. Those bound to a wheel chair for instance can experience an Appalachian trail hike. HHMI events can be scheduled and followed by individuals or groups. Virtual Reality Chair Chairs, such as, for example, movie theater chairs, may be fitted with a HHMI construction in the form of a covering or movie goers can wear an HHMI garment when attending the theater. The chair and/or the garment is configured to receive and apply haptic, visual and audio data creating a more immersive experience for example, for a 3D movie.

Movies could be made such that actual actors wear HHMI garments worn, following and recording their movements in the movie scenes. The movements of an actor in a scene can be translated into haptic data with the finished product of a movie or entertainment streamed with data added into the movie and wirelessly communicated to a viewer wearing an HHMI or haptic sleeve, allowing later translation to a viewer, wirelessly from code embedded in the movie data and interpreted by an HHMI garment worn by the viewer. Additionally, or alternatively, additional data, such as cartoon graphics or CGI can be synchronized with haptic cues coded to the movie data for wireless dissemination during the movie to the viewer.

Audience Feedback Data can be collected for data base and/or Big Data analysis for use by the entertainment industry and other to understand details about a person's reaction to a movie scene. For example, was the viewed material exciting, and did the measurements of a study group confirm that most watching it were in a dense bubble that indicated high excitement because of HHMI measurements taken compiled, and analyzed. The HHMI creates a wearable membrane of data collection between the body of the wearer that detects, makes sense of, processes and stores all manners of data for big data collection storage, and analyzing. Data collected by the HHMI makes a human being into a part of the IOT (internet of things), in fact it creates a new type of data realm, the IOH (internet of humans). Collection data would be accomplished by detecting heart rate, blood pressure, sweat, brain waves, and the like. A built in microprocessor receives data from bio sensor chips, and from detect dry electrodes, that monitor reactions in the body of a person viewing entertainment, or any other viewable material that, during the viewing of, data collection is desired to measure reaction to that material. In combination with augmented reality and virtual reality vision and auditory systems the HHMI is used as a wearable electronic data collecting membrane, or layer, between the body of the wearer and a wireless detection point. Anonymous (or encrypted) data is compiled by the microprocessor and off loaded to a cloud connected SAN storage array (allowing random access), or local array, local or within a cloud containing a DB of the collected data on for instance an oracle cloud machine, on oracle, SQL, Sybase and/or other DBs, and then real-time data analysis can be performed within/by a cluster of VMware (or like technology) virtual machines that use AI or smart stable or unstable sorting algorithms, divide and conquer, Treesort, Burstsort Randomized or non or any other existing or future sorting algorithm desired based on data to be sorted. Data is then organized and the organized data stored as with HDFS which stores large files (typically in the range of gigabytes to terabytes) across multiple machines. The sorted data is then analyzed by technologies such as SAS, Dataspora, Clear Story and Opera to mention just a few. The resulting data can be offered as data as a service (HDFS map-reduce or Apache SPARKworking with WindowsAzure as an example), or as traditional data in the form of: data reports, visualized data, analytical data. Data sets can contain predictive analysis, reaction analysis, sense and respond, behavioral insights, risk analytics, query based data reports, simulation based data reports real time or stored, disease trends, health of HHMI user, health demographics, travel destination popularity, population demographics, etcetera. (Note: I believe encryption of data needs to happen in the HHMI prior to wireless transmission).

Interpersonal Enhanced Experience Interpersonal experiences are enhanced by VR and haptic appliance to all manners of interactions over distance, such as but not limited to chats, dating sites, adult phone line calls, meetings with therapists that may not be in your area but are best equipped to deal with your issues, Business meetings, Walks down virtual landscapes holding hands, remote physical therapy where the therapist and patient are separated by large distances, Young adults at university needing reassurance perhaps just a conversation and a hug from mom. In the case of sensitive data a data tunnel is created from therapist direct to HHMI only de-encrypted by fingerprint which HHMI stores to know its owner. The tunnel is a VPN from point to point, encrypted or non encrypted data travels between. Through augmented reality, virtual reality head sets and gear, auditory components and the HHMI, an immersive (for instance) therapy session occurs over distance, the data is wirelessly uploaded to CPU power set aside for the appointment (JFC) within a cluster of virtual machines connected to dedicated SAN or local storage in rack as in the case of an Oracle cloud machine. In the case of a therapist visit the encrypted data is tunneled to a wireless point at the caregivers site and then wirelessly downloaded to a microprocessor on the therapists HHMI decoded by it based on unique recognition such as a fingerprint. In a HHMI glove the finger is in constant contact with surface, if contact is broken, the data ceases and the VPN tunnel is closed. Astronauts and those doing activities that most people will never experience can likewise be experienced in VR and somewhat enhanced by HHMI. Drones or robots operating on other planets or in orbit can allow someone to virtually experience extraterrestrial environments.

There are a lot of life forms that it may be interesting to experience. A lion for instance. Or a Dolphin. To experience a Dolphins swim through the ocean, and its interactions with other Dolphins and the environment. Perhaps even a haptic way with VR to experience sonar perceptions. While suspended in an isolation tank. The dolphin can be outfitted with an HHMI and sensors to transmit both the feelings of swimming through the ocean wirelessly to a satellite and perhaps sonar perceptions, which can then send to internet and again target those HHMI purchasers by identity or serial number etcetera. Sonar perceptions can be interpreted by a microprocessor in the same way it is today when we use sonar devices. This could we militarized. A Dolphin can be controlled such that underwater espionage is carried out.

Relief of Anxiety Disorders Sufferers of anxiety disorders could be helped by the invention. The HHMI can be configured with software and hardware that provides a massage experience, and may include other relaxation-inducing possibilities such as warmth, a mild electro stimulus that has been meted out to a pre measured threshold at which anxiety is reduced, at an individual level via the electrodes in the HHMI and the use of TENS type electrolysis. In conjunction with augmented reality, virtual reality head set and auditory, a peaceful scene could be presented to relax the sufferers.

Simulated Weight Lifting The HHMI can simulate weight lifting, in so much as it creates a counter force to your muscles that is translatable to a pound measurement. For instance while trying to make a curling action the HHMI sleeve resists the action of it's user. During the exercise your body's data of movement could be recorded and extrapolations drawn such as strength or muscle density based on the level of your resistance to the HHMI's counter. A virtual exercise instruction/instructor would be created, and the haptic device in full body form providing all kinds of feedback and work outs suggestions, even diet. Amusement Park Rides Amusement park rides, ghost tours in which a participator is wearing an HHMI, and being "scared" by stimulations that intersect visual and auditory. Holo Deck type experiences that happen in a wireless virtual world tunneled into by fingerprint (for proof of purchase), such as gaming, support forums, learning forums. Rides or fright tours, ghost tours, in which the rider or attendee is outfitted with some form of an HHMI, whose internal microprocessor is commanded at certain points in the ride or tour to cause a stimulation in the HHMI wearers musculature, such that for instance a person attending a ghost tour feels that they were grabbed by an unseen presence. Rides that are virtual such as a VR helmet visually delivered roller coaster ride, where the chairs on which the riders sit sway and dip according to the ride map, also wear HHMIs or the chair itself is outfitted with HHMI so that the pressure of their bodies put them in close contact with the send and receive electrodes and circuitry, the data for a sensory event can be sent wirelessly or wirelined based on the script of the virtual amusement ride, or ghost tour. The stimulation via HHMI when a drone operator (or any operator of any vehicle) crosses a GPS point, such as another country, state, mental state (enemy), or over water. Or approaching GPS danger points (volcanos).

Deep Immersive Training A VR or AR system can include a computer generated scene that shows an audience and or other performers. For example, the user can be shown an experience of public speaking and allowed to rehearse a presentation as if he or she were in front of a live audience. The virtual audience provides visual and auditory cues that can represents a similar audience as would be expected during the live presentation. A musician can play with actual and/or virtual band members, and also experience the sights and sounds of an actual real-world performance. An experience can be created that trains one to perform as a stand up comic, actor, priest, business person, politician, school teacher, student, or other role that places the trainee in front of a live audience. Actual or virtual props and setting and scene components can be included in the experience, such as a teleprompter or podium. The HHMI can be used to include touch and movement feedback and sensations to further deepen the trainees immersion, and provide an experience conducive to the intended training.

First Responder Medial Glove: A glove with Kinaptic bi-directional pads on the palm and finger areas. On the back of the hand area, an embedded LCD and/or an attachment point for securing a cell phone and connecting to the glove via BLE or WIFI (or "other" wireless). Using the glove, "detect" muscle activity, EMG, EKG, skin temperature, 02 levels, galvanic skin response, ultrasound narrow beam images, etc. and in "apply" mode apply soothing TENS and EMS to the muscles for relaxation and massage.

The uses of this type of glove are numerous. For example, for a "first responder", this glove could be used to detect heart rate, respiration and other "vital signs" while still allowing the first responder to use their hands as they normally would. Used by a massage therapist, these gloves would allow muscle "deep massage" and stimulation during normal massage therapy activity. In addition, they would allow the masseuse the ability to measure muscle activity and response (apply and detect), perhaps ultimately allowing some level of added insight into the patient's localized pain areas, etc.

Figure 25A:
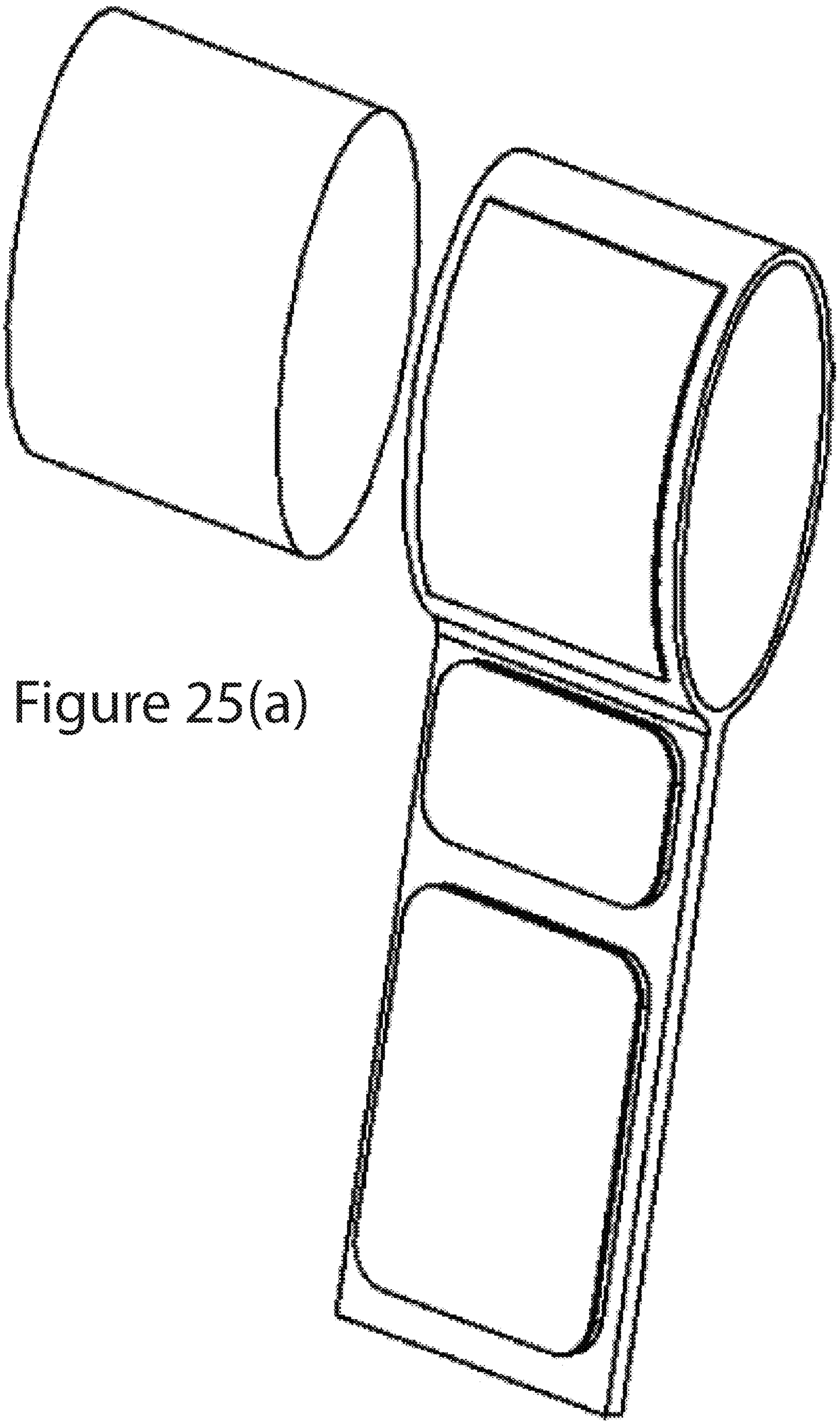
FIG. 25(*a*) is a perspective view of dry electrode insert having a receiving space and showing a separate pneumatic urging member.
Figure 25B:
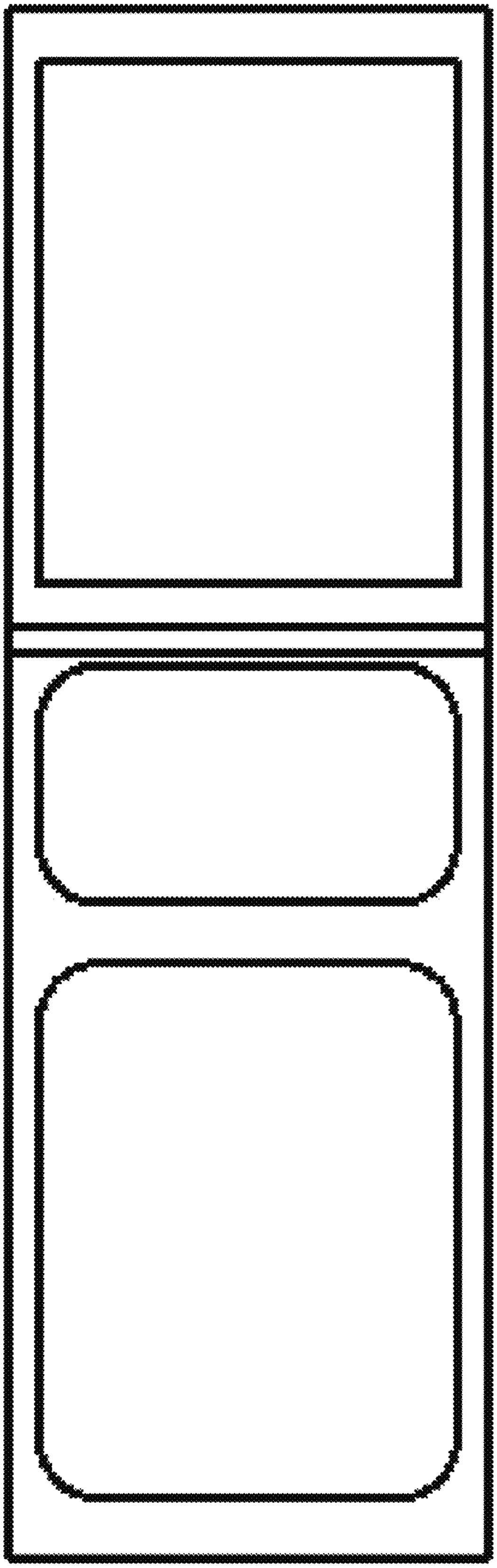

As shown, for example, in FIG. 25(*a*) 29(*d*), in accordance with a non-limiting exemplary embodiment, an apparatus comprises a housing with at least one electrode supportable by the housing. The at least one electrode for applying stimulation electrical signals to skin of a user. At least one urging member is supportable by the housing adjacent to the at least one electrode for urging the at least one electrode towards the skin of the user.

An electrode insert can be provided supportable by the housing and separate from the housing. That is, the electrode insert and the housing are separate components allowing the insert to be positioned relative to the housing to benefit the ergonomics or other application factors for an individual user or specific application. The electrode insert includes the at least one electrode.

The electrode insert further can include the at least one urging member. The electrode insert and the housing interact to cooperatively hold the at least one electrode in electrical contact with the skin of the user. For example, in the exemplary embodiments shown herein, the electrode insert is held snug against the skin of the user by the housing. The housing can comprise an elastic fabric for applying a squeezing force against the electrode insert for cooperatively acting with the least one urging member for holding and urging the at least one electrode in electrical contact with the skin of the user.

The at least one electrode may comprise a conductive fabric electrode sewn to at least one of the housing and the electrode insert. The at least one electrode can comprise a dry electrode formed by at least one of digital inkjet printing, screen printing, doctor blading, stamping, dip coating and spray painting of a conductive ink. The urging member may comprise at least one of a pneumatic bladder, a foam block, a wire spring, and an elastic fabric. The volume (and hence the pressure applied as the urging force) of the pneumatic bladder can be adjustable, for example, using an air pump. Additional urging members can be included between the housing and the electrode insert to provide a custom fit for a particular user's body, preference, or a specific application of the inventive electrical signal detector and/or applier system.

The inventive electrical signal detector and/or applier system may be fabricated, for example, by providing a housing substrate. At least one electrode is fixed to the housing substrate, the at least one electrode for applying stimulation electrical signals to skin of a user. At least one urging member is fixed to the housing substrate. The at least one urging member is disposed adjacent to the at least one electrode for urging the at least one electrode towards the skin of the user. For example, a combination of urging members and electrodes can be formed and or fixed to the house substrate along with other electrodes and or urging members formed or fixed to the electrode insert.

The at least one electrode may comprise a dry electrode pre-printed on a print medium, and wherein the at least one electrode is fixed to the housing substrate by adhering the print medium to the housing substrate. The at least one electrode may comprise a dry electrode fixed to the housing substrate and or electrode insert by printing the dry electrode onto the housing substrate.

Figure 30A:
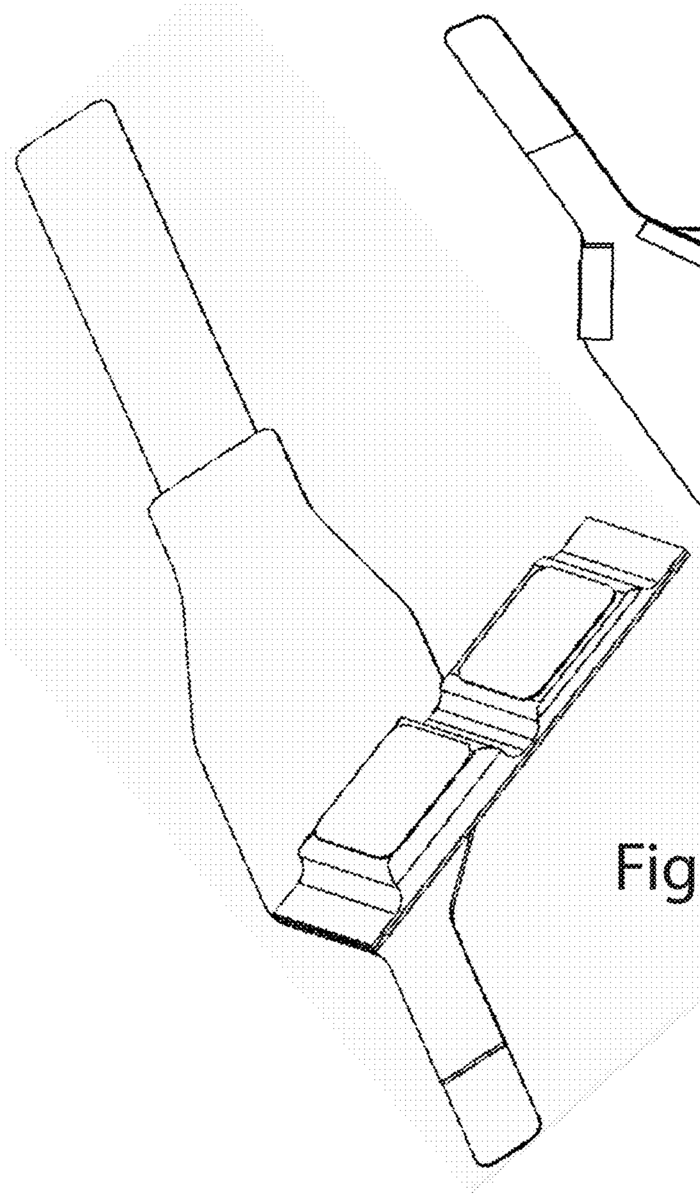
FIG. 30(*a*) shows the front of another embodiment of the inventive electrical signal detector and/or applier system.
Figure 30B:
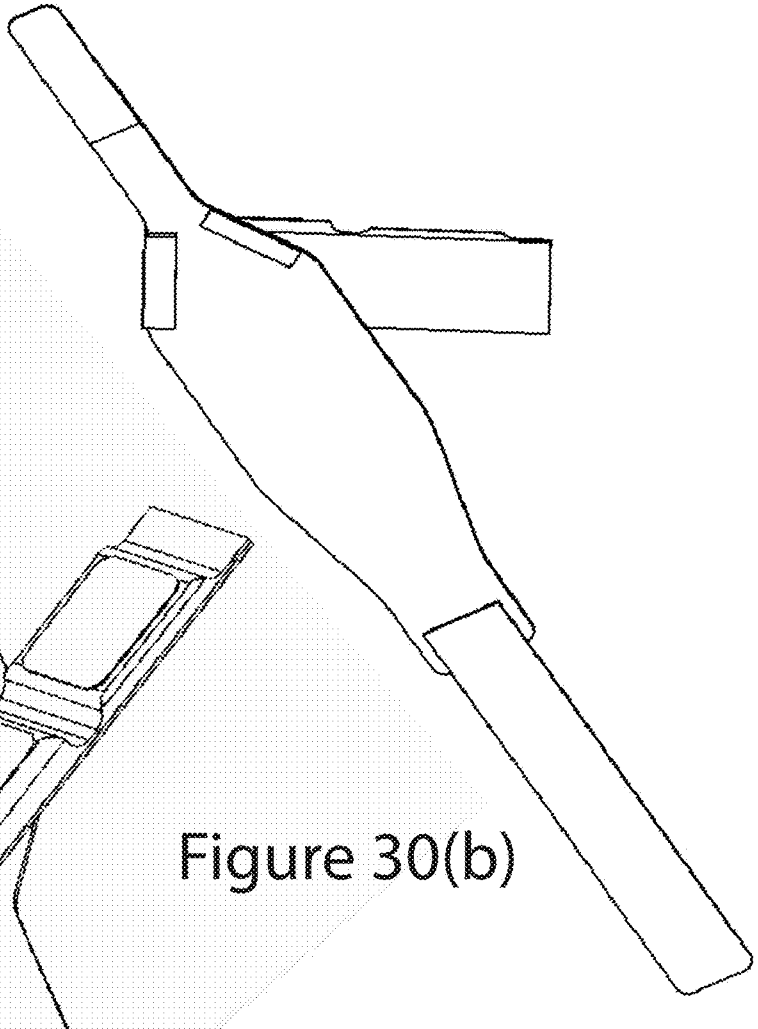
Figure 31A:
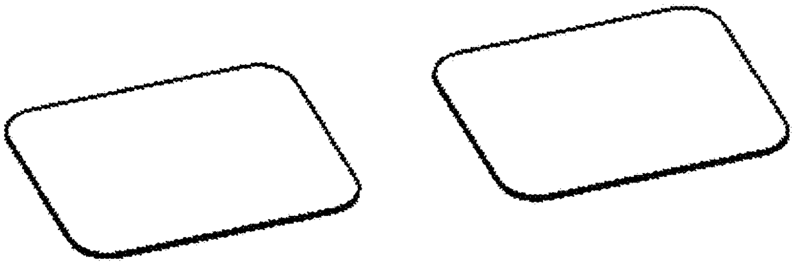
FIG. 31(*a*) show printed electrodes having a hotmelt sheet adhesive.
Figure 31B:
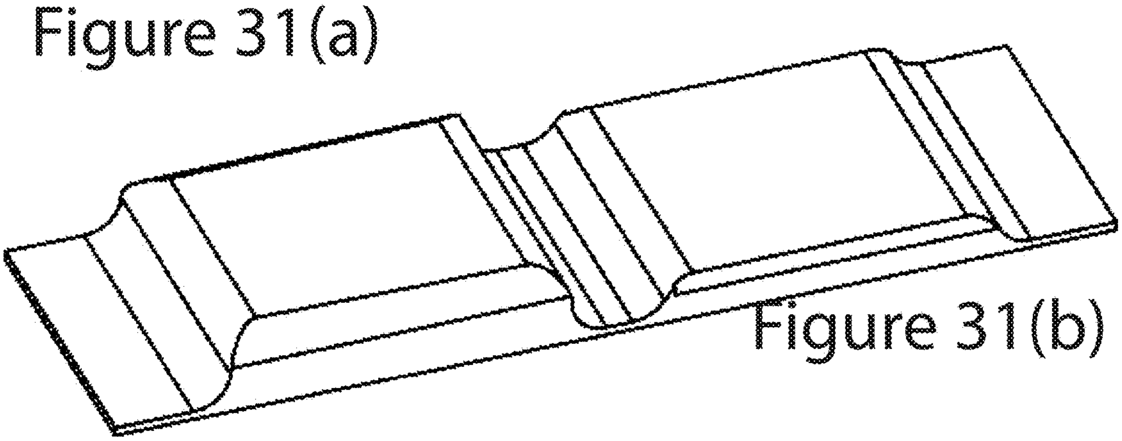
Figure 31C:
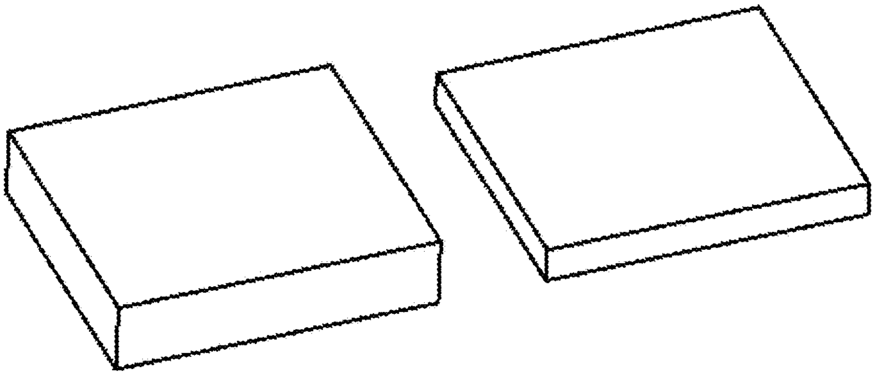
Figure 31D:
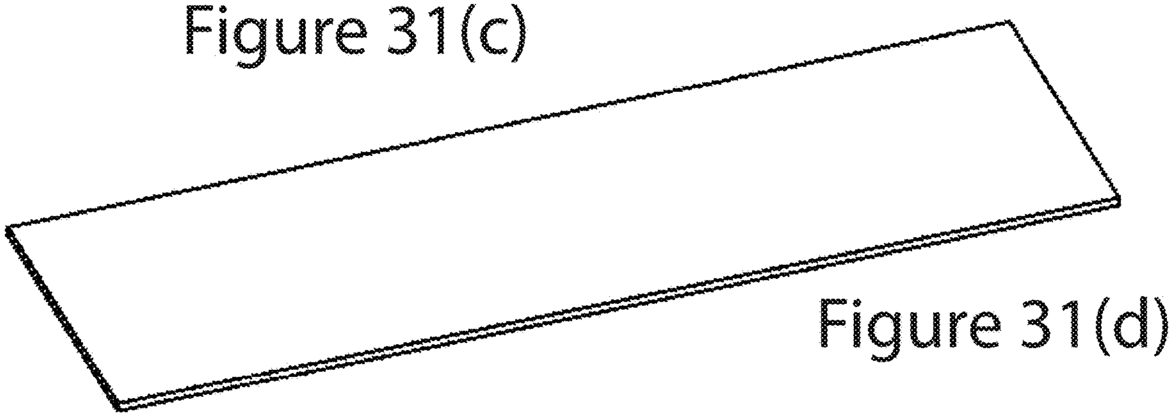
Figure 38:
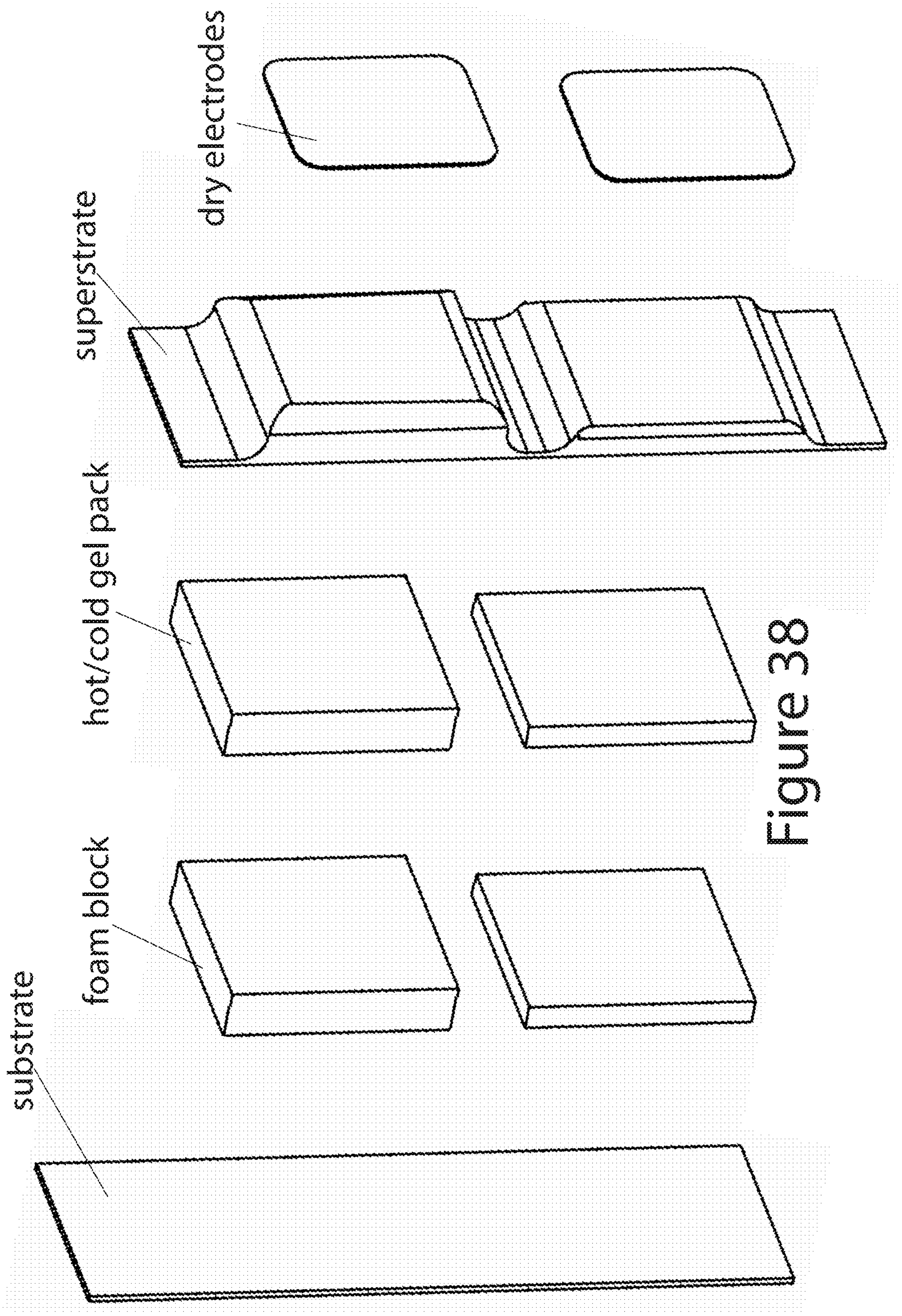
FIG. 38 is an exploded view of an embodiment of the electrical signal detector and/or applier system.
Figure 39A:
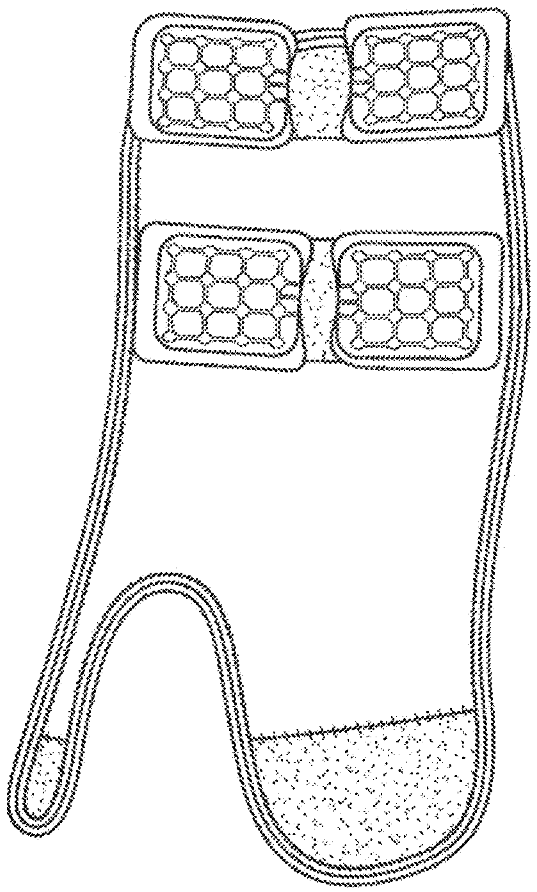
FIG. 39(*a*) shows an alternative embodiment showing a wrist sleeve having dry electrode units.
Figure 39B:
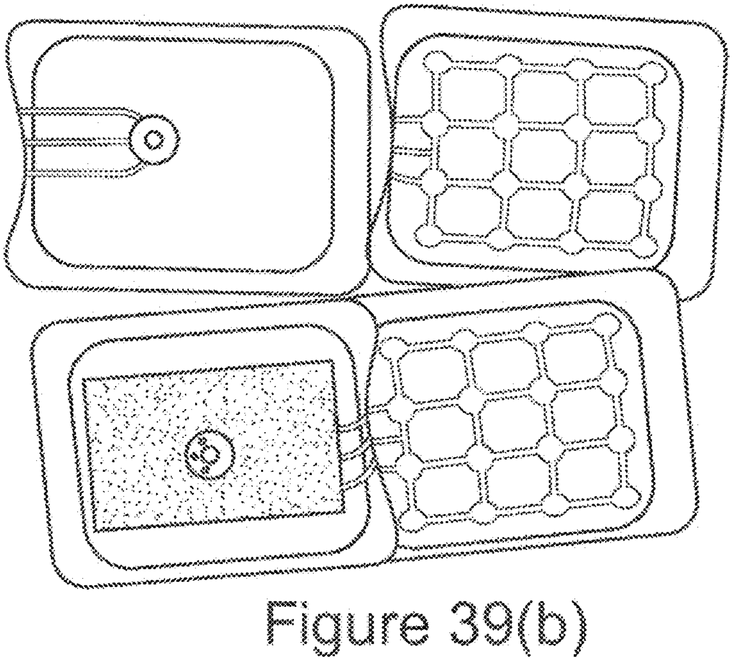

The urging member may a respective foam block configured and dimensioned for urging a corresponding electrode towards the skin a the user. A cavity can be formed in the housing substrate and or in the electrode insert. The cavity is positioned adjacent to a corresponding electrode. The at least one urging member comprises compressible block configured and dimensioned to be received in the cavity effective for urging In accordance with a non-limiting exemplary embodiment shown, for example, in FIGS. 30(*a*) through 37(*b*), an apparatus is provided for applying an electrical stimulation to skin of a user for mitigating pain. The apparatus comprises a housing with at least one electrode supportable by the housing for applying stimulation electrical signals to skin of a user. At least one urging member is supportable by the housing adjacent to the at least one electrode for urging the at least one electrode towards the skin of the user. FIG. 38 is an exploded view of an embodiment of the electrical signal detector and/or applier system. FIG. 39(*a*) shows an alternative embodiment showing a wrist sleeve having dry electrode units. FIG. 39(*b*) shows the front and back of dry electrode units. The dry electrode units include a velcro hook patch that match up with a velcro loop fabric on the inside of the wrist sleeve. The printed dry electrode pattern terminates in a press fit connected snap. The snap connects to a wire that connects with a TENS unit for applying a transcutaneous electrical nerve stimulation signal. A pair of dry electrode units connects with the TENS unit via wires that snap to the snap connectors. Each electrode unit is constructed so that at least one electrode supportable by the housing for applying stimulation electrical signals to skin of a user. In use, the dry electrode unit is held in place via the velcro patch to the wrist sleeve and a foam block urging member urges the printed electrode towards the skin of the user.

FIG. 40(*a*) illustrates an electrode pattern for the electrical signal detector and/or applier system. FIG. 40(*b*) shows a gesture control cuff turned inside out to show the electrodes of the electrical signal detector and/or applier system. The at least one electrode may comprise a plurality of individually addressable electrodes supported by the housing. The individually addressable electrodes are for at least one of applying stimulation electrical signals to skin of a user and detecting biometric electrical signals from the skin of the user. At least one of a signal detector for detecting the biometric electrical signals and a signal generator for generating the stimulation electrical signals. An electrode multiplex circuit for addressing the plurality of individually addressable electrodes by at least one of routing the biometric electrical signals from the skin of the user through more than one of the plurality of individually addressable electrodes to the signal detector and routing the stimulation electrical signals from the signal generator through more than one of the plurality of individually addressable electrode to the skin of the user. A microprocessor controls at least one of the signal detector, the signal generator, the electrode multiplex circuit.

The microprocessor controls the electrode multiplex circuit to route the biometric electrical signals from the skin of the user sequentially through more than one of the plurality of individually addressable electrodes to the signal detector. The microprocessor controls the electrode multiplex circuit to route the biometric electrical signals from the skin of the user simultaneously through more than one of the plurality of individually addressable electrodes to the signal detector. The microprocessor controls the electrode multiplex circuit to route the stimulation electrical signals from the signal generator simultaneously through more than one of the plurality of individually addressable electrodes to the skin of the user. The microprocessor controls the electrode multiplex circuit to route the stimulation electrical signals from the signal generator sequentially through more than one of the plurality of individually addressable electrodes to the skin of the user. The microprocessor controls the electrode multiplex circuit to route the stimulation electrical signals from the signal generator simultaneously through more than one of the plurality of individually addressable electrodes to the skin of the user.

A signal multiplex circuit controlled by the microprocessor can be provided for routing the electrical signals from the signal generator to skin of the user through the electrode multiplex circuit and to the signal detector from the skin of the user through the electrode multiplex circuit. A memory controlled by the microprocessor can be provided for storing data dependent on the biometric electrical signals; and a communication module for transmitting the stored data for analysis by a remote network device. The housing may comprise an elastic fabric material, where the individually addressable electrodes are dry electrodes formed on the housing and or the electrode insert by printing elastic conductive ink. A same individually addressable electrode of the plurality of individually addressable electrodes can be provided that both detects the biometric electrical signals from the skin and applies the stimulation electrical signals to the skin.

The microprocessor controls the electrode multiplex circuit to address the plurality of electrodes for sampling the biometric electrical signals at a sampling rate effective for the detection by the signal detector of the biometric signals as electromyographic signals originating from subcutaneous motor units indicative of muscle contractions from two or more muscles of the user. The microprocessor controls the electrode multiplex circuit to address the plurality of electrode for applying the stimulation electrical signals as application pulses at a pulse rate effective to cause involuntary contractions of the muscles of the user. The microprocessor controls the electrode multiplex circuit to address the plurality of individually addressable electrodes by at least one of sequentially and simultaneously routing both the biometric electrical signals from the skin of the user through more than one of the plurality of individually addressable electrodes to the signal detector and routing the stimulation electrical signals from the signal generator through more than one of the plurality of individually addressable electrode to the skin of the user. At least one of an inertial measurement unit, an accelerometer, a sensor, a detector and a transducer can also be supported by the housing.

Figures 42A, 42B:
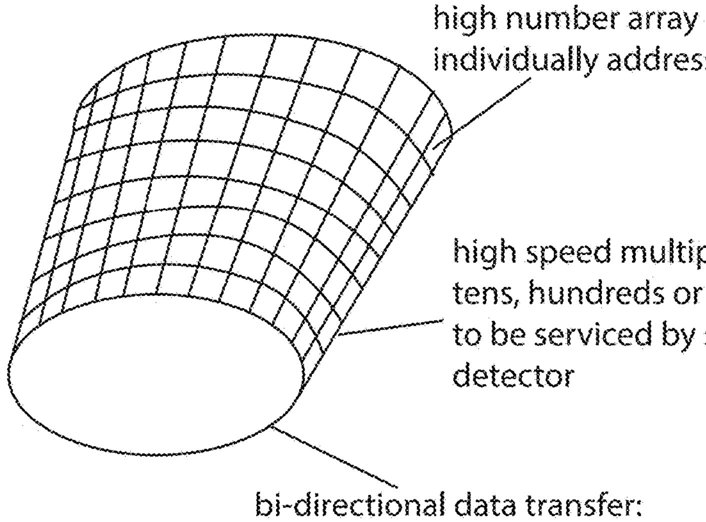
FIG. 42(*a*) shows the cross sectional stack of materials and the interface between the HHMI and the skin of the user.
Figure 43:
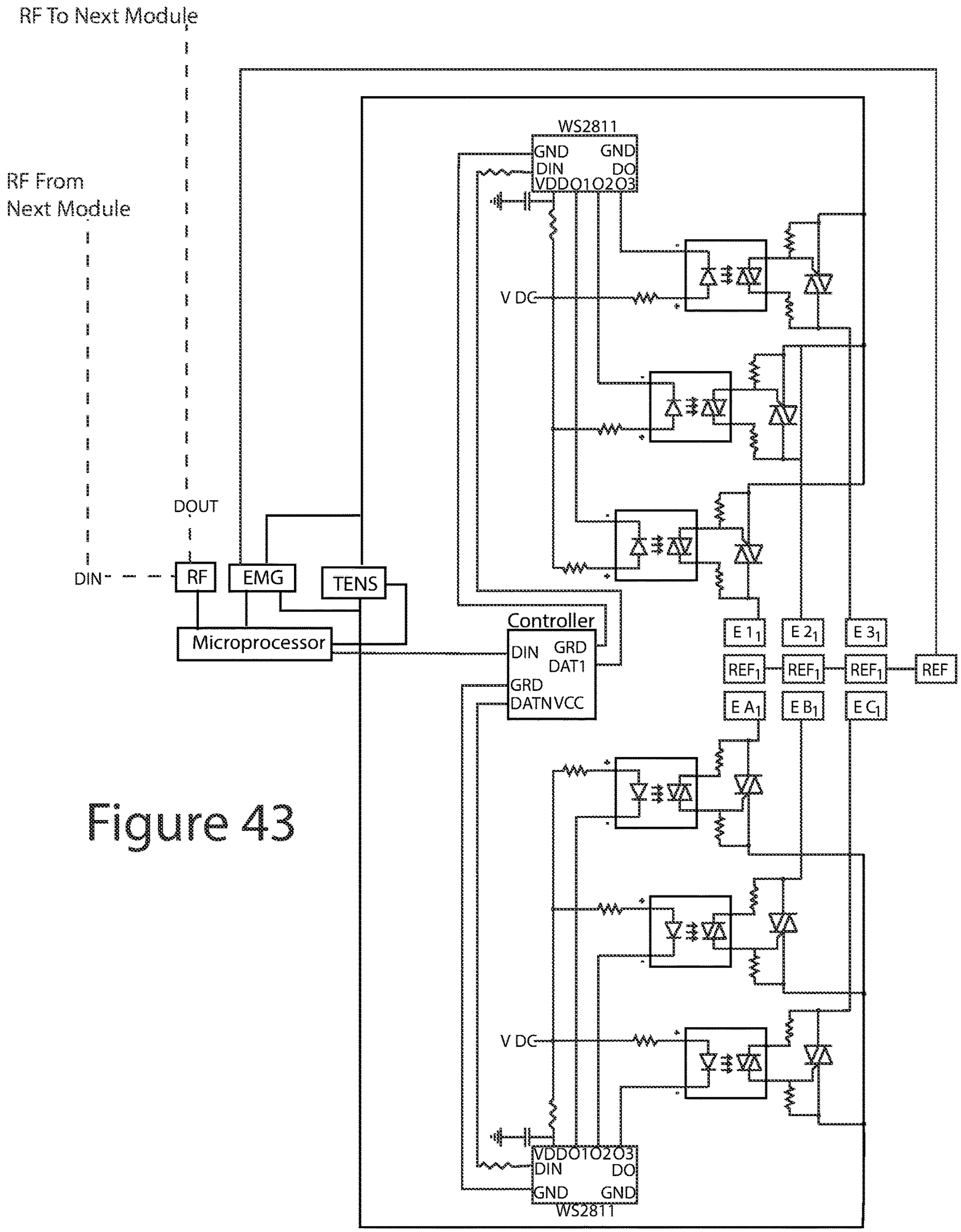
FIG. 43 is a schematic showing a repeatable module that includes a communication network element (RF) for receiving and transmitting synchronized data.

FIG. 42(*a*) shows the cross sectional stack of materials and the interface between the HHMI and the skin of the user. FIG. 42(*b*) shows a section of a sleeve illustrating a large number array of individually addressable electrodes. FIG. 43 is a schematic showing a repeatable module that includes a communication network element (RF) for receiving and transmitting synchronized data. The module includes a microprocessor that controls the contains of the other components.

As an example, the microprocessor can be used to synchronize the detection and application of electrical signals to and from the user, and can be used in concert with a number of other modules which may all be under the control of a centralized CPU (remote from or worn by the user). As one example, WS2811-type micro controllers can be used to receive data (DIN) from a serial bit stream, and strip off the data relative to the components under its control (e.g., multiplex switch units, triacs, transistors, etc.). These components may, for example, maintain the application or detection of electrical signals to/from the skin of the user. The number of electrodes that are serviced by a single TENS unit and/or a single EMG unit can be very large, tens, hundred or even thousands of individually addressable electrodes can be serviced by the single TENS unit or EMG unit under the control of the microprocessor. A full system (e.g., a full haptic suit) may be constructed, for example, where a large number of electrodes on leggings are separately control and serviced a relatively smaller number of TENS and/or EMG units. A torso suit may have a separate configuration of electrodes, control circuitry etc., with the two wearable garments, the leggings and the torso suit, synchronized through a central CPU.

The electrodes may be individually addressable so that when in the on-state a direction of current flow of the applied electrical signals can be selectively at least one of positive or negative. The biological component may comprises a component of at least one of a muscle, nervous, lymphatic, organ, skin, sensory and other biological system of the user. The electrode may be individually addressable in accordance with pulse width modulation so that the effective electrical energy of the applied electrical signals flowing through the at least one electrode to the biological component can be independently reduced relative to the applied electrical signals without pulse width modulation. The response of the muscle and nerves will tend to integrate an applied pulse electrical signal.

Another electrode of the plurality of electrodes may be individually addressable in accordance with pulse width modulation so that the effective electrical energy of the applied electrical signals flowing through the other electrode to the biological component is different than the effective electrical energy of the applied electrical signals flowing through the first electrode to the biological component. This enables different areas of the biological component to receive different effective electrical energies of the same applied electrical signals. A portion of the plurality of electrodes may be selectively driven as groups forming an electrode pattern conforming to a target area of the biological component.

Transistors can be used to switch a haptic signal under the control of a controller. The controller is in turn controlled by a microprocessor. The control and microprocessor can be integrated together, or separated elements. For example, the microprocessor can be a smart phone or other readily available electronic device, or it can be a dedicated device. The controller may be a small integrated circuit device that is associated with an electrode or group of electrodes and disposed within flexible circuit layers of the HHMI. The electrical signals may be applied as haptic sensory cues received by the user as computer controlled serially generated electrical signals.

The electrical signals invoke may invoke at least one of an involuntary body part movement having a predetermined motion dependent on the computer controlled serially generated electrical signals and a perception having a predetermined touch sensation dependent on the computer controlled serially generated electrical signals.

In a medical use example, the onset of an involuntary tremor motion is detected in a body part (e.g., a Parkinsonian arm/hand tremor) by amplifying the electrical activity in the muscles and nerves. This detected electrical activity is then used to determine the characteristics of an electrical signal that is then applied back to the muscles and nerves to mitigate the tremor motion. The electrical signals are detected and transmitted through surface contact with the skin, the product is a wireless, wearable electronic, with no chemicals or invasive and dangerous procedures.

Using a driver, such as WS2812 also provides an advantage in that software and circuit devices, such as the Arduino, can be readily adapted for the HHMI use speeding the development and providing the potential for open source advancements. The electrical circuits may include regulators to ensure that the electrical signal applied is always within a safety constraint. As another similar example driver, the WS2811 8-bit PWM driver controls three LED (RGB) channels (total of 24 bits) and provides a potential integrated circuit that has a construction and functionality useful for illustrating some of the inventive concepts of the electrical circuits shown herein. The use of these example drivers is for illustrative purposes, there being other discrete electronic and integrated solutions that could be used.

Like persistence of vision, the detected and applied signals can be samples that are representative of muscle activity/detection and pulses that are effective to cause precise involuntary muscle pulses that appear smooth. The applied signal can be as complex as necessary so that, for example, a varying PWM pulse can be applied at varying effective strengths to nearly instantaneously varying locations and surface areas of the user's skin.

The haptic sensory cues may stimulate a somatosensory system of a user comprising at least one receptor including thermoreceptors, photoreceptors, mechanoreceptors and chemoreceptors to cause the user to perceive an experience of at least one of proprioception, mechanoreception, thermoception, and nociception. The haptic sensory cues may be generated in synchronization dependent on time sequential data. The electrical signals simultaneously stimulate both the involuntary body part movement and the perception by the user related to the sense of touch.

Haptic electrical signals can be applied having a complex electrical characteristic having varying effective electrical energy applied as pulses at specific electrodes to cause precise movements and perceived sensations. The same electrodes can be used to apply the electrical signal generated by the controller or microprocessor and to detect the myographic data. The microprocessor controls the electronic circuit so that the haptic signals are selectively applied to the electrodes, and the myographic data are selectively detected from the same electrodes.

The HHMI has many small electrodes that are individually addressable to form localized groups conforming to the correct location and size of the patient's body to optimally apply precisely targeted electrical signals and control subtle movement, such as finger, arm and hand movements. As shown the same electrodes that apply the computer-generated signal, using a different addressing scheme that may include ground or reference (REF) electrodes positioned at bony parts of the arm, are locally group by the driving circuitry and software to form detection regions at isolated muscles and nerves.

The use of the HHMI technology as the membrane between man and machine has application for swarming UAVs. For example, a number of squadrons of drones can go out on patrol of a wide area conflict zone with hotspot potentials. Each squadron can be commanded by a respective remote-from-the-battlefield soldier who controls a master drone with the rest of the drones in his squadron flying semi-autonomously along side the master in formation. When a hotspot is identified, this squadron of drones is in place for other soldier-pilots to jump in and take command of an individual drone so that each drone in the squadron is immediately in place and now has the human "wetware" interfacing the remote drone for focused control and an orchestrated response to the hotspot. The other soldier-pilots can be the other squadron operators (who may leave their drone squadrons hovering, or put them into auto-pilot to rally to the hot spot) or additional personnel located at a geographically remote area(s).

For example, the HHMI/VR First Person View will put a remote operator in control of a very close range drone (relative to the bad guys) with the situational awareness at the level of total VR immersion. Combine this with the solder-operator squadron. The solder-operator is like a cat with nine lives if he commands a squadron of 9 semi-autonomous drones. The MVP focus remains since we have to solve the problem of the HHMI membrane (the HHMI wearable electronic garment is built upon the dry electrode insert of the pain mitigation sleeves).

Figure 44A:
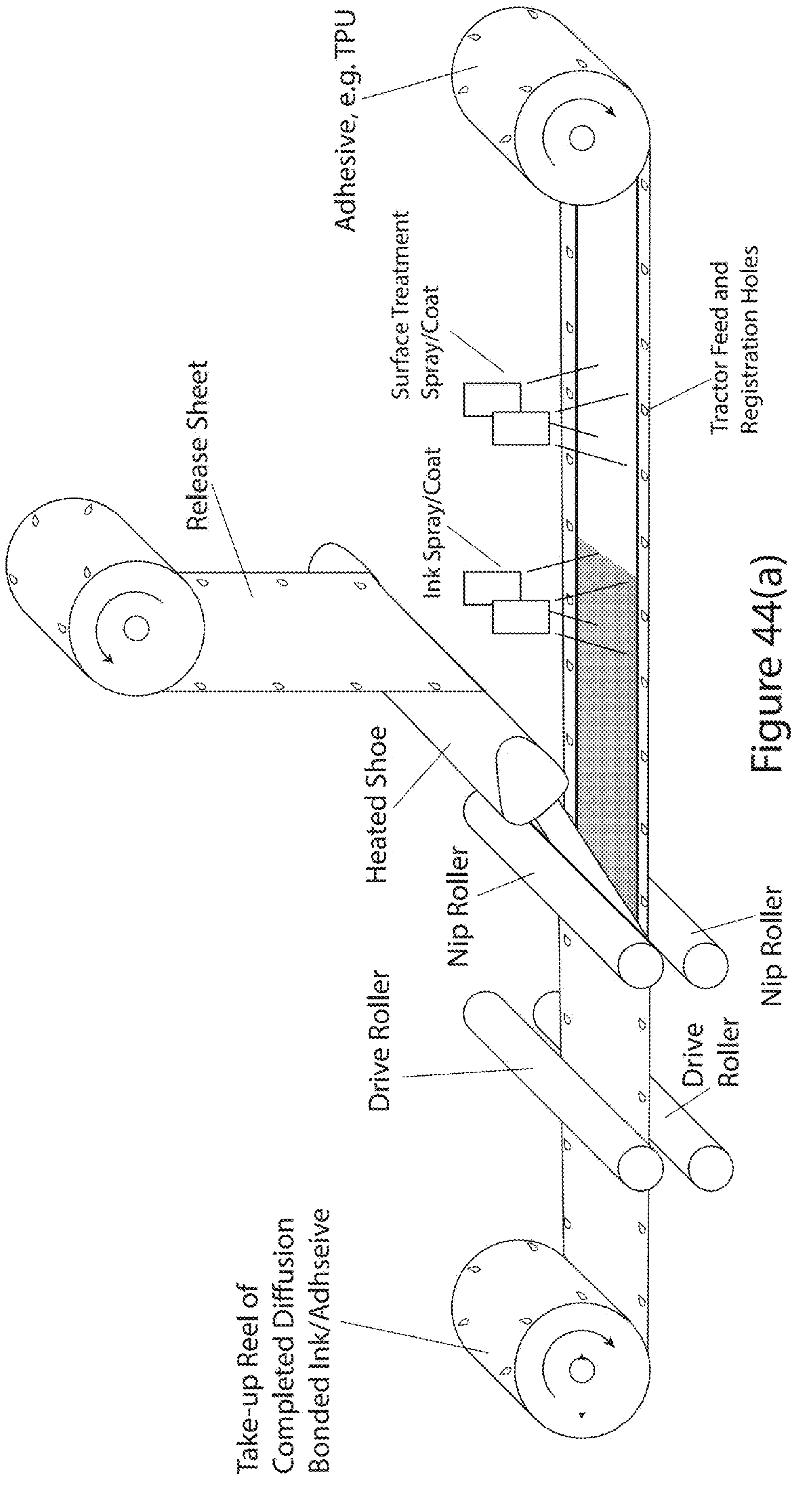
FIG. 44(*a*) illustrates a roll-to-roll manufacturing process for manufacturing a robust exposed electrode materials using a print media surface pre-treatment, an elastic ink printing, and a heat and pressure post-treatment FIG. 44(*b*) illustrates a roll-to-roll manufacturing process for making a robust exposed electrode formed as a patterned elastic conductive ink on TPU adhered to fabric.
Figure 44B:
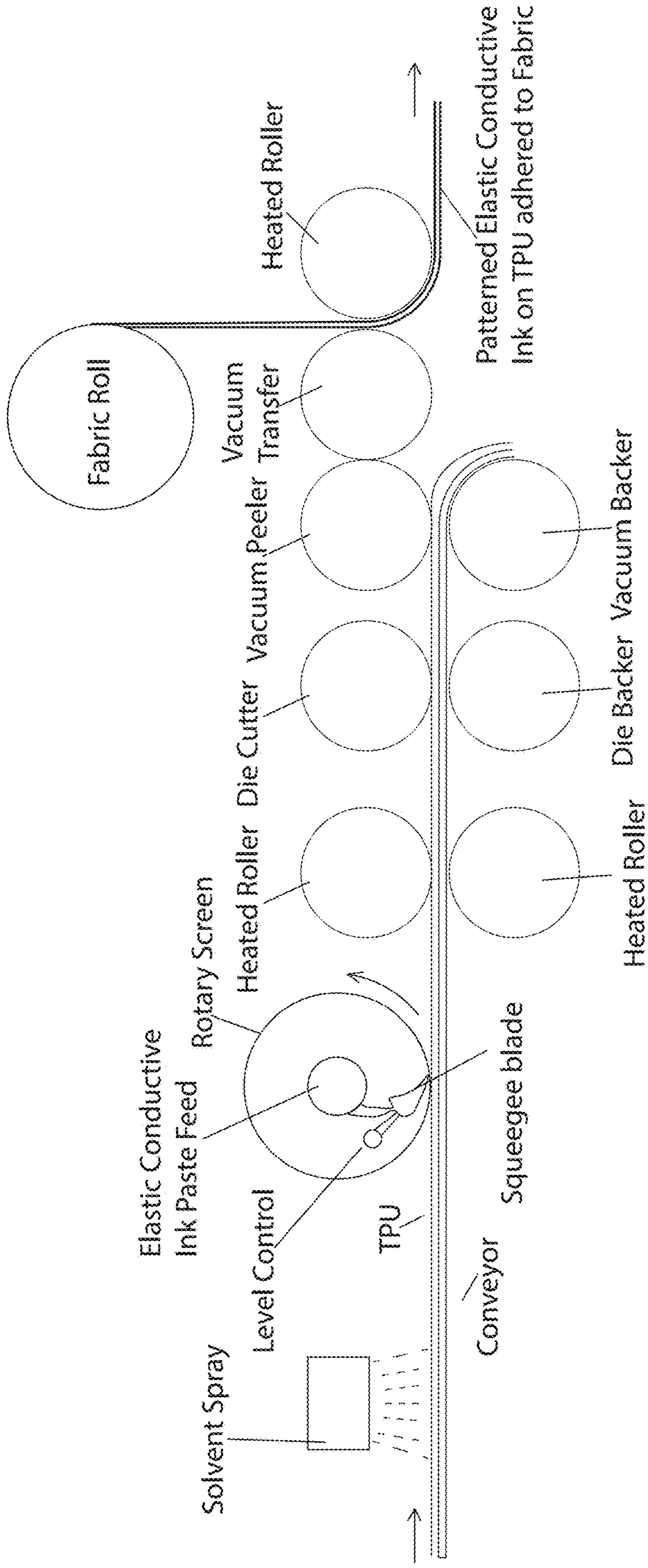
Figure 44C:
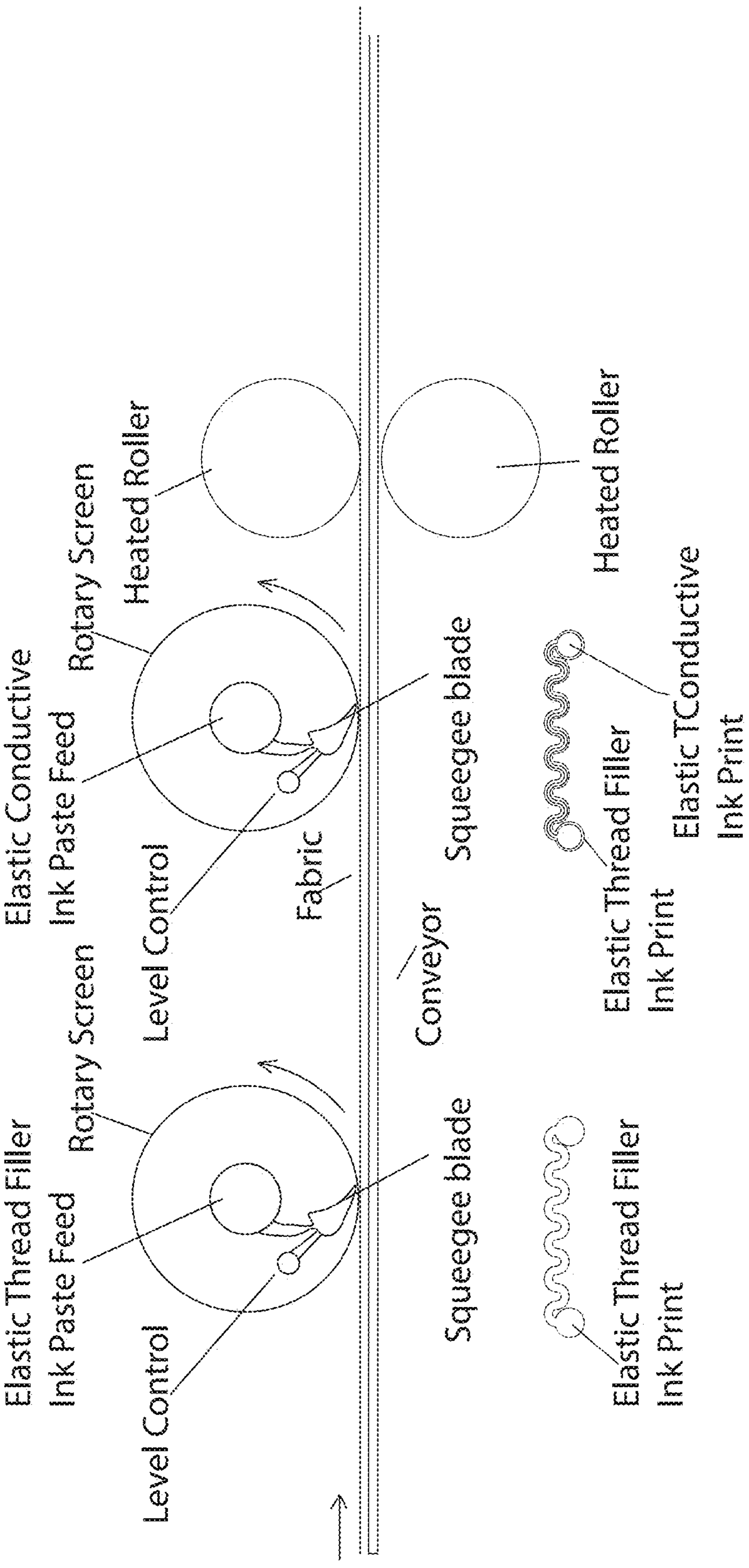
Figure 45:
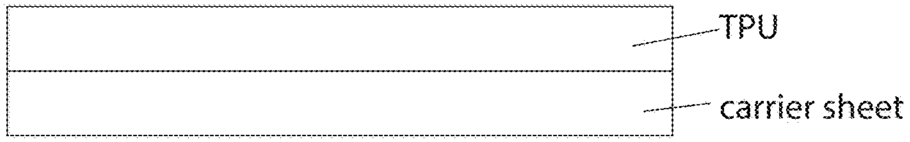
FIG. 45 shows a step in the process of forming a robust exposed electrode showing the step of providing a TPU print media on a carrier sheet.
Figure 46:
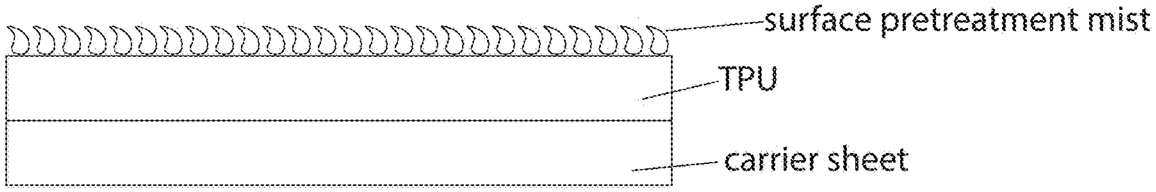
FIG. 46 shows a step of pre-treating the top surface of the TPU print media using a solvent mist.
Figure 47:
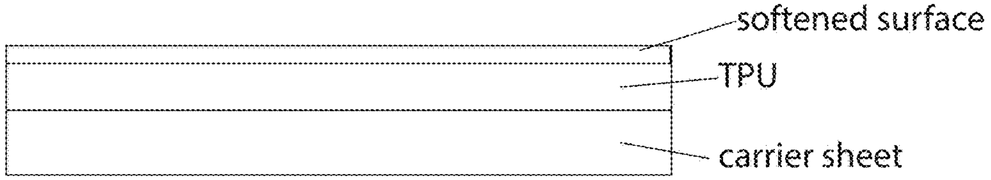
FIG. 47 shows a step of the pre-treatment creating a softened top surface of the TPU print media.

FIG. 44(*a*) through 53 show exemplary embodiments of methods of making an electrode for a wearable electronic. An adhesive print media layer is provided. A surface treatment is performed to a top surface of the print media layer. An elastic conductive ink is deposited onto the print media layer. The elastic conductive ink comprises a conductive particulate disposed in a binder. A diffusion bond is formed between the top surface of the print media layer and the elastic conductive ink. The diffusion bond forming is facilitated by the surface treatment.

The adhesive print media layer can be provided as a roll of material on a carrier substrate. Performing the surface treatment to the top surface, depositing the elastic conductive ink and forming the diffusion bond may be done sequentially in a roll-to-roll process. The surface treatment may comprise at least one of heat and solvent softening of the top surface of the print media layer. The diffusion bond can be formed by at least one of a heat treatment and a pressure operation. The diffusion bond can be formed at a heat treatment temperature above 95° C.

At least one of the surface treatment and depositing can be done using at least one of a spray coating, dip coating, screen printing, rotary screen printing, rotogravure printing, off-set printing and digital printing. The diffusion bond can be formed at a heat treatment temperature above the softening point of the adhesive print media layer. The diffusion bond can be formed at a heat treatment temperature between 110° C. and 165° C. and a pressure between 2.8 bar and 4.2 bar. The surface treatment may comprise softening the top surface and the diffusion bond is formed by pressing the binder and conductive particulate into the softened top surface under heat and pressure.

The surface treatment may comprise applying a solvent to top surface, allowing the solvent time to soften a thickness of the top surface effective for a portion of the binder and conductive particulate of the elastic conductive ink to infiltrate into the thickness of the top surface during the step of forming a diffusion bond. The diffusion bond can be formed using a heated roller with a roll surface temperature between 225° C. and 325° C., a roller pressure of at least 1.5 bar and a speed of the print media layer passing through the heated roller between 1.0 m/minute and 1.5 m/minute.

The solvent may comprise an organic solvent, and may be selected to achieve a relatively lesser degree of solvation with relatively greater swelling of the top surface. Alternatively, the solvent may be selected to achieve a high degree of solvation of the top surface. The solvent may include at least one of Dichloromethane (CH2 Cl2), Dimethyl formamide (C3H7 NO) and Methanol (CH3 OH). As described in U.S. Pat. No. 4,383,867, which is incorporated by reference herein, a solvent mixture that achieves a relatively lesser degree of solvation with relatively greater swelling of the top surface of the adhesive print media may include by Ingredient Percent by Volume: Dichloromethane (CH2 Cl2) 70%; Dimethyl formamide (C3H7 NO) 20%; and Methanol (CH3 OH) 10%. The adhesive print media layer may comprise a polyurethane, and may include a polymer chain including ethyl carbamate C3H7NO2.

Similarly to the description of a roll-to-roll manufacturing process described above an electronic device, such as a sensor, active or passive electronic circuit element, packaged or bare die electronic device, touch sensor, chemistry sensor, heat sensor, pressure sensor, heart beat monitor, blood oxygen sensor, or other sensor, transducer, or electrical circuit element described herein or otherwise available, may be embedded in an encapsulating adhesive layer and in electrical communication with the elastic conductive ink. The encapsulating adhesive layer is provided on the diffusion bonded elastic conductive ink. A predetermined pattern of semiconductor devices is fixed to the encapsulating adhesive layer. As an example of a vertical electrode arrangement, the semiconductor devices can each have a top device conductor and a bottom device conductor. As an example of a horizontal electrode arrangement, the semiconductor device has conductors on the top or bottom of the device.

A top substrate having a conductive portion disposed thereon can be provided to form a lamination package comprising the elastic conductive ink fusion bonded to the adhesive print media layer, the encapsulating adhesive layer, and the top substrate. As an example of connecting the electrodes of a vertical electrode arrangement semiconductor device, the lamination package may be driven through a roll or press laminator whereby the encapsulating adhesive layer insulates and binds the top substrate to the adhesive print media layer so that one of the top device conductor and bottom device conductor of the semiconductor devices is brought into electrical communication with the conductive portion of the top substrate, and so that the other of said top device conductor and bottom device conductor of each said semiconductor element is in electrical communication with the elastic conductive ink. Examples of a similar roll-to-roll bare die lamination process is described, for example, in U.S. Pat. Nos. 7,052,924, 7,217,956, 7,259,030, 7,427,782, 7,677,943, 7,723,733, 7,858,994, 7,863,760, 7,952,107, 8,129,730, which are incorporated by reference herein.

Figure 54:
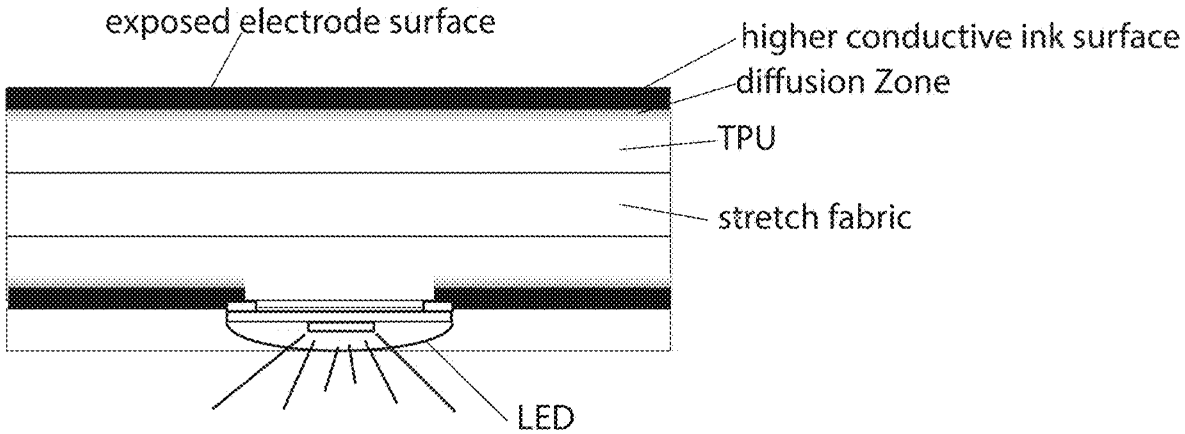
FIG. 54 shows a configuration of a robust exposed electrode facing inwards towards the skin of a user and adhered to a stretch fabric with an embedded LED adhered to the stretch fabric and facing outward from the skin of the user.
Figure 55:
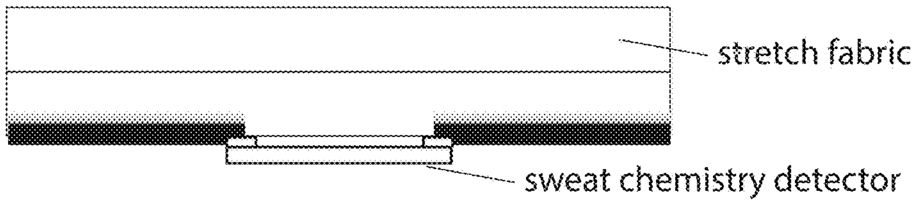
FIG. 55 shows a configuration of a robust sweat chemistry detector fixed to printed electric leads formed from a elastic conductive ink diffusion bonded to a TPU print media and adhered to a stretch fabric
Figure 56:
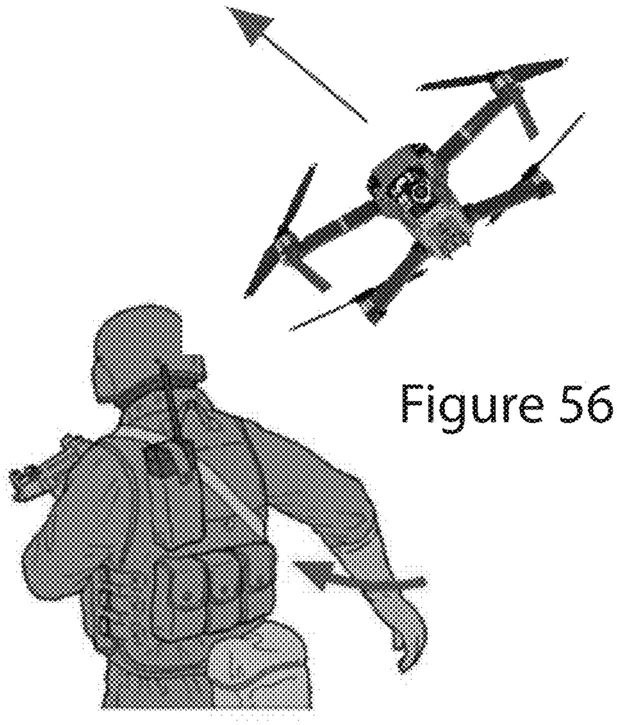
FIG. 56 illustrates a use of the HHMI configured for determining control intentions from silent communication hand and arm signals.
Figure 57:
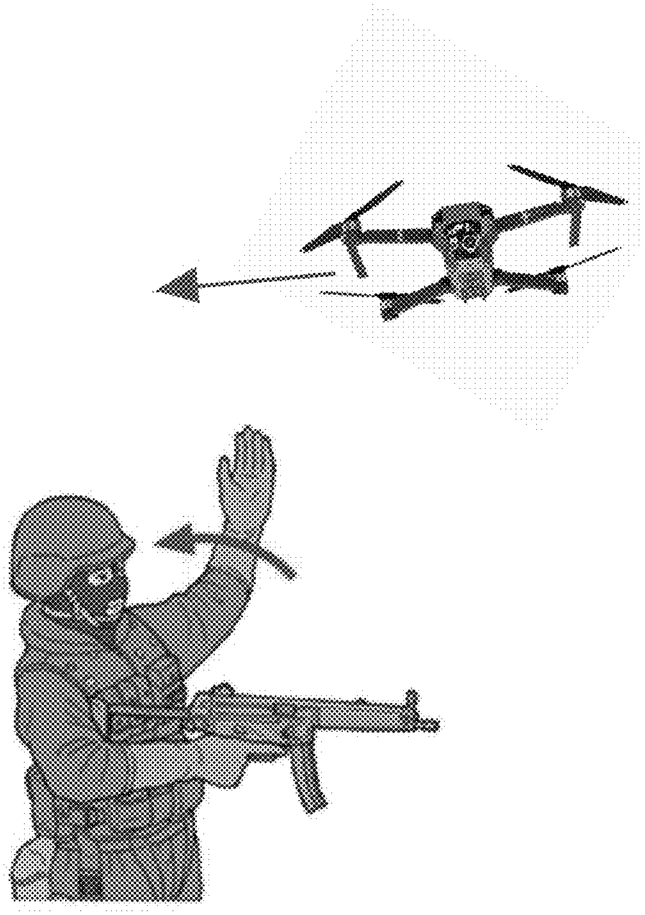
FIG. 57 illustrate the use of the HHMI configured for determining control intentions from silent communication hand and arm signals.
Figure 58:
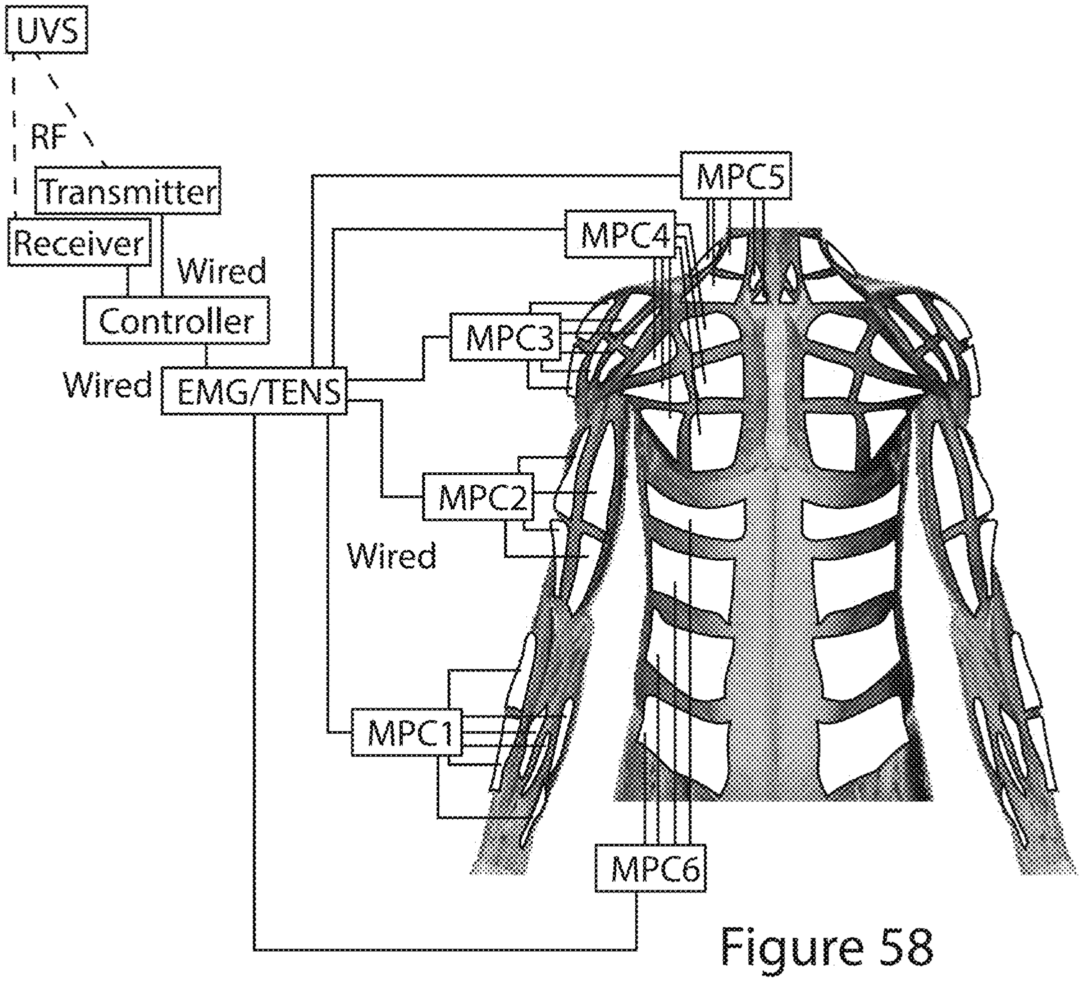
FIG. 58 illustrates a configuration of the HHMI as a SmartShirt™ having individually addressable electrodes configured and dimensioned relative to the underlying muscles of the user.
Figure 59:
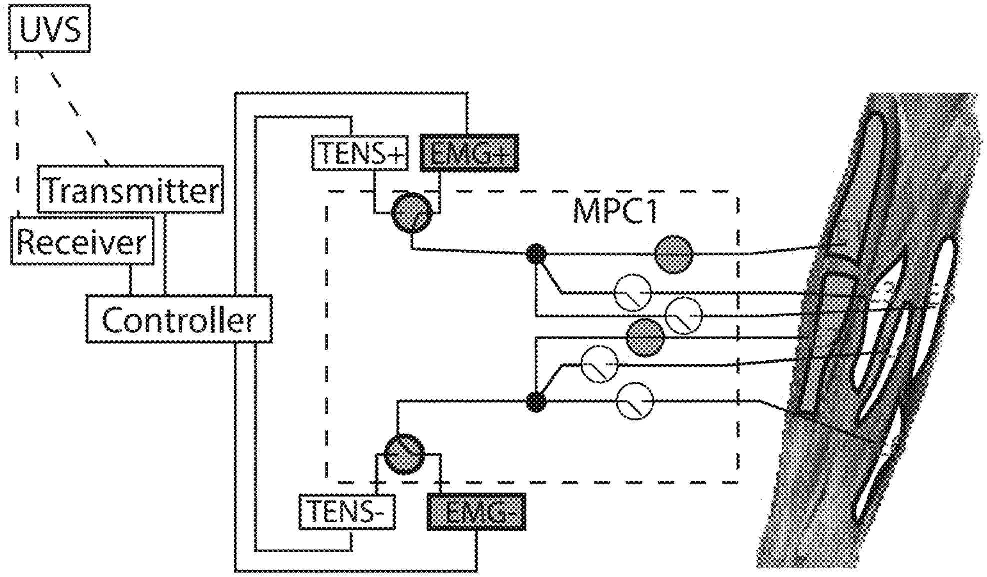
FIG. 59 is a detailed view showing a multiple plex circuit connected to a number of individually addressable electrodes on the forearm of the user.
Figure 60:
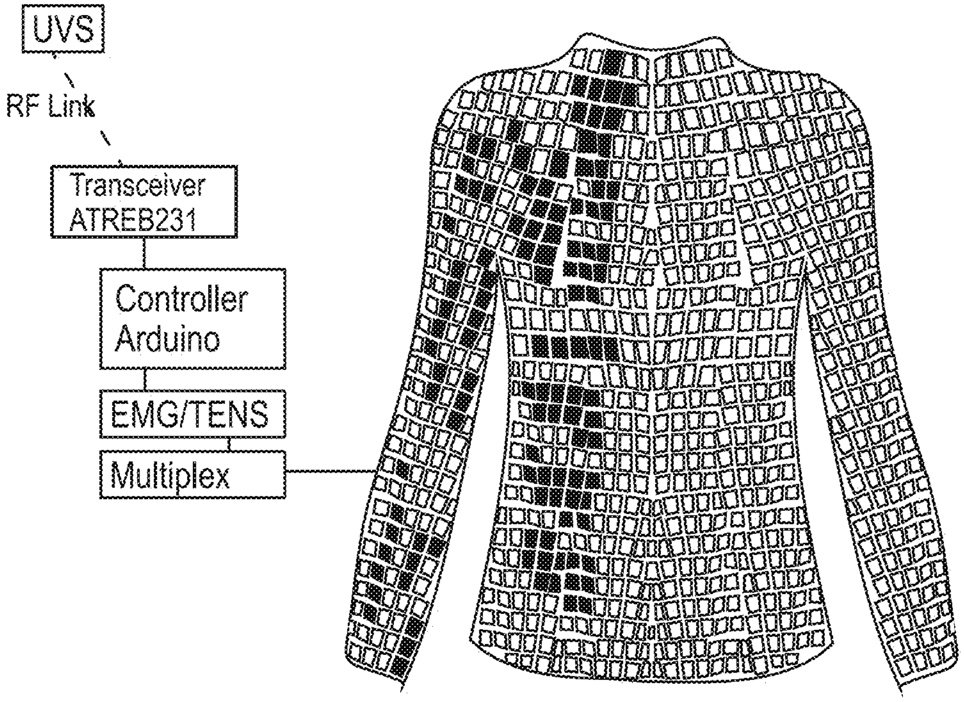
FIG. 60 shows the HHMI configured as a SmartShirt™ with a large number of individually addressable electrodes connected to EMG detector(s) and TENS signal generator(s) through a multiplex circuit under the control of a microcontroller.

FIG. 54 shows a configuration of a robust exposed electrode facing inwards towards the skin of a user and adhered to a stretch fabric with an embedded LED adhered to the stretch fabric and facing outward from the skin of the user. FIG. 55 shows a configuration of a robust sweat chemistry detector fixed to printed electric leads formed from a elastic conductive ink diffusion bonded to a TPU print media and adhered to a stretch fabric. FIG. 56 illustrates a use of the HHMI configured for determining control intentions from silent communication hand and arm signals. FIG. 57 illustrate the use of the HHMI configured for determining control intentions from silent communication hand and arm signals. FIG. 58 illustrates a configuration of the HHMI as a SmartShirt™ having individually addressable electrodes configured and dimensioned relative to the underlying muscles of the user. FIG. 59 is a detailed view showing a multiple plex circuit connected to a number of individually addressable electrodes on the forearm of the user. FIG. 60 shows the HHMI configured as a SmartShirt™ with a large number of individually addressable electrodes connected to EMG detector(s) and TENS signal generator(s) through a multiplex circuit under the control of a microcontroller;

Hand and Arm signals are used by the military for communication between personnel when a radio silence is in effect or when there is a need to remain undetected. Through the use of hand signals, military leaders, such as team leaders, squad leaders, platoon leaders, etc., keep command and control over their particular element and event. New recruits are taught to use the proper hand and arm signals found in the field manual. However, it is not uncommon for units to adopt and/or create their own signals. These signals ultimately become a standard operating procedure (SOP).

The HHMI can be configured as a wearable electronic that effectively uses the naturally occurring electrical signals of the human body to determine the control intentions from the movement and position of a user's hands and arms.

As shown, for example, in FIGS. 58-60, the HHMI includes a high-speed multiplex circuit drives a densely populated high-resolution array of individually addressable electrodes. The HHMI provides the critical interface between "man and machine", enabling a host of patented and patent-pending applications for fitness, healthcare, drone control, virtual reality, gaming, military, sports training, big data collection and analysis. The HHMI can be configured, for example, for intuitively controlling a semi-autonomous unmanned vehicle using the military's hand and arm signals.

HHMI is configured as a light weight, wireless, high resolution electrical signal sensing/applying wearable electronic for the detection of the operator control intentions (for example, to control a robot's flight) and for the application of enhanced haptic cues (for example, to experience the robot's flight conditions). The interface is in the form of a comfortable, easily worn garment that the operator wears with limited weight and bulk, and very little restriction of movement.

The HHMI is made from a multilayered, flexible and light weight structure. The layers of the HHMI include compression layers that bias inward and wraps around an object, such as an arm, when configured as a sleeve, or the operator's back, shoulders, stomach and torso when configured as a shirt. The HHMI may thus be configured as a wearable electronic with the individually addressable electrodes urged into effective face-to-face electrical contact with the skin of the operator.

The HHMI may be constructed as a conformable, comfortable, but fairly tightfitting garment to hold the electrodes in direct face-to-face electrical contact with the skin. The HHMI is used to apply electrical stimulation through the skin to provide haptic cues, and to detect EMG signals from the muscles and nerves beneath the skin.

A plurality of individually addressable electrodes are supported by a stretch fabric base layer that places the electrodes in direct face-to-face contact with the skin. The individually addressable electrodes are capable of applying stimulation electrical signals to skin of an operator and detecting biometric electrical signals from the skin of the operator. A signal detector (EMG Sensor Module) detects the biometric electrical signals and a signal generator (TENS Signal Module) generates the stimulation electrical signals. An Electrode Multiplex Circuit addresses the plurality of individually addressable electrodes by routing the biometric electrical signals from the skin of the operator through the individually addressable electrodes to the signal detector and routing the stimulation electrical signals from the signal generator through the individually addressable electrode to the skin of the operator. A microprocessor controls the signal detector, the signal generator, and the electrode multiplex circuit.

The HHMI can be configured as a SmartShirt™ with a number of Individually Addressable Electrodes (IAE) in contact with the skin and located and dimensioned relative to the underlying muscles. The IAEs are formed using a Robust Exposed Electrode Printing (REEP™) process and applied to the fabric of the HHMI garment through a heat press lamination process. In the REEP™ process, a stretchable conductive ink (e.g., DuPont's PE971) is printed onto a pre-treated Thermoplastic Polyurethane (TPU) adhesive substrate, the printed TPU is then subjected to heat and pressure to cure the printed ink and form a robust diffusion bond between the ink layer and the TPU substrate.

Groupings of IAEs are associated with a respective Multiplex Circuit (e.g. MPC1). The connection from the IAEs to the MPCs is through conductive leads printed and/or sewn into the HHMI garment. The conductive leads are integrally connected with the IAEs and terminate in female snap connectors. The MPC is connected with its associated group of the IAEs through mating male snap connectors.

As shown in more detail in the FIG. 59, the EMG/TENS module is connected to each MPC through a relay controlled by a microcontroller (Controller). The green colored elements denote the path of EMG signals detected from the operator's brachioradialis muscle which causes the forearm to bend at the elbow. The connection from the MPCs to the EMG/TENS module is wired, as is the connection from the EMG/TENS module to the Controller (which may be contained within a small housing attached to, for example, the lower back portion of the HHMI garment). As shown, each MPC is a series of solid state relays (or other circuit equivalents) that route the signals to/from the human body, and from/to the TENS module and the EMG module. Under the control of the Controller, the MPC routes the signals so that the EMG generated by the motor units causing each particular muscle to contract can be detected by the EMG module. In this way, the HHMI significantly reduces cost, power, bulk, weight and failure modes since one EMG module can service multiples of the IAEs (similarly, the TENS module is multiplexed with multiple IAEs).

The Controller includes the electronics, memory, software and hardware necessary to analyze the detected electrical signals and determine the control intentions of the operator. These control intentions are converted into the appropriate signals and transmitted from a Transmitter through a Radio Frequency (RF) link to a remote Unmanned Vehicle System (UVS). The Contoller also includes the HW/SW necessary to receive telemetry from the UVS and convert the received signals into appropriate haptic feedback applied as a TENS signal routed through the MCP and IAEs to the skin of the operator.

Using the HHMI wearable electronic garment, the determination of the control intentions of the operator is achieved through the detection of the EMG signals that correspond to a particular hand and arm signal. Accelerometers and IMUs can also be employed to increase the accuracy of the determined control intention.

The flight of a semi-autonomous drone can be controlled and moved into position using hand signals that are the same or similar to those used for conveying silent information between human soldiers. In the case of the drone control, only the signals that are relevant to the remote control of the unmanned vehicle will be detected and analyzed. As an example, a sweeping motion of the hand and arm that silently conveys "move forward" generates particular EMG signals coming from the muscles and nerves of the operator's shoulder, upper arm and forearm. The HHMI captures the EMG signals, determines which muscles are generating them along with other indicators of a control intention such as motor units recruitment and signal intensity. From this detected EMG data, the silent control intention of "move forward" is determined. A transceiver sends the appropriate RF signals to the drone, indicating that the drone is to "move forward."

In addition to the use of controlling an UVS based on intuitive hand and arm signals, as a source of haptic feedback during flight, electrical stimulation can be applied through the skin using the same IAEs that are used for EMG detection. The feedback can create a slight or more intense urging sensation, that urges the operator to move a body part, such as his arm, to a desired position. The desired body position can be related to a sensed parameter, such as flex, rotation, tilt, pitch, yaw, temperature, vibration, and other detectable stresses or conditions of a mechanical component (wing, fuselage, control surfaces, etc.) of the UVS. The sensed parameter could be air pressure experienced at a wing control surface while maneuvering. The sensed parameter is transmitted from the drone causing a computer controlled TENS cue (electrical stimulation) resulting in an auto-action response in the hand of the operator feeling pressure to assume a position directly related to the drone's control surface. The pressure to move the hand is the result of muscle movements caused by the TENS cue. The operator experiences the sensation of resistance or pressure because of the computer controlled electrical signals applied to the operator's own sensory/muscular physiology. In addition to pressure and resistance, the physical sensation of vibrations, knocks and even scratches can be perceived as the result of transcutaneous computer generated electrical signal stimulation. The muscle movements and touch sensations are involuntarily and automatic. There are no mechanical force simulators involved, although there can be.

In addition to the use of controlling an UVS based on intuitive hand and arm signals, the HHMI undergarment can be worn by an operator for adding a new layer of perception during, for example, a combat situation. Typically, the visual and auditory senses of a warfighter are saturated during the high intensity of a combat situation. The HHMI undergarment can add a new way to convey information to the warfighter using tactile information that can be a supplement to the audio and visual information being received. The tactile information may be, for example, an indication of the location of a rallying point. The location of an enemy, such as by detecting a muzzle blast, can be sensed, for example, using audio sensors that are tuned to detect the muzzle blast, and the direction of the enemy can be conveyed using the HHMI undergarment, through a haptic sensation or even by causing an involuntary turning or urging of the warfighter. Sensors and transmitters or other data links can be used as well to convey details about the warfighter's physical condition including heart rate, blood pressure, body temperature and other vital signs and health related conditions.

The HHMI opens new avenues in human/machine interaction and control, that also impacts areas of accelerated learning, physical training and rehabilitation. The ability to identify muscle groups at a sufficient level of definition, and the ability to apply electrical signals at a similar level, enables an HHMI system in which previously-known actions and muscle movements could be developed for improved physical training and correction of physical motion. Muscle memory associated with nearly all kinds of human activities can be more quickly developed to learn, for example, a musical instrument or sport technique. For military applications, beyond the robotics and drones, rapid muscle memory buildup enhances training in basic and advanced weapons use. Additionally, new forms of safety restraints could be imagined in which the human operator is prevented from taking an action that may result in injury or a catastrophic vehicle accident.

In the case of military drones, it is desirable that the operators be given much time at the controls of the remote drone in order to learn the subtleties of remote controlling a drone or robot. For example, in the case of a flying drone, the operators can be provided with a flight simulation so that the cost and time involved in flying an actual drone is avoided. The operator can also be given a more immersive experience without having to fly the actual drone. In this case, the operator may use a recorded actual drone mission, and receive haptic, visual and audio cues that replicate the experience of the remote drone operator during the actual mission. The actual mission can include a predetermined course, so that the operator knows what to anticipate before the haptic audio and visual cues are applied.

The SmartShirt™ is designed and constructed to be a modular unit and communicate with external devices through wired or radio frequency links. As a Controller used for the prototype SmartShirt™, the Arduino Uno RB-Ard-83 Microcontroller and integrated WiFi board is a good design choice and is included here as an exemplary microcontroller. There are other microcontrollers available, and different functionalities may be divided among two or more controller units, some located attached to or embedded in the HHMI wearable electronic, and others in communication, for example, through an RF or wired link, to the wearable electronic.

As an example EMG detection, the MPC1 shown in more detail in FIG. 58 and FIG. 59 is associated with the brachioradialis muscle samples an EMG signal indicating that the operator has cased his forearm to bend at the elbow, and IMU and accelerometer sensors indicate that the movement and position of the operator's hand indicates the signaling of a "move forward" hand and arm signal. The EMG detection is received from the EMG module as a voltage signal on a pin(s) of the Arduino which then controls the transceiver to send an appropriate control signal to a remote UVS, telling the UVS that the operator has signaled the "move forward" command.

As shown in FIG. 60, the link between the Arduino Microcontroller of the SmartShirt™ and the UVS may be in the 2.4 GHz band to be consistent with most radio-control system providers. There is a multitude of single-chip receivers, transmitters, and transceivers available. FIG. 60 shows the HHMI configured as a SmartShirt™ with a large number of individually addressable electrodes connected to EMG detector(s) and TENS signal generator(s) through a multiplex circuit under the control of a microcontroller. All critical data must be acknowledged and the established protocols with ack/nack used to assure error-free delivery of packets when conditions permit. 2.4 GHz protocols have higher bandwidth data rates and allow audio and video streams independent of control links. This may be used advantageously during rapid prototype iterations, for example, where various COTS chipsets and hardware/software solutions can be used so that audio and video links are streaming concurrently with control and status information on different channels.

The availability of Wi-Fi tablets, smartphones, laptops, and notebooks also make the 2.4 GHz bands desirable since a reliable and low-cost control platform is readily available on most smartphones. An app can be your controller. ZigBee remote controls can also be used as low-cost testers.

As an example solution, the Atmel AT86RF231-ZUR, is a small 32-pin dedicated transceiver that can be used for 700, 800, 900 MHz and 2.4 GHz designs. Atmel's ATREB231FE2-EK Reference Design provides details to start designing the system.

Figure 61:
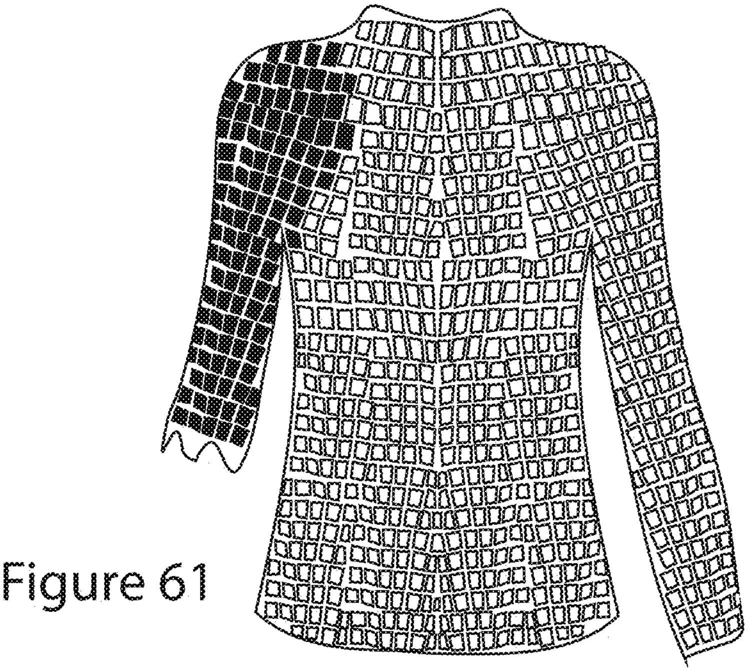
FIG. 61 shows the HHMI configured as a SmartShirt™ having rapid blood loss detection capability, and auto-tourniquet capability provided by application of TENS signals to the muscles above a catastrophic injury resulting in sudden blood loss.

Stopping Blood Loss: FIG. 61 shows the HHMI configured as a SmartShirt™ having rapid blood loss detection capability, and auto-tourniquet capability provided by application of TENS signals to the muscles above a catastrophic injury resulting in sudden blood loss. Another use of the HHMI with embedded devices can include detecting blood loss from an inflicted wound on a limb of the user, and stopping or slowing the blood loss through an action similar to the application of a tourniquet. The HHMI can include a traumatic injury detector that includes, for example, monitoring for a drop in blood pressure in combination with an excessive detection of moisture. A moisture sensor can be associated with one or more of the individually addressable electrodes so that the location of a particular moisture sensor can be determined. In this use, the HHMI may be configured as an undergarment and can include a selectively constricting mechanism, such as pneumatic cuffs, located at the upper arm and upper thigh. When an indication is received that an injury has been sustained that may result in critical loss of blood (e.g., detecting a drop in blood pressure along with excessive moisture), the location of the excessive moisture is determined. If the location is determined to be at a limb where pressure applied to an artery will slow the loss of blood, a microprocessor controls the pressurization of a pneumatic cuff located to put pressure on the artery and slow the loss of blood from the detected wound. A kill switch can be included so that the user or responder can quickly release the pressure in the pneumatic cuff.

Humanistic intelligence is a new scientific breakthrough where the wearer and the computer with its associated input and output facilities are not seen as separate entities; The computer is treated as a second brain and its sensory modalities as additional senses, in which synthetic synesthesia merges with the wearer's senses. A soldier on a battle field can be kept safer, and kept in prime fighting condition, during battle, by applying humanistic intelligence to the HHMI (Haptic/human machine interface).

The smart HHMI includes addressable electrodes deployed all over the soldiers body, as a body tight outfit containing and being controlled by a micro-processor, with enough power to detect, analyze, and react to situations a soldier entering, or in, battle will experience, and to intervene on the soldiers welfares behalf. The problem this application will be addressing is a soldier cannot, as a physiological being, always control his or her emotions, or thoughts. There are times when those emotions or thought trends are at odds with the soldiers well being in so far as the soldier could be stated to be/or not to be, at a perfect level of awareness, keenness, sharpness for battle, also loosely called "battle readiness." For instance a soldier experiencing extreme fear or anxiety would likely be in a lesser state of battle readiness than a soldier who remains calm.

Yet the only choices that soldier has for dealing with his anxiety, which could become a panic attack and thus not only poorly effect but destroy his battle readiness, would be to retreat, to stop during battle to inject an anti-anxiety drug into himself, or to have a medic trailing beside each soldier with a device telling the medic what the soldiers system needs in order to equalize.

Another benefit to be disclosed made possible by the HHMI membrane covering the soldier's body is a smart tourniquet, a HHMI wide (body wide) function able to detect, analyze and react to a wound of any magnitude sustained by the soldier. Again, until now a wounded soldier has the following options: He can get himself (magnitude of wound allowing) to safety where a battle field medic can stop blood loss and perform other beneficial actions such that the soldiers life is saved. If the wound is too severe, other soldiers must react to the wounded soldier's need by leaving battle to carry or otherwise transport the soldier to a safe zone, where again a medic would take whatever steps were needed to save the soldiers life.

The problems with the above scenarios are many. Although the soldier would expectedly have some simple medical knowledge about his condition, the shallowness of that knowledge coupled with the shock of the wound makes him a poor choice as caregiver after receiving a wound of any sort. Second, he can be expected to think less than clearly amid the shock of being wounded, and the chaos of the battle field. His condition also takes out at least one other healthy soldier (one who is not wounded and thus able to think without pain or distraction in any way comparable to the wounded soldier) out of action, while getting the wounded soldier to safety.

Third, for the same reasons as the wounded soldier, the unwounded soldier is not the best choice for battlefield medical attention. Basic tourniquet application has not changed much in the past century, at least as far as when applied on the battlefield.

However, a body wide smart membrane, analyzing biometric data from the soldiers body as well as data available to it by being in contact with the soldiers skin, and with a DB either in a cloud that the HHMI can wirelessly access while in battle for consultation and comparison, as well as an on board mini DB should wireless go down, makes the HHMI the perfect defensive weapon, whose main purpose is to keep the soldier healthy and more importantly a survivor of a battle. It does this by allowing the soldier to stay at the highest state of battle readiness while battle worthy, and if the soldiers condition is determined to be less than battle worthy, allows him to extract himself alone, without straining those soldiers still in battle worthy conditions, without removing soldiers still healthy from the fighting, and giving the soldier who has become less than battle worthy through wounds or other conditions the BEST chance of escaping to safety, for treatment.

In accordance with the present invention, the HHMI will analyze the soldiers bio metrics. A high heart rate coupled with sweating and perhaps certain brain waves are detected, and the HHMI will categorize these bio metrics into a "condition," such as anxiety, nausea, fear, frenzied, low energy, etcetera and then the HHMI will calculate a dose of a drug meant to equalize, or bring back under control, the detected undesirable condition. To keep the soldier in battle readiness, the HHMI will then instruct a built-in panel of needles to flip from a flat position to a vertical one, and then the HHMI will constrict, the constriction both forcing the needed drug to be pushed up the needle and also causing the needle to puncture the soldiers skin such that the drug is delivered into a muscle group causing near immediate effect.

Alternatively, upon detection of a wound, the HHMI will not only deliver the calculated drug types and doses (pain killer, onsite coagulant, anti-anxiety, adrenaline) to keep the wounded soldiers mind keen, but will also apply electrical pulses or waves such that the muscle group immediately above the wound site are caused to tensionize around the main artery leading to the wound site, thereby slowing blood flow to the wound. At the same time the HHMI will constrict around the site itself, and between the two functions, and/or combinations of those functions, be able to slow the blood loss to nearly nothing. The soldier is thereby allowed to leave the battle field without disrupting the fighting of other still battle worthy soldiers, and get himself to safety alone.

In extreme wounds, such as the loss of a lower leg, the HHMI can tense up to the point that it acts as another limb, or instructs an exoskeleton (such as a hydraulic suit) around the soldier to use the HHMI's ability to read what brain to muscle instructions are being sent to the no longer existing musculature of the lower leg for example, and conveying in micro seconds those brain commands to the exoskeleton or tensed HHMI so that the order is carried out: the most likely example being "run" as in run to safety.

All of the HHMI's on the battle field will be in contact with each other, and a HUD will show commanding officers the state of each soldier, as being battle worthy, ready, non worthy or ready, wounded, MIA or out of action/extracted. Chances of survival of any wounded individual will or can also be displayed as a percentage on any HUD. Death of course can be detected and transmitted as a cessation of bio-signals, such as brain waves, and heartbeat.

A body of data that becomes a bio-metric picture of a battlefield is again and again collected from battles, one possible use for this data is detecting individuals whose special brain wave patterns, or genetics, make them good selections for a highly specialized mission, or military group.

Diabetes Shorts: The HHMI can be configured and used to mitigate, prevent, control and possibly reverse type 2 diabetes. As shown in FIG. 62 and FIG. 63, There are large and powerful muscle groups of the human body easily accessible to TENS. The HHMI configured as a pair of shorts can be used to apply TENS signals to these large muscle groups, causing involuntary muscle contraction which result in a non-drug, non-surgical check on unhealthy bodily activities related to glucose uptake, intercellular Glute 4 concentration, insulin sensitivity and glucose metabolism. As an example, the HHMI configured as compression shorts lined with the inventive dry electrode system delivers TENS or NMES to the quadriceps, hamstrings and gluteal muscles FIG. 55 shows a configuration of a robust sweat chemistry detector fixed to printed electric leads formed from a elastic conductive ink diffusion bonded to a TPU print media and adhered to a stretch fabric.

FIG. 62 and FIG. 63 shows the location of TENS or NMES signal applying electrodes on the large muscles of the lower body of a diabetic user. FIG. 64 and FIG. 65 shows an HHMI configuration as diabetes shorts with electrodes located for applying TENS or NMES signals to the large muscles of the lower body of a diabetic user.

Diabetes is one of the fastest growing preventable diseases in the world. Diabetes is a condition when the blood glucose levels remain at elevated levels for long periods of time. Glucose a substrate of carbohydrates are free floating within the blood stream. Glucose is an energy source utilized by every cell in the body. Glucose homeostasis is needed for the body to maintain health. Glucose intake, production and removal are all vital in this process. Removal is accomplished by the liver, skeletal muscle and adipocytes. Skeletal muscle plays a major role postprandial; nearly 90% of the glucose disposal following a meal is through skeletal muscle uptake. (see, for example, DeFronzo. R. A., Funnarsson, R., Bjorkman, O., Olsson, M., and Wahre, J. (1985) Effects of insulin on peripheral and splanchnic glucose metabolism in moimsulin-dependent (type2) diabetes mellitus. J. Clinic. Invest. 76: 149-155)

Unlike the liver which has the capability of absorbing glucose to store as glycogen and also secrete glucose back into the blood stream; the skeletal muscle is a one way street. It absorbs glucose and stores it as glycogen. The glycogen stays within the muscle until it is utilized as energy.

The absorption process is a combination of two factors. The first is insulin mediated glucose uptake and the second is muscle contraction. Under sedentary conditions the glucose uptake into body tissues is under the control of insulin. At the muscle level insulin mediates either glucose storage as glycogen or metabolizes it through glycolysis and the citric acid cycle. Through physical activity (muscle contraction) glucose uptake takes place within skeletal muscle (see, for example, Richter, E., Mikines, K., Galbo, H., and Kiens, B., (1989). Effect of exercise on insulin action in human skeletal muscle. J. Appl. Physiol. 99(2): 876-885).

Despite two separate pathways for glucose uptake both stimulate cellular activities. They both stimulate glucose transporters (example Glute 4), this transporter is utilized during insulin mediated uptake and is reported 5-15 fold when stimulated by muscle contraction. (see, for example, Richter, E., Mikines, K., Galbo, H., and Kiens, B., (1989). Effect of exercise on insulin action in human skeletal muscle. J. Appl. Physiol. 99(2): 876-885). Muscle contractions not only increase muscle insulin sensitivity, responsiveness, but also stimulate the glucose transport independent of insulin. Research has proven that the combination of insulin and muscle contraction is the best way to absorb and utilized glucose.

In diabetes one of two issues are present. 1. The pancreas beta cells are damaged lacking production of insulin. 2. Insulin resistance, the inability of cells to absorb blood glucose via insulin. With the ability to create muscle contractions in individuals who may not have the time to exercise or the ability to do so due to pain, the Kinaptic Diabetes Shorts can give them the benefit of exercise while performing their daily activities which may include sitting at a desk for prolong periods of time. This garment may be worn under the user's daily clothing and provide NMES to the large leg muscles including the quadriceps, hamstrings and gluteals.

A small study explored the use of NMES on glucose metabolism and A1C in type 2 diabetics. The patients used a NMES suit 2 times a week for 20 min a session. There were documented improvements in A1c and glucose metabolism after 10 weeks. (see, for example, Dolan, P., Tapscott, E., Dorton, P., and Dohm, G. (1993) Role of transverse tubules in insulin stimulated muscle glucose transport. J. Cell Biochem. 52:1-7)

Another study showed that utilizing NMES in a 4 channel pulsed biphasic scheme of the lower body muscles decreased A1c in what they describe as an aerobic NMES stimulation system. (see, for example, Crowe, Louse., Caulfield, Brian, (2012) Aerobic neuromuscular electrical stimulation—an emerging technology to improve haemoglobin A1c in type 2 diabetes mellitus: results of a pilot study. J. BMJ Open. 2012; 2(3): e000219). NMES has been shown to improve Vo2 max and help achieve the American College of Sports Medicine weekly aerobic requirements in sedentary individuals. (see, for example, Amanda Carty, MSc, Kirsti McCormack, BSc, Garrett F. Coughlan, PhD, Louis Crowe, MB, BCh, BAO, Brian Caulfield, PhD, (2012) Increased Aerobic Fitness After Neuromuscular Electrical Stimulation Training in Adults With Spinal Cord Injury. Arch Phys Med Rehabil 2012; 93:790-5; van Buuren Frank, Horstkotte Dieter, Mellwig Klaus Peter, Frund Andreas, Vlachojannis Marios, Bogunovic Nicola, Dimitriadis Zisis, Vortherms Jirgen, Humphrey Reed, and Niebauer Josef. Diabetes Technology & Therapeutics. May 2015, 17(6): 413-419. doi: 10.1089/dia.2014.0315.)

The human skeletal muscle holds approximately 500 g of glycogen with larger skeletal muscles housing larger amounts than smaller muscle groups. By targeting the large muscle groups of the legs it allows the Kinaptic Diabetes Shorts to utilize these large deposits of glycogen and improve the insulin resistance of these muscles.

Figure 66:
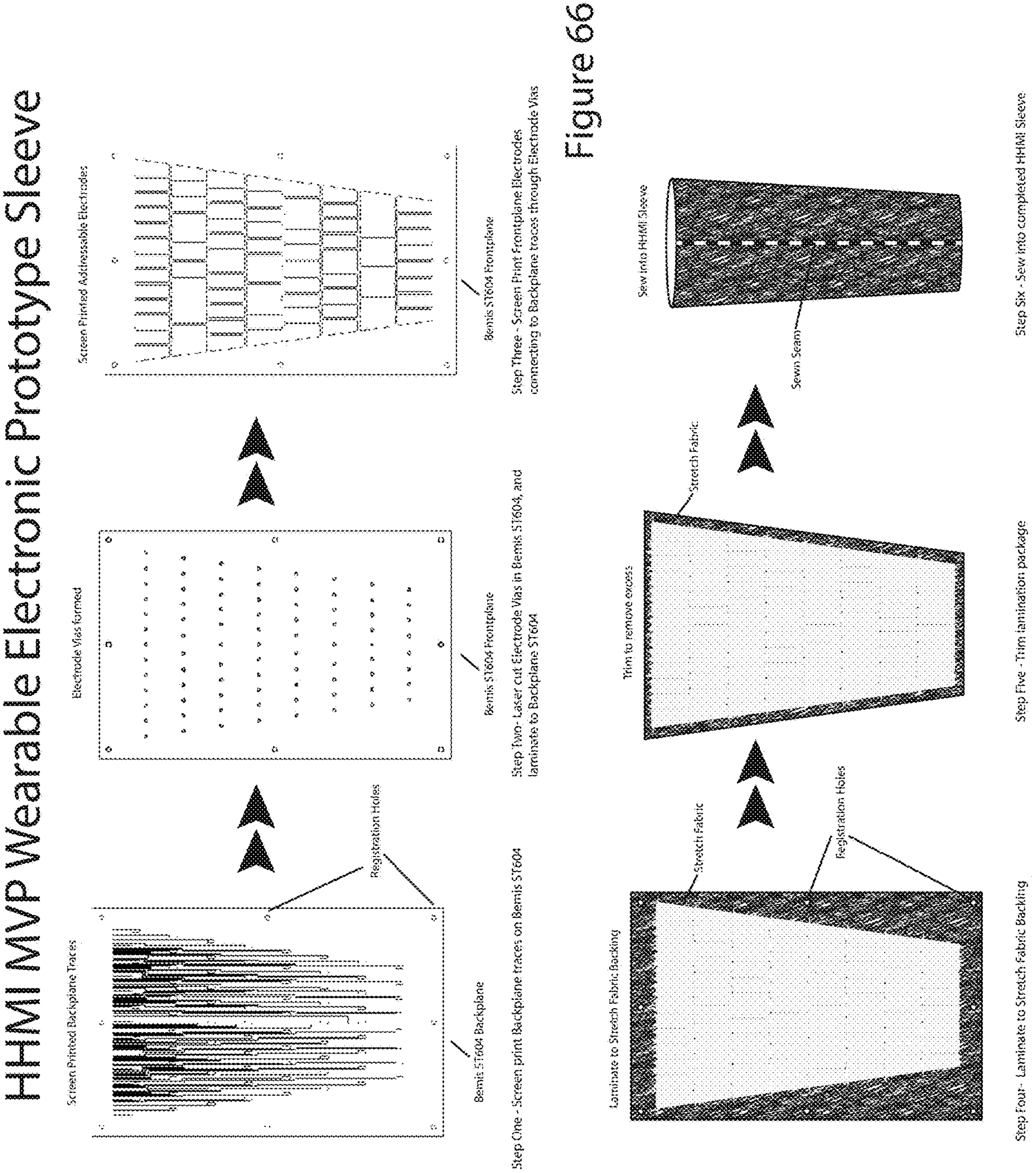
FIG. 66 shows a construction of an HHMI configuration using an adhesive layer having a preprinted electrode pattern, where the adhesive layer is laminated to a stretch fabric substrate and sewn to form an HHMI sleeve.

The exemplary embodiments herein describe methods, apparatus, computer code, applications and techniques for a wearable electronic, such as a haptic human/machine and human/human interface (HHMI). FIG. 66 shows a construction of an HHMI configuration using an adhesive layer having a preprinted electrode pattern, where the adhesive layer is laminated to a stretch fabric substrate and sewn to form an HHMI sleeve.

Example Configuration (Step One): A 12"×18.5" sheet of Bemis ST604 is laser cut with registration holes and placed on a screen printing jig to form the Backplane. DuPont 973 Elastic Conductive Ink is screen printed to form the Backplane Traces on the Backplane.

(Step Two): A second 12"×18.5" sheet of Bemis ST604 is laser cut with registration holes and electrode vias, then placed on the screen printing jig to form the Frontplane.

(Step Three): The Backplane and Frontplane are assembled on lamination jig and laminated together forming a lamination package and sandwiching the Backplane Traces between layers of Bemis ST604. The lamination package is placed on the screen printing jig. DuPont 973 Elastic Conductive Ink is screen printed to form the Addressable Electrodes on the Frontplane.

(Step Four): A 12"×18.5" piece of Lycra stretch material is laser cut with registration holes. The Lycra stretch material and the lamination package are assembled on the lamination jig and laminated together to form the HHMI sleeve preform.

(Step Five): The HHMI sleeve preform is laser cut to trim excess materials.

(Step Six): The trimmed HHMI sleeve preform is sewn to form the completed HHMI sleeve.

The HHMI may be provided as a wearable housing supporting the apparatus to provide a user-wearable electronic device. The wearable housing may comprise a multilayered flexible electronic circuit including an electrode layer comprised of a plurality of electrodes having a conductive face disposed for making electrical contact with a biological system of the user and at least one additional layer including at least one of an electrical circuit layer, an electrical insulating layer, an electrical conducting layer, and a flexible covering. A rigid or semi-rigid outer housing may be provided, which may also incorporate other useful devices such as a display, TENS signal generator, RF communication transmit/receiver, battery, memory, central processing unit (CPU) and a wired or wireless computer interface. All or some of these devices can be embedded within the HHMI garment as described herein.

The HHMI is constructed of layers of thin flexible materials, such as conductive stretchable fabrics, flexible insulators, flexible circuit boards, and the like. The materials may be woven, spun, closed cell, open cell, thin film, or other suitable structure. Layers, bonded layers, and constituent elements of the HHMI may be printed using a 3D printer, or formed by a batch or roll-to-roll manufacturing process including lamination, screen printing, ink jet printing, self-assembly, vapor deposited, sprayed or dip coated. The HHMI can be fabricated as a sleeve, glove, legging, shirt, full body suit, etc., and has a flexible and comfortable snug fit that urges the electrodes into face-to-face surface contact with the skin of the user. The electrode construction described herein provides thin, flexible structures designed specifically for compression face-to-face contact. Whatever the case, the transference of the electrical signal between the electrically conductive surface of the electrode and the skin of the user is effectively accommodated. An exemplary embodiment of the HHMI is constructed as a thin, flexible sleeve unobtrusively worn by the user, and the connection between the sleeve and microprocessor can be direct or via wireless networking, such as optical, or RF (e.g., Bluetooth, WiFi, etc.). The HHMI may be embodied in a lightweight, comfortable, haptic sleeve having electrode size and density enabling automatic calibration to the unique physiology of a user.

Figure 67:
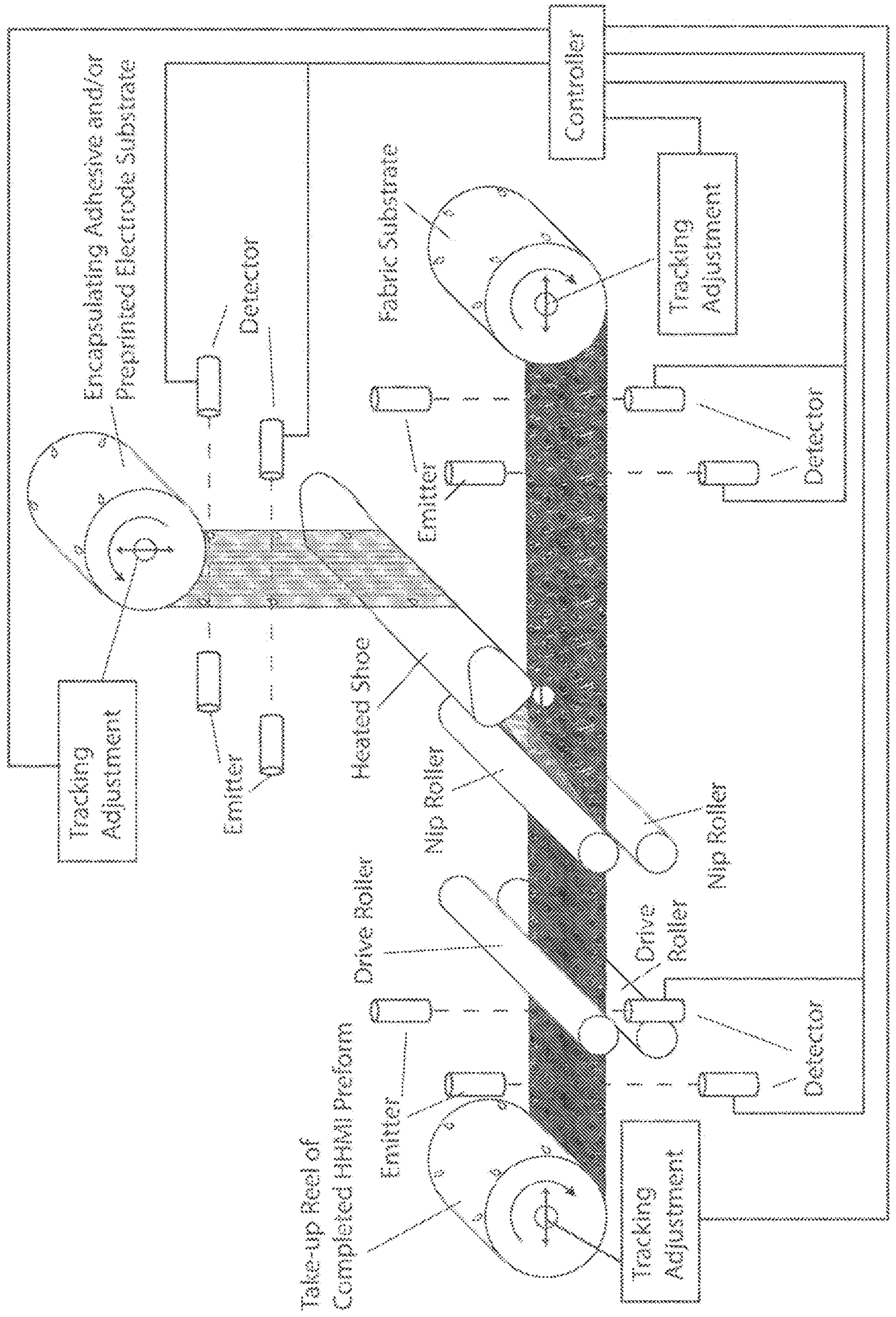
FIG. 67 schematically illustrates a roll-to-roll lamination process for mass producing an HHMI preform including an adhesive print media layer having a preprinted electrode pattern laminated to a stretch fabric substrate.

FIG. 67 schematically shows a roll-to-roll manufacturing process for manufacturing, for example, at least one of the exemplary embodiments shown herein. The HHMI can be configured as a sleeve, legging, jumpsuit, coverall, jacket, trouser, cap, glove or other wearable electronic. The HHMI may be comprised of a multilayered structure with the electrodes in contact with the skin of the user, insulation and wiring layers, and the sleeve covering. The layers, such as the outer covering may be, for example, a thin, multi-axial stretchable fabric. The fabric can be electrically insulating, and contain conductive threads, patches, coatings or inks to conduct the detected and applied electrical signals. In some of the drawings the electrodes are illustrated as being on the outside of the sleeve to show the concept of electrode size and location. In an exemplary embodiment, the sleeve is made from an opaque Lycra material with flexible conductive fabric electrodes disposed on the interior of the sleeve and in direct face-to-face electrical contact with the skin on the arm of the user. The fabric of the outer cover or other layer provides sufficient compression to urge the electrodes into face-to-face electrical contact with the skin of the arm. In addition, or alternatively, straps, bands, bladders, Velcro or other such mechanisms can be used for urging the electrodes into face-to-face electrical communication with the user's skin. Flexible and conductive fabrics and/or threads, such as mixes of one or more of copper/stainless-steel/nylon/polyester fabric and/or threads can be used to make electrode patches and/or traces that are highly conductive, thin and flexible. Signal cross talk, interference from or to the electronics of the HHMI may be mitigated with shielding layers separating, as necessary, the conductive pathways and electrically active components.

An exemplary embodiment pertains to a method of making a wearable electronic. The inventive roll-to-roll fabrication process starts with a supply roll of bottom substrate material, such as an elastic fabric. A supply roll of a hotmelt adhesive sheet, which may include one or more layers of pre-printed print media and embedded electronic and mechanical devices, is brought into contact with the bottom substrate. An embedded device die (or other mechanical, RF, semiconductor or electronic circuit elements) can be pre-embedded into the hotmelt adhesive sheet off-line in a separate operation, or in-line as described elsewhere herein. A warm tacking pressure roller system can be used to soften the hotmelt adhesive and secure it to the bottom substrate. The hotmelt adhesive sheet can include a release sheet that protects the embedded semiconductor elements and keeps the adhesive from sticking to itself in the roll. A top substrate having a conductive layer can be provided, and/or additional layers of conductor, insulators, devices, etc., can be provided to create a multilayered circuit board-type of structure. The hotmelt adhesive sheet with the printed electrodes, traces and embedded device(s) is inserted between the elastic fabric and any additional top layer(s) (if any) to form a lamination package. The lamination package is run through hot fusing pressure rollers to melt the hotmelt adhesive sheet and electrically insulate and connect (as determined by the conductive print and the embedded devices) and bind the lamination package materials together. The rollers may be heated, or separate heating zones can be provided for heat activating the adhesive.

In accordance with an inventive method of making a wearable electronic, a bottom substrate comprising a flexible, elastic material is provided. An adhesive print media layer is provided having a preprinted conductive pattern. The adhesive print media layer is disposed on top of the bottom substrate. The adhesive print media layer is activated to bind the preprinted conductive pattern to the flexible, elastic material. The flexible, elastic material may comprise a stretch fabric. The preprinted conductive pattern comprising electrodes may be configured for making face to face contact with the skin of user for at least one of detecting electrical signals from the skin of the user and applying electrical signals to the skin of the user. An electronic device may be embedded in an encapsulating adhesive layer and in electrical communication with the preprinted conductive pattern. The electronic device may be embedded in the encapsulating adhesive layer and brought into electrical communication with the preprinted conductive pattern when the encapsulating adhesive layer is thermally activated.

A predetermined pattern of semiconductor devices may be fixed to the encapsulating adhesive layer. As an example, the semiconductor devices may each have a top device conductor and a bottom conductor. A top substrate may be provided having a conductive pattern disposed thereon to form a lamination package comprising the bottom substrate, the preprinted conductive pattern on the adhesive print media layer, the encapsulating adhesive layer and the top substrate. The top substrate may be provided as a complete matching sheet or roll that matches the adhesive and preprinted adhesive print media. Alternatively, the top substrate can be a conductive patch, such as a piece of ITO coated plastic sheet, where the ITO acts as a transparent conductor. The lamination package is laminated so that the encapsulating adhesive layer insulates and binds the top substrate to the bottom substrate so that one of the top device conductor and bottom device conductor of the semiconductor devices is in electrical communication with the conductive pattern of the top substrate and so that the other of said top device conductor and bottom device conductor of each said semiconductor element is in electrical communication with the electrically conductive layer of the preprinted conductive pattern.

At least one of the bottom substrate, the adhesive print media layer, the encapsulating adhesive layer are provided as respective rolls of material. The step of disposing may comprise fusing at least two of the bottom substrate the adhesive print media layer, the encapsulating adhesive layer are provided as respective rolls of material together in a continuous roll lamination process.

The semiconductor device may be at least one of electrostatically and magnetically attracted onto the adhesive layer. The semiconductor device may be placed onto the adhesive layer using a pick and place machine. The semiconductor device may be placed onto the adhesive layer by transferring said semiconductor device from a relatively lower tack adhesive to a relatively higher tack adhesive.

Figure 68:
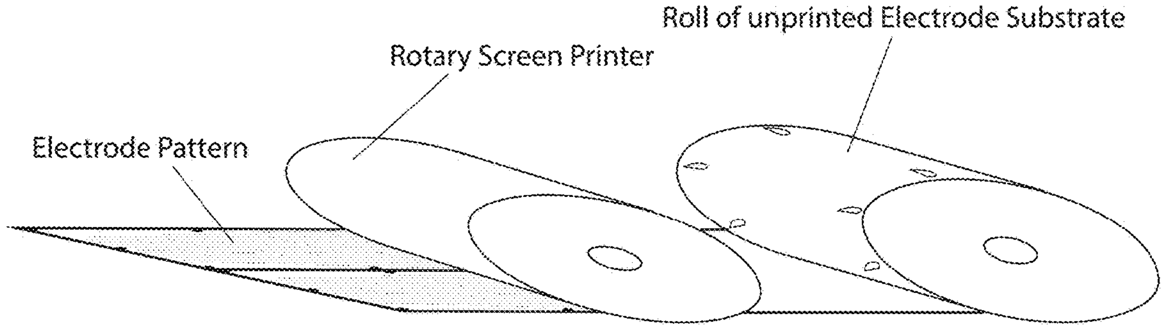
FIG. 68 shows a roll of an adhesive print media layer having an elastic conductive ink electrode pattern printed thereon through a rotary screen printing process.
Figure 69:
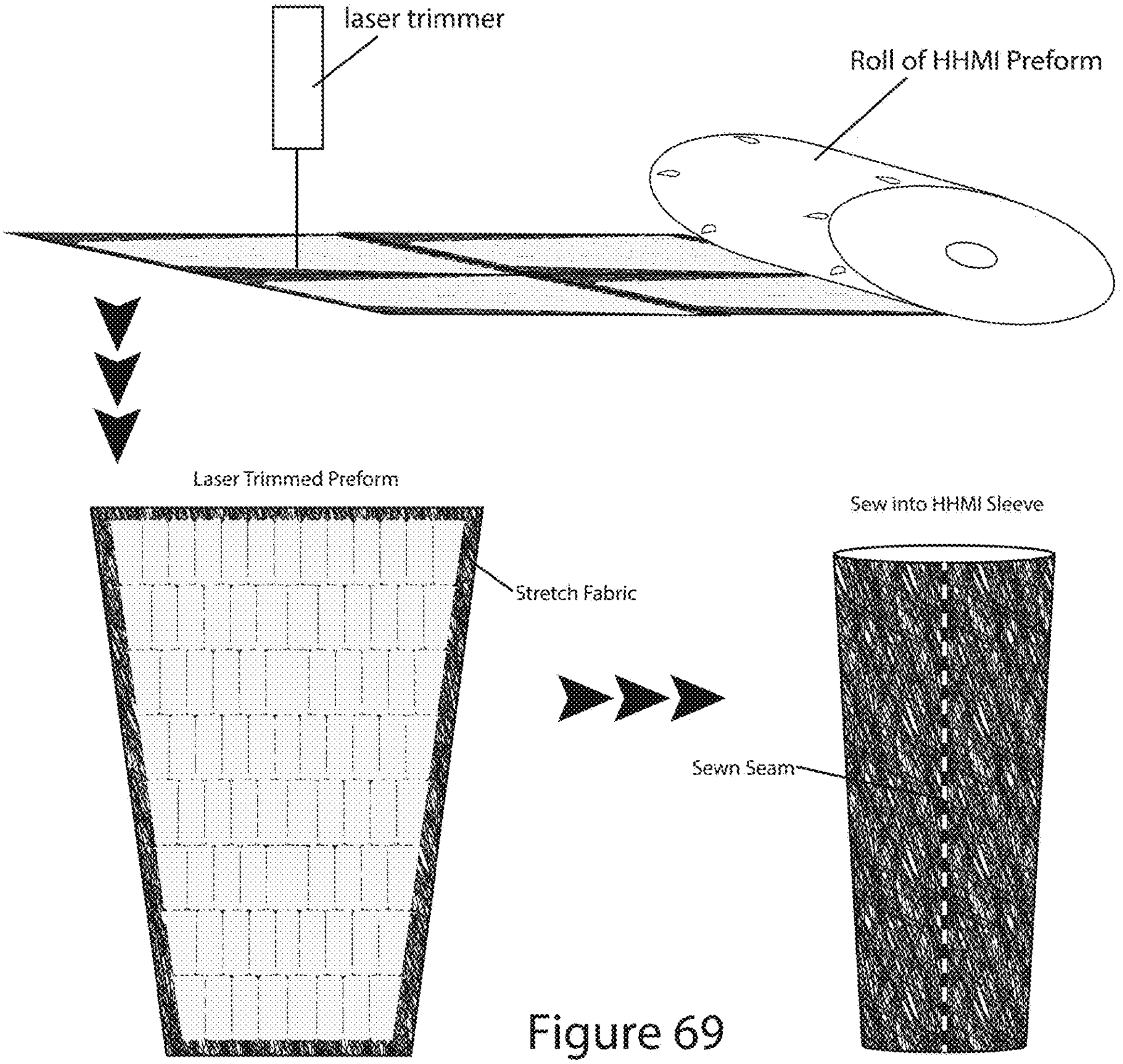
FIG. 69 shows a roll of HHMI preform formed in the roll-to-roll manufacturing process laser trimmed and sewn into an HHMI sleeve.

FIG. 68 shows a roll of adhesive layer having an elastic conductive ink electrode pattern printed thereon through a rotary screen printing process. FIG. 69 shows a roll of HHMI preform formed in the roll-to-roll manufacturing process laser trimmed and sewn into an HHMI sleeve.

In an optional manufacturing technique, bare die and packaged semiconductor devices can be connected during the lamination process. Applicant has discovered that as the hotmelt sheet is softened, for example, during a roll lamination process, the embedded device die breakthrough the adhesive so that an electrode of the device comes into electrical contact with the conductive layers in the lamination package (for example, the conductive pattern printed on the print media, or other layer in another lamination material that is oriented and positioned to make contact with the conductor when the device breaks through the hot melt adhesive layer that it is embedded within). Thus, for example, in the case of a simple semiconductor device, a pn junction diode, the p and n sides of each embedded diode device die are automatically connected to a top conductive layer and a bottom conductive surface that is strategically disposed in the lamination package for making such contact. Each embedded device can be completely encapsulated within the hotmelt adhesive and the substrates for a waterproof and robust construction. In addition, the embedded device die is each permanently secured between the substrates fully encased within the flexible, hotmelt adhesive sheet layer and substrates.

The protective barrier of the adhesive provides a water proof, dust proof thermally advantageous protection of, for example, a package SMT device and, also secures the electrical connection of the two bottom conductors (or multiple conductors). However, for example, in the case of an LED or optical sensor, the optical properties of the protective barrier are not likely to be a better light transmission match than the lens material or optical stack that makes up the packaged lamp from the emissive LED surface to the top of the lens open to the outside. Accordingly, FIG. 70 shows a release sheet that is removed exposing a light emitting lens or a detecting top face while leaving the rest of a packaged SMT LED embedded in a thermally active adhesive and in face-to-face electrical contact with a conductor(s) of one or more of the materials in the lamination package. FIG. 71 illustrates the embedding the packaged SMT LED in a thermally active adhesive and forcing it under the pressure of the lamination rollers into direct face-to-face electrical contact with a printed electronic pattern. In accordance with this aspect of the invention, the emitting face of packaged lamps or the detecting face of, for example, an optical detector, is left exposed while leaving the vulnerable SMT LED (or bare die) nearly fully embedded in a barrier and/or thermally advantageous binding film (the adhesive, adhesive/phase change material layers, adhesive with phase change domains, adhesive with phase change wells, etc., as shown and described herein and also as might otherwise logically be used to achieve the intended purpose of tending to maximize light output, lower cost, ease manufacturing, reduce manufacturing capital equipment, reduce failure modes and provide device protection).

FIG. 72 shows an embedded packaged semiconductor device having the top face (which can be an emitter or detector, transducer, or other active portion) exposed once the release sheet is removed, with the rest of the device embedded in a thermally active adhesive and in direct face-to-face electrical contact with the printed flex circuit conductors. When the release sheet is peeled away, for example, in the case of an LED, the light emitting lens is exposed while leaving the rest of a packaged SMT LED embedded in a barrier layer of thermally active adhesive.

As shown and described herein, sensor, emitter, bare die and packaged semiconductor electronics can be embedded within the construction of the HHMI garment. The hot-melt materials provide barrier, shock absorbing and retention properties making the emitted device protected and robust. The embedded device can act as a sensor, indicator, emitter, detector, for uses including, but not limited to pulse, oxygen, moisture, blood chemistry (including glucose, salt, alcohol, pathogen, toxic factors, and other health conditions obtainable from the body).

Figure 73:
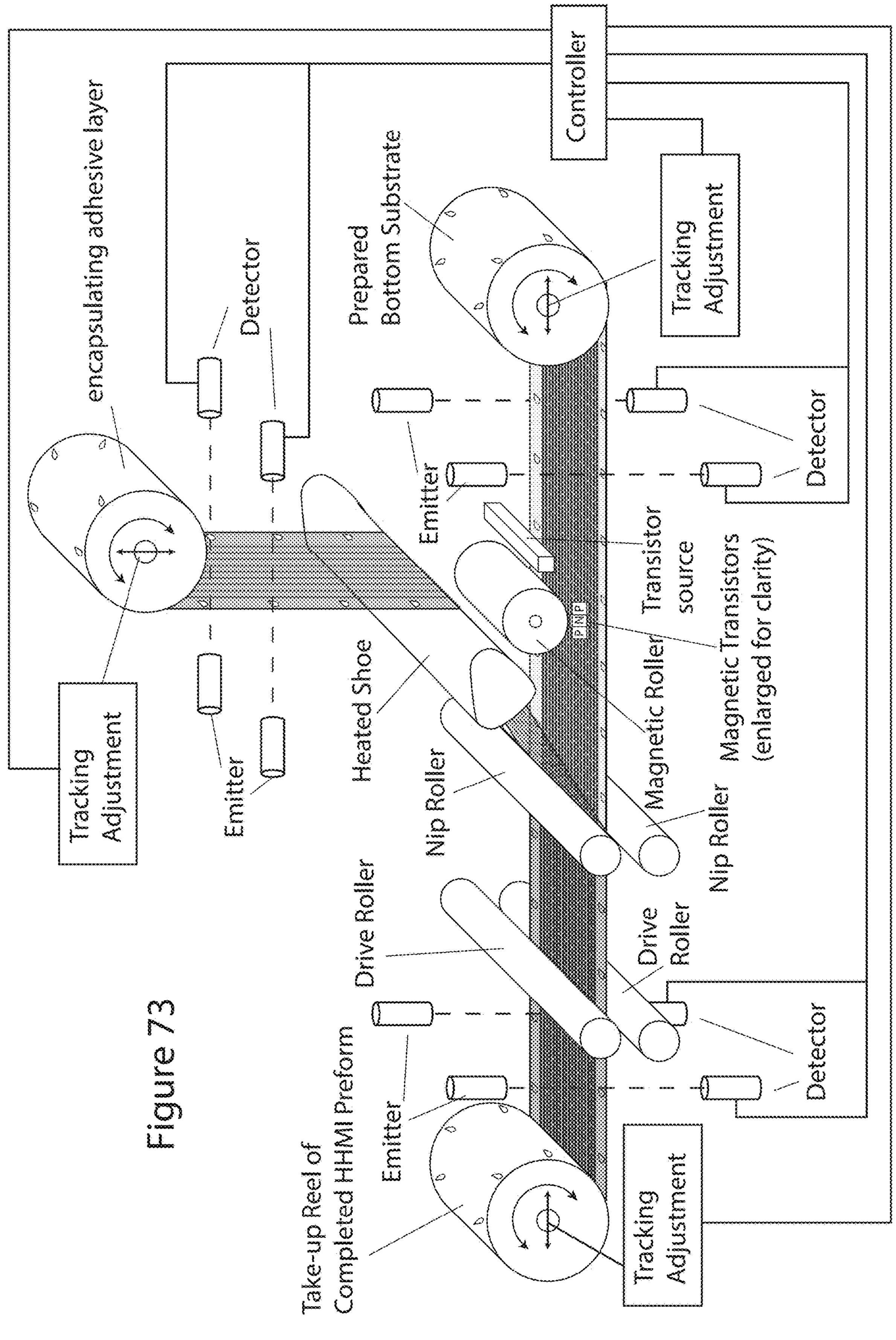
FIG. 73 schematically shows a roll-to-roll manufacturing process for manufacturing, for example, at least one of the exemplary embodiments shown herein, where a magnetically attractive semiconductor device is magnetically attracted and placed onto the encapsulating adhesive layer or the adhesive print media during the roll-to-roll manufacturing process.

FIG. 73 schematically shows a roll-to-roll manufacturing process for manufacturing, for example, at least one of the exemplary embodiments shown herein. In accordance with the exemplary roll-to-roll manufacturing process, an electronic device, such as a bare die or packaged semiconductor detector, emitter, sensor, electronic circuit element, or other small device (collectively, "embedded device") that can be beneficially embedded in the HHMI wearable electronic construction is made available. For example, the embedded device may be attracted to a magnetic (or electrostatic) rotating drum and transferred to an adhesive or transfer sheet. An embedded device source provides a hopper located adjacent to a rotating drum, similar to a toner cartridge of a conventional laser printer or copier and the many different conventional mechanisms for selectively directing toner onto a flexible substrate (e.g., paper sheet), can be utilized in accordance with the exemplary roll-to-roll manufacturing process to create a rapid, low cost, wearable electronic assembly process without the need to individually pick and place, for example, a bare die or packaged semiconductor, or many other fabrication steps that would be typically associated with creating a printed circuit embedded within a wearable electronic.

The inventive wearable electronic can have a very simple device architecture including a bottom substrate (typically, a stretch fabric such as Lycra or Spandex), a hotmelt adhesive (which may include an embedded device) can include a conductive electrode and circuit pattern screen printed ink, such as DuPont PE971, pre-printed onto a roll of print media such as Bemis ST604. The Bemis ST604 includes a hotmelt adhesive layer which can be provide as, or in addition to, the hotmelt encapsulating adhesive and vice versa. A top substrate may also be provided that can include, for example, insulated and non-insulated sections that allow for the direct face-to-face electrical communication between the skin of a wearer of the wearable electronic and an element of the wearable electronic such as the individually addressable electrodes, sensor and the like. The pre-printed print media and the hotmelt adhesive can be prepared ahead of time as a completed roll of materials that includes conductive electrodes, circuit patterns, and packaged and/or bare die electronics fixed to the circuit patterns. The bottom substrate, the hotmelt adhesive (with the embedded device) and the top substrate can thus be provided as rolls of material. The rolls are brought together in a continuous roll fabrication process, resulting in the high-speed production of a wearable electronic device. The inventive roll-to-roll fabrication process enables a high yield, lower cost manufacturing of a wearable electronic garment that can optionally include embedded semiconductor electronic circuits. Also, the exemplary embodiment results in devices with a unique, very thin form factor that is extremely flexible, waterproof and highly robust.

Figure 74:
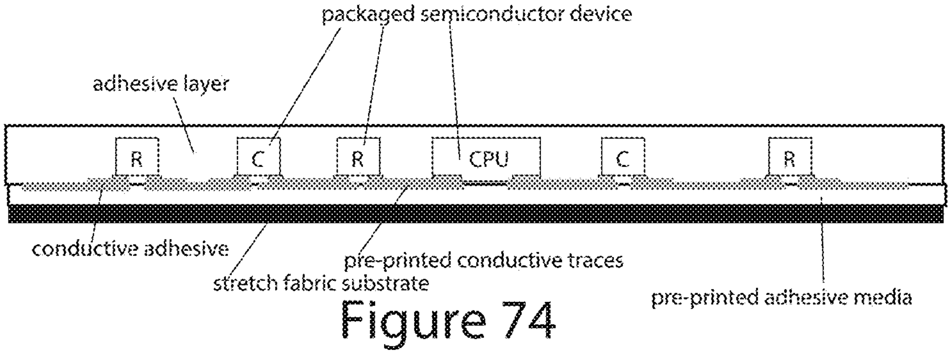
FIG. 74 is a cross sectional view showing an HHMI configuration formed on a stretch fabric substrate with an adhesive print media having a printed conductive trace pattern for forming an electronic circuit with packaged semiconductor electronic devices embedded in an encapsulating adhesive layer.
Figure 75:
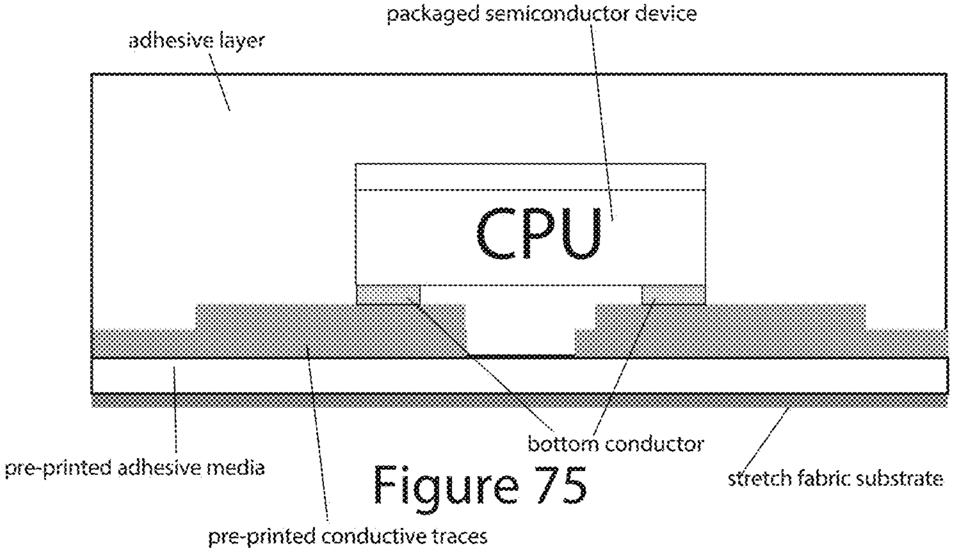

FIG. 74 is a cross sectional view showing an HHMI configuration formed on a stretch fabric substrate with an adhesive media having a printed conductive trace pattern for forming an electronic circuit with packaged semiconductor electronic devices embedded in an encapsulating adhesive layer. FIG. 75 is an isolated cross-sectional view showing an HHMI configuration formed on a stretch fabric substrate with an adhesive media having a printed conductive trace pattern for forming an electronic circuit with a CPU packaged semiconductor electronic device embedded in an encapsulating adhesive layer.

FIGS. 76-84 show exemplary embodiments of methods of making an electrode for a wearable electronic. In accordance with the disclosed exemplary methods, a Robust Exposed Electrode Printing (REEP™) process results in a conductive, elastic, adhesive material that has many applications for wearable electronics and printed circuit board manufacturing.

Figure 76:
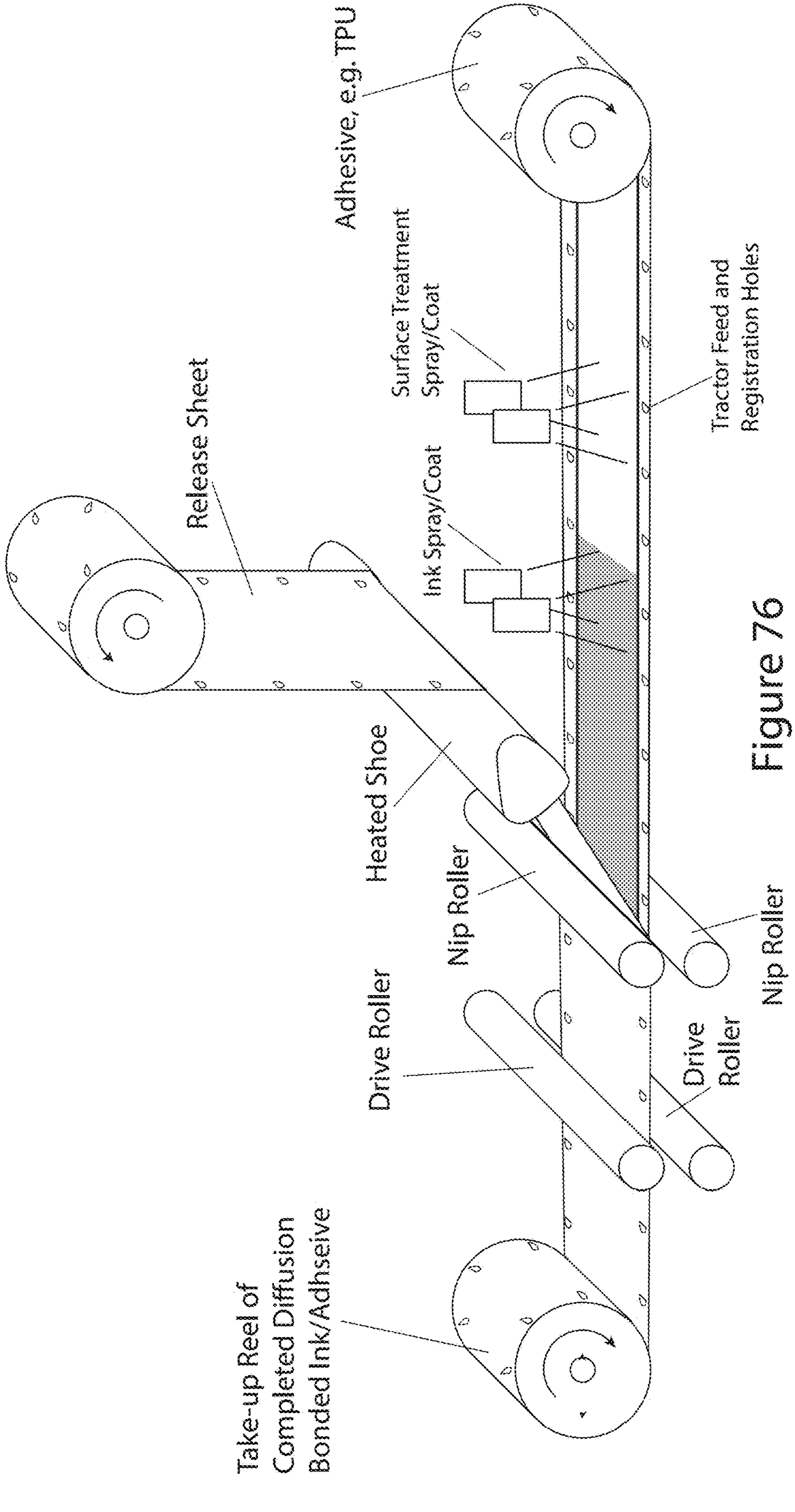

FIG. 76 illustrates a roll-to-roll manufacturing process for manufacturing a robust exposed electrode material using a print media surface pre-treatment, an elastic ink printing, and a heat and pressure post-treatment. A continuous roll of print media, such as a TPU adhesive, feeds towards a first state where a surface treatment is performed. The print media may be carried on a suitable carrier sheet or it could be free standing. Additionally, or alternatively, other layers can be included with the print media include a moldable plastic substrate, an insulator, a bonding adhesive that becomes softened at a different temperature than the TPU, fabric, or pre-formed layers of a multi-layer electronic circuit (in which can the roll-to-roll process is used to make a multi-layered circuit board-type device). The surface treatment can be, for example, one or more of a solvent application, a heat treatment, or other operation that softens and/or swells the surface of the print media making it more receptive forming a diffusion bond with a conductive ink and/or conductive particulate which is applied downstream. The exemplary roll-to-roll process includes stations where the conditions, steps and materials used at each station will affect the process balance and the achievement of the intended output material. For example, the surface treatment may be left out of the roll-to-roll process depending on throughput and the downstream processing conditions. For example, a slower throughput, higher downstream processing temperatures, longer dwell time between ink application and pressure/heat application, and other factors may allow for the pre-treatment station to be avoided or less surface pre-treatment.

After the pre-treatment station, a conductive ink that is properly thinned is deposited on the print media surface. The deposition can be performed by any suitable coating operation. For example, spray coating may be used to achieve overall coverage of the print media surface, while rotary screen printing may be used to create selected conductive patterns on the print media. Speed past the spray coating heads or multiple deposition stations can be used to build up a desired thickness while aiding in balancing the overall throughput of the roll-to-roll manufacturing process.

A release sheet passes over a heated shoe to pre-heat the release sheet. Additionally, or alternatively, a second heated shoe (not shown) can also be used heat the coated print media. Other heating methods can also be used, including heated rollers, radiant lamps, convention or conduction heat source, etc., providing for a suitable heating of the print media and make it receptive to form a diffusion bond with the conductive material coated on its surface.

To form the diffusion bond between the conductive material and the print media, a pair of nip rollers apply pressure to the heated print media/conductive material. Nip rolls or pinch rolls are powered rolls that are used to press two or more sheets together to form a laminated product. The high pressure created at the nip point brings the sheets into intimate contact, and can squeeze out any bubbles or blisters that might cause a defective bond.

It is noted that the formation of the diffusion bond may be formed on pre-cured printed ink on TPU. With the application of heat and pressure as disclosed herein, the conductive particulate and binder of the conductive ink is forced into a forming along with the TPU material a gradient where at the surface and below the surface towards the bulk of the TPU, a gradient of material concentrations are achieved where greater conductive material is located towards the surface and greater insulative TPU material is located towards the TPU bulk or bottom of the TPU sheet. As an alternative, in addition to or instead of conductive ink, a conductive particulate, such as silver particles, copper particles, organic conductors, carbon, carbon nanotubes, graphene, or other conductive material, can be applied in a wet or dry coating operation and then driven into and intimately fixed to the TPU through the application of heat and pressure, for example, at the nip rollers.

Drive rollers pull the lamination materials (conductive material coated TPU, carrier sheet and release sheet). A take-up reel of completed diffusion bonded ink/adhesive may be the final step in the roll-to-roll manufacturing process creating a starting material for further processing into a wearable electronic, printed circuit board, or other useful article. Alternatively, additional processing steps may be provided in line, including the addition of electronic devices such as packaged or bare die electronic circuit devices, bio-sensors, ambient environment sensors, transmitters/receivers, processors, antennas, power supplying devices, energy harvesting devices, graphics, barrier layers, etc.

In accordance with a non-limiting embodiment, the above-described roll-to-roll process, or a similar batch process, can be employed in a method for making low temperature printed circuit board. An adhesive print media layer is provided. An elastic conductive ink is deposited onto the print media layer. The elastic conductive ink comprises a conductive particulate disposed in a binder. A diffusion bond is formed between the top surface of the print media layer and the elastic conductive ink, wherein the diffusion bond forming is facilitated by the surface treatment. The diffusion bond enables a direct face-to-face electrical and mechanical connection between the elastic conductive ink and electrodes of a semiconductor device. A surface treatment may be performed to a top surface of the print media layer, wherein the diffusion bond forming is facilitated by the surface treatment.

The adhesive print media layer is provided as a roll of material on a carrier substrate; and performing the surface treatment to the top surface, depositing of the elastic conductive ink and forming the diffusion bond are done sequentially in a roll-to-roll process.

A predetermined pattern of semiconductor devices may be fixed to the elastic conductive ink diffusion bonded to the print media layer. The semiconductor devices each have a top device conductor and a bottom device conductor. At least one of heat and pressure is applied to electrically and mechanically connect the semiconductor device to the elastic conductive ink diffusion bonded to the print media.

The elastic conductive ink can patterned as lead lines and connection lands for forming a printed circuit. The connection of the predetermined pattern of the semiconductor devices forms an electronic circuit having the semiconductor devices electrically and mechanically connected to the connection lands and the lead lines provide for the flow of electrons between the semiconductor devices during the operation of the printed circuit.

Figure 77:
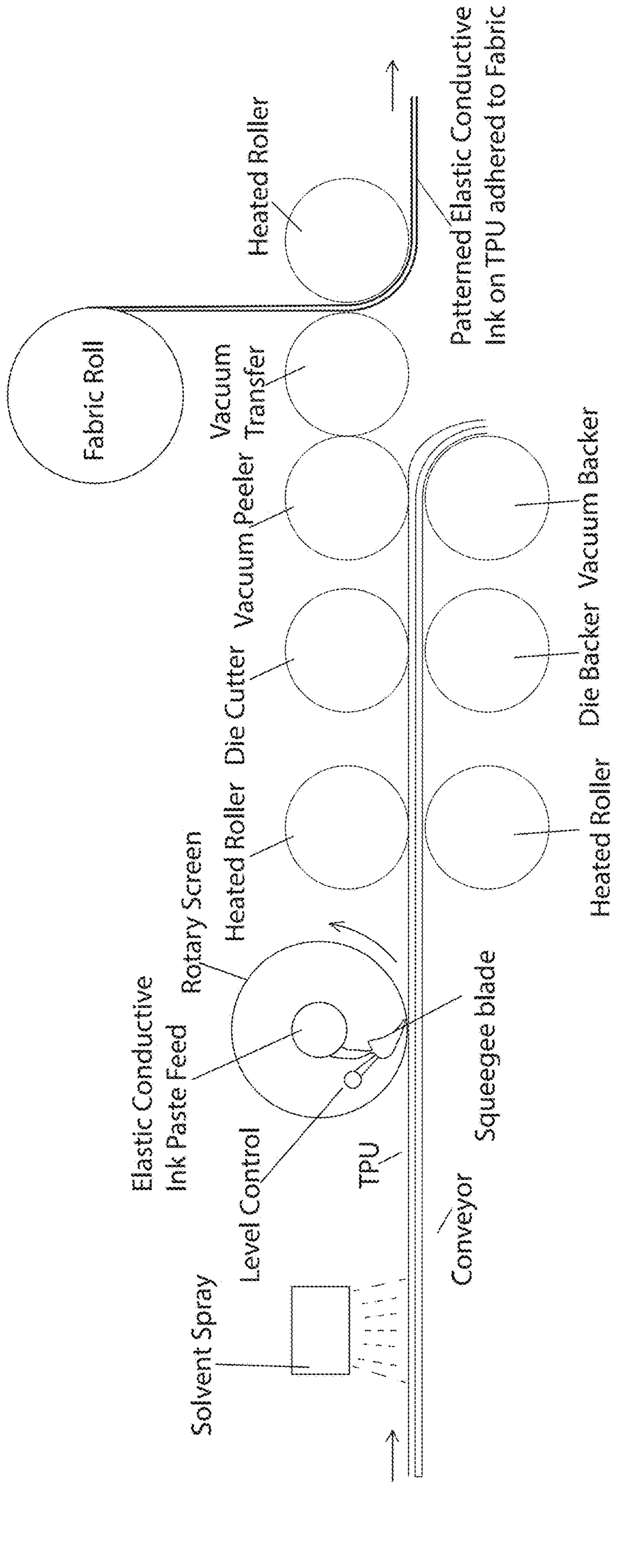

FIG. 77 illustrates a roll-to-roll manufacturing process for making a robust exposed electrode formed as a patterned elastic conductive ink on TPU adhered to fabric. In this non-limiting, exemplary embodiment, a conveyor moves a TPU passed a solvent spray station where a mist of solvent is applied to pre-treat the surface of the TPU. A rotary screen printing stage next coats the pre-treated TPU surface with an elastic conductive ink or paste. The rotary screen can have, for example, a printed circuit pattern, or could provide for wide area coverage of the conductive ink. Heated rollers apply heat and pressure to the coated TPU to form a diffusion bond and drive off solvent from the coating and TPU surface. A die cutting station can utilize a rotary die and die backer to cut the diffusion bonded TPU into desired shapes or patches. At a vacuum peeler station, the cut TPU patches are removed from the conveyor as separated units. These separated patches are then transferred at a vacuum transfer station to reverse the orientation of the TPU patch so that the conductive surface now faces a drum or roller of the vacuum station and what was the bottom surface of the TPU is now facing out. A fabric roll is fed between the vacuum transfer drum and a heated roller so that the TPU patch is laminated to the fabric with the conductive surface facing out and left exposed. The output of this exemplary roll-to-roll process is a diffusion bonded pattered conductive ink on TPU patch adhered to the fabric. This material may then become the starting material for a wearable electronic. Instead of fabric, other suitable materials, such as plastic, paper, adhesive, or any other suitable substrate may be used.

Figure 78:
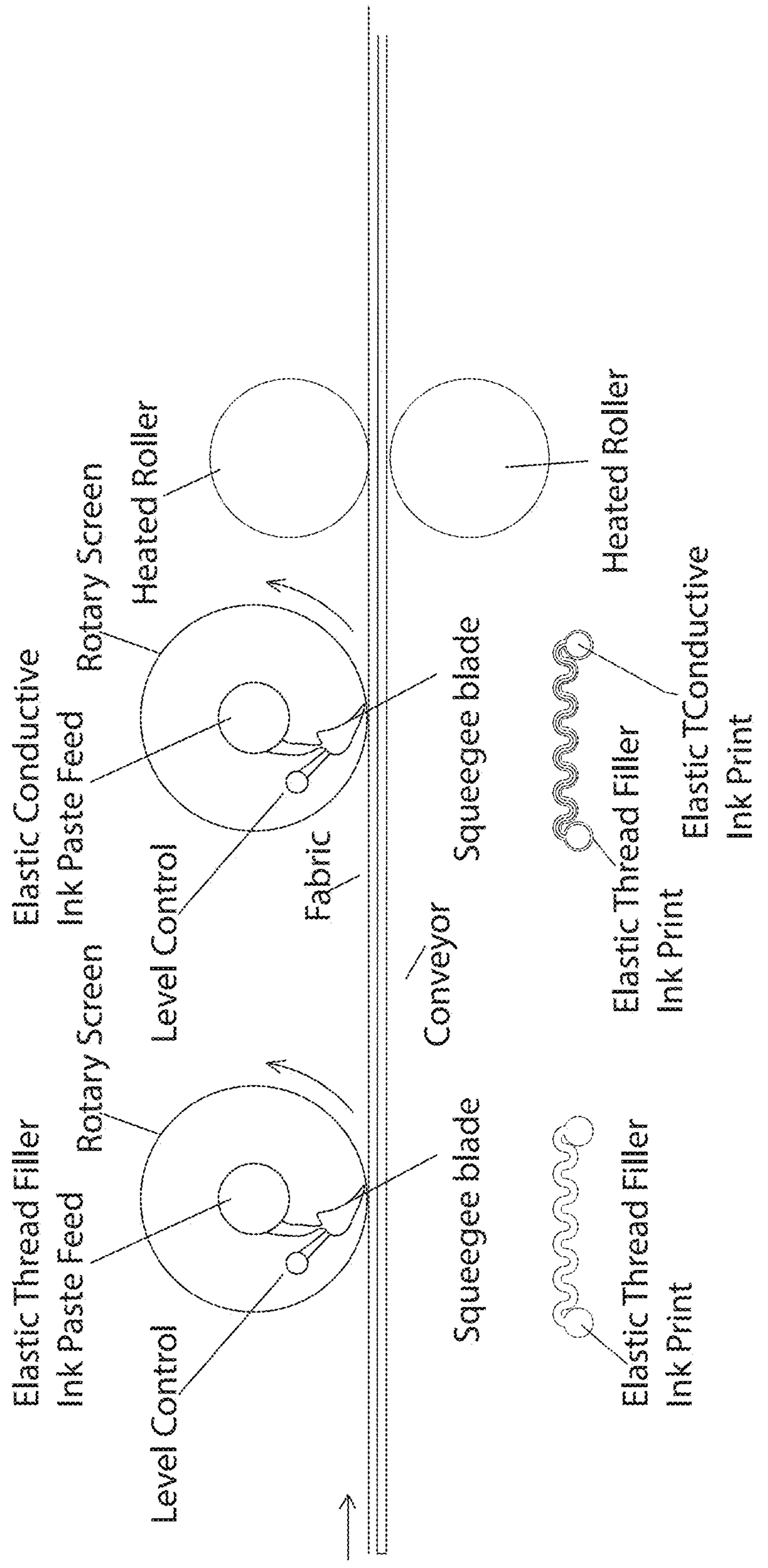

FIG. 78 illustrates a roll-to-roll direct-to-fabric printing for forming a patterned elastic conductive ink print over a patterned elastic thread filler ink formed directly on fabric. In this non-limiting, exemplary embodiment an elastic thread filler ink is first printed onto a fabric substrate using a first rotary screen printing station. At a second rotary screen printing station, an elastic conductive ink is printed over the elastic thread filler print. Additional heat, solvent, pressure, etc., treatment station(s) may be provided between the first and the second rotary printing stations. At a heated roller station, heat and pressure may be applied if desired to form a diffusion bond between the elastic thread filler material and the elastic conductive ink material, and/or adhere the printed materials to the fabric. In line with the processing of the fabric with the printed inks, additional processing, such as a pick and place operation, may be performed to add, for example, electronic circuit devices, sensors, mechanical elements, connectors, or other elements onto the printed inks and/or the fabric.

Figure 79:
Figure 80:
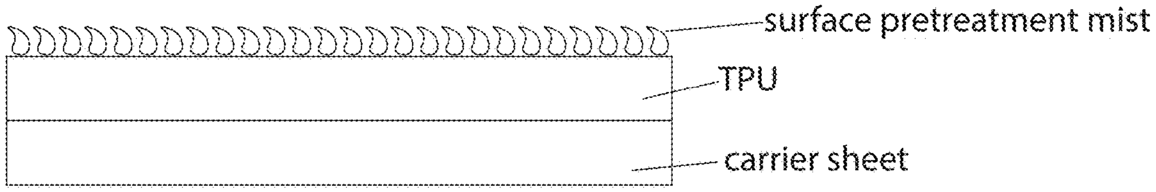
Figure 81:
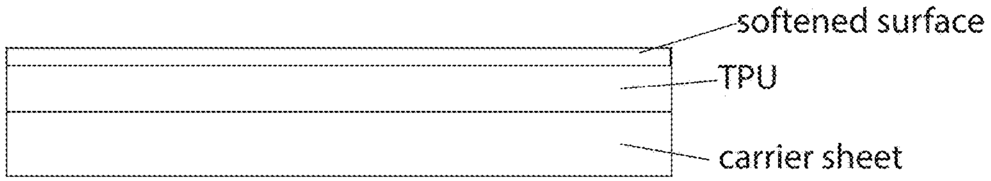
Figure 82:
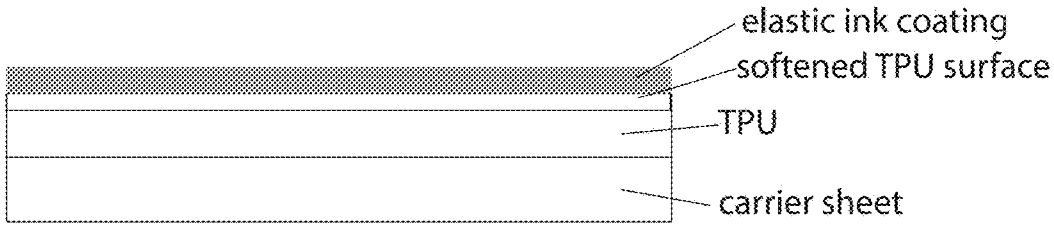
Figure 83:
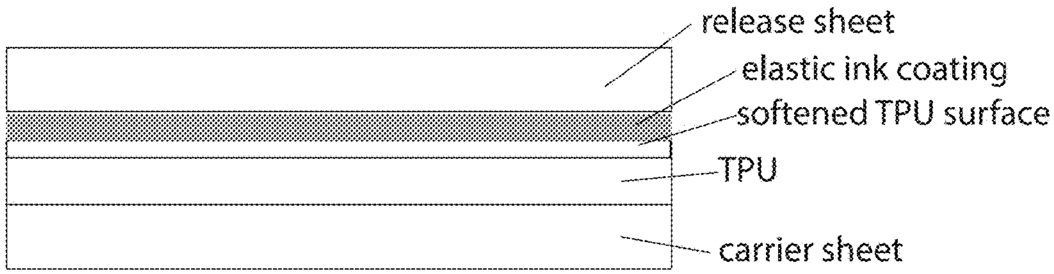
Figure 84:
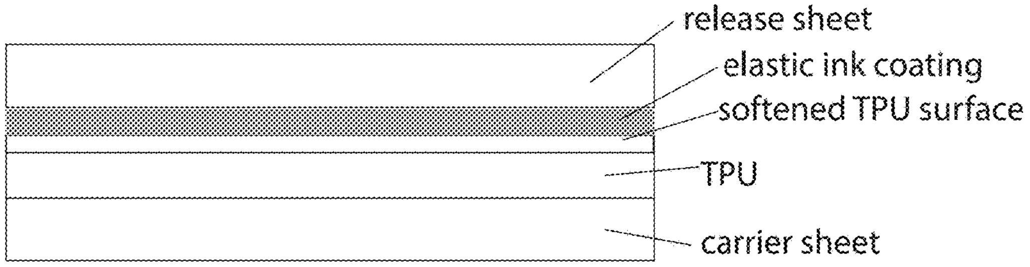

In accordance with a non-limiting, exemplary embodiment of the REEP™ process, an adhesive print media layer is provided. FIG. 79 shows a step in the process of forming a robust exposed electrode showing the step of providing a TPU print media on a carrier sheet. A surface treatment is performed to a top surface of the print media layer. FIG. 80 shows a step of pre-treating the top surface of the TPU print media using a solvent mist. FIG. 81 shows a step of the pre-treatment creating a softened top surface of the TPU print media. An elastic conductive ink is deposited onto the print media layer. The elastic conductive ink comprises a conductive particulate disposed in a binder. FIG. 82 shows a step of applying an elastic conductive ink coating on the softened top surface of the TPU print media. FIG. 83 shows a step of providing a release sheet on top of the uncured elastic ink coating on the softened top surface of the TPU print media. A diffusion bond is formed between the top surface of the print media layer and the elastic conductive ink. The diffusion bond forming may be facilitated by the surface treatment. FIG. 84 shows a step forming a diffusion bond between the elastic ink and the TPU print media by applying heat and pressure to cure the elastic conductive ink coating, drive off at least a portion of any remaining solvents from the top surface pre-treatment and from within the coating of elastic conductive ink.

Figure 85:
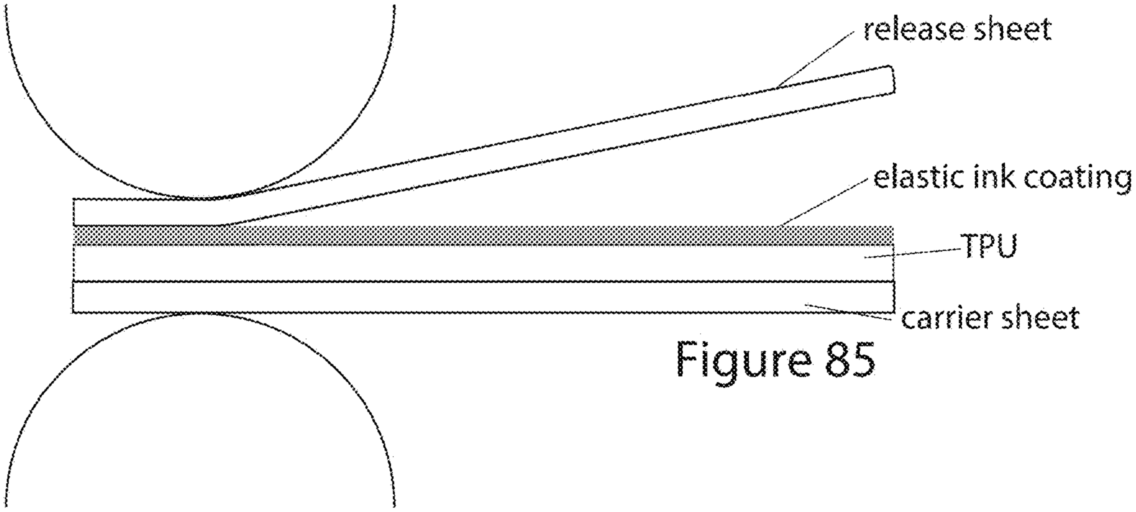

FIG. 85 illustrates the roll-to-roll process of forming a diffusion bond by applying heat and pressure to cure the elastic conductive ink coating using heated rollers. The adhesive print media layer can be provided as a roll of material on a carrier substrate. Performing the surface treatment to the top surface, depositing the elastic conductive ink and forming the diffusion bond may be done sequentially in a roll-to-roll process. The surface treatment may comprise at least one of heat and solvent softening of the top surface of the print media layer. The diffusion bond can be formed by at least one of a heat treatment and a pressure operation. The diffusion bond can be formed at a heat treatment temperature above 95° C. A non-limiting example of a suitable adhesive print media layer is Bemis 3914, a thermoplastic polyurethane (TPU) sold by Bemis, located in Massachusetts.

At least one of the surface treatment and depositing can be done using at least one of a spray coating, dip coating, screen printing, rotary screen printing, rotogravure printing, off-set printing, ink jet, and digital printing. The diffusion bond can be formed at a heat treatment temperature above the softening point of the adhesive print media layer. The diffusion bond can be formed at a heat treatment temperature between 110° C. and 165° C. and a pressure between 2.8 bar and 4.2 bar. The surface treatment may comprise softening the top surface and the diffusion bond is formed by pressing the binder and conductive particulate into the softened top surface under heat and pressure.

The surface treatment may comprise applying a solvent to top surface, allowing the solvent time to soften a thickness of the top surface effective for a portion of the binder and conductive particulate of the elastic conductive ink to infiltrate into the thickness of the top surface during the step of forming a diffusion bond. The diffusion bond can be formed using a heated roller with a roll surface temperature between 225° C. and 325° C., a roller pressure of at least 1.5 bar and a speed of the print media layer passing through the heated roller between 1.0 m/minute and 1.5 m/minute.

The solvent may comprise an organic solvent, and may be selected to achieve a relatively lesser degree of solvation with relatively greater swelling of the top surface. Alternatively, the solvent may be selected to achieve a high degree of solvation of the top surface. The solvent may include at least one of Dichloromethane (CH2 Cl2), Dimethyl formamide (C3H7 NO) and Methanol (CH3 OH). As described in U.S. Pat. No. 4,383,867, which is incorporated by reference in its entirety herein, a solvent mixture that achieves a relatively lesser degree of solvation with relatively greater swelling of the top surface of the adhesive print media may include by Ingredient Percent by Volume: Dichloromethane (CH2 Cl2) 70%; Dimethyl formamide (C3H7 NO) 20%; and Methanol (CH3 OH) 10%.

The adhesive print media layer may comprise a polyurethane, and may include a polymer chain including ethyl carbamate C3H7NO2. The pre-treatment of the adhesive print media can be performed by one of more of a heat treatment, solvent treatment, prior to the step of depositing the elastic conductive ink. Alternatively, a non-limiting, exemplary embodiment, the pre-treatment step may be avoided, with the deposition of the elastic conductive ink being performed on an untreated top surface of the adhesive print media layer. As another alternative, non-limiting, exemplary embodiment, the pre-treatment of the adhesive print media layer may be performed prior to the deposition of the elastic conductive ink, and a comingling of the constituent parts of the softened adhesive print media layer and the elastic conductive ink may form the diffusion bond with or without the application of either or both heat and pressure. However, in the preferred embodiment of a roll-to-roll manufacturing process, the application of heat and pressure has been experimentally shown to be effective for forming the desired diffusion bond (with and without the pre-treatment step). On the other hand, it has been experimentally shown that following a typical curing process, for example, following the manufacturers recommendations for curing the DuPont PE971 elastic conductive ink, does not result in the robust exposed electrode that is obtained following the inventive processing steps described herein. In an experimental comparison of the conventional curing of the DuPont PE971 elastic conductive ink printed on Bemis 3914 TPU, samples of the printed TPU was cured in a heat tunnel for about 5 minutes at a temperature of about 130° C. Other samples were prepared following the inventive REEP™ process described herein. Subsequent testing of this conventionally cured elastic conductive ink on TPU showed a greater degree of ink material removed using an adhesive tape peel test as compared with the same ink and TPU materials processed with the inventive REEP™ process.

Figure 86:
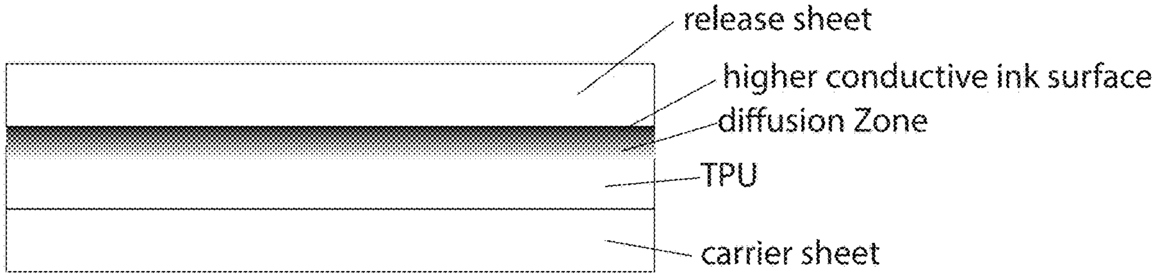

FIG. 86 shows the diffusion bond formed by applying heat and pressure to uncured elastic conductive ink coated on the softened top surface of a pre-treated TPU print media. FIG. 87 shows a robust exposed electrode having a higher conductive ink surface bonded through a diffusion bond to the TPU print media adhered to a stretch fabric. The diffusion bond creates a robust electrically conductive surface that may be kept exposed, such as for use in detecting and/or applying electrical signals to the skin. The diffusion bond also prepares the surface of the conductive material coated TPU to receive a packaged or bare die semiconductor device, and make direct face-to-face electrical contact between an electrode of the semiconductor device and the conductive particulate embedded in and integrally formed with the conductive material/TPU diffusion bond. These conductive particulates are in suitable concentration and electrical communication among the particulate so that electrons can flow through the conductive constituents included in the diffusion bond and the electrode of the semiconductor device.

Similarly to the description of a roll-to-roll manufacturing process shown, for example, in FIGS. 66-73 an electronic device, such as a sensor, active or passive electronic circuit element, packaged or bare die electronic device, touch sensor, chemistry sensor, heat sensor, pressure sensor, heart beat monitor, blood oxygen sensor, or other sensor, transducer, or electrical circuit element described herein or otherwise available, may be embedded in an encapsulating adhesive layer and in electrical communication with the elastic conductive ink. The encapsulating adhesive layer is provided on the diffusion bonded elastic conductive ink. A predetermined pattern of semiconductor devices is fixed to the encapsulating adhesive layer. As an example of a vertical electrode arrangement, the semiconductor devices can each have a top device conductor and a bottom device conductor. As an example of a horizontal electrode arrangement, the semiconductor device has conductors on the top or bottom of the device.

A top substrate having a conductive portion disposed thereon can be provided to form a lamination package comprising the elastic conductive ink fusion bonded to the adhesive print media layer, the encapsulating adhesive layer, and the top substrate. As an example of connecting the electrodes of a vertical electrode arrangement semiconductor device, the lamination package may be driven through a roll or press laminator whereby the encapsulating adhesive layer insulates and binds the top substrate to the adhesive print media layer so that one of the top device conductor and bottom device conductor of the semiconductor devices is brought into electrical communication with the conductive portion of the top substrate, and so that the other of said top device conductor and bottom device conductor of each said semiconductor element is in electrical communication with the elastic conductive ink. Examples of a similar roll-to-roll bare die lamination process is described, for example, in U.S. Pat. Nos. 7,052,924, 7,217,956, 7,259,030, 7,427,782, 7,677,943, 7,723,733, 7,858,994, 7,863,760, 7,952,107, 8,129,730, as well as U.S. patent application Ser. No. 15/186,401, filed Jun. 17, 2016, claiming priority of provisional patent application 62/181,710, filed Jun. 18, 2015, all of which are incorporated by reference in their entirety herein. FIG. 88 shows a configuration of a robust exposed electrode facing inwards towards the skin of a user and adhered to a stretch fabric with an embedded LED adhered to the stretch fabric and facing outward from the skin of the user.

FIG. 89 shows a configuration of a robust sweat chemistry detector fixed to printed electric leads formed from an elastic conductive ink diffusion bonded to a TPU print media and adhered to a stretch fabric. An example of a robust sweat chemistry detector can be found in U.S. Pat. No. 8,841,239 B2, which is incorporated by reference in its entirety herein.

As described in more detail herein, REEP™ processed materials were discovered to be capable of forming a very low temperature printed circuit board (PCB) (as compared with the elevated temperatures necessary for a conventional solder flow PCBs). Importantly, the materials prepared following the exemplary embodiments described herein for the REEP™ process have been shown to be able to electrically connect surface mount electronic devices, including electronic devices such as light emitting diodes, capacitors, resistors, and transistors without the need for additional conductive glues or solder.

FIG. 90 is a cross-sectional view showing a surface mount electronic device electrically and mechanically connected without conductive glues or solder to REEP™ processed conductive leads disposed on a thermoplastic insulative adhesive and/or disposed on a PCB substrate. The PCB substrate may be made from paper, plastic, fabric, wood, metal, thermally transmissive heat sinking material, included as a daughterboard on a conventional printed circuit board motherboard (and vice-versa), or any other suitable material. The PCB substrate may also be thermoformable, such as using vacuum forming, into a three-dimensional object.

FIG. 91 illustrates REEP™ processed conductive lead having an embedded conductive thread for providing a lower resistance electric pathway. The embedded conductive thread can be added to the diffusion zone of material comprised of the constituent parts of the TPU and conductive ink either before or after the process steps forming the diffusion bond. For example, the conductive thread may be tacked in place on the softened top surface of the TPU prior to the step of coating the elastic conductive ink. Alternatively, the conductive thread can be placed onto the uncured elastic conductive ink prior to the process steps forming the diffusion bond. As another alternative, the conductive thread can be placed onto the diffusion bonded surface of the conductive ink, and then heat and/or pressure applied to embed the conductive thread into the diffusion zone of material comprised of the constituent parts of the TPU and conductive ink.

FIG. 92 illustrates a low temperature printed circuit made from an all-additive process. A conductive pattern of REEP™ processed material is disposed on a low temperature PCB substrate. The conductive pattern creates the conductive pathways (lead lines) that enable electrons to flow through discreet electronic circuit elements (R1—resistor, C—capacitor, LED, T—transistor) mechanically and electrically connected to the conductive pattern. As an example, the conductive pattern can be formed by printed a pattern of elastic conductive ink onto a TPU substrate. Alternatively, pre-made REEP™ processed material may be cut into the conductive pattern using, for example, a laser or vinyl cutter, and then adhered (conductive side up) to a base PCB substrate. In any case, the REEP™ disclosed here converts the printed elastic conductive ink on the TPU into a material that is able to electrically connect with and mechanically fix surface mount electronic devices. The inherent resistance (e.g., R2) can be advantageously utilized, for example, to provide a currently limiting resistance associated with an electronic circuit device, such as an LED, or an additional SMT resistor can be include with the appropriate electrical connection between, in the case of the example, circuit, the capacitor and the LED.

As shown in FIG. 92, the surface mount electronic devices are placed onto the pre-disposed conductive pattern to form the electronic circuit shown schematically in FIG. 93. FIG. 93 is a schematic of an electronic circuit that includes a resistor/capacitor timing circuit for controlling a transistor to cause an LED to blink. Of course, the electronic circuit can be more or less complex, and many surface mount electronic devices are available and usable in the inventive REEP™ low temperature PCB construction. FIG. 94 is an example of a surface mount transistor, having overall dimensions of about 3 mm by about 2.5 mm, and provides an indication of the scale of the printed circuit, although the printed circuit size is not in any way limited to the example shown herein.

The discrete SMT electronic devices are placed on the conductive pattern of REEP™ processed material. The conductive pattern may be made tacky by applying heat to facilitate the rapid placement of the SMT devices using a conventional pick and place machine (where the REEP™ PCB may or may not need to be first mounted on a carrier, depending on what PCB substrate is used).

Once the SMT electronic devices have been populated, heat and pressure is applied to form an electrical connection between the electronic devices and the conductive pattern. This heat and pressure can be applied using a roll laminator, thereby enabling the REEP™ process to be adaptable to roll-to-roll manufacturing. In this case, all or some of the various processing steps described herein can be performed in a single, efficient, continuous manufacturing line. Alternatively, the heat and pressure can be applied using a platen laminator. Once exposed to the heat and pressure, the discrete SMT electronic devices are securely fixed to the conductive pattern and brought into electrical communication with the elastic conductive ink forming a constituent part of the diffusion bonded ink and TPU.

FIG. 95 shows an example of a sine wave shape printed conductive circuit line made using the REEP™ process and laminated to a fabric PCB substrate suitable for making a wearable electronic device. The conductive circuit line may include an embedded conductive thread or other conductivity/connection enhancing element. The embedded conductive thread may be incorporated and embedded into the sine wave shape printed conductive circuit line during the processing an elastic conductive ink diffusion bonded onto a TPU adhesive, or it could be added in a subsequent process.

FIG. 95 shows an example of a sine wave shape printed conductive circuit line made using the REEP™ process and laminated to a fabric PCB substrate suitable for making a wearable electronic device. FIG. 96 shows a sine way printed circuit line formed using the REEP™ processed material. FIG. 97 shows a low temperature printed circuit board built on a paper substrate using the REEP™ processed materials for connecting a surface mount LED, where the LED includes a connection enhancing additional TPU patch that includes a light diffusing particulate, showing that the LED has been put into electrical communication with a battery without the use of an additional conductive glue or solder. The low temperature PCB process includes the steps of making an electrical and mechanical connection through a simple heat and pressure lamination step without the need for additional conductive glue, solder, or any other material or process.

FIG. 98 shows an experimental attempt to connect a surface mount LED to conductive lines using the same TPU and conductive ink as used in the REEP™ processed material shown in FIG. 32. However, as shown, the LED has not been put into electrical communication with a battery having an ink curing process consistent with the conventional process recommended by the ink manufacturer for curing a conductive ink printed on TPU.

FIG. 97 shows a low temperature printed circuit board built on a paper substrate using the REEP™ processed materials for connecting a surface mount LED, where the LED includes a connection enhancing additional TPU patch that includes a light diffusing particulate, showing that the LED has been put into electrical communication with a battery without the use of an additional conductive glue or solder. FIG. 98 shows an experimental attempt to connect a surface mount LED to conductive lines using the same TPU and conductive ink as used in the REEP™ processed material.

FIG. 99 shows a low temperature printed circuit board with a blue LED and a green LED electrically connected through a simple one-step heat and pressure lamination process directly onto conductive lead lines formed from REEP™ processed materials having an elastic conductive ink diffusion bonded to an adhesive print media. FIG. 100 shows the blue and green LED shown in FIG. 99 having a patch of light diffusion material applied in a heat and pressure lamination process, which also more securely fixes the surface mount electronic devices to the REEP™ processed material. FIG. 101 shows an experimental light diffusion patch made from silver-coated glass spheres bonded to the same TPU and similar processing steps as used in the REEP™ processed materials.

FIG. 102 illustrates a roll-to-roll process with multiple spray coating passes for creating a completed roll of diffusion bonded elastic conductive ink on adhesive. An adhesive substrate, such as TPU, is provided having a top surface. The adhesive is provided as a roll of material that is conveyed through various process stations in the roll-to-roll process. A top surface of the adhesive is sprayed with solvent to soften the top surface in preparation of receiving a conductive particulate. A layer of conductive particulate is applied, for example, from a conductive ink spray station on the top surface. A flash dry station can be provided to semi-cure the conductive ink spray before a second conductive ink spray station applied another layer of the conductive particulate. Multiple stations can be provided as necessary to build up a desired thickness of the conductive particulate. Flash dry stations and/or heated rollers can be provided between the conductive ink spray stations to semi-cure, cure and/or embed the conductive particulate into the adhesive top surface. The conductive particulate is embedded into the softened top surface of the adhesive substrate to form a conductive surface. After forming the conductive layer, a second or multiple additional layers of conductive particulate can be formed on the conductive surface, and embedded into the conductive surface. Through this process, a desired conductivity can be provided for the conductive surface through the successive build up, curing and embedding processes, with the conductive particulate securely embedded within a matrix of the adhesive.

FIG. 103 is a flow chart showing the steps for forming an adhesive with particulate in an adhesive substrate. An adhesive is provided having a top surface (Step One). FIG. 104 is a cross section of a TPU substrate on carrier sheet. The top surface of the adhesive may be softened in preparation of receiving the conductive particulate (Step Two).

Typically, a conductive ink includes binder material mixed with conductive particulate. A solvent keeps the binder material in an unhardened state prior to and during printing. During a curing process, the solvent is removed and the binder hardens to secure the conductive particulate to the substrate. This conventional conductive ink has a drawback in the binder typically being an electrically insulative material, limiting the conductivity of the electrically conductive structure formed from the conductive particulate and binder.

In accordance with the exemplary embodiments, instead of a binder and solvent system for carrying the conductive particulate, the binder may be omitted. For example, FIG. 105 is a cross section showing a carrier fluid with dispersed conductive particulate disposed on the top surface of the TPU substrate. The carrier fluid may be a solvent that softens the top surface of the TPU substrate to make it more receptive of embedding the conductive particulate (without binder) to create a conductive surface by forming a diffusion bond of the conductive particulate in the TPU substrate.

A layer of conductive particulate is formed on the top surface (Step Three). FIG. 106 is a cross section showing a softened TPU zone formed on the top surface of the TPU substrate. The conductive particulate is embedded in the softened top surface to form a diffusion bond (Step Four). FIG. 107 is a cross section showing the conductive particulate embedded in the TPU substrate with a diffusion zone formed between a more conductive top surface and the bulk of the TPU substrate.

FIG. 108 illustrate an electrostatic digital printing station of a wearable electronic digital manufacturing process. FIG. 109 is a close-up view showing the transfer of conductive particulate from a coating drum to a photoreceptor drum to a substrate of the electrostatic digital printing station. FIG. 110 illustrates a roll-to-roll wearable electronic digital manufacturing process.

As shown in FIGS. 107 and 108, a microprocessor controls the wearable electronics digital manufacturing system and receives a digital manufacturing signal that includes electrically conductive pattern image artwork and other details needed to form an electrically conductive surface on a substrate. The electrically conductive pattern is formed, for example, from conductive particulate that is disposed onto a substrate, such as an adhesive, fabric, TPU, or the like, and then fused to the substrate. The substrate with the fused conductive pattern can then be applied to a fabric, printed circuit board substrate, or other suitable material.

The microprocessor activates a corona wire. This is a high-voltage wire that gives a static electric charge to charge up a photoreceptor drum. The photoreceptor drum gains a positive charge spread uniformly across its surface. The microprocessor controls a laser to draw an image from the digital manufacturing signal onto the photoreceptor drum. As in a conventional laser printer, a laser beam may be reflected off a moving mirror that scans it over the photoreceptor drum. Where the laser beam hits the photoreceptor drum, the positive charge at the location of the incident beam on the photoreceptor drum creates an area of negative charge.

An electrostatic image builds up on the rotating photoreceptor drum. For example, where there are areas that are not part of the electrically conductive pattern, a positive charge is disposed on the photoreceptor drum. On the other hand, where the electrically conductive pattern is present, a negative charge is disposed on the photoreceptor drum.

A coating drum touching the photoreceptor drum coats it with tiny particles of powdered conductive particulate (like the toner in a conventional laser printer). The conductive particulate may be, for example, silver, silver chloride, aluminum, copper, alloy, organic conductors, or other micro or nano-scale conductive particulate. The conductive particulate is given a positive electrical charge, and is electrostatically attracted to the parts of the photoreceptor drum that have the negative charge. As the photoreceptor drum rotates, the conductive pattern in the image in the digital manufacturing signals builds up on the drum.

A substrate feeds up toward the photoreceptor drum. As the substrate moves along, the substrate is given a strong positive electrical charge by another corona wire or other static electric inducing mechanism (not shown).

When the substrate moves near the photoreceptor drum, the positive charge on the substrate attracts the negatively charged conductive particulate away from the photoreceptor drum. The electrically conductive pattern of conductive particulate is then transferred from the photoreceptor drum onto the substrate.

As shown in FIG. 110, the substrate with the conductive particulate disposed on its surface passes through two hot rollers. The heat and pressure from the rollers embed the conductive particulate particles permanently into the substrate and form a diffusion bond, where there is a higher concentration of overlapping conductive particulate mixed in and adhered at the surface of the substrate and gradually a higher concentration of the substrate material in the conductive particulate/substrate mix towards the bottom of the substrate.

FIG. 111 is a digitally printable exposed electrode pattern. This pattern is an example of a printed electronic image that is applied, for example, to a stretch fabric to create a wearable electronic pattern. In this case, the wearable electronic is disposable as a forearm sleeve with the electrodes disposed to obtain EMG signals from the muscles in the forearm of a user to detect muscle contractions used for a biometric "gesture control" system. The pattern has eight gangs of three individually addressable electrodes. Each gang includes a central reference electrode and a top and bottom detection electrode. The electrodes are used to detect EMG signals from the muscles in the forearm. When applied to a stretch fabric, in any of the exemplary processes described herein, a soft wearable electronic construction enables a Haptic Human/Machine Interface that has the ability to detect, analyze and apply electrical signals to/from the human body. This pattern also has the capability of adding sweat chemistry detection. For example, sweat chemistry sensors can be included for fitness and health related uses (for example, continuous diabetes monitoring of glucose and ketones—without requiring any drawing of blood). The pattern has terminations with snap connectors to transition from the printed ink to the electronics.

A print media layer is provided. A layer of conductive particulate is deposited onto a top layer of the print media layer. The conductive particulate is embedded into the top surface of the print media to form a conductive surface on the top surface of the print media layer. A surface treatment is performed to a top surface of the print media layer. The embedding is facilitated by the surface treatment. The materials, including the print media layer, may be provided as a roll of material on a carrier substrate. The surface treatment to the top surface, depositing of the conductive particulate and embedding may be done sequentially in a roll-to-roll process.

The surface treatment may comprise at least one of heat and solvent softening of the top surface of the print media layer. The embedding may be performed by at least one of a heat treatment and a pressure operation.

The conductive particulate may be electrostatically attractive. The depositing is performed by attracting the electrostatically attractive conductive particulate onto an electrostatically charged surface and transferring the electrostatically attractive conductive particulate from the electrostatically charged surface and onto the top surface of the print media layer.

The electrostatically charged surface may be selectively patterned with positive and negative charge to selectively attract the electrostatically attractive conductive particulate in a predetermined pattern. The predetermined pattern of electrostatically attractive conductive particulate can be transferred onto the top surface of the print media in a transferred pattern. The transferred pattern of electrostatically attractive conductive particulate may be embedded in the top surface of the print media to form the electrically conductive surface having the transferred pattern.

Figure 48:
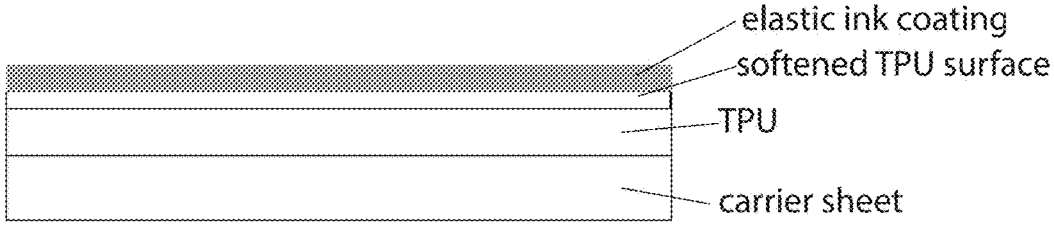
FIG. 48 shows a step of applying an elastic conductive ink coating on the softened top surface of the TPU print media.
Figure 49:
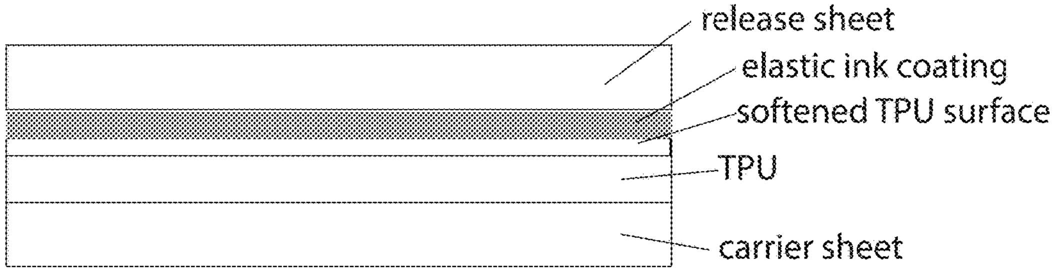
FIG. 49 shows a step of providing a release sheet on top of the uncured elastic ink coating on the softened top surface of the TPU print media.
Figure 50:
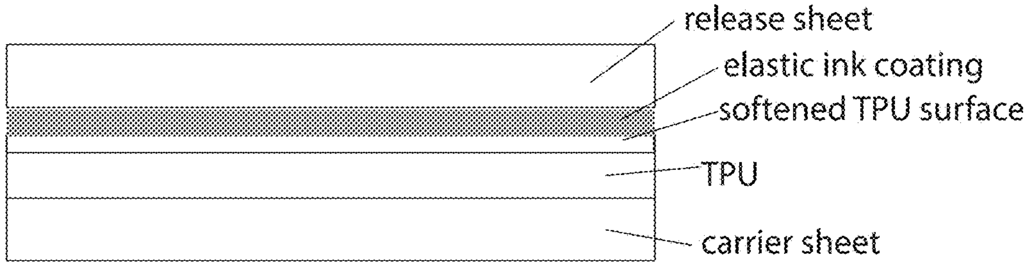
FIG. 50 shows a step forming a diffusion bond between the elastic ink and the TPU print media by applying heat and pressure to cure the elastic conductive ink coating, drive off at least a portion of any remaining solvents from the top surface pre-treatment and from within the coating of elastic conductive ink.
Figure 51:
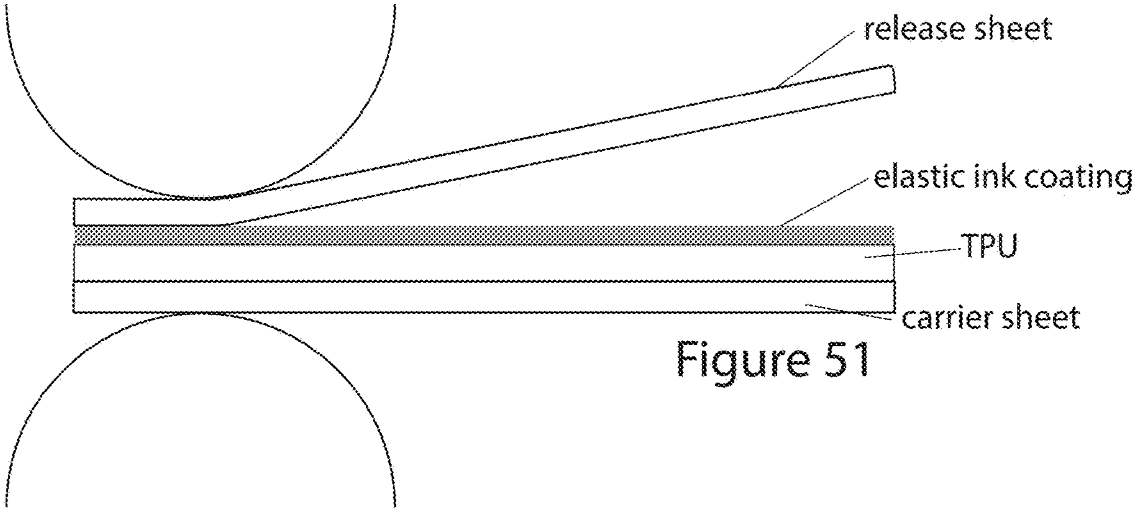
FIG. 51 illustrates the roll-to-roll process of forming a diffusion bond by applying heat and pressure to cure the elastic conductive ink coating using heated rollers.
Figure 52:
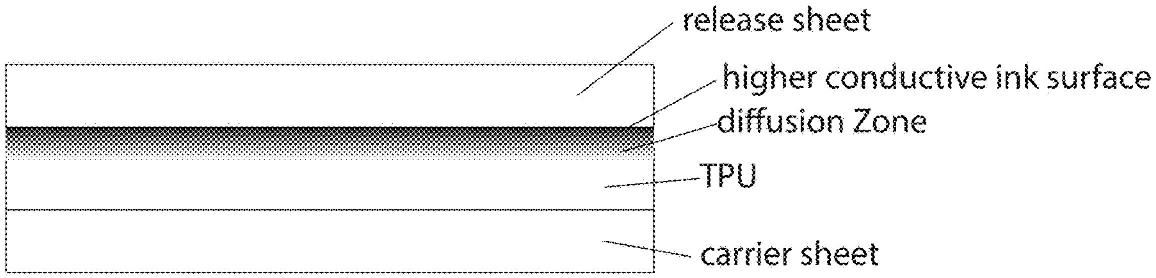
FIG. 52 shows the diffusion bond formed by applying heat and pressure to uncured elastic conductive ink coated on the softened top surface of a pre-treated TPU print media.
Figure 53:
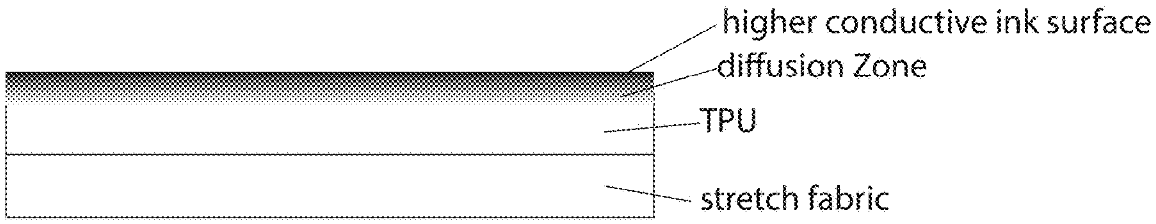
FIG. 53 shows a robust exposed electrode having a higher conductive ink surface bonded through a diffusion bond to the TPU print media adhered to a stretch fabric.

The electrostatically charged surface can be selectively patterned depending on a received digital manufacturing signal received over a network. The transferred pattern is dependent on the received digital manufacturing signal. FIG. 112 illustrates a multiple pass, roll-to-roll digital manufacturing line for building up high density conductive particulate into a digitally printed electronically conductive pattern. FIG. 48 is a cross section showing a patterned deposited first layer of conductive particulate on a TPU substrate.

An electronic device can be embedded in the conductive surface and in electrical communication with the conductive surface. FIG. 113 is a cross section showing an embedded first layer of conductive particulate on the TPU substrate. FIG. 114 is a cross section showing the embedded first layer and a patterned deposited second layer of conductive particulate on the TPU substrate. FIG. 115 is a cross section showing the embedded first layer and an embedded second layer of conductive particulate on the TPU substrate. FIG. 116 is a cross section showing the embedded first layer and the embedded second layer of conductive particulate with a patterned insulative adhesive overcoat on the TPU substrate. FIG. 117 is a cross section showing the embedded first layer and the embedded second layer of conductive particulate with the patterned insulative adhesive overcoat having an SMT semiconductor device adhered to the insulative adhesive and electrically connected to the embedded first and second layers of conductive particulate on the TPU substrate. FIG. 118 is a cross section showing the SMT semiconductor device adhered to the insulative adhesive and further fixed and protected with a protective insulative overcoating. FIG. 119 is a cross section showing the SMT semiconductor device that has been brought into face to face electrical communication with the patterned embedded conductive particulate and fixed in place on the TPU substrate through the application of heat and pressure, and further fixed and protected with a protective insulative overcoating. FIG. 120 is a cross section showing an SMT LED adhered to the insulative adhesive, with an optical overcoating and further fixed and protected with a protective insulative flood coating.

A predetermined pattern of semiconductor devices can be fixed to the conductive surface. The semiconductor devices may each have a top device conductor and a bottom device conductor. At least one of heat and pressure can be applied to electrically and mechanically connect the semiconductor device to the conductive surface on the print media. The conductive particulate can be patterned as lead lines and connection lands for forming a printed circuit. The connection of the predetermined pattern of the semiconductor devices forms an electronic circuit having the semiconductor devices electrically and mechanically connected to the connection lands and the lead lines provide for the flow of electrons between the semiconductor devices during the operation of the printed circuit.

The conductive surface can be selectively patterned in a predetermined pattern. The predetermined pattern of the conductive surface can be transferred as a transferred pattern onto a substrate. The transferred pattern of conductive particulate can then be embedded in the substrate. The conductive surface can be selectively patterned in the predetermined pattern depending on a received digital manufacturing signal received over a network. The transferred pattern is dependent on the received digital manufacturing signal, so that, for example, a user can be digitally measured at a different date and or time as the manufacturing of a wearable electronic that is designed to fit the digitally measured user with a high degree of precision. The digital measurement can include the user's geometry, and also the underlying muscles, bones, nerves, organs and other biological structures beneath the user's skin. EMG, X-Ray, MRI, PET and other biological scanning techniques can be used, in addition to or instead of, for example, laser measurements of the user's body geometry.

FIG. 121 is a cross section showing a bare die electronic element, such as an LED, connected to a conductive transparent surface of a top patch or sheet of transparent substrate applied to a TPU having a conductive surface. FIG. 122 is a cross section showing a bare die electronic element, such as an LED, connected to a printed ink conductive translucent surface of a top patch or sheet of transparent substrate applied to a TPU having a conductive surface. FIG. 123 is a cross section showing a bare die electronic element, such as an LED, connected to a printed ink conductive translucent surface and printed ink higher conductivity lead lines printed on a TPU having a conductive surface. FIG. 124 is a cross section showing a hotmelt adhesive on a bottom release sheet. FIG. 125 is a cross section showing a bare die LED partially embedded in a softened top surface of the hotmelt adhesive. FIG. 126 is a cross section showing a top release sheet forming a lamination package with the hotmelt adhesive on the bottom release sheet; FIG. 127 is a cross section showing the bare die LED driven thorough the hotmelt adhesive. FIG. 128 is a cross section showing the top and bottom release sheets removed from the hotmelt adhesive with the bare die LED embedded having a top and bottom electrode expose. FIG. 129 is a flow chart of a process for forming a sheet of adhesive with embedded bare die LED, each LED having its top and bottom electrode exposed.

The conductive surface can be selectively patterned in the predetermined pattern by at least one of laser cutting, die cutting, and CNC knife cutting. The inventive roll-to-roll process is capable of a high degree of recycling. For example, a scrap portion of the conductive surface that is not transferred to the fabric can be obtained from the carrier sheet. A recycling operation can be performed on the scrap portion, where the recycling operation comprises, for example, at least one of a heat and/or solvent processing. The conductive particulate can have a composition, concentration, geometry and/or orientation that is used to create a desired electrical characteristic, so that for example, a resistance value can be set by printing a particulate layer having a predetermined particle concentration, composition, etc. Different printing stages, or similar to a color laser printer, different conductive particulate cartridges, can be used to hold different type of particulate with compositions that enable the building up desired resistor, capacitor, semiconductor properties according to a desire printed circuit construction.

In accordance with a non-limiting embodiment, an adhesive substrate having a top surface is provided, A layer of conductive particulate is formed on the top surface. The top surface can be softened in preparation of receiving the conductive particulate. The conductive particulate is embedded into the softened top surface of the adhesive substrate to form a conductive surface.

A second layer of conductive particulate can be formed on the conductive surface. The second layer of conductive particulate is then embedded into the conductive surface. Alternatively, or additionally, multiple layers of particulate can be built up with conductive, semi-conductive, p-material, n-material, adhesive, heat transporting, phase-change, and other properties. The embedding can be done in subsequent passes through heat and pressure rollers between building up the layers, or layers can be built up and then subjected to a coalescing/embedding heat and pressure operation.

FIG. 130 is a cross section showing a TPU substrate with a conductive surface on a carrier sheet. FIG. 131 is a cross section showing a hotmelt adhesive with embedded bare die LED adhered to the conductive surface. FIG. 132 is a cross section showing a conductive lead line printed on a top surface of the hotmelt. FIG. 133 is a cross section showing a translucent printed conductor connecting the top electrode to the conductive lead line.

FIG. 134 is a flow chart of a process for forming an electronic circuit by printing a translucent conductive ink and conductive lead lines on a sheet of hotmelt adhesive with embedded bare die LED. FIG. 135 is a cross section showing a TPU substrate with a conductive surface on a carrier sheet. FIG. 136 is a cross section showing an adhesive hotmelt adhered to the TPU substrate to embed the conductive surface into a bottom surface of the hotmelt adhesive. FIG. 137 is a cross section showing a bare die LED partially embedded in a softened top surface of the hotmelt adhesive. FIG. 138 is a cross section showing the bare die LED driven thorough the hotmelt adhesive with a bottom electrode connecting with the conductive surface. FIG. 139 is a cross section showing a conductive lead line and a translucent printed conductor connecting the top electrode of the LED to the conductive lead line printed on a top surface of the hotmelt.

FIG. 140 is a flow chart of a process for forming an electronic circuit by printing a translucent conductive ink and conductive lead lines on a sheet of hotmelt adhesive with embedded bare die LED. In accordance with a non-limiting embodiment, a layer of conductive particulate is formed onto an electrostatic surface. The layer of conductive particulate is transferred from the charged electrostatic surface to a top surface of a substrate. The conductive particulate is embedded into the top surface of the substrate to form a conductive surface.

A second layer of conductive particulate can be formed onto a charged electrostatic surface after the first layer of conductive particulate has been embedded or to build up a thickness or mixture of conductive particulate. The second layer of conductive particulate is transferred from the charged electrostatic surface onto the conductive surface.

The conductive particulate is embedded into the conductive surface. The conductive particulate can have a composition, concentration, geometry and/or orientation for creating a desired electrical characteristic. The electrodes of one or more electronic devices can be embedded in the conductive surface to electrically connect the electrodes of the electronic devices to the conductive surface.

Embodiments herein may be implemented in software (executed by one or more processors), hardware (e.g., an application specific integrated circuit), or a combination of software and hardware. In an example embodiment, the software (e.g., application logic, an instruction set) is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain, store, and/or transport the instructions for use by or in connection with an instruction execution system, apparatus, or device, such as a computer.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations set out in the claims.

It is noted herein that while the above describes example embodiments of the invention, these descriptions should not be viewed in a limiting sense. Rather, there are several variations and modifications which may be made without departing from the scope of the present invention as defined in the appended claims.

The invention claimed is:

1. A method of making an electrode for a wearable electronic, comprising:

providing an elastic adhesive print media layer;

performing a surface treatment to a top surface of the print media layer, wherein the surface treatment comprises applying a solvent to the top surface and allowing the solvent time to soften a thickness of the top surface;

depositing an elastic conductive ink onto the print media layer, wherein the elastic conductive ink comprises a conductive particulate disposed in a binder;

forming a diffusion bond between the top surface of the print media layer and the elastic conductive ink, wherein the diffusion bond forming is facilitated by the surface treatment, and wherein the softened thickness of the top surface is effective for a portion of the binder and conductive particulate of the elastic conductive ink to infiltrate into the thickness of the top surface during the step of forming the diffusion bond; and applying heat and pressure to form an electrically conductive interface between the print media layer and the conductive ink using a heated surface with a surface temperature between 225° C. and 325° C., a pressure of at least 1.5 bar to form the elastic print media layer having the top surface of the diffusion bonded electrode being is electrically conductive to apply an electrical signal to, or detect an electrical signal from, nerves or muscles of the human body through the skin.

2. The method of claim 1; wherein the adhesive print media layer is provided as a roll of material on a carrier substrate; and performing the surface treatment to the top surface, depositing of the elastic conductive ink and forming the diffusion bond are done sequentially in a roll-to-roll process.

3. The method of claim 1; wherein the surface treatment comprises at least one of heat and solvent softening of the top surface of the print media layer.

4. The method of claim 1; wherein the solvent comprises an organic solvent.

5. The method according to claim 1; wherein the solvent is selected to achieve a slight degree of solvation with maximum swelling of the top surface.

6. The method of claim 1; wherein the solvent is selected to achieve a high degree of solvation of the top surface.

7. The method of claim 1; wherein the solvent includes at least one of Dichloromethane (CH2Cl2), Dimethyl formamide (C3H7NO) and Methanol (CH3OH).

8. The method according to claim 1, wherein the adhesive print media layer comprises a polyurethane.

9. The method according to claim 1; wherein the adhesive print media layer comprises a polymer chain including ethyl carbamate C3H7NO2.

* * * * *